US010622094B2

(12) United States Patent
Kim et al.

(10) Patent No.: US 10,622,094 B2
(45) Date of Patent: Apr. 14, 2020

(54) METHODS AND PROCESSES FOR NON-INVASIVE ASSESSMENT OF GENETIC VARIATIONS

(71) Applicant: SEQUENOM, INC., San Diego, CA (US)

(72) Inventors: Sung K. Kim, Glendale, CA (US); Gregory Hannum, San Diego, CA (US); Jennifer Geis, San Diego, CA (US); Cosmin Deciu, San Diego, CA (US)

(73) Assignee: Sequenom, Inc., San Diego, CA (US)

( * ) Notice: Subject to any disclaimer, the term of this patent is extended or adjusted under 35 U.S.C. 154(b) by 701 days.

(21) Appl. No.: 14/311,070

(22) Filed: Jun. 20, 2014

(65) Prior Publication Data

US 2015/0005176 A1 Jan. 1, 2015

Related U.S. Application Data

(60) Provisional application No. 61/838,048, filed on Jun. 21, 2013.

(51) Int. Cl.
| | | |
|---|---|---|
| *G16B 30/00* | (2019.01) | |
| *C12Q 1/6816* | (2018.01) | |
| *G16B 20/00* | (2019.01) | |
| *C12Q 1/6872* | (2018.01) | |
| *C12Q 1/6869* | (2018.01) | |
| *G06F 19/00* | (2018.01) | |

(52) U.S. Cl.
CPC ........... *G16B 30/00* (2019.02); *C12Q 1/6816* (2013.01); *C12Q 1/6869* (2013.01); *C12Q 1/6872* (2013.01); *G06F 19/34* (2013.01); *G16B 20/00* (2019.02)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 5,075,212 A | 12/1991 | Rotbart | |
| 5,091,652 A | 2/1992 | Mathies et al. | |
| 5,432,054 A | 7/1995 | Saunders et al. | |
| 5,445,934 A | 8/1995 | Fodor | |
| 5,670,325 A | 9/1997 | Lapidus et al. | |
| 5,720,928 A | 2/1998 | Schwartz et al. | |
| 5,786,146 A | 7/1998 | Herman et al. | |
| 5,928,870 A | 7/1999 | Lapidus et al. | |
| 5,939,598 A | 8/1999 | Kucherlapati et al. | |
| 6,015,714 A | 6/2000 | Baldarelli et al. | |
| 6,090,550 A | 7/2000 | Collinge et al. | |
| 6,100,029 A | 8/2000 | Lapidus et al. | |
| 6,214,558 B1 | 4/2001 | Shuber et al. | |
| 6,214,560 B1 | 4/2001 | Yguerabide et al. | |
| 6,235,475 B1 | 5/2001 | Brenner et al. | |
| 6,258,540 B1 | 7/2001 | Lo et al. | |
| 6,263,286 B1 | 7/2001 | Gilmanshin et al. | |
| 6,403,311 B1 | 6/2002 | Chan | |
| 6,566,101 B1 | 5/2003 | Shuber et al. | |
| 6,617,133 B1 | 9/2003 | Noda et al. | |
| 6,772,070 B2 | 8/2004 | Gilmanshin et al. | |
| 6,818,395 B1 | 11/2004 | Quake et al. | |
| 6,927,028 B2 | 8/2005 | Dennis et al. | |
| 6,936,422 B2 | 8/2005 | El sohl et al. | |
| 7,005,264 B2 | 2/2006 | Su et al. | |
| 7,169,560 B2 | 1/2007 | Lapidus et al. | |
| 7,279,337 B2 | 10/2007 | Zhu | |
| 7,282,337 B1 | 10/2007 | Harris | |
| 7,947,454 B2 | 5/2011 | Akeson et al. | |
| 7,960,105 B2 | 6/2011 | Schwartz et al. | |
| 7,972,858 B2 | 7/2011 | Meller et al. | |
| 8,467,976 B2 | 6/2013 | Lo et al. | |
| 8,620,593 B2 | 12/2013 | Lo et al. | |
| 8,688,388 B2 | 4/2014 | Dzakula et al. | |
| 9,260,745 B2 | 2/2016 | Rava et al. | |
| 2001/0014850 A1 | 8/2001 | Gilmanshin et al. | |
| 2001/0049102 A1 | 12/2001 | Huang et al. | |
| 2002/0006621 A1 | 1/2002 | Bianchi | |
| 2002/0045176 A1 | 4/2002 | Lo et al. | |
| 2002/0110818 A1 | 8/2002 | Chan | |
| 2002/0119469 A1 | 8/2002 | Shuber et al. | |
| 2002/0164629 A1 | 11/2002 | Quake et al. | |
| 2003/0013101 A1 | 1/2003 | Balasubramanian | |
| 2003/0082600 A1 | 5/2003 | Olek et al. | |
| 2003/0180779 A1 | 9/2003 | Lofton-Day et al. | |
| 2003/0207326 A1 | 11/2003 | Su et al. | |
| 2003/0232346 A1 | 12/2003 | Su | |
| 2004/0081993 A1 | 4/2004 | Cantor et al. | |
| 2004/0110208 A1 | 6/2004 | Chan et al. | |

(Continued)

FOREIGN PATENT DOCUMENTS

| | | |
|---|---|---|
| WO | WO 00/006770 | 2/2000 |
| WO | WO 01/032887 | 5/2001 |

(Continued)

OTHER PUBLICATIONS

Office Action dated Jul. 7, 2016 in U.S. Appl. No. 13/781,530, filed Feb. 28, 2013 and published as US 2014-0100792 on Apr. 10, 2014.
International Search Report and Written Opinion dated Sep. 24, 2014 in International Application No. PCT/US2014/043497, filed on Jun. 20, 2014.
Liu et al., "CUSHAW: a CUDA compatible short read aligner to large genomes based on the Burrows-Wheeler transform" Bioinformatics (2012) 28(14):1830-1837.

(Continued)

*Primary Examiner* — John S Brusca

(74) *Attorney, Agent, or Firm* — Fish & Richardson P.C.

(57) ABSTRACT

Provided herein are methods, processes, systems, machines and apparatuses for non-invasive assessment of genetic variations.

20 Claims, 25 Drawing Sheets

(56) References Cited

U.S. PATENT DOCUMENTS

| | | |
|---|---|---|
| 2004/0137470 A1 | 7/2004 | Dhallan et al. |
| 2005/0019784 A1 | 1/2005 | Su et al. |
| 2005/0095599 A1 | 5/2005 | Pittaro et al. |
| 2005/0112590 A1 | 5/2005 | Boom et al. |
| 2005/0147980 A1 | 7/2005 | Berlin et al. |
| 2005/0164241 A1 | 7/2005 | Hahn et al. |
| 2005/0227278 A1 | 10/2005 | Wall |
| 2005/0287592 A1 | 12/2005 | Kless |
| 2006/0046258 A1 | 3/2006 | Lapidus et al. |
| 2006/0063171 A1 | 3/2006 | Akeson et al. |
| 2006/0068440 A1 | 3/2006 | Chan et al. |
| 2006/0252071 A1 | 11/2006 | Lo et al. |
| 2007/0065823 A1 | 3/2007 | Dressman et al. |
| 2007/0202525 A1 | 8/2007 | Quake et al. |
| 2008/0020390 A1 | 1/2008 | Mitchell et al. |
| 2008/0070792 A1 | 3/2008 | Stoughton et al. |
| 2008/0081330 A1 | 4/2008 | Kahvejian et al. |
| 2008/0138809 A1 | 6/2008 | Kapur et al. |
| 2008/0187915 A1 | 8/2008 | Polonsky et al. |
| 2008/0233575 A1 | 9/2008 | Harris |
| 2009/0026082 A1 | 1/2009 | Rothberg et al. |
| 2009/0029377 A1 | 1/2009 | Lo et al. |
| 2009/0075252 A1 | 3/2009 | Harris |
| 2009/0129647 A1 | 5/2009 | Dimitrova et al. |
| 2009/0191565 A1 | 7/2009 | Lapidus et al. |
| 2009/0197257 A1 | 8/2009 | Harris |
| 2009/0317817 A1 | 12/2009 | Oeth et al. |
| 2009/0317818 A1 | 12/2009 | Ehrich et al. |
| 2010/0105049 A1 | 4/2010 | Ehrich et al. |
| 2010/0112575 A1 | 5/2010 | Fan et al. |
| 2010/0112590 A1 | 6/2010 | Lo et al. |
| 2010/0138165 A1 | 6/2010 | Fan et al. |
| 2010/0151471 A1 | 6/2010 | Faham et al. |
| 2010/0216151 A1 | 8/2010 | Lapidus et al. |
| 2010/0216153 A1 | 8/2010 | Lapidus et al. |
| 2010/0109197 A1 | 9/2010 | Hansen et al. |
| 2010/0261285 A1 | 10/2010 | Goldstein et al. |
| 2010/0310421 A1 | 12/2010 | Oliver et al. |
| 2010/0330557 A1 | 12/2010 | Yakhini et al. |
| 2011/0086769 A1 | 4/2011 | Oliphant et al. |
| 2011/0159601 A1 | 6/2011 | Golovchenko et al. |
| 2011/0171634 A1 | 7/2011 | Xiao et al. |
| 2011/0174625 A1 | 7/2011 | Akeson et al. |
| 2011/0177498 A1 | 7/2011 | Clarke et al. |
| 2011/0177517 A1 | 7/2011 | Rava et al. |
| 2011/0201507 A1 | 8/2011 | Rava et al. |
| 2011/0224087 A1 | 9/2011 | Quake et al. |
| 2011/0230358 A1 | 9/2011 | Rava |
| 2011/0288780 A1 | 11/2011 | Rabinowitz et al. |
| 2011/0294699 A1 | 12/2011 | Lee et al. |
| 2011/0312503 A1 | 12/2011 | Chuu et al. |
| 2011/0319272 A1 | 12/2011 | Fan et al. |
| 2012/0046877 A1 | 2/2012 | Hyland et al. |
| 2012/0122701 A1 | 5/2012 | Ryan et al. |
| 2012/0165203 A1 | 6/2012 | Quake et al. |
| 2012/0184449 A1 | 7/2012 | Hixson et al. |
| 2012/0214678 A1 | 8/2012 | Rava et al. |
| 2012/0264115 A1 | 10/2012 | Rava |
| 2012/0270212 A1 | 10/2012 | Rabinowitz et al. |
| 2012/0270739 A1 | 10/2012 | Rava et al. |
| 2013/0012399 A1 | 1/2013 | Meyers |
| 2013/0022977 A1 | 1/2013 | Lapidus et al. |
| 2013/0034546 A1 | 2/2013 | Rava et al. |
| 2013/0059733 A1 | 3/2013 | Lo et al. |
| 2013/0085681 A1 | 4/2013 | Deciu et al. |
| 2013/0096011 A1 | 4/2013 | Rava et al. |
| 2013/0130921 A1 | 5/2013 | Gao et al. |
| 2013/0130923 A1 | 5/2013 | Ehrich et al. |
| 2013/0150253 A1 | 6/2013 | Deciu et al. |
| 2013/0196317 A1 | 8/2013 | Lapidus et al. |
| 2013/0237431 A1 | 9/2013 | Lo et al. |
| 2013/0245961 A1 | 9/2013 | Lo et al. |
| 2013/0261983 A1 | 10/2013 | Dzakula et al. |
| 2013/0288244 A1 | 10/2013 | Deciu et al. |
| 2013/0304392 A1 | 11/2013 | Deciu et al. |
| 2013/0309666 A1 | 11/2013 | Deciu et al. |
| 2013/0310260 A1 | 11/2013 | Kim et al. |
| 2013/0325360 A1 | 12/2013 | Deciu et al. |
| 2013/0338933 A1 | 12/2013 | Deciu et al. |
| 2014/0019064 A1 | 1/2014 | Lo et al. |
| 2014/0038830 A1 | 2/2014 | Srinivasan et al. |
| 2014/0100792 A1 | 4/2014 | Deciu et al. |
| 2014/0180594 A1 | 6/2014 | Kim et al. |
| 2014/0235474 A1 | 8/2014 | Tang et al. |
| 2014/0242588 A1 | 8/2014 | Van Den Boom et al. |
| 2014/0322709 A1 | 10/2014 | Lapidus et al. |
| 2015/0100244 A1 | 4/2015 | Hannum |
| 2015/0347676 A1 | 12/2015 | Zhao et al. |
| 2016/0034640 A1 | 2/2016 | Zhao et al. |
| 2016/0110497 A1 | 4/2016 | Dzakula et al. |
| 2018/0230532 A1 | 8/2018 | Kim et al. |

FOREIGN PATENT DOCUMENTS

| | | |
|---|---|---|
| WO | WO 2002/042496 | 5/2002 |
| WO | WO 03/000920 | 1/2003 |
| WO | WO 03/106620 | 12/2003 |
| WO | WO 05/023091 | 3/2005 |
| WO | WO 06/056480 | 6/2006 |
| WO | WO 07/140417 | 12/2007 |
| WO | WO 07/147063 | 12/2007 |
| WO | WO 08/121828 | 10/2008 |
| WO | WO 09/007743 | 1/2009 |
| WO | WO 2009/013496 | 1/2009 |
| WO | WO 09/032779 | 3/2009 |
| WO | WO 09/032781 | 3/2009 |
| WO | WO 09/046445 | 4/2009 |
| WO | WO 10/004265 | 1/2010 |
| WO | WO 10/033578 | 3/2010 |
| WO | WO 10/033639 | 3/2010 |
| WO | WO 10/056728 | 5/2010 |
| WO | WO 10/059731 | 5/2010 |
| WO | WO 10/065470 | 6/2010 |
| WO | WO 10/115016 | 10/2010 |
| WO | WO 11/034631 | 3/2011 |
| WO | WO 11/038327 | 3/2011 |
| WO | WO 11/050147 | 4/2011 |
| WO | WO 11/057094 | 5/2011 |
| WO | WO 2011/054936 | 5/2011 |
| WO | WO 2011/057094 | 5/2011 |
| WO | WO 11/087760 | 7/2011 |
| WO | WO 11/090556 | 7/2011 |
| WO | WO 11/090558 | 7/2011 |
| WO | WO 11/090559 | 7/2011 |
| WO | WO 11/091063 | 7/2011 |
| WO | WO 11/102998 | 8/2011 |
| WO | WO 11/143659 | 11/2011 |
| WO | WO 11/146632 | 11/2011 |
| WO | WO 12/012703 | 1/2012 |
| WO | WO 12/088348 | 6/2012 |
| WO | WO 12/088456 | 6/2012 |
| WO | WO 2012/093331 | 7/2012 |
| WO | WO 12/103031 | 8/2012 |
| WO | WO 12/108920 | 8/2012 |
| WO | WO 12/118745 | 9/2012 |
| WO | WO 12/177792 | 12/2012 |
| WO | WO 13/000100 | 1/2013 |
| WO | WO 2013/041921 | 3/2013 |
| WO | WO 13/052907 | 4/2013 |
| WO | WO 13/052913 | 4/2013 |
| WO | WO 13/055817 | 4/2013 |
| WO | WO 13/109981 | 7/2013 |
| WO | WO 2013/177086 | 11/2013 |
| WO | WO 13/192562 | 12/2013 |
| WO | WO 2014/039556 | 3/2014 |
| WO | WO 14/055774 | 4/2014 |
| WO | WO 14/055790 | 4/2014 |
| WO | WO 14/116598 | 7/2014 |
| WO | WO 2014/165596 | 10/2014 |
| WO | WO 2014/190286 | 11/2014 |
| WO | WO 2015/040591 | 3/2015 |
| WO | WO 2015/051163 | 4/2015 |

(56) References Cited

FOREIGN PATENT DOCUMENTS

| WO | WO 2015/054080 | 4/2015 |
|---|---|---|
| WO | WO 2015/183872 | 12/2015 |
| WO | WO 16/019042 | 2/2016 |

OTHER PUBLICATIONS

Office Action dated Oct. 6, 2014 in U.S. Appl. No. 13/754,817, filed Jan. 30, 2013 and published as US 2013-0150253 on Jun. 13, 2013.
Chen et al., "A method for noninvasive detection of fetal large deletions/duplications by low coverage massively parallel sequencing" Prenatal Diagnosis (2013) 33(6):584-590, and supplementary material pp. 1-6.
Hsu et al., "A model-based circular binary segmentation algorithm for the analysis of array CGH data" BMC Research Notes (2011) 4:394.
Kim et al., "Identification of significant regional genetic variations using continuous CNV values in aCGH data" Genomics (2009) 94(5):317-323.
Oh et al., "CAM: a web tool for combining array CGH and microarray gene expression data from multiple samples" Computers in Biology and Medicine (2009) 40(9):781-785.
International Search Report and Written Opinion dated Dec. 17, 2014 in International Application No. PCT/US2014/039389, filed on May 23, 2014 and published as WO 2014/190286 on Nov. 27, 2014.
International Preliminary Report on Patentability dated Dec. 31, 2014 in International Application No. PCT/US2013/047131, filed on Jun. 21, 2013 and published as WO 2013/192562 on Dec. 27, 2013.
Hinds et al., "Whole-genome patterns of common DNA variation in three human populations" Science (2005) 307:1072-1079.
Pushkarev et al., "Single-molecule sequencing of an individual human genome" Nature Biotechnology (2009) 27(9):847-852.
Office Action dated Oct. 22, 2015 in U.S. Appl. No. 13/781,530, filed Feb. 28, 2013 and published as US 2014-0100792 on Apr. 10, 2014.
Office Action dated Oct. 27, 2015 in U.S. Appl. No. 13/333,842, filed Dec. 21, 2011 and published as US 2012/0184449 on Jul. 19, 2012.
Invitation to Pay Additional Fees and Partial International Search Report dated Oct. 14, 2015 in International Application No. PCT/US2015/042701, filed on Jul. 29, 2015.
Yu et al., "Size-based molecular diagnostics using plasma DNA for noninvasive prenatal testing" PNAS USA (2014) 111(23):8583-8588.
International Search Report and Written Opinion dated Oct. 2, 2015 in International Application No. PCT/US2015/032550, filed on May 27, 2015 and published as WO 2015/183872 on Dec. 3, 2015.
Yu et al., "Noninvasive prenatal molecular karyotyping from maternal plasma" PLoS One (2013) 8(4):e60968.
Bollen, "Bioconductor: Microarray versus next-generation sequencing tool sets" retrieved from the internet: http://dspace.library.uu.nl/bitstream/handle/1874/290489/Sander_Bollen_writing_assignment.pdf, retrieved on Sep. 23, 2015.
International Preliminary Report on Patentability dated Dec. 3, 2015 in International Application No. PCT/US2014/039389, filed on May 23, 2014 and published as WO 2014/190286 on Nov. 27, 2014.
Office Action dated Aug. 31, 2016 in U.S. Appl. No. 13/782,857, filed Mar. 1, 2013 and published as US 2013-0310260 on Nov. 21, 2013.
Agarwal et al., "Commercial landscape of noninvasive prenatal testing in the United States" Prenatal Diagnosis (2013) 33(6):521-531.
Dan et al., "Clinical application of massively parallel sequencing-based prenatal noninvasive fetal trisomy test for trisomies 21 and 18 in 11,105 pregnancies with mixed risk factors" Prenatal Diagnosis (2012) 32:1225-1232.
Office Action dated Jul. 27, 2015 in U.S. Appl. No. 13/782,857, filed Mar. 1, 2013 and published as US 2013-0310260 on Nov. 21, 2013.
International Preliminary Report on Patentability dated Aug. 6, 2015 in International Application No. PCT/US2014/012369, filed Jan. 21, 2014 and published as WO 2014/116598 on Jul. 31, 2014.
Supplementary Partial European Search Report dated Aug. 10, 2015 in European Application No. EP11745050.2, filed on Feb. 9, 2011 and published as EP 2 536 852 on Dec. 26, 2012.
Office Action dated Aug. 27, 2015 in U.S. Appl. No. 13/933,935, filed Jul. 2, 2013 and published as US 2013-0304392 on Nov. 14, 2013.
Office Action dated Sep. 1, 2015 in U.S. Appl. No. 13/829,164, filed Mar. 14, 2013 and published as US 2013-0288244 on Oct. 31, 2014.
Office Action dated Sep. 8, 2015 in U.S. Appl. No. 13/669,136, filed Nov. 5, 2012 and published as US 2013-0085681 on Apr. 4, 2013.
Office Action dated Sep. 8, 2015 in U.S. Appl. No. 13/797,508, filed Mar. 12, 2013 and published as US 2013-0261983 on Oct. 3, 2013.
Office Action dated Sep. 18, 2015 in U.S. Appl. No. 12/727,824, filed Mar. 19, 2010 and published as US 2010-0216153 on Aug. 26, 2010.
Office Action dated Sep. 22, 2015 in U.S. Appl. No. 13/779,638, filed Feb. 27, 2013 and published as US 2013-0309666 on Nov. 21, 2013.
Office Action dated Sep. 28, 2015 in U.S. Appl. No. 14/187,876, filed Feb. 24, 2014 and published as US 2014-0322709 on Oct. 30, 2014.
Office Action dated Oct. 2, 2015 in U.S. Appl. No. 13/754,817, filed Jan. 30, 2013 and published as US 2013-0150253 on Jun. 13, 2013.
Office Action dated Oct. 2, 2015 in U.S. Appl. No. 13/782,883, filed Mar. 1, 2013 and published as US 2014-0180594 on Jun. 26, 2014.
International Preliminary Report on Patentability dated Oct. 15, 2015 in International Application No. PCT/US2014/032687, filed on Apr. 2, 2014 and published as WO 2014/165596 on Oct. 9, 2014.
Romiguier et al., "Contrasting GC-content dynamics across 33 mammalian genomes: relationship with life-history traits and chromosome sizes" Genome Research (2010) 20:1001-1009.
National Human Genome Research Institute, Chromosomes fact sheet , (http://www.genome.gov/26524120, downloaded Sep. 9, 2015).
Leek et al., "Tackling the widespread and critical impact of batch effects in high-throughput data" Nature Reviews Genetics (2010) 11:733-739.
The International SNP Map Working Group "A map of human genome sequence variation containing 1.42 million single nucleotide polymorphisms" Nature (2001) 409:928-933.
Fan et al., "Analysis of the size distributions of fetal and maternal cell-free DNA by paired-end sequencing" Clinical Chemistry (2010) 56(8):1279-1286.
Alkan et al., "Personalized copy number and segmental duplication maps using next-generation sequencing", Nature Genetics, vol. 41, No. 10, Oct. 30, 2009 (Oct. 30, 2009), pp. 1061-1067, and Supplementary Information 1-68.
Adinolfi et al., "Rapid detection of aneuploidies by microsatellite and the quantitative fluorescent polymerase chain reaction." Prenat Diagn. Dec. 1997;17(13):1299-311.
Akeson et al., "Microsecond Time-Scale Discrimination Among Polycytidylic Acid, Polyadenylic Acid, and Polyuridylic Acid as Homopolymers or as Segments Within Single RNA Molecules," Biophysical Journal vol. 77 Dec. 1999 3227-3233.
Alkan, C., et al., Personalized copy number and segmental duplication maps using nextgeneration sequencing. Nat Genet, 2009. 41(10): p. 1061-7.
Amicucci et al., "Prenatal Diagnosis of Myotonic Dystrophy Using Fetal DNA Obtained from Maternal Plasma," Clin. Chem. 46:301-302, 2000.
Anantha et al., "Porphyrin binding to quadrupled T4G4." Biochemistry. Mar. 3, 1998;37(9):2709-14.
Armour et al., "Measurement of locus copy number by hybridisation with amplifiable probes." Nucleic Acids Res. Jan. 15, 2000;28(2):605-9.
Armour et al., "The detection of large deletions or duplications in genomic DNA." Hum Mutat. Nov. 2002;20(5):325-37.
Ashkenasy et al., "Recognizing a Single Base in an Individual DNA Strand: A Step Toward Nanopore DNA Sequencing," Angew Chem Int Ed Engl. Feb. 18, 2005; 44(9): 1401-1404.

(56) References Cited

OTHER PUBLICATIONS

Ashoor, et al., (2012): Chromosome-selective sequencing of maternal plasma cell-free DNA for first trimester detection of trisomy 21 and trisomy 18, American Journal of Obstetrics and Gynecology, doi: 10.1016/j.ajog.2012.01.029.
Aston et al. "Optical mapping and its potential for large-scale sequencing project," (1999) Trends Biotechnol. 17(7):297-302.
Aston et al. "Optical mapping: an approach for fine mapping," (1999) Methods Enzymol. 303:55-73.
Avent et al., "Non-invasive diagnosis of fetal sex; utilization of free fetal DNA in maternal plasma and ultrasound," Prenatal Diagnosis, 2006, 26: 598-603.
Beaucage and Caruthers, Tetrahedron Letts., 22:1859-1862 (1981).
Berger et al., "Universal bases for hybridization, replication and chain termination," (2000) Nucleic Acids Res. 28(15): 2911-2914.
Bergstrom et al. "Synthesis, Structure, and Deoxyribonucleic Acid Sequencing with a Universal Nucleoside: 1-(2'-Deoxy-.beta.-D-ribofuranosyl)-3-nitropyrrole," (1995) J. Am. Chem. Soc. 117, 1201-1209.
Brizot et al., "Maternal serum hCG and fetal nuchal translucency thickness for the prediction of fetal trisomies in the first trimester of pregnancy." Br J Obstet Gynaecol. Feb. 1995;102(2):127-32.
Brizot et al., "Maternal serum pregnancy-associated plasma protein A and fetal nuchal translucency thickness for the prediction of fetal trisomies in early pregnancy." Obstet Gynecol. Dec. 1994;84(6):918-22.
Brown and Lin "Synthesis and duplex stability of oligonucleotides containing adenine-guanine analogues," (1991) Carbohydrate Research 216, 129-139.
Brown et al. A step-by-step guide to non-linear regression analysis of experimental data using a Microsoft Excel spreadsheet Computer Methods and Programs in Biomedicine vol. 65, pp. 191-200 (2001).
Brown, L., et al., Validation of QF-PCR for prenatal aneuploidy screening in the United States. Prenat Diagn, 2006. 26(11): p. 1068-74.
Brünger, "Free R value: a novel statistical quantity for assessing the accuracy of crystal structures," Nature 355, 472-475 (Jan. 30, 1992); doi:10.1038/355472a0.
Bullard et al., "Evaluation of statistical methods for normalization and differential expression in mRNA-Seq experiments," Bioinformatics 2010, 11:94, pp. 1-13.
Burlingame et al. Anal. Chem. 70:647R-716R (1998).
Campbell et al., "Identification of somatically acquired rearrangements in cancer using genome-wide massively parallel paired-end sequencing." Nat Genet. Jun. 2008;40(6):722-9. doi: 10.1038/ng.128. Epub Apr. 27, 2008.
Canick et al., "DNA sequencing of maternal plasma to identify Down syndrome and other trisomies in multiple gestations," Prenat Diagn. May 14, 2012:1-5.
Canick, et al., "A New Prenatal Blood Test for Down Syndrome (RNA)," Jul. 2012 found on the internet at: clinicaltrials.gov/show/A15NCT00877292.
Carlson et al., "Molecular Definition of 22q11 Deletions in 151 Velo-Cardio-Facial Syndrome Patients," The American Journal of Human Genetics, vol. 61, Issue 3, 620-629, Sep. 1, 1997.
Chan et al. "Size Distribution of Maternal and Fetal DNA in Maternal Plasma," (2004) Clin. Chem. 50:88-92.
Chen et al., "Noninvasive Prenatal Diagnosis of Fetal Trisomy 18 and Trisomy 13 by Maternal Plasma DNA Sequencing," PLoS One, Jul. 2011, vol. 6, Issue 7, e21791, pp. 1-7.
Chiang et al., High-resolution mapping of copy-number alterations with massively parallel sequencing, Nat Methods. Jan. 2009 ; 6(1): 99-103.
Chim et al. (2008). "Systematic search for placental DNA-methylation markers on chromosome 21: toward a maternal plasma-based epigenetic test for fetal trisomy 21." Clin Chem 54(3): 500-11.
Chiu et al. "Maternal plasma DNA analysis with massively parallel sequencing by ligation for noninvasive prenatal diagnosis of trisomy 21." Clin Chem 56(3): 459-63.(2010).

Chiu et al. (2008). "Noninvasive prenatal diagnosis of fetal chromosomal aneuploidy by massively parallel genomic sequencing of DNA in maternal plasma." Proc Natl Acad Sci U S A 105(51): 20458-20463.
Chiu et al., "Non-invasive prenatal assessment of trisomy 21 by multiplexed maternal plasma DNA sequencing: large scale validity study," BMJ 2011;342:c7401, 1-9.
Chiu et al., "Prenatal exclusion of thalassaemia major by examination of maternal plasma," Lancet 360:998-1000, 2002.
Chu et al. (2009). "Statistical model for whole genome sequencing and its application to minimally invasive diagnosis of fetal genetic disease." Bioinformatics 25(10): 1244-50.
Cohen et al. (2005): GC Composition of the Human Genome: In Search of Isochores. Mole Biol. Evol. 22(5):1260-1272.
Costa et al., "New Strategy for Prenatal Diagnosis of X-Linked Disorders" N. Engl. J. Med. 346:1502, 2002.
Current Protocols in Molecular Biology, John Wiley&Sons, N.Y. 6.3.1-6.3.6(1989).
D'Alton ME., "Prenatal diagnostic procedures." Semin Perinatol. Jun. 1994;18(3):140-62.
Dan et al., "Prenatal detection of aneuploidy and imbalanced chromosomal arrangements by massively parallel sequencing," PLoS One 7(2): e27835. (2012).
Data Sheet: Illumina Sequencing: TruSeq RNA and DNA Sample Preparation Kits v2, Publication No. 970-2009-039 Apr. 27, 2011.
Davanos et al., "Relative quantitation of cell-free fetal DNA in maternal plasma using autosomal DNA markers" Clinica Chimica Acta (2011) 412:1539-1543.
Deamer et al., "Nanopores and Nucleic Acids: Prospects for ultrarapid sequencing." Focus Tibtech Apr. 2000, (vol. 18) pp. 147-151.
Derrien et al. (2012) Fast Computation and Applications of Genome Mappability. PLoS One 7(1): e30377, doi:10.1371/journal.pone.0030377.
Ding et al., "A high-throughput gene expression analysis technique using competitive PCR and matrix-assisted laser desorption ionization time-of-flight MS." Proc Natl Acad Sci U S A. Mar. 18, 2003;100(6):3059-64. Epub Mar. 6, 2003.
DNAcopy [online],[retrieved on Apr. 24, 2013], retrieved from the internet <URL:* >http://bioconductor.org/packages/2.12/bioc/html/DNAcopy.html.
Dohm et al., "Substantial biases in ultra-short read data sets from high-throughput DNA sequencing," Nucleic Acids Res. Sep. 2008;36(16):e105. Epub Jul. 26, 2008.
Donoho and Johnstone (1995), "WaveLab and Reproducible Research," Stanford University, Stanford CA 94305, USA, pp. 1-27.
Edelmann, L., et al., A common molecular basis for rearrangement disorders on chromosome 22q11. Hum Mol Genet, 1999. 8(7): p. 1157-67.
Egger et al., "Reverse transcription multiplex PCR for differentiation between polio- and enteroviruses from clinical and environmental samples." J Clin Microbiol. Jun. 1995;33(6):1442-7.
Ehrich et al., Noninvasive detection of fetal trisomy 21 by sequencing of DNA in maternal blood: a study in a clinical setting, American Journal of Obstetrics and Gynecology—Amer J Obstet Gynecol, vol. 204, No. 3, pp. 205.e1-205.e11, 2011 DOI: 10.1016/j.
Eiben et al., "First-trimester screening: an overview." J Histochem Cytochem. Mar. 2005;53(3):281-3.
Ensenauer, R.E., et al., Microduplication 22q11.2, an emerging syndrome: clinical, cytogenetic, and molecular analysis of thirteen patients. Am J Hum Genet, 2003. 73(5): p. 1027-40.
Fan et al., (2008). "Noninvasive diagnosis of fetal aneuploidy by shotgun sequencing DNA from maternal blood." Proc Natl Acad Sci U S A 105(42): 16266-71.
Fan et al., (2010). "Sensitivity of noninvasive prenatal detection of fetal aneuploidy from maternal plasma using shotgun sequencing is limited only by counting statistics." PLoS One 5(5): e10439.
Gebhard et al., "Genome-wide profiling of CpG methylation identifies novel targets of aberrant hypermethylation in myeloid leukemia." Cancer Res. Jun. 15, 2006;66(12):6118-28.
Goya, R., et al. (2010) SNVMix: predicting single nucleotide variants from nextgeneration sequencing of tumors, *Bioinformatics*, 26, 730-736.

(56) References Cited

OTHER PUBLICATIONS

Haar, Alfred (1910) "Zur Theorie der orthogonalen Funktionensysteme", Mathematische Annalen 69 (3): 331-371, English translation "On the Theory of Orthogonal Function Systems" 1-37.
Hahn et al., "Cell-free nucleic acids as potential markers for preeclampsia." Placenta. Feb. 2011;32 Suppl:S17-20. doi: 10.1016/j.placenta.2010.06.018.
Harris et al., "Single-molecule DNA sequencing of a viral genome." Science. Apr. 4, 2008;320(5872):106-9. doi: 10.1126/science.1150427.
Hill, Craig, "Gen-Probe Transcription-Mediated Amplification: System Principles," Jan. 1996 httl://www.gen-probe.com/pdfs/tma_whiteppr.pdf.
Hsu, S. Self, D. Grove, T. Randolph, K. Wang, J. Delrow, L. Loo, and P. Porter, "Denoising array-based comparative genomic hybridization data using wavelets", Biostatistics (Oxford, England), vol. 6, No. 2, pp. 211-226, 2005.
Hulten et al., "Rapid and simple prenatal diagnosis of common chromosome disorders: advantages and disadvantages of the molecular methods FISH and QF-PCR." Reproduction. Sep. 2003;126(3):279-97.
Human Genome Mutations, D. N. Cooper and M. Krawczak, BIOS Publishers, 1993.
Hupe,P. et al. (2004) "Analysis of array CGH data: from signal ratio to gain and loss of DNA regions", Bioinformatics, 20, 3413-3422.
Hudson et al., "An STS-Based Map of the Human Genome," Science, vol. 270, pp. 1945-1954 (1995).
Innis et al., PCR Protocols: A Guide to Methods and Applications, Innis et al., eds, 1990.
International Human Genome Sequencing Consortium Initial sequencing and analysis of the human genome Nature vol. 409, pp. 860-921 (2001).
James/James "Mathematics Dictionary," Fifth Edition, Chapman & Hall, International Thomson Publishing, 1992, pp. 266-267_270.
Jensen et al. "High-Throughput Massively Parallel Sequencing for Fetal Aneuploidy Detection from Maternal Plasma" Mar. 6, 2013. PLoS One 8(3): e57381.
Jensen et al., "Detection of microdeletion 22q11.2 in a fetus by next-generation sequencing of maternal plasma," Clin Chem. Jul. 2012;58(7):1148-1151.
Jiang et al., "*FetalQuant*: Deducing Fractional Fetal DNA Concentration from Massively Parallel Sequencing of DNA in Maternal Plasma," Bioinformatics, Nov. 15, 2012;28(22):2883-2890.
Jing et al. (1998) Proc Natl Acad Sci USA. 95(14):8046-51.
Jorgez et al.. "Improving Enrichment of Circulating Fetal DNA for genetic Testing: Size Fractionatiion Followed by Whole Gene Amplification." Fetal Diagnosis and Therapy, Karger Basel, CH, vol. 25, No. 3 Jan. 1, 2009, pp. 314-319.
Jurinke et al. (2004) Mol. Biotechnol. 26, 147-164.
Kalinina et al., "Nanoliter scale PCR with TaqMan detection." Nucleic Acids Res. May 15, 1997;25(10):1999-2004.
Kitzman et al., (2012): Noninvasive whole-genome sequencing of a human fetus. Science Translational Medicine, 4 (137):137ra76.
Kulkarni et al., "Global DNA methylation patterns in placenta and its association with maternal hypertension in pre-eclampsia." DNA Cell Biol. Feb. 2011;30(2):79-84. doi: 10.1089/dna.2010.1084. Epub Nov. 2, 2010.
Lai et al. (1999) Nat Genet. 23(3):309-13.
Lai et al., (2005). Comparative analysis of algorithms for identifying amplifications and deletions in array CGH data. Bioinformatics, 21, 19:3763-70.
Langmead et al., "Ultrafast and memory-efficient alignment of short DNA sequences to the human genome." Genome Biol. 2009;10(3):R25. doi: 10.1186/gb-2009-10-3-r25. Epub Mar. 4, 2009.
Li et al., "Mapping short DNA sequencing reads and calling variants using mapping quality scores." Genome Res. Nov. 2008;18(11):1851-8. doi: 10.1101/gr.078212.108. Epub Aug. 19, 2008.
Liao et al., (2012): Noninvasive Prenatal Diagnosis of Fetal Trisomy 21 by Allelic Ratio Analysis Using Targeted Massively Parallel Sequencing of Maternal Plasma DNA. PLoS One, 7(5):e38154, p. 1-7.
Liao, G.J., et al., Targeted massively parallel sequencing of maternal plasma DNA permits efficient and unbiased detection of fetal alleles. Clin Chem, 2010. 57(1): p. 92-101.
Lin and Brown, (1989) Nucleic Acids Res. 17:10373-10383.
Lin and Brown, (1992) Nucleic Acids Res. 20:5149-5152.
Lo "Recent advances in fetal nucleic acids in maternal plasma." J Histochem Cytochem. Mar. 2005;53(3):293-296.
Lo et al. (1997). "Presence of fetal DNA in maternal plasma and serum." Lancet 350(9076): 485-487.
Lo et al. (2007). "Digital PCR for the molecular detection of fetal chromosomal aneuploidy." Proc Natl Acad Sci U S A 104(32): 13116-21.
Lo et al. (2007). "Plasma placental RNA allelic ratio permits noninvasive prenatal chromosomal aneuploidy detection." Nat Med 13(2): 218-23.
Lo et al., "Prenatal Diagnosis of Fetal RhD Status by Molecular Analysis of Maternal Plasma," N. Engl. J. Med. 339:1734-1738, 1998.
Lo et al., "Quantative Abnormalities of Fetal NDA in Maternal Serum in Preeclampsia," Clin. Chem. 45:184-188, 1999.
Lo et al.,"Increased Fetal DNA Concentrations in the Plasma of Pregnant Women Carrying Fetuses with Trisomy 21," Clin. Chem. 45:1747-1751, 1999.
Lo YM, et al.(1998) Am J Hum Genet 62:768-775.
Lo, Y.M., et al., Maternal plasma DNA sequencing reveals the genome-wide genetic and mutational profile of the fetus. Sci Transl Med, 2010. 2(61): p. 61ra91.
Loakes and Brown (1994) Nucleic Acids Res. 22, 4039-4043.
Lun et al. (2008). "Microfluidics digital PCR reveals a higher than expected fraction of fetal DNA in maternal plasma." Clin Chem 54(10): 1664-72.
Mann et al., "Development and implementation of a new rapid aneuploidy diagnostic service within the UK National Health Service and implications for the future of prenatal diagnosis." Lancet. Sep. 29, 2001;358(9287):1057-61.
Margulies et al., "Genome sequencing in microfabricated high-density picolitre reactors." Nature. Sep. 15, 2005;437(7057):376-80. Epub Jul. 31, 2005.
Mazloom, Amin, "Gender Prediction with Bowtie Alignments using Male Specific Regions," May 10, 2012.
Metzker ML., "Sequencing technologies—the next generation." Nat Rev Genet. Jan. 2010;11(1):31-46. doi: 10.1038/nrg2626. Epub Dec. 8, 2009.
Miller et al., Consensus statement: chromosomal microarray is a first-tier clinical diagnostic test for individuals with developmental disabilities or congenital anomalies. Am J Hum Genet, 2010. 86(5): p. 749-64.
Moudrianakis et al., "Base Sequence Determination in Nucleic Acids with the Electron Microscope, III. Chemistry and Microscopy of Guanine-Labeled DNA." Proc Natl Acad Sci U S A. Mar. 1965;53:564-571.
Nakano et al., "Single-molecule PCR using water-in-oil emulsion." J Biotechnol. Apr. 24, 2003;102(2):117-1+A11024.
Nason, G.P. (2008) "Wavelet methods in Statistics", table of contents. R. Springer, New York ISBN: 978-0-387-75960-9 (Print) 978-0-387-75961-6 (Online).
Needham-VanDevanter et al., "Characterization of an adduct between CC-1065 and a defined oligodeoxynucleotide duplex." Nucleic Acids Res. Aug. 10, 1984;12(15):6159-68.
Ng et al. (2003). "mRNA of placental origin is readily detectable in maternal plasma." Proc Natl Acad Sci U S A 100(8): 4748-53.
Nguyen, NHA, "Denoising of Array-Based DNA Copy Number Data Using the Dual-tree Complex Wavelet Transform," Bioinformatics and Bioengineering, 2007. BIBE 2007. Proceedings of the 7th IEEE International Conference, Boston MA, on Oct. 14-17, 2007, pp. 137-144.
Nichols et al. "A universal nucleoside for use at ambiguous sites in DNA primers," (1994) Nature 369, 492-493.

(56) References Cited

OTHER PUBLICATIONS

Nicolaides et al., "One-stop clinic for assessment of risk of chromosomal defects at 12 weeks of gestation." J Matern Fetal Neonatal Med. Jul. 2002;12(1):9-18.
Nolte FS., "Branched DNA signal amplification for direct quantitation of nucleic acid sequences in clinical specimens." Adv Clin Chem. 1998;33:201-35.
Nygren, A. O., J. Dean, et al. (2010) "Quantification of fetal DNA by use of methylation-based DNA discrimination." Clin Chem 56(10): 1627-35.
Ohno, S. (1967). Sex chromosomes and Sex-linked Genes. Berlin, Springer. p. 111.
Old et al. (2007). "Candidate epigenetic biomarkers for non-invasive prenatal diagnosis of Down syndrome." Reprod Biomed Online 15(2): 227-35.
Olshen et al., "Circular binary segmentation for the analysis of array-based DNA copy number data," Biostatistics. Oct. 2004;5(4):557-572.
Oudejans et al. (2003). "Detection of chromosome 21-encoded mRNA of placental origin in maternal plasma." Clin Chem 49(9): 1445-9.
Palomaki et al., DNA sequencing of maternal plasma to detect Down syndrome: an international clinical validation study. Genet Med., Nov. 2011;13(11):913-920.
Palomaki, et al. "DNA sequencing of maternal plasma reliably identifies trisomy 18 and trisomy 13 as well as Down syndrome: an international collaborative study" Genet Med 2012;14:296-305.
Pandya et al., "Screening for fetal trisomies by maternal age and fetal nuchal translucency thickness at 10 to 14 weeks of gestation." Br J Obstet Gynaecol. Dec. 1995;102(12):957-62.
Pearson and Regnier, "High-Performance Anion-Exchange Chromatogrtaphy of Oligonucleotides," J. Chrom., 255:137-149, 1983.
Pekalska et al., "Classifiers for dissimilarity-based pattern recognition," 15th International Conference on Pattern Recognition (ICPR'00), vol. 2, Barcelona, Spain, Sep. 3-8, 2000, pp. 12-16.
Pertl et al., "Rapid molecular method for prenatal detection of Down's syndrome." Lancet. May 14, 1994;343(8907):1197-8.
Peters et al. "Noninvasive Prenatal Diagnosis of a Fetal Microdeletion Syndrome," Correspondence to the Editor, New England Journal of Medicine, 365:19 Nov. 10, 2011, pp. 1847-1848.
Poon et al., "Differential DNA methylation between fetus and mother as a strategy for detecting fetal DNA in maternal plasma." Clin Chem. Jan. 2002;48(1):35-41.
Product Sheet for: Nextera™ DNA Sample Prep Kit (Illumina®-Compatible) Cat. Nos. GA09115, GA091120, GA0911-50, GA0911-96, and GABC0950, from: Epicentre, an Illumina Company, Literature # 307, Jun. 2011.
Qu et al., "Analysis of drug-DNA binding data." Methods Enzymol. 2000;321:353-69.
Robin, N.H. and R.J. Shprintzen, Defining the clinical spectrum of deletion 22q11.2. J Pediatr, 2005. 147(1): p. 90-6.
Romero and Rotbart in Diagnostic Molecular Biology: Principles and Applications pp. 401-406; Persing et al., eds., Mayo Foundation, Rochester, Minn., 1993.
Ross et al., "The DNA sequence of the human X chromosome." Nature. Mar. 17, 2005;434(7031):325-337.
Roth, A., et al. (2012) JointSNVMix: a probabilistic model for accurate detection of somatic mutations in normal/tumour paired next-generation sequencing data, Bioinformatics, 28, 907-913.
Saito et al., "Prenatal DNA diagnosis of a singlegene disorder from maternal plasma," Lancet 356:1170, 2000.
Sambrook and Russell, Molecular Cloning: A Laboratory Manual 3d ed., 2001.
Schouten et al., "Relative quantification of 40 nucleic acid sequences by multiplex ligation-dependent probe amplification." Nucleic Acids Res. Jun. 15, 2002;30(12):e57.
Schwinger et al., "Clinical utility gene card for: DiGeorge syndrome, velocardiofacial syndrome, Shprintzen syndrome, chromosome 22q11.2 deletion syndrome (22q11.2, TBX1)," European Journal of Human Genetics (2010) 18, published online Feb. 3, 2010.
Sehnert et al., "Optimal Detection of Fetal Chromosomal Abnormalities by Massively Parallel DNA Sequencing of Cell-Free Fetal DNA from Maternal Blood," Clinical Chemistry, 57:7, pp. 1042-1049 (2011).
Sekizawa et al., "Cell-free Fetal DNA is increased in Plasma of Women with Hyperemisis Gravidarum," Clin. Chem. 47:2164-2165, 2001.
Shah, S.P., et al. (2009) Mutational evolution in a lobular breast tumour profiled at single nucleotide resolution, Nature, 461, 809-813.
Shen et al., "A hidden Markov model for copy number variant prediction from whole genome resequencing data". BMC Bioinformatics, 2011. 12(Suppl 6):54, p. 1-7.
Sherman, S. L., E. G. Allen, et al. (2007). "Epidemiology of Down syndrome." Ment Retard Dev Disabil Res Rev 13(3): 221-7.
Shin, M., L. M. Besser, et al. (2009). "Prevalence of Down syndrome among children and adolescents in 10 regions of the United States." Pediatrics 124(6): 1565-71.
Skaletsy et al., "The male-specific region of the human Y chromosome is a mosaic of discrete sequence classes." Nature. Jun. 19, 2003;423(6942):825-37.
Slater et al., "Rapid, high throughput prenatal detection of aneuploidy using a novel quantitative method (MLPA)." J Med Genet. Dec. 2003;40(12):907-12.
Snijders et al., "Assembly of microarrays for genome-wide measurement of DNA copy number." Nat Genet. Nov. 2001;29(3):263-4.
Snijders et al., "First-trimester ultrasound screening for chromosomal defects." Ultrasound Obstet Gynecol. Mar. 1996;7(3):216-26.
Snijders et al., "UK multicentre project on assessment of risk of trisomy 21 by maternal age and fetal nuchal-translucency thickness at 10-14 weeks of gestation. Fetal Medicine Foundation First Trimester Screening Group." Lancet. Aug. 1, 1998;352(9125):343-6.
Soni et al., "Progress toward ultrafast DNA sequencing using solid-state nanopores." Clin Chem. Nov. 2007;53(11):1996-2001. Epub Sep. 21, 2007.
Sparks et al., (2012): "Selective analysis of cell-free DNA in maternal blood for evaluation of fetal trisomy," Prenatal Diagnosis, 32, 3-9.
Sparks et al., (2012): Non-invasive Prenatal Detection and Selective Analysis of Cell-free DNA Obtained from Maternal Blood: Evaluation for Trisomy 21 and Trisomy 18, American Journal of Obstetrics and Gynecology, pp. 319.e1-319.e9, doi: 10.1016/j.ajog.2012.01.030.
Srinivasan et al., Noninvasive Detection of Fetal Subchromosome Abnormalities via Deep Sequencing of Maternal Plasma, The American Journal of Human Genetics (2013) 167-176.
Stagi et al., "Bone density and metabolism in subjects with microdeletion of chromosome 22q11 (del22q11)." Eur J Endocrinol, 2010. 163(2): p. 329-37.
Stanghellini, I., R. Bertorelli, et al. (2006). "Quantitation of fetal DNA in maternal serum during the first trimester of pregnancy by the use of a DAZ repetitive probe." Mol Hum Reprod 12(9): 587-91.
Strachan, The Human Genome, T. BIOS Scientific Publishers, 1992.
Tabor et al. (1986). "Randomised controlled trial of genetic amniocentesis in 4606 low-risk women." Lancet 1(8493): 1287-93.
Timp et al., "Nanopore Sequencing: Electrical Measurements of the Code of Life," IEEE Trans Nanotechnol. May 1, 2010; 9(3): 281-294.
Van den Berghe H, Parloir C, David G et al. A new characteristic karyotypic anomaly in lymphoproliferative disorders. Cancer 1979; 44: 188-95.
Veltman et al., "High-throughput analysis of subtelomeric chromosome rearrangements by use of array-based comparative genomic hybridization." Am J Hum Genet. May 2002;70(5):1269-76. Epub Apr. 9, 2002.
Venkatraman, ES, Olshen, AB (2007) "A faster circular binary segmentation algorithm for the analysis of array CGH data", Bioinformatics, 23, 6:657-63.

(56) References Cited

OTHER PUBLICATIONS

Verbeck et al. In the Journal of Biomolecular Techniques (vol. 13, Issue 2, 56-61).
Verma et al., "Rapid and simple prenatal DNA diagnosis of Down's syndrome." Lancet. Jul. 4, 1998;352(9121):9-12.
Vincent et al., "Helicase-dependent isothermal DNA amplification." EMBO Rep. Aug. 2004;5(8):795-800. Epub Jul. 9, 2004.
Voelkerding et al., "Next-generation sequencing: from basic research to diagnostics." Clin Chem. Apr. 2009;55(4):641-58. doi: 10.1373/clinchem.2008.112789. Epub Feb. 26, 2009.
Vogelstein et al., "Digital PCR." Proc Natl Acad Sci U S A. Aug. 3, 1999;96(16):9236-41.
Wang and S. Wang, "A novel stationary wavelet denoising algorithm for array-based DNA copy number data", International Journal of Bioinformatics Research and Applications, vol. 3, No. 2, pp. 206-222, 2007.
Wapner et al., "First-trimester screening for trisomies 21 and 18." N Engl J Med. Oct. 9, 2003;349(15):1405-13.
WaveThresh (WaveThresh : Wavelets statistics and transforms [online],[retrieved on Apr. 24, 2013], retrieved from the internet <URL:*>http://cran.r-project.org/web/packages/wavethresh/index.html<>) and a detailed description of WaveThresh ( Package 'wavethresh' [online, PDF], Apr. 2, 2013, [retrieved on Apr. 24, 2013], retrieved from the internet <URL:*>http://cran.r-project.org/web/packages/wavethresh/wavethresh.pdf<>).
Willenbrock H, Fridlyand J. A comparison study: applying segmentation to array CGH data for downstream analyses. Bioinformatics Nov. 15, 2005;21(22):4084-91.
Wright et al., "The use of cell-free fetal nucleic acids in maternal blood for non-invasive diagnosis," Human Reproduction Update 2009, vol. 15, No. 1, pp. 139-151.
Wu et al., "Genetic and environmental influences on blood pressure and body mass index in Han Chinese: a twin study," (Feb. 2011) Hypertens Res. Hypertens Res 34: 173-179; advance online publication, Nov. 4, 2010.
Zhang et al., "A single cell level based method for copy number variation analysis by low coverage massively parallel sequencing," PLoS One 8(1): e54236. doi:10.1371/journal.pone.0054236 (2013).
Zhao et al., "Quantification and application of the placental epigenetic signature of the RASSF1A gene in maternal plasma." Prenat Diagn. Aug. 2010;30(8):778-82. doi: 10.1002/pd.2546.
Zhong et al., "Elevation of both maternal and fetal extracellular circulating deoxyribonucleic acid concentrations in the plasma of pregnant women with preeclampsia," Am. J. Obstet. Gynecol. 184:414-419, 2001.
Zhong et al., "Cell-free fetal DNA in the maternal circulation does not stem from the transplacental passage of fetal erythroblasts" Molecular Human Reproduction (2002) 8(9):864-870.
Zhou et al., "Recent Patents of Nanopore DNA Sequencing Technology: Progress and Challenges," Recent Patents on DNA & Gene Sequences 2010, 4, 192-201.
Zhou et al., "Detection of DNA copy number abnormality by microarray expression analysis" Hum. Genet. (2004) 114:464-467.
Zimmermann, B., X. Y. Zhong, et al. (2007). "Real-time quantitative polymerase chain reaction measurement of male fetal DNA in maternal plasma." Methods Mol Med 132: 43-9.
International Preliminary Report on Patentability and Written Opinion dated Jan. 9, 2014 in International Application No. PCT/US2012/043388, filed on Jun. 20, 2012 and published as WO 2012/177792 on Dec. 27, 2012.
International Search Report and Written Opinion dated Apr. 5, 2013 in International Application No. PCT/US2012/043388 filed: Jun. 20, 2012 and published as: WO 12/177792 Dec. 27, 2012.
International Search Report and Written Opinion dated Jul. 4, 2013 in International Application No. PCT/US2013/022290 filed: Jan. 18, 2013, and published as: WO/2013/109981 on Jul. 25, 2013.
International Search Report and Written Opinion dated Mar. 6, 2013 in International Application No. PCT/US2012/059592 filed: Oct. 10, 2012.
International Search Report and Written Opinion dated Sep. 26, 2012 in International Application No. PCT/US2011/066639 filed: Dec. 21, 2011 and published as: WO 12/088348 Jun. 28, 2012.
Invitation to Pay Additional Fees and Partial Search Report dated Jan. 18, 2013 in International Application No. PCT/US2012/059592 filed: Oct. 10, 2012.
Invitation to Pay Additional Fees and Partial Search Report dated Jul. 3, 2013 in International Application No. PCT/US2012/059123 filed: Oct. 5, 2012 and published as: WO/2013/052913 on Apr. 11, 2013.
International Search Report and Written Opinion dated Sep. 9, 2013 in International Application No. PCT/US2012/059123, filed on Oct. 5, 2012 and published as WO/2013/052913 on Apr. 11, 2013.
International Search Report and Written Opinion dated Sep. 9, 2013 in International Application No. PCT/US2012/059114, filed on Oct. 5, 2012 and published as WO/2013/052907 on Apr. 11, 2013.
International Search Report and Written Opinion dated Sep. 18, 2013 in International Application No. PCT/US2013/047131, filed on Jun. 21, 2013 and published as WO 2013/192562 on Dec. 27, 2013.
International Search Report and Written Opinion dated Dec. 13, 2013 in International Application No. PCT/US2013/063287, filed Oct. 3, 2013.
International Preliminary Report on Patentability dated Feb. 27, 2014 in International Application No. PCT/US2012/059123, filed on Oct. 5, 2012 and published as WO 2013/052913 on Apr. 11, 2013.
Office Action dated, Feb. 20, 2013 in U.S. Appl. No. 13/656,328, filed Oct. 19, 2012, not yet published.
Office Action dated Feb. 15, 2013 in U.S. Appl. No. 13/669,136, filed Nov. 5, 2012 and published as: US 2013-0085681 on Apr. 4, 2013.
Office Action dated May 7, 2013 in U.S. Appl. No. 13/754,817, filed Jan. 30, 2013.
Office Action dated May 3, 2013 in U.S. Appl. No. 13/333,842, filed Dec. 21, 2011 and published as:-2012/0184449 on: Jul. 19, 2012.
Office Action dated Aug. 22, 2013 in U.S. Appl. No. 13/797,508, filed Mar. 12, 2013.
Office Action dated Sep. 11, 2013 in U.S. Appl. No. 13/829,164, filed Mar. 14, 2013.
Office Action dated Sep. 12, 2013 in U.S. Appl. No. 13/669,136, filed Nov. 5, 2012 and published as: US 2013-0085681 on Apr. 4, 2013.
Office Action dated Sep. 12, 2013 in U.S. Appl. No. 13/656,328, filed Oct. 19, 2012 and published as US 2013-0103320 on Apr. 25, 2013.
Office Action dated Oct. 16, 2013 in U.S. Appl. No. 13/933,935, filed Jul. 2, 2013 and published as US 2013-0304392 on Nov. 14, 2013.
Office Action dated Oct. 17, 2013 in U.S. Appl. No. 13/669,136, filed Nov. 5, 2012 and published as US 2013-0085681 on Apr. 4, 2013.
Office Action dated Oct. 18, 2013 in U.S. Appl. No. 13/656,328, filed Oct. 19, 2012 and published as US 2013-0103320 on Apr. 25, 2013.
Office Action dated Dec. 26, 2013 in U.S. Appl. No. 13/797,508, filed Mar. 12, 2013 and published as US 2013-0261983 on Oct. 3, 2013.
Office Action dated Jan. 17, 2014 in U.S. Appl. No. 13/333,842, filed Dec. 21, 2011 and published as US 2012/0184449 on Jul. 19, 2012.
Office Action dated Jan. 27, 2014 in U.S. Appl. No. 13/829,164, filed Mar. 14, 2013 and published as US 2013-0288244 on Oct. 31, 2014.
Office Action dated Jan. 30, 2014 in U.S. Appl. No. 13/933,935, filed Jul. 2, 2013 and published as US 2013-0304392 on Nov. 14, 2013.
Office Action dated Apr. 7, 2014 in U.S. Appl. No. 13/754,817, filed Jan. 30, 2013 and published as US 2013-0150253 on Jun. 13, 2013.
International Preliminary Report on Patentability and Written Opinion dated Apr. 24, 2014 in International Application No. PCT/US2012/059592, filed on Oct. 10, 2012 and published as WO 2013/055817 on Apr. 18, 2013.

(56) References Cited

OTHER PUBLICATIONS

International Search Report and Written Opinion dated Apr. 2, 2014 in International Application No. PCT/US2013/063314, filed on Oct. 3, 2013 and published as WO 2014/055790 on Apr. 10, 2014.
International Search Report and Written Opinion dated May 9, 2014 in International Application No. PCT/US2014/012369, filed Jan. 21, 2014.
International Preliminary Report on Patentability dated Jun. 9, 2014 in International Application No. PCT/US2012/059114, filed on Oct. 5, 2012 and published as WO 2013/052907 on Apr. 11, 2013.
International Search Report and Written Opinion dated Jul. 14, 2014 in International Application No. PCT/US2014/032687, filed on Apr. 2, 2014.
Office Action dated Jul. 28, 2014 in U.S. Appl. No. 13/797,508, filed Mar. 12, 2013 and published as US 2013-0261983 on Oct. 3, 2013.
International Preliminary Report on Patentability dated Jul. 31, 2014 in International Application No. PCT/US2013/022290, filed on Jan. 18, 2013 and published as WO 2013/109981 on Jul. 25, 2013.
Office Action dated Aug. 13, 2014 in U.S. Appl. No. 13/829,164, filed Mar. 14, 2013 and published as US 2013-0288244 on Oct. 31, 2014.
Office Action dated Aug. 13, 2014 in U.S. Appl. No. 13/669,136, filed Nov. 5, 2012 and published as US 2013-0085681 on Apr. 4, 2013.
Office Action dated Aug. 14, 2014 in U.S. Appl. No. 13/933,935, filed Jul. 2, 2013 and published as US 2013-0304392 on Nov. 14, 2013.
Office Action dated Apr. 16, 2015 in U.S. Appl. No. 13/669,136, filed Nov. 5, 2012 and published as US 2013-0085681 on Apr. 4, 2013.
Office Action dated Apr. 16, 2015 in U.S. Appl. No. 13/933,935, filed Jul. 2, 2013 and published as US 2013-0304392 on Nov. 14, 2013.
International Preliminary Report on Patentability dated Apr. 16, 2015 in International Application No. PCT/US2013/063314, filed on Oct. 3, 2013 and published as WO 2014/055790 on Apr. 10, 2014.
International Preliminary Report on Patentability dated Apr. 16, 2015 in International Application No. PCT/US2013/063287, filed Oct. 3, 2013.
Office Action dated Apr. 17, 2015 in U.S. Appl. No. 13/829,164, filed Mar. 14, 2013 and published as US 2013-0288244 on Oct. 31, 2014.
Office Action dated Apr. 21, 2015 in U.S. Appl. No. 13/754,817, filed Jan. 30, 2013 and published as US 2013-0150253 on Jun. 13, 2013.
Office Action dated May 12, 2015 in U.S. Appl. No. 13/669,136, filed Nov. 5, 2012 and published as US 2013-0085681 on Apr. 4, 2013.
Office Action dated May 13, 2015 in U.S. Appl. No. 13/333,842, filed Dec. 21, 2011 and published as US 2012/0184449 on Jul. 19, 2012.
Office Action dated Mar. 11, 2016 in U.S. Appl. No. 13/782,857, filed Mar. 1, 2013 and published as US 2013-0310260 on Nov. 21, 2013.
Office Action dated Mar. 22, 2016 in U.S. Appl. No. 12/727,824, filed Mar. 19, 2010 and published as US 2010-0216153 on Aug. 26, 2010.
Zhao et al., "Detection of fetal subchromosomal abnormalities by sequencing circulating cell-free DNA from maternal plasma" Clinical Chemistry (2015) 61(4):608-616.
Lefkowitz et al., "Clinical validation of a noninvasive prenatal test for genomewide detection of fetal copy number variants" American Journal of Obstetrics & Gynecology (Dec. 2, 2015) S0002-9378(16)00318-5. doi: 10.1016/j.ajog.2016.02.030. [Epub ahead of print].
Avent, "Refining noninvasive prenatal diagnosis with single-molecule next-generation sequencing" Clin. Chem. (2012) 58(4):657-658.

Boeva et al., "Control-free calling of copy number alterations in deep-sequencing data using GC-content normalization" Bioinformatics (2011) 27(2):268-269.
Chung et al., "Discovering transcription factor binding sites in highly repetitive regions of genomes with multi-read analysis of ChIP-Seq data" PLoS Computational Biology (2011) 7(7):e1002111.
Chandrananda et al., "Investigating and correcting plasma DNA sequencing coverage bias to enhance aneuploidy discovery" PloS One (2014) 9:e86993.
Benjamini et al., "Summarizing and correcting the GC content bias in high-throughput sequencing" Nucleic Acids Research (2012) 40(10):e72.
International Preliminary Report on Patentability dated Apr. 14, 2016 in International Application No. PCT/US2014/058885, filed on Oct. 2, 2014 and published as WO 2015/051163 on Apr. 9, 2015.
International Preliminary Report on Patentability dated Apr. 21, 2016 in International Application No. PCT/US2014/059156, filed on Oct. 3, 2014 and published as WO 2015/054080 on Apr. 16, 2015.
Yuk et al., "Genomic Analysis of Fetal Nucleic Acids in Maternal Blood" Annual Review of Genomics and Human Genetics (2012) 13:285-306.
Office Action dated Apr. 26, 2016 in U.S. Appl. No. 13/797,508, filed Mar. 12, 2013 and published as US 2013-0261983 on Oct. 3, 2013.
Office Action dated Apr. 27, 2016 in U.S. Appl. No. 13/829,164, filed Mar. 14, 2013 and published as US 2013-0288244 on Oct. 31, 2014.
Office Action dated Apr. 27, 2016 in U.S. Appl. No. 13/933,935, filed Jul. 2, 2013 and published as US 2013-0304392 on Nov. 14, 2013.
International Search Report and Written Opinion dated Feb. 18, 2015 in International Application No. PCT/US2014/058885, filed on Oct. 2, 2014.
Office Action dated Mar. 19, 2015 in U.S. Appl. No. 13/797,508, filed Mar. 12, 2013 and published as US 2013-0261983 on Oct. 3, 2013.
Shendure et al., "Next-generation DNA sequencing" in Nature Biotechnology (2008) 26:1135-1145.
Bianchi et al., "Isolation of fetal DNA from nucleated erythrocytes in maternal blood," PNAS, 1990,87(9): 3279-3283.
Borsenberger et al, "Chemically Labeled Nucleotides and Oligonucleotides Encode DNA for Sensing with Nanopores," J. Am. Chem. Soc., 131, 7530-7531, 2009.
Branton et al, "The potential and challenges of nanopore sequencing", Nature Biotechnology, 26:1146-1153, 2008.
Braslaysky et al., "Sequence information can be obtained from single DNA molecules," PNAS, 2003, 100(7): 3960-3964.
Bruch et al., Trophoblast-like cells sorted from peripheral maternal blood using flow cytometry: a multiparametric study involving transmission electron microscopy and fetal DNA amplification,: Prenatal Diagnosis 11:787-798, 1991.
Cann et al., "A heterodimeric DNA polymerase: evidence that members of Euryarchaeota possess a distinct DNA polymerase." 1998, Proc. Natl. Acad. Sci. USA 95:14250.
Cariello et al., "Fidelity of Thermococcus litoralis DNA polymerase (Vent) in PCR determined by denaturing gradient gel electrophoresis," Nucleic Acids Res. Aug. 11, 1991;19(15):4193-8.
Chien et al., "Deoxyribonucleic acid polymerase from the extreme thermophile Thermus aquaticus, " 1976, J. Bacteoriol, 127: 1550-1557.
Costa et al., "Fetal RHD genotyping in maternal serum during the first trimester of pregnancy" British Journal of Haematology (2002) 119:255-260.
Cunningham et al., in Williams Obstetrics, McGraw-Hill, New York, p. 942, 2002.
Dhallan et al., "Methods to increase the percentage of free fetal DNA recovered from the maternal circulation," J. Am. Med. Soc. 291(9): 1114-1119, Mar. 2004).
Diaz and Sabino, "Accuracy of replication in the polymerase chain reaction. Comparison between Thermotoga maritima DNA polymerase and Thermus aquaticus DNA polymerase." Diaz RS, Sabino EC. 1998 Braz J. Med. Res, 31: 1239.

(56) References Cited

OTHER PUBLICATIONS

DNA Replication 2nd edition, Kornberg and Baker, W. H. Freeman, New York, N.Y. (1991).
Drmanac et al., "Sequencing by hybridization: towards an automated sequencing of one million M13 clones arrayed on membranes," Electrophoresis, 13(8): p. 566-573, 1992.
Herzenberg et al., "Fetal cells in the blood of pregnant women: detection and enrichment by fluorescence-activated cell sorting," PNAS 76:1453-1455, 1979.
Hinnisdaels et al., "Direct cloning of PCR products amplified with Pwo DNA polymerase," 1996, Biotechniques, 20: 186-188.
Huber et al. "High-resolution liquid chromatography of DNA fragments on non-porous poly(styrene-divinylbenzene) particles," Nucleic Acids Res. 21(5):1061-1066, 1993.
Huse et al., "Accuracy and quality of massively parallel DNA pyrosequencing" Genome Biology (2007) 8(7):R143.
Johnston et al., "Autoradiography using storage phosphor technology," Electrophoresis. May 1990;11(5):355-360.
Joos et al., "Covalent attachment of hybridizable oligonucleotides to glass supports," Analytical Biochemistry 247:96-101, 1997.
Juncosa-Ginesta et al., "Improved efficiency in site-directed mutagenesis by PCR using a *Pyrococcus* sp. GB-D polymerase," 1994, Biotechniques, 16(5): pp. 820-823.
Kato et al., "A new packing for separation of DNA restriction fragments by high performance liquid chromatography," J. Biochem, 95(1):83-86, 1984.
Khandjian, "UV crosslinking of RNA to nylon membrane enhances hybridization signals," Mol. Bio. Rep. 11: 107-115, 1986.
Kornberg and Baker, W. H. Freeman, New York, N.Y. (1991).
Lecomte and Doubleday, "Selective inactivation of the 3' to 5' exonuclease activity of *Escherichia coli* DNA polymerase I by heat," 1983, Polynucleotides Res. 11:7505-7515.
Levin, "It's prime time for reverse transcriptase," Cell 88:5-8 (1997).
Li et al., "Detection of paternally inherited fetal point mutations for beta-thalassemia using size-fractionated cell-free DNA in maternal plasma.," J. Amer. Med. Assoc. 293:843-849, 2005.
Lo et al., "Fetal DNA in maternal plasma: application to non-invasive blood group genotyping of the fetus" Transfus. Clin. Biol. (2001) 8:306-310.
Lundberg et al., "High-fidelity amplification using a thermostable DNA polymerase isolated from Pyrococcus furiosus," 1991 Gene, 108:1-6.
Mitchell & Howorka, "Chemical tags facilitate the sensing of individual DNA strands with nanopores," Angew. Chem. Int. Ed. 47:5565-5568, 2008.
Myers and Gelfand, "Reverse transcription and DNA amplification by a Thermus thermophilus DNA polymerase," Biochemistry 1991, 30:7661-7666.
Nevin, N.C., "Future direction of medical genetics", The Ulster Medical Journal, vol. 70, No. 1, (2001), pp. 1-2.
Ng et al. "The Concentration of Circulating Corticotropin-releasing Hormone mRNA in Maternal Plasma Is Increased in Preeclampsia," Clinical Chemistry 49:727-731, 2003.
Nordstrom et al., "Characterization of bacteriophage T7 DNA polymerase purified to homogeneity by antithioredoxin immunoadsorbent chromatography," 1981, J. Biol. Chem. 256:3112-3117.
Oroskar et al., "Detection of immobilized amplicons by ELISA-like techniques." Clin. Chem. 42:1547-1555, 1996.
PCT International Search Report and Written Opinion of the international Searching Authority for International Application No. PCT/US11/24132, dated Aug. 8, 2011. 15 pages.
Purnell and Schmidt, "Discrimination of single base substitutions in a DNA strand immobilized in a biological nanopore," ACS Nano, 3:2533, 2009.
Sambrook, Chapter 10 of Molecular Cloning, a Laboratory Manual, 3.sup.ed Edition, J. Sambrook, and D. W. Russell, Cold Spring Harbor Press (2001).
Smid et al., "Evaluation of Different Approaches for Fetal DNA Analysis from Maternal Plasma and Nucleated Blood Cells," Clinical Chemistry, 1999, 45(9): 1570-1572.
Smith et al., "Direct mechanical measurements of the elasticity of single DNA molecules by using magnetic beads," Science 258:5085, pp. 1122-1126, Nov. 13, 1992.
Stenesh and McGowan, "DNA polymerase from mesophilic and thermophilic bacteria. III. Lack of fidelity in the replication of synthetic polydeoxyribonucleotides by DNA polymerase from Bacillus licheniformis and Bacillus stearothermophilus," 1977, Biochim Biophys Acta 475:32-41.
Stoddart et al, "Single-nucleotide discrimination in immobilized DNA oligonucleotides with a biological nanopore," Proc. Nat. Acad. Sci. 2009, 106(19): pp. 7702-7707.
Takagi et al., "Characterization of DNA polymerase from *Pyrococcus* sp. strain KOD1 and its application to PCR," 1997, Appl. Environ. Microbiol. 63(11): pp. 4504-4510.
Taylor et al., "Characterization of chemisorbed monolayers by surface potential measurements," J. Phys. D. Appl. Phys. 24(8):1443-1450, 1991.
Verma, "The reverse transcriptase," Biochim Biophys Acta 473(1):1-38 (Mar. 21, 1977).
Wei, Chungwen et al., "Detection and Quantification by Homogenous PCR of Cell-free Fetal DNA in Maternal Plasma", Clinical Chemistry, vol. 47, No. 2, (2001), pp. 336-338.
Wu et al., "Reverse Transcriptas," CRC Crit. Rev Biochem. 3(3): pp. 289-347 (Jan. 1975).
Yershov et al., "DNA analysis and diagnostics on oligonucleotide microchips," Proc. Natl. Acad. Sci. 93(10): pp. 4913-4918 (May 14, 1996).
Yoon et al., "Sensitive and accurate detection of copy number variants using read depth of coverage" Genome Research (2009) 19:1586-1592.
Office Action dated Aug. 22, 2013 in U.S. Appl. No. 13/619,039, filed Sep. 14, 2012 and published as: US 2013/0022977 on: Jan. 24, 2013.
Office Action dated Jan. 10, 2013 in U.S. Appl. No. 13/619,039, filed Sep. 14, 2012 and published as: US 2013/0022977 on: Jan. 24, 2013.
Office Action dated Jul. 14, 2014 in U.S. Appl. No. 12/727,824, filed Sep. 13, 2012 and published as: US 2010/0216153 on: Aug. 26, 2010.
Office Action dated Oct. 18, 2011 in U.S. Appl. No. 12/727,824, filed Sep. 13, 2012 and published as: US 2010/0216153 on: Aug. 26, 2010.
Office Action dated May 16, 2011 in U.S. Appl. No. 12/727,824, filed Sep. 13, 2012 and published as: US 2010/0216153 on: Aug. 26, 2010.
Office Action dated Feb. 25, 2015 in U.S. Appl. No. 12/727,824, filed Sep. 13, 2012 and published as: US 2010/0216153 on: Aug. 26, 2010.
Office Action dated May 29, 2015 in U.S. Appl. No. 14/187,876, filed Feb. 24, 2014 and published as US 2014-0322709 on Oct. 30, 2014.
Kim et al., "Determination of fetal DNA fraction from the plasma of pregnant women using sequence read counts" Prenat. Diagn. (2015) 35(8):810-815.
Extended European Search Report dated Dec. 2, 2015 in European Application No. EP11745050.2, filed on Feb. 9, 2011 and published as EP 2 536 852 on Dec. 26, 2012.
Omont et al., "Gene-based bin analysis of genome-wide association studies" BMC Proceedings (2008) 2 (Suppl 4):S6.
Trapnell and Salzberg, "How to map billions of short reads onto genomes" Nat. Biotechnol. (2009) 27(5):455-457.
International Search Report and Written Opinion dated Jan. 5, 2016 in International Application No. PCT/US2015/042701, filed on Jul. 29, 2015.
Office Action dated Feb. 1, 2016 in U.S. Appl. No. 13/669,136, filed Nov. 5, 2012 and published as US 2013-0085681 on Apr. 4, 2013.
Canick et al., "The impact of maternal plasma DNA fetal fraction on next generation sequencing tests for common fetal aneuploidies" Prenat. Diagn. (2013) 33(7):667-674.

(56) References Cited

OTHER PUBLICATIONS

Hudecova et al., "Maternal plasma fetal DNA fractions in pregnancies with low and high risks for fetal chromosomal aneuploidies" PLoS One (2014) 9(2):e88484.
Palomaki et al., "DNA sequencing of maternal plasma to detect Down syndrome: an international clinical validation study" Genet Med. (2011) 13:913-920, and Expanded Methods Appendix A, pp. 1-65.
Office Action dated Feb. 12, 2016 in U.S. Appl. No. 13/797,930, filed Mar. 12, 2013 and published as US 2013-0325360 on Dec. 5, 2013.
Forabosco et al., "Incidence of non-age-dependent chromosomal abnormalities: a population-based study on 88965 amniocenteses" European Journal of Human Genetics (2009) 17:897-903.
Grati, "Chromosomal Mosaicism in Human Feto-Placental Development: Implications for Prenatal Diagnosis" J. Clin. Med. (2014) 3:809-837.
Office Action dated Feb. 23, 2016 in U.S. Appl. No. 14/812,432, filed Jul. 29, 2015 and published as US 2016-0034640 on Feb. 4, 2016.
Office Action dated Mar. 3, 2016 in U.S. Appl. No. 13/829,373, filed Mar. 14, 2013 and published as US 2013-0338933 on Dec. 19, 2013.
Office Action dated May 26, 2016 in U.S. Appl. No. 13/782,883, filed Mar. 1, 2013 and published as US 2014-0180594 on Jun. 26, 2014.
Office Action dated Jan. 6, 2017 in U.S. Appl. No. 13/829,373, filed Mar. 14, 2013 and published as US 2013-0338933 on Dec. 19, 2013.
Office Action dated Feb. 23, 2017 in U.S. Appl. No. 13/782,857, filed Mar. 1, 2013 and published as US 2013-0310260 on Nov. 21, 2013.
Office Action dated Mar. 23, 2017 in U.S. Appl. No. 13/782,883, filed Mar. 1, 2013 and published as US 2014-0180594 on Jun. 26, 2014.
Office Action dated Apr. 7, 2017 in U.S. Appl. No. 13/781,530, filed Feb. 28, 2013 and published as US 2014-0100792 on Apr. 10, 2014.
Office Action dated Nov. 13, 2017 in U.S. Appl. No. 13/782,857, filed Mar. 1, 2013 and published as US 2013-0310260 on Nov. 21, 2013.
Office Action dated Sep. 13, 2017 in U.S. Appl. No. 13/782,857, filed Mar. 1, 2013 and published as US 2013-0310260 on Nov. 21, 2013.
Office Action dated Sep. 21, 2017 in U.S. Appl. No. 13/782,883, filed Mar. 1, 2013 and published as US 2014-0180594 on Jun. 26, 2014.
Rijnders et al., "Clinical Applications of Cell-Free Fetal DNA From Maternal Plasma" Am. J. Obstet. Gynecol. (2004) 103(1):157-164.
Xue et al., "Optimizing the yield and utility of circulating cell-free DNA from plasma and serum" Clinica Chimica Acta (2009) 404:100-104.
Office Action dated Oct. 19, 2017 in U.S. Appl. No. 13/781,530, filed Feb. 28, 2013 and published as US 2014-0100792 on Apr. 10, 2014.
Non-final office action dated Sep. 20, 2018 in U.S. Appl. No. 13/781,530, filed Feb. 28, 2013; 15 pages.
Non-final office action dated Sep. 21, 2018 in U.S. Appl. No. 13/782,883, filed Mar. 1, 2013; 10 pages.

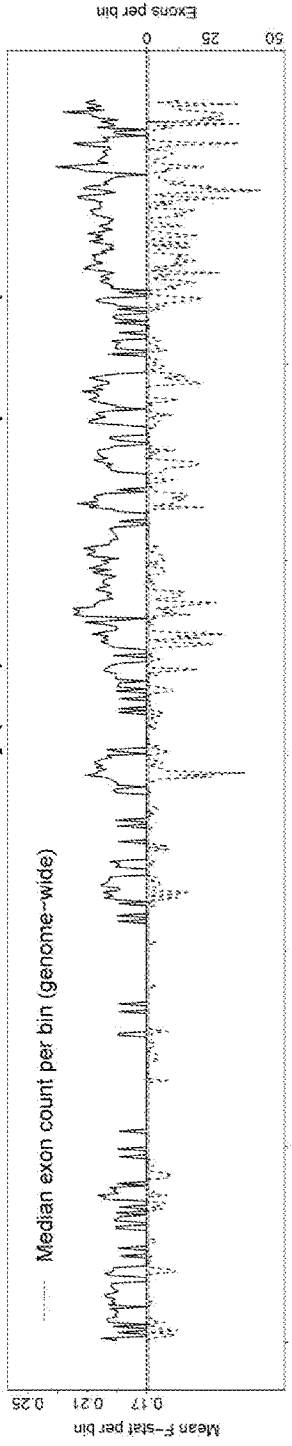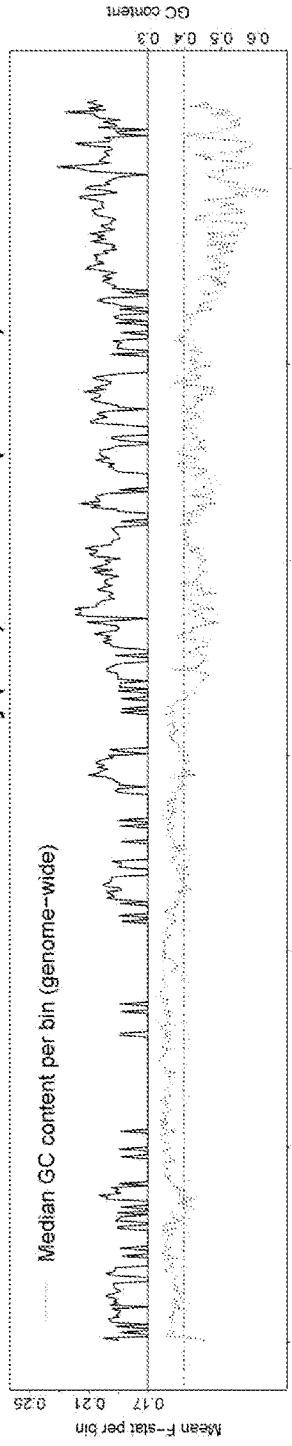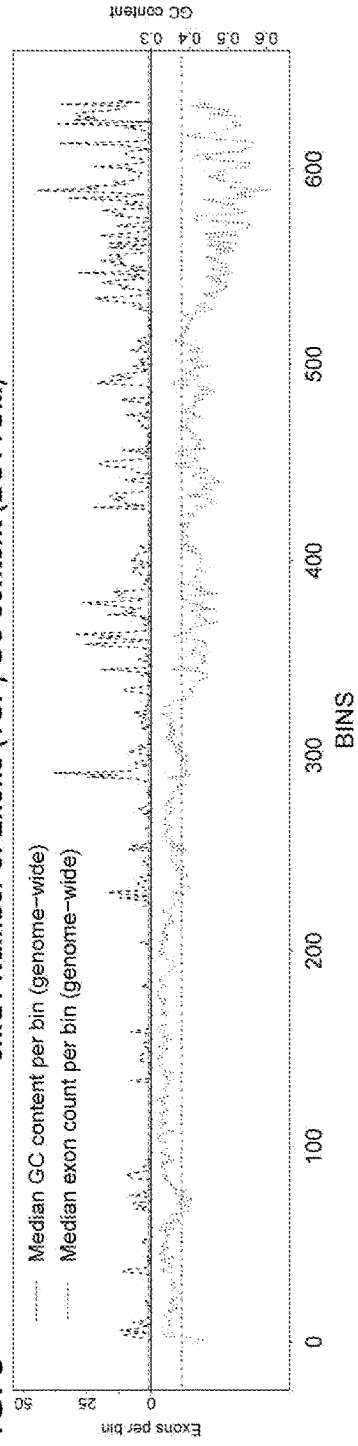
FIG. 7 chr21 F-stat fetal enriched only (TOP) number of exons (BOTTOM)
FIG. 8 chr21 F-stat fetal enriched only (TOP) GC content (BOTTOM)
FIG. 9 chr21 Number of Exons (TOP) GC content (BOTTOM)

FIG. 23

| Flow Cell | Samples | Read length | Biochemistry | automated bead cleanup | Study | Plate | FOA | NTC | Pooled |
|---|---|---|---|---|---|---|---|---|---|
| RDFC0050 | 32 | 36 | ENZ | YES | 480v2 | | 32/32 | 0 | 0 |
| RDFC0051 | 32 | 36 | ENZ | YES | 480v2 | | 32/32 | 0 | 0 |
| RDFC010044 | 96 | 45 | ENZ | NO | WI | 19 | 88/96 | 1 | 1 |
| RDFC010045 | 96 | 45 | TRUSEQ | YES | WI | EPT | 0/96 | 0 | 0 |
| RDFC010049 | 96 | 36 | ENZ | NO | WI | 17 | 84/96 | 1 | 1 |
| RDFC010050 | 96 | 36 | ENZ | NO | WI | 18 | 90/96 | 1 | 1 |
| RDFC010232 | 96 | 36 | TRUSEQ | YES | CEW1 | PE_P2 | 88/96 | 0 | 8 |
| RDFC010239 | 96 | 36 | TRUSEQ | YES | CEW1 | PE_P1 | 88/96 | 0 | 8 |

METHODS AND PROCESSES FOR NON-INVASIVE ASSESSMENT OF GENETIC VARIATIONS

RELATED PATENT APPLICATIONS

This patent application claims the benefit of U.S. provisional patent application No. 61/838,048 filed on Jun. 21, 2013, entitled METHODS AND PROCESSES FOR NON-INVASIVE ASSESSMENT OF GENETIC VARIATIONS, naming Sung K. Kim et al. as inventors. The entire content of the foregoing application is incorporated herein by reference, including all text, tables and drawings.

FIELD

Technology provided herein relates in part to methods, processes, machines and apparatuses for non-invasive assessment of genetic variations.

BACKGROUND

Genetic information of living organisms (e.g., animals, plants and microorganisms) and other forms of replicating genetic information (e.g., viruses) is encoded in deoxyribonucleic acid (DNA) or ribonucleic acid (RNA). Genetic information is a succession of nucleotides or modified nucleotides representing the primary structure of chemical or hypothetical nucleic acids. In humans, the complete genome contains about 30,000 genes located on twenty-four (24) chromosomes (see The Human Genome, T. Strachan, BIOS Scientific Publishers, 1992). Each gene encodes a specific protein, which after expression via transcription and translation fulfills a specific biochemical function within a living cell.

Many medical conditions are caused by one or more genetic variations. Certain genetic variations cause medical conditions that include, for example, hemophilia, thalassemia, Duchenne Muscular Dystrophy (DMD), Huntington's Disease (HD), Alzheimer's Disease and Cystic Fibrosis (CF) (Human Genome Mutations, D. N. Cooper and M. Krawczak, BIOS Publishers, 1993). Such genetic diseases can result from an addition, substitution, or deletion of a single nucleotide in DNA of a particular gene. Certain birth defects are caused by a chromosomal abnormality, also referred to as an aneuploidy, such as Trisomy 21 (Down's Syndrome), Trisomy 13 (Patau Syndrome), Trisomy 18 (Edward's Syndrome), Monosomy X (Turner's Syndrome) and certain sex chromosome aneuploidies such as Klinefelter's Syndrome (XXY), for example. Another genetic variation is fetal gender, which can often be determined based on sex chromosomes X and Y. Some genetic variations may predispose an individual to, or cause, any of a number of diseases such as, for example, diabetes, arteriosclerosis, obesity, various autoimmune diseases and cancer (e.g., colorectal, breast, ovarian, lung).

Identifying one or more genetic variations or variances can lead to diagnosis of, or determining predisposition to, a particular medical condition. Identifying a genetic variance can result in facilitating a medical decision and/or employing a helpful medical procedure. In certain embodiments, identification of one or more genetic variations or variances involves the analysis of cell-free DNA. Cell-free DNA (CF-DNA) is composed of DNA fragments that originate from cell death and circulate in peripheral blood. High concentrations of CF-DNA can be indicative of certain clinical conditions such as cancer, trauma, burns, myocardial infarction, stroke, sepsis, infection, and other illnesses. Additionally, cell-free fetal DNA (CFF-DNA) can be detected in the maternal bloodstream and used for various noninvasive prenatal diagnostics.

The presence of fetal nucleic acid in maternal plasma allows for non-invasive prenatal diagnosis through the analysis of a maternal blood sample. For example, quantitative abnormalities of fetal DNA in maternal plasma can be associated with a number of pregnancy-associated disorders, including preeclampsia, preterm labor, antepartum hemorrhage, invasive placentation, fetal Down syndrome, and other fetal chromosomal aneuploidies. Hence, fetal nucleic acid analysis in maternal plasma can be a useful mechanism for the monitoring of feto-maternal well-being.

SUMMARY

Provided herein, in certain aspects, is a method for estimating a fraction of fetal nucleic acid in a test sample from a pregnant female, comprising (a) obtaining counts of sequence reads mapped to portions of a reference genome, which sequence reads are reads of circulating cell-free nucleic acid from a test sample from a pregnant female, (b) weighting, using a microprocessor, (i) the counts of the sequence reads mapped to each portion, or (ii) other portion-specific parameter, to a portion-specific fraction of fetal nucleic acid according to a weighting factor independently associated with each portion, thereby providing portion-specific fetal fraction estimates according to the weighting factors, where each of the weighting factors have been determined from a fitted relation for each portion between (i) a fraction of fetal nucleic acid for each of multiple samples, and (ii) counts of sequence reads mapped to each portion, or other portion-specific parameter, for the multiple samples and (c) estimating a fraction of fetal nucleic acid for the test sample based on the portion-specific fetal fraction estimates.

Also provided herein is a method for estimating a fraction of fetal nucleic acid in a test sample from a pregnant female, comprising (a) obtaining counts of sequence reads mapped to portions of a reference genome, which sequence reads are reads of circulating cell-free nucleic acid from a test sample from a pregnant female, (b)(i) adjusting, using a microprocessor, the counts of the sequence reads mapped to each portion according to a weighting factor independently assigned to each portion, thereby providing adjusted counts for the portions, or (b)(ii) selecting, using a microprocessor, a subset of portions, thereby providing a subset of counts, where the adjusting in (b)(i) or the selecting in (b)(ii) is according to portions to which an increased amount of reads from fetal nucleic acid are mapped, and (c) estimating a fraction of fetal nucleic acid for the test sample based on the adjusted counts or the subset of counts.

Also provided herein is a method for increasing the accuracy of the estimation of a fraction of fetal nucleic acid in a test sample from a pregnant female, comprising obtaining counts of sequence reads mapped to portions of a reference genome, which sequence reads are reads of circulating cell-free nucleic acid from a test sample from a pregnant female, where at least a subset of the counts obtained are derived from a region of the genome that contributes a greater number of counts derived from fetal nucleic acid relative to total counts from the region than counts of fetal nucleic acid relative to total counts of another region of the genome.

Also provided herein is a system, machine or apparatus comprising one or more microprocessors and memory, which memory comprises instructions executable by the one or more microprocessors and which instructions executable by the one or more microprocessors are configured to (a) access nucleotide sequence reads mapped to portions of a reference genome, which sequence reads are reads of circulating cell-free nucleic acid from a test sample from a pregnant female, (b) weight (i) the counts of the sequence reads mapped to each portion, or (ii) other portion-specific parameter, to a portion-specific fraction of fetal nucleic acid according to a weighting factor independently associated with each portion, thereby providing portion-specific fetal fraction estimates according to the weighting factors, where each of the weighting factors have been determined from a fitted relation for each portion between (i) a fraction of fetal nucleic acid for each of multiple samples, and (ii) counts of sequence reads mapped to each portion, or other portion-specific parameter, for the multiple samples and (c) estimate a fraction of fetal nucleic acid for the test sample based on the portion-specific fetal fraction estimates.

Also provided herein is a machine comprising one or more microprocessors and memory, which memory comprises instructions executable by the one or more microprocessors and which memory comprises nucleotide sequence reads mapped to portions of a reference genome, which sequence reads are reads of circulating cell-free nucleic acid from a test sample from a pregnant female, and which instructions executable by the one or more microprocessors are configured to (a) weight, using a microprocessor, (i) the counts of the sequence reads mapped to each portion, or (ii) other portion-specific parameter, to a portion-specific fraction of fetal nucleic acid according to a weighting factor independently associated with each portion, thereby providing portion-specific fetal fraction estimates according to the weighting factors, where each of the weighting factors have been determined from a fitted relation for each portion between (i) a fraction of fetal nucleic acid for each of multiple samples, and (ii) counts of sequence reads mapped to each portion, or other portion-specific parameter, for the multiple samples and (b) estimate a fraction of fetal nucleic acid for the test sample based on the portion-specific fetal fraction estimates.

Also provided herein is a non-transitory computer-readable storage medium with an executable program stored thereon, where the program instructs a microprocessor to perform the following: (a) access nucleotide sequence reads mapped to portions of a reference genome, which sequence reads are reads of circulating cell-free nucleic acid from a test sample from a pregnant female, (b) weight, using a microprocessor, (i) the counts of the sequence reads mapped to each portion, or (ii) other portion-specific parameter, to a portion-specific fraction of fetal nucleic acid according to a weighting factor independently associated with each portion, thereby providing portion-specific fetal fraction estimates according to the weighting factors, where each of the weighting factors have been determined from a fitted relation for each portion between (i) a fraction of fetal nucleic acid for each of multiple samples, and (ii) counts of sequence reads mapped to each portion, or other portion-specific parameter, for the multiple samples and (c) estimate a fraction of fetal nucleic acid for the test sample based on the portion-specific fetal fraction estimates.

Certain aspects of the technology are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 7 shows a pairwise comparison of FRS (left vertical axis, upper histogram) and the number of exons per 50 kb portion (right vertical axis, lower histogram) for chromosome 21. Portions are shown on the bottom, horizontal X-axis.

FIG. 8 shows a pairwise comparison of FRS (left vertical axis, upper histogram) and the GC content per 50 kb portion (right vertical axis, lower histogram) for chromosome 21. Portions are shown on the bottom, horizontal X-axis.

FIG. 9 shows a pairwise comparison of the number of exons per 50 kb portion (left vertical axis, upper histogram) and the GC content per 50 kb portion (right vertical axis, lower histogram) for chromosome 21. Portions are shown on the bottom, horizontal X-axis.

FIG. 23 shows a table presenting a description of data used for certain analyses.

DETAILED DESCRIPTION

Figure 1:
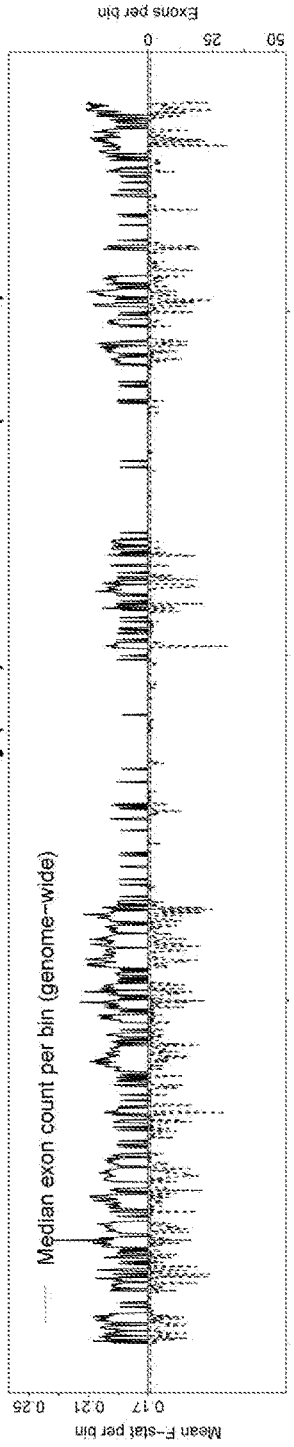
FIG. 1 shows a pairwise comparison of FRS (left vertical axis, upper histogram) and the number of exons per 50 kb bin (right vertical axis, lower histogram) for chromosome 13. Portions are shown on the bottom, horizontal X-axis.
Figure 2:
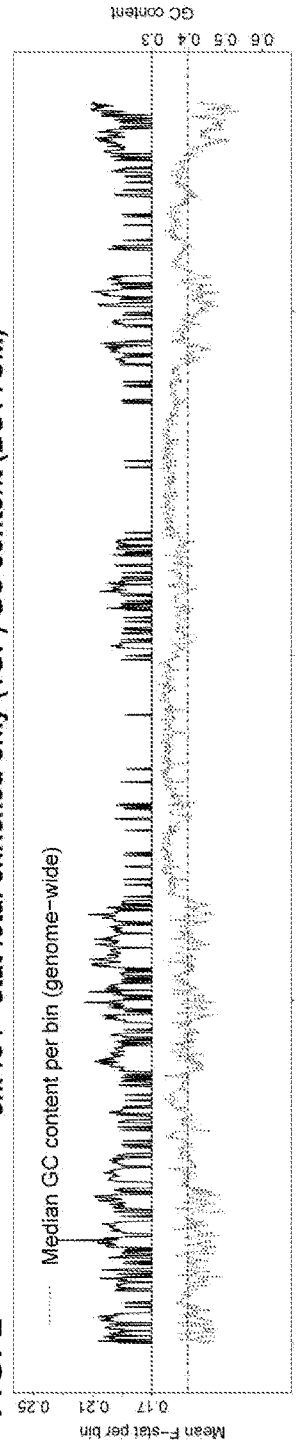
FIG. 2 shows a pairwise comparison of FRS (left vertical axis, upper histogram) and the GC content per 50 kb bin (right vertical axis, lower histogram) for chromosome 13. Portions are shown on the bottom, horizontal X-axis.
Figure 3:
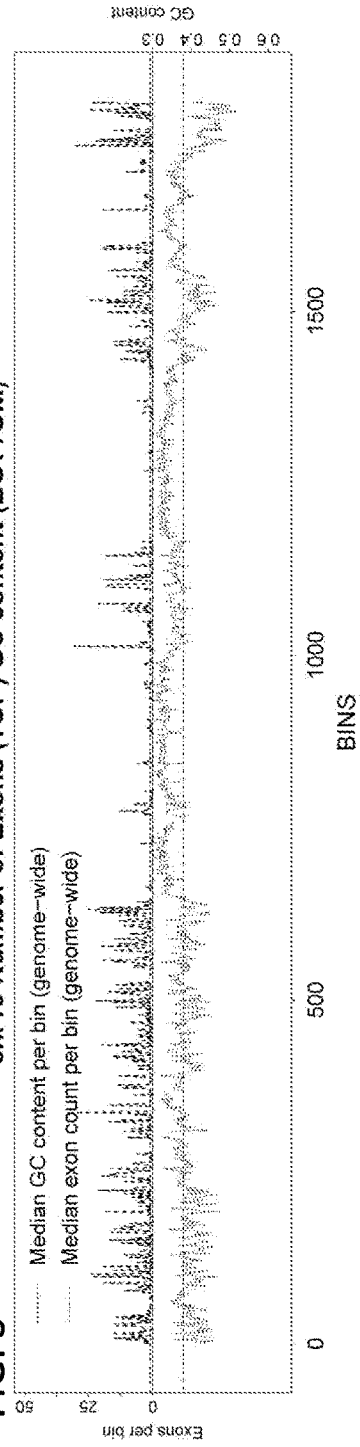
FIG. 3 shows a pairwise comparison of the number of exons per 50 kb portion (left vertical axis, upper histogram) and the GC content per 50 kb portion (right vertical axis, lower histogram) for chromosome 13. Portions are shown on the bottom, horizontal X-axis.
Figure 4:
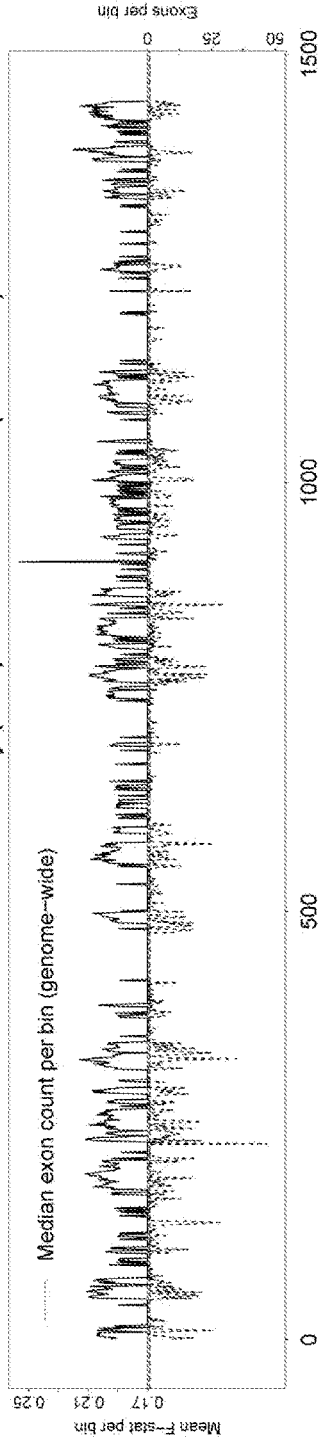
FIG. 4 shows a pairwise comparison of FRS (left vertical axis, upper histogram) and the number of exons per 50 kb portion (right vertical axis, lower histogram) for chromosome 18. Portions are shown on the bottom, horizontal X-axis.
Figure 5:
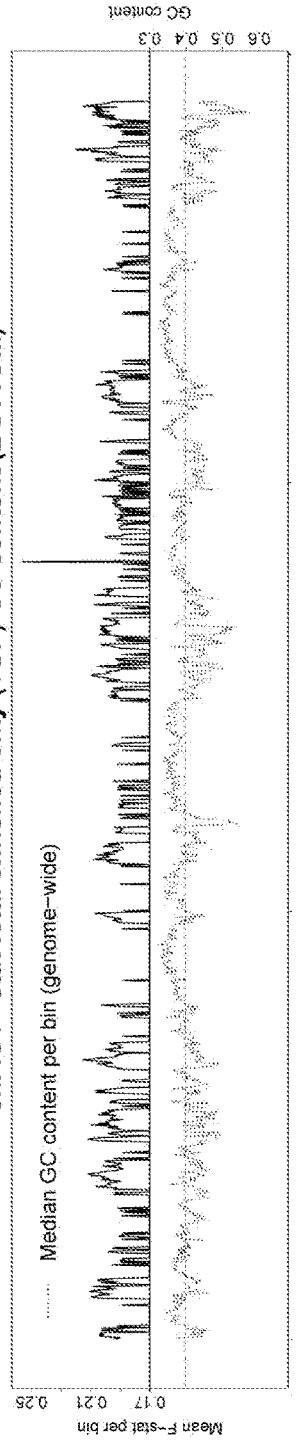
FIG. 5 shows a pairwise comparison of FRS (left vertical axis, upper histogram) and the GC content per 50 kb portion (right vertical axis, lower histogram) for chromosome 18. Portions are shown on the bottom, horizontal X-axis.
Figure 6:
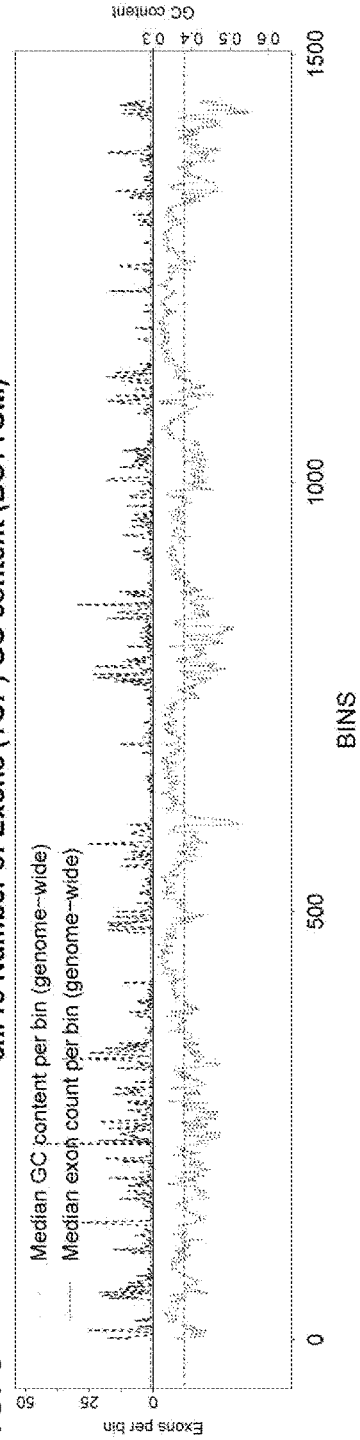
FIG. 6 shows a pairwise comparison of the number of exons per 50 kb portion (left vertical axis, upper histogram) and the GC content per 50 kb portion (right vertical axis, lower histogram) for chromosome 18. Portions are shown on the bottom, horizontal X-axis.

Provided herein are methods for analyzing polynucleotides in a nucleic acid mixture which include, for example, methods for determining the presence or absence of a genetic variation. Assessment of a genetic variation, such as, for example, a fetal aneuploidy, from a maternal sample typically involves sequencing of the nucleic acid present in the sample, mapping sequence reads to certain regions in the genome, quantifying the sequence reads for the sample, and analyzing the quantification. Such methods often directly analyze the nucleic acid in the sample and obtain nucleotide sequence reads for all or substantially all of the nucleic acid in the sample, which can be expensive and can generate superfluous and/or irrelevant data. Certain sequence-based and/or length-based separation approaches combined with certain sequence-based and/or length-based analysis, however, can generate specific information about targeted genomic regions, such as, for example a specific chromosome, and in some instances, can differentiate nucleic acid fragment origins, such as maternal versus fetal origins. Certain methods may include use of a sequencing methods, enrichment techniques and length-based analysis. Certain methods described herein, in some embodiments, may be performed without determining nucleotide sequences of the nucleic acid fragments. Provided herein are methods for analyzing polynucleotides in a nucleic acid mixture (e.g., determining the presence or absence of a fetal aneuploidy) using a combination of sequence-based and/or length-based separation and analysis approaches.

Also provided are methods, processes and machines useful for identifying a genetic variation. Identifying a genetic variation sometimes comprises detecting a copy number variation and/or sometimes comprises adjusting a level comprising a copy number variation. In some embodiments, a level is adjusted providing an identification of one or more genetic variations or variances with a reduced likelihood of a false positive or false negative diagnosis. In some embodiments, identifying a genetic variation by a method described herein can lead to a diagnosis of, or determining a predisposition to, a particular medical condition. Identifying a genetic variance can result in facilitating a medical decision and/or employing a helpful medical procedure.

Also provided herein are systems, machines and modules that, in some embodiments, carry out the methods described herein.

Samples

Provided herein are methods and compositions for analyzing nucleic acid. In some embodiments, nucleic acid fragments in a mixture of nucleic acid fragments are analyzed. A mixture of nucleic acids can comprise two or more nucleic acid fragment species having different nucleotide sequences, different fragment lengths, different origins (e.g., genomic origins, fetal vs. maternal origins, cell or tissue origins, sample origins, subject origins, and the like), or combinations thereof.

Nucleic acid or a nucleic acid mixture utilized in methods and apparatuses described herein often is isolated from a sample obtained from a subject. A subject can be any living or non-living organism, including but not limited to a human, a non-human animal, a plant, a bacterium, a fungus or a protist. Any human or non-human animal can be selected, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be a male or female (e.g., woman, a pregnant woman). A subject may be any age (e.g., an embryo, a fetus, infant, child, adult).

Nucleic acid may be isolated from any type of suitable biological specimen or sample (e.g., a test sample). A sample or test sample can be any specimen that is isolated or obtained from a subject or part thereof (e.g., a human subject, a pregnant female, a fetus). Non-limiting examples of specimens include fluid or tissue from a subject, including, without limitation, blood or a blood product (e.g., serum, plasma, or the like), umbilical cord blood, chorionic villi, amniotic fluid, cerebrospinal fluid, spinal fluid, lavage fluid (e.g., bronchoalveolar, gastric, peritoneal, ductal, ear, arthroscopic), biopsy sample (e.g., from pre-implantation embryo), celocentesis sample, cells (blood cells, placental cells, embryo or fetal cells, fetal nucleated cells or fetal cellular remnants) or parts thereof (e.g., mitochondrial, nucleus, extracts, or the like), washings of female reproductive tract, urine, feces, sputum, saliva, nasal mucous, prostate fluid, lavage, semen, lymphatic fluid, bile, tears, sweat, breast milk, breast fluid, the like or combinations thereof. In some embodiments, a biological sample is a cervical swab from a subject. In some embodiments, a biological sample may be blood and sometimes plasma or serum. The term "blood" as used herein refers to a blood sample or preparation from a pregnant woman or a woman being tested for possible pregnancy. The term encompasses whole blood, blood product or any fraction of blood, such as serum, plasma, buffy coat, or the like as conventionally defined. Blood or fractions thereof often comprise nucleosomes (e.g., maternal and/or fetal nucleosomes). Nucleosomes comprise nucleic acids and are sometimes cell-free or intracellular. Blood also comprises buffy coats. Buffy coats are sometimes isolated by utilizing a ficoll gradient. Buffy coats can comprise white blood cells (e.g., leukocytes, T-cells, B-cells, platelets, and the like). In certain embodiments buffy coats comprise maternal and/or fetal nucleic acid. Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3-40 milliliters) often is collected and can be stored according to standard procedures prior to or after preparation. A fluid or tissue sample from which nucleic acid is extracted may be acellular (e.g., cell-free). In some embodiments, a fluid or tissue sample may contain cellular elements or cellular remnants. In some embodiments fetal cells or cancer cells may be included in the sample.

A sample often is heterogeneous, by which is meant that more than one type of nucleic acid species is present in the sample. For example, heterogeneous nucleic acid can include, but is not limited to, (i) fetal derived and maternal derived nucleic acid, (ii) cancer and non-cancer nucleic acid, (iii) pathogen and host nucleic acid, and more generally, (iv) mutated and wild-type nucleic acid. A sample may be heterogeneous because more than one cell type is present, such as a fetal cell and a maternal cell, a cancer and non-cancer cell, or a pathogenic and host cell. In some embodiments, a minority nucleic acid species and a majority nucleic acid species is present.

For prenatal applications of technology described herein, fluid or tissue sample may be collected from a female at a gestational age suitable for testing, or from a female who is being tested for possible pregnancy. Suitable gestational age may vary depending on the prenatal test being performed. In certain embodiments, a pregnant female subject sometimes is in the first trimester of pregnancy, at times in the second trimester of pregnancy, or sometimes in the third trimester of pregnancy. In certain embodiments, a fluid or tissue is collected from a pregnant female between about 1 to about 45 weeks of fetal gestation (e.g., at 1-4, 4-8, 8-12, 12-16, 16-20, 20-24, 24-28, 28-32, 32-36, 36-40 or 40-44 weeks of fetal gestation), and sometimes between about 5 to about 28 weeks of fetal gestation (e.g., at 6, 7, 8, 9, 10, 11, 12, 13, 14, 15, 16, 17, 18, 19, 20, 21, 22, 23, 24, 25, 26 or 27 weeks of fetal gestation). In certain embodiments a fluid or tissue sample is collected from a pregnant female during or just after (e.g., 0 to 72 hours after) giving birth (e.g., vaginal or non-vaginal birth (e.g., surgical delivery)).

Acquisition of Blood Samples and Extraction of DNA

Methods herein often include separating, enriching and analyzing fetal DNA found in maternal blood as a non-invasive means to detect the presence or absence of a maternal and/or fetal genetic variation and/or to monitor the health of a fetus and/or a pregnant female during and sometimes after pregnancy. Thus, the first steps of practicing certain methods herein often include obtaining a blood sample from a pregnant woman and extracting DNA from a sample.

Acquisition of Blood Samples

A blood sample can be obtained from a pregnant woman at a gestational age suitable for testing using a method of the present technology. A suitable gestational age may vary depending on the disorder tested, as discussed below. Collection of blood from a woman often is performed in accordance with the standard protocol hospitals or clinics generally follow. An appropriate amount of peripheral blood, e.g., typically between 5-50 ml, often is collected and may be stored according to standard procedure prior to further preparation. Blood samples may be collected, stored or transported in a manner that minimizes degradation or the quality of nucleic acid present in the sample.

Preparation of Blood Samples

An analysis of fetal DNA found in maternal blood may be performed using, e.g., whole blood, serum, or plasma. Methods for preparing serum or plasma from maternal blood are known. For example, a pregnant woman's blood can be placed in a tube containing EDTA or a specialized commercial product such as Vacutainer SST (Becton Dickinson, Franklin Lakes, N.J.) to prevent blood clotting, and plasma can then be obtained from whole blood through centrifugation. Serum may be obtained with or without centrifugation-following blood clotting. If centrifugation is used then it is typically, though not exclusively, conducted at an appropriate speed, e.g., 1,500-3,000 times g. Plasma or serum may be subjected to additional centrifugation steps before being transferred to a fresh tube for DNA extraction.

In addition to the acellular portion of the whole blood, DNA may also be recovered from the cellular fraction, enriched in the buffy coat portion, which can be obtained following centrifugation of a whole blood sample from the woman and removal of the plasma.

Extraction of DNA

There are numerous known methods for extracting DNA from a biological sample including blood. The general methods of DNA preparation (e.g., described by Sambrook and Russell, Molecular Cloning: A Laboratory Manual 3d ed., 2001) can be followed; various commercially available reagents or kits, such as Qiagen's QIAamp Circulating Nucleic Acid Kit, QiaAmp DNA Mini Kit or QiaAmp DNA Blood Mini Kit (Qiagen, Hilden, Germany), GenomicPrep™ Blood DNA Isolation Kit (Promega, Madison, Wis.), and GFX™ Genomic Blood DNA Purification Kit (Amersham, Piscataway, N.J.), may also be used to obtain DNA from a blood sample from a pregnant woman. Combinations of more than one of these methods may also be used.

In some embodiments, the sample may first be enriched or relatively enriched for fetal nucleic acid by one or more methods. For example, the discrimination of fetal and maternal DNA can be performed using the compositions and processes of the present technology alone or in combination with other discriminating factors. Examples of these factors include, but are not limited to, single nucleotide differences between chromosome X and Y, chromosome Y-specific sequences, polymorphisms located elsewhere in the genome, size differences between fetal and maternal DNA and differences in methylation pattern between maternal and fetal tissues.

Other methods for enriching a sample for a particular species of nucleic acid are described in PCT Patent Application Number PCT/US07/69991, filed May 30, 2007, PCT Patent Application Number PCT/US2007/071232, filed Jun. 15, 2007, U.S. Provisional Application Nos. 60/968,876 and 60/968,878 (assigned to the Applicant), (PCT Patent Application Number PCT/EP05/012707, filed Nov. 28, 2005) which are all hereby incorporated by reference. In certain embodiments, maternal nucleic acid is selectively removed (either partially, substantially, almost completely or completely) from the sample.

The terms "nucleic acid" and "nucleic acid molecule" may be used interchangeably throughout the disclosure. The terms refer to nucleic acids of any composition from, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA, microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A template nucleic acid in some embodiments can be from a single chromosome (e.g., a nucleic acid sample may be from one chromosome of a sample obtained from a diploid organism). Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues. The term nucleic acid is used interchangeably with locus, gene, cDNA, and mRNA encoded by a gene. The term also may include, as equivalents, derivatives, variants and analogs of RNA or DNA synthesized from nucleotide analogs, single-stranded ("sense" or "antisense", "plus" strand or "minus" strand, "forward" reading frame or "reverse" reading frame) and double-stranded polynucleotides. The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons). Deoxyribonucleotides include deoxyadenosine, deoxycytidine, deoxyguanosine and deoxythymidine. For RNA, the base cytosine is replaced with uracil. A template nucleic acid may be prepared using a nucleic acid obtained from a subject as a template.

Nucleic Acid Isolation and Processing

Nucleic acid may be derived from one or more sources (e.g., cells, serum, plasma, buffy coat, lymphatic fluid, skin, soil, and the like) by methods known in the art. Any suitable method can be used for isolating, extracting and/or purifying DNA from a biological sample (e.g., from blood or a blood product), non-limiting examples of which include methods of DNA preparation (e.g., described by Sambrook and Russell, Molecular Cloning: A Laboratory Manual 3d ed., 2001), various commercially available reagents or kits, such as Qiagen's QIAamp Circulating Nucleic Acid Kit, QiaAmp DNA Mini Kit or QiaAmp DNA Blood Mini Kit (Qiagen, Hilden, Germany), GenomicPrep™ Blood DNA Isolation Kit (Promega, Madison, Wis.), and GFX™ Genomic Blood DNA Purification Kit (Amersham, Piscataway, N.J.), the like or combinations thereof.

Cell lysis procedures and reagents are known in the art and may generally be performed by chemical (e.g., detergent, hypotonic solutions, enzymatic procedures, and the like, or combination thereof), physical (e.g., French press, sonication, and the like), or electrolytic lysis methods. Any suitable lysis procedure can be utilized. For example, chemical methods generally employ lysing agents to disrupt cells and extract the nucleic acids from the cells, followed by treatment with chaotropic salts. Physical methods such as freeze/thaw followed by grinding, the use of cell presses and the like also are useful. High salt lysis procedures also are commonly used. For example, an alkaline lysis procedure may be utilized. The latter procedure traditionally incorporates the use of phenol-chloroform solutions, and an alternative phenol-chloroform-free procedure involving three solutions can be utilized. In the latter procedures, one solution can contain 15 mM Tris, pH 8.0; 10 mM EDTA and 100 ug/ml Rnase A; a second solution can contain 0.2N NaOH and 1% SDS; and a third solution can contain 3M KOAc, pH 5.5. These procedures can be found in Current Protocols in Molecular Biology, John Wiley & Sons, N.Y., 6.3.1-6.3.6 (1989), incorporated herein in its entirety.

Nucleic acid may be isolated at a different time point as compared to another nucleic acid, where each of the samples is from the same or a different source. A nucleic acid may be from a nucleic acid library, such as a cDNA or RNA library, for example. A nucleic acid may be a result of nucleic acid purification or isolation and/or amplification of nucleic acid molecules from the sample. Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acids can include extracellular nucleic acid in certain embodiments. The term "extracellular nucleic acid" as used herein can refer to nucleic acid isolated from a source having substantially no cells and also is referred to as "cell-free" nucleic acid, "circulating cell-free nucleic acid" (e.g., CCF fragments) and/or "cell-free circulating nucleic acid". Extracellular nucleic acid can be present in and obtained from blood (e.g., from the blood of a pregnant female). Extracellular nucleic acid often includes no detectable cells and may contain cellular elements or cellular remnants. Non-limiting examples of acellular sources for extracellular nucleic acid are blood, blood plasma, blood serum and urine. As used herein, the term "obtain cell-free circulating sample nucleic acid" includes obtaining a sample directly (e.g., collecting a sample, e.g., a test sample) or obtaining a sample from another who has collected a sample. Without being limited by theory, extracellular nucleic acid may be a product of cell apoptosis and cell breakdown, which provides basis for extracellular nucleic acid often having a series of lengths across a spectrum (e.g., a "ladder").

Extracellular nucleic acid can include different nucleic acid species, and therefore is referred to herein as "heterogeneous" in certain embodiments. For example, blood serum or plasma from a person having cancer can include nucleic acid from cancer cells and nucleic acid from non-cancer cells. In another example, blood serum or plasma from a pregnant female can include maternal nucleic acid and fetal nucleic acid. In some instances, fetal nucleic acid sometimes is about 5% to about 50% of the overall nucleic acid (e.g., about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49% of the total nucleic acid is fetal nucleic acid). In some embodiments, the majority of fetal nucleic acid in nucleic acid is of a length of about 500 base pairs or less (e.g., about 80, 85, 90, 91, 92, 93, 94, 95, 96, 97, 98, 99 or 100% of fetal nucleic acid is of a length of about 500 base pairs or less). In some embodiments, the majority of fetal nucleic acid in nucleic acid is of a length of about 250 base pairs or less (e.g., about 80, 85, 90, 91, 92, 93, 94, 95, 96, 97, 98, 99 or 100% of fetal nucleic acid is of a length of about 250 base pairs or less). In some embodiments, the majority of fetal nucleic acid in nucleic acid is of a length of about 200 base pairs or less (e.g., about 80, 85, 90, 91, 92, 93, 94, 95, 96, 97, 98, 99 or 100% of fetal nucleic acid is of a length of about 200 base pairs or less). In some embodiments, the majority of fetal nucleic acid in nucleic acid is of a length of about 150 base pairs or less (e.g., about 80, 85, 90, 91, 92, 93, 94, 95, 96, 97, 98, 99 or 100% of fetal nucleic acid is of a length of about 150 base pairs or less). In some embodiments, the majority of fetal nucleic acid in nucleic acid is of a length of about 100 base pairs or less (e.g., about 80, 85, 90, 91, 92, 93, 94, 95, 96, 97, 98, 99 or 100% of fetal nucleic acid is of a length of about 100 base pairs or less). In some embodiments, the majority of fetal nucleic acid in nucleic acid is of a length of about 50 base pairs or less (e.g., about 80, 85, 90, 91, 92, 93, 94, 95, 96, 97, 98, 99 or 100% of fetal nucleic acid is of a length of about 50 base pairs or less). In some embodiments, the majority of fetal nucleic acid in nucleic acid is of a length of about 25 base pairs or less (e.g., about 80, 85, 90, 91, 92, 93, 94, 95, 96, 97, 98, 99 or 100% of fetal nucleic acid is of a length of about 25 base pairs or less).

Nucleic acid may be provided for conducting methods described herein without processing of the sample(s) containing the nucleic acid, in certain embodiments. In some embodiments, nucleic acid is provided for conducting methods described herein after processing of the sample(s) containing the nucleic acid. For example, a nucleic acid can be extracted, isolated, purified, partially purified or amplified from the sample(s). The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. The term "isolated nucleic acid" as used herein can refer to a nucleic acid removed from a subject (e.g., a human subject). An isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" as used herein can refer to a nucleic acid provided that contains fewer non-nucleic acid components (e.g., protein, lipid, carbohydrate) than the amount of non-nucleic acid components present prior to subjecting the nucleic acid to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. The term "purified" as used herein can refer to a nucleic acid provided that contains fewer nucleic acid species than in the sample source from which the nucleic acid is derived. A composition comprising purified nucleic acid may be about 90%, 91%, 92%, 93%, 94%, 95%, 96%, 97%, 98%, 99% or greater than 99% free of other nucleic acid species. For example, fetal nucleic acid can be purified from a mixture comprising maternal and fetal nucleic acid. In certain examples, nucleosomes comprising small fragments of fetal nucleic acid can be purified from a mixture of larger nucleosome complexes comprising larger fragments of maternal nucleic acid.

In some embodiments nucleic acids are fragmented or cleaved prior to, during or after a method described herein. Fragmented or cleaved nucleic acid may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000 or 9000 base pairs. Fragments can be generated by a suitable method known in the art, and the average, mean or nominal length of nucleic acid fragments can be controlled by selecting an appropriate fragment-generating procedure.

Nucleic acid fragments may contain overlapping nucleotide sequences, and such overlapping sequences can facilitate construction of a nucleotide sequence of the non-fragmented counterpart nucleic acid, or a segment thereof. For example, one fragment may have subsequences x and y and another fragment may have subsequences y and z, where x, y and z are nucleotide sequences that can be 5 nucleotides in length or greater. Overlap sequence y can be utilized to facilitate construction of the x-y-z nucleotide sequence in nucleic acid from a sample in certain embodiments. Nucleic acid may be partially fragmented (e.g., from an incomplete or terminated specific cleavage reaction) or fully fragmented in certain embodiments.

In some embodiments nucleic acid is fragmented or cleaved by a suitable method, non-limiting examples of which include physical methods (e.g., shearing, e.g., sonication, French press, heat, UV irradiation, the like), enzymatic processes (e.g., enzymatic cleavage agents (e.g., a suitable nuclease, a suitable restriction enzyme, a suitable methylation sensitive restriction enzyme)), chemical methods (e.g., alkylation, DMS, piperidine, acid hydrolysis, base hydrolysis, heat, the like, or combinations thereof), processes described in U.S. Patent Application Publication No. 20050112590, the like or combinations thereof.

As used herein, "fragmentation" or "cleavage" refers to a procedure or conditions in which a nucleic acid molecule, such as a nucleic acid template gene molecule or amplified product thereof, may be severed into two or more smaller nucleic acid molecules. Such fragmentation or cleavage can be sequence specific, base specific, or nonspecific, and can be accomplished by any of a variety of methods, reagents or conditions, including, for example, chemical, enzymatic, physical fragmentation.

As used herein, "fragments", "cleavage products", "cleaved products" or grammatical variants thereof, refers to nucleic acid molecules resultant from a fragmentation or cleavage of a nucleic acid template gene molecule or amplified product thereof. While such fragments or cleaved products can refer to all nucleic acid molecules resultant from a cleavage reaction, typically such fragments or cleaved products refer only to nucleic acid molecules resultant from a fragmentation or cleavage of a nucleic acid template gene molecule or the segment of an amplified product thereof containing the corresponding nucleotide sequence of a nucleic acid template gene molecule. The term "amplified" as used herein refers to subjecting a target nucleic acid in a sample to a process that linearly or exponentially generates amplicon nucleic acids having the same or substantially the same nucleotide sequence as the target nucleic acid, or segment thereof.

In certain embodiments the term "amplified" refers to a method that comprises a polymerase chain reaction (PCR). For example, an amplified product can contain one or more nucleotides more than the amplified nucleotide region of a nucleic acid template sequence (e.g., a primer can contain "extra" nucleotides such as a transcriptional initiation sequence, in addition to nucleotides complementary to a nucleic acid template gene molecule, resulting in an amplified product containing "extra" nucleotides or nucleotides not corresponding to the amplified nucleotide region of the nucleic acid template gene molecule). Accordingly, fragments can include fragments arising from segments or parts of amplified nucleic acid molecules containing, at least in part, nucleotide sequence information from or based on the representative nucleic acid template molecule.

As used herein, the term "complementary cleavage reactions" refers to cleavage reactions that are carried out on the same nucleic acid using different cleavage reagents or by altering the cleavage specificity of the same cleavage reagent such that alternate cleavage patterns of the same target or reference nucleic acid or protein are generated. In certain embodiments, nucleic acid may be treated with one or more specific cleavage agents (e.g., 1, 2, 3, 4, 5, 6, 7, 8, 9, 10 or more specific cleavage agents) in one or more reaction vessels (e.g., nucleic acid is treated with each specific cleavage agent in a separate vessel). The term "specific cleavage agent" as used herein refers to an agent, sometimes a chemical or an enzyme that can cleave a nucleic acid at one or more specific sites.

Nucleic acid also may be exposed to a process that modifies certain nucleotides in the nucleic acid before providing nucleic acid for a method described herein. A process that selectively modifies nucleic acid based upon the methylation state of nucleotides therein can be applied to nucleic acid, for example. In addition, conditions such as high temperature, ultraviolet radiation, x-radiation, can induce changes in the sequence of a nucleic acid molecule. Nucleic acid may be provided in any suitable form useful for conducting a suitable sequence analysis.

Nucleic acid may be single or double stranded. Single stranded DNA, for example, can be generated by denaturing double stranded DNA by heating or by treatment with alkali, for example. In certain embodiments, nucleic acid is in a D-loop structure, formed by strand invasion of a duplex DNA molecule by an oligonucleotide or a DNA-like molecule such as peptide nucleic acid (PNA). D loop formation can be facilitated by addition of E. Coli RecA protein and/or by alteration of salt concentration, for example, using methods known in the art.

Genomic Targets

In some embodiments, target nucleic acids, also referred to herein as target fragments, include polynucleotide fragments from a particular genomic region or plurality of genomic regions (e.g., single chromosome, set of chromosomes, and/or certain chromosome regions). In some embodiments, such genomic regions can be associated with fetal genetic abnormalities (e.g., aneuploidy) as well as other genetic variations including, but not limited to, mutations (e.g., point mutations), insertions, additions, deletions, translocations, trinucleotide repeat disorders, and/or single nucleotide polymorphisms (SNPs). In some embodiments, reference nucleic acids, also referred to herein as reference fragments, include polynucleotide fragments from a particular genomic region or plurality of genomic regions not associated with fetal genetic abnormalities. In some embodiments, target and/or reference nucleic acids (i.e., target fragments and/or reference fragments) comprise nucleotide sequences that are substantially unique to the chromosome of interest or reference chromosome (e.g., identical nucleotide sequences or substantially similar nucleotide sequences are not found elsewhere in the genome).

In some embodiments, fragments from a plurality of genomic regions are assayed. In some embodiments, target fragments and reference fragments from a plurality of genomic regions are assayed. In some embodiments, fragments from a plurality of genomic regions are assayed to determine the presence, absence, amount (e.g., relative amount) or ratio of a chromosome of interest, for example. In some embodiments, a chromosome of interest is a chromosome suspected of being aneuploid and may be referred to herein as a "test chromosome". In some embodiments, fragments from a plurality of genomic regions is assayed for a presumed euploid chromosome. Such a chromosome may be referred to herein as a "reference chromosome". In some embodiments, a plurality of test chromosomes is assayed. In some embodiments, test chromosomes are selected from among chromosome 13 (Chr13), chromosome 18 (Chr18) and chromosome 21 (Chr21). In some embodiments, reference chromosomes are selected from among chromosomes 1, 2, 3, 4, 5, 6, 7, 8, 9, 10, 11, 12, 13, 14, 15, 16, 17, 18, 19, 20, 21, 22, X and Y, and sometimes, reference chromosomes are selected from autosomes (i.e., not X and Y). In some embodiments, chromosome 20 (Chr20) is selected as a reference chromosome. In some embodiments, chromosome 14 is selected as a reference chromosome. In some embodiments, chromosome 9 is selected as a reference chromosome. In some embodiments, a test chromosome and a reference chromosome are from the same individual. In some embodiments, a test chromosome and a reference chromosome are from different individuals.

In some embodiments, fragments from at least one genomic region are assayed for a test and/or reference chromosome. In some embodiments, fragments from at least 10 genomic regions (e.g., about 20, 30, 40, 50, 60, 70, 80 or 90 genomic regions) are assayed for a test chromosome and/or a reference chromosome. In some embodiments, fragments from at least 100 genomic regions (e.g., about 200, 300, 400, 500, 600, 700, 800 or 900 genomic regions) are assayed for a test chromosome and/or a reference chromosome. In some embodiments, fragments from at least 1,000 genomic regions (e.g., about 2000, 3000, 4000, 5000, 6000, 7000, 8000 or 9000 genomic regions) are assayed for a test chromosome and/or a reference chromosome. In some embodiments, fragments from at least 10,000 genomic regions (e.g., about 20,000, 30,000, 40,000, 50,000, 60,000, 70,000, 80,000 or 90,000 genomic regions) are assayed for a test chromosome and/or a reference chromosome. In some embodiments, fragments from at least 100,000 genomic regions (e.g., about 200,000, 300,000, 400,000, 500,000, 600,000, 700,000, 800,000 or 900,000 genomic regions) are assayed for a test chromosome and/or a reference chromosome.

Enrichment and Separation of Subpopulations of Nucleic Acid

In some embodiments, nucleic acid (e.g., extracellular nucleic acid) is enriched or relatively enriched for a subpopulation or species of nucleic acid. Nucleic acid subpopulations can include, for example, fetal nucleic acid, maternal nucleic acid, nucleic acid comprising fragments of a particular length or range of lengths, or nucleic acid from a particular genome region (e.g., single chromosome, set of chromosomes, and/or certain chromosome regions). Such enriched samples can be used in conjunction with a method provided herein. Thus, in certain embodiments, methods of the technology comprise an additional step of enriching for a subpopulation of nucleic acid in a sample, such as, for example, fetal nucleic acid. In certain embodiments, a method for determining fetal fraction described herein also can be used to enrich for fetal nucleic acid. In certain embodiments, maternal nucleic acid is selectively removed (partially, substantially, almost completely or completely) from the sample. In certain embodiments, enriching for a particular low copy number species nucleic acid (e.g., fetal nucleic acid) may improve quantitative sensitivity. Methods for enriching a sample for a particular species of nucleic acid are described, for example, in U.S. Pat. No. 6,927,028, International Patent Application Publication No. WO2007/140417, International Patent Application Publication No. WO2007/147063, International Patent Application Publication No. WO2009/032779, International Patent Application Publication No. WO2009/032781, International Patent Application Publication No. WO2010/033639, International Patent Application Publication No. WO2011/034631, International Patent Application Publication No. WO2006/056480, and International Patent Application Publication No. WO2011/143659, all of which are incorporated by reference herein.

In some embodiments, nucleic acid is enriched for certain target fragment species and/or reference fragment species. In certain embodiments, nucleic acid is enriched for a specific nucleic acid fragment length or range of fragment lengths using one or more length-based separation methods described below. In certain embodiments, nucleic acid is enriched for fragments from a select genomic region (e.g., chromosome) using one or more sequence-based separation methods described herein and/or known in the art. Certain methods for enriching for a nucleic acid subpopulation (e.g., fetal nucleic acid) in a sample are described in detail below.

Some methods for enriching for a nucleic acid subpopulation (e.g., fetal nucleic acid) that can be used with a method described herein include methods that exploit epigenetic differences between maternal and fetal nucleic acid. For example, fetal nucleic acid can be differentiated and separated from maternal nucleic acid based on methylation differences. Methylation-based fetal nucleic acid enrichment methods are described in U.S. Patent Application Publication No. 2010/0105049, which is incorporated by reference herein. Such methods sometimes involve binding a sample nucleic acid to a methylation-specific binding agent (methyl-CpG binding protein (MBD), methylation specific antibodies, and the like) and separating bound nucleic acid from unbound nucleic acid based on differential methylation status. Such methods also can include the use of methylation-sensitive restriction enzymes (as described above; e.g., HhaI and HpaII), which allow for the enrichment of fetal nucleic acid regions in a maternal sample by selectively digesting nucleic acid from the maternal sample with an enzyme that selectively and completely or substantially digests the maternal nucleic acid to enrich the sample for at least one fetal nucleic acid region.

Another method for enriching for a nucleic acid subpopulation (e.g., fetal nucleic acid) that can be used with a method described herein is a restriction endonuclease enhanced polymorphic sequence approach, such as a method described in U.S. Patent Application Publication No. 2009/0317818, which is incorporated by reference herein. Such methods include cleavage of nucleic acid comprising a non-target allele with a restriction endonuclease that recognizes the nucleic acid comprising the non-target allele but not the target allele; and amplification of uncleaved nucleic acid but not cleaved nucleic acid, where the uncleaved, amplified nucleic acid represents enriched target nucleic acid (e.g., fetal nucleic acid) relative to non-target nucleic acid (e.g., maternal nucleic acid). In certain embodiments, nucleic acid may be selected such that it comprises an allele having a polymorphic site that is susceptible to selective digestion by a cleavage agent, for example.

Some methods for enriching for a nucleic acid subpopulation (e.g., fetal nucleic acid) that can be used with a method described herein include selective enzymatic degradation approaches. Such methods involve protecting target sequences from exonuclease digestion thereby facilitating the elimination in a sample of undesired sequences (e.g., maternal DNA). For example, in one approach, sample nucleic acid is denatured to generate single stranded nucleic acid, single stranded nucleic acid is contacted with at least one target-specific primer pair under suitable annealing conditions, annealed primers are extended by nucleotide polymerization generating double stranded target sequences, and digesting single stranded nucleic acid using a nuclease that digests single stranded (i.e. non-target) nucleic acid. In certain embodiments, the method can be repeated for at least one additional cycle. In certain embodiments, the same target-specific primer pair is used to prime each of the first and second cycles of extension, and In certain embodiments, different target-specific primer pairs are used for the first and second cycles.

In some embodiments, nucleic acid is enriched for fragments from a select genomic region (e.g., chromosome) using one or more sequence-based separation methods described herein. In some embodiments, nucleic acid is enriched for a specific polynucleotide fragment length or range of fragment lengths and for fragments from a select genomic region (e.g., chromosome) using a combination of length-based and sequence-based separation methods. Such length-based and sequence-based separation methods are described in further detail below.

Some methods for enriching for a nucleic acid subpopulation (e.g., fetal nucleic acid) that can be used with a method described herein include massively parallel signature sequencing (MPSS) approaches. MPSS typically is a solid phase method that uses adapter (i.e. tag) ligation, followed by adapter decoding, and reading of the nucleic acid sequence in small increments. Tagged PCR products are typically amplified such that each nucleic acid generates a PCR product with a unique tag. Tags are often used to attach the PCR products to microbeads. After several rounds of ligation-based sequence determination, for example, a sequence signature can be identified from each bead. Each signature sequence (MPSS tag) in a MPSS dataset is analyzed, compared with all other signatures, and all identical signatures are counted.

In certain embodiments, certain enrichment methods (e.g., certain MPS and/or MPSS-based enrichment methods) can include amplification (e.g., PCR)-based approaches. In certain embodiments, loci-specific amplification methods can be used (e.g., using loci-specific amplification primers). In certain embodiments, a multiplex SNP allele PCR approach can be used. In certain embodiments, a multiplex SNP allele PCR approach can be used in combination with uniplex sequencing. For example, such an approach can involve the use of multiplex PCR (e.g., MASSARRAY system) and incorporation of capture probe sequences into the amplicons followed by sequencing using, for example, the Illumina MPSS system. In certain embodiments, a multiplex SNP allele PCR approach can be used in combination with a three-primer system and indexed sequencing. For example, such an approach can involve the use of multiplex PCR (e.g., MASSARRAY system) with primers having a first capture probe incorporated into certain loci-specific forward PCR primers and adapter sequences incorporated into loci-specific reverse PCR primers, to thereby generate amplicons, followed by a secondary PCR to incorporate reverse capture sequences and molecular index barcodes for sequencing using, for example, the Illumina MPSS system. In certain embodiments, a multiplex SNP allele PCR approach can be used in combination with a four-primer system and indexed sequencing. For example, such an approach can involve the use of multiplex PCR (e.g., MASSARRAY system) with primers having adaptor sequences incorporated into both loci-specific forward and loci-specific reverse PCR primers, followed by a secondary PCR to incorporate both forward and reverse capture sequences and molecular index barcodes for sequencing using, for example, the Illumina MPSS system. In certain embodiments, a microfluidics approach can be used. In certain embodiments, an array-based microfluidics approach can be used. For example, such an approach can involve the use of a microfluidics array (e.g., Fluidigm) for amplification at low plex and incorporation of index and capture probes, followed by sequencing. In certain embodiments, an emulsion microfluidics approach can be used, such as, for example, digital droplet PCR.

In certain embodiments, universal amplification methods can be used (e.g., using universal or non-loci-specific amplification primers). In certain embodiments, universal amplification methods can be used in combination with pull-down approaches. In certain embodiments, a method can include biotinylated ultramer pull-down (e.g., biotinylated pull-down assays from Agilent or IDT) from a universally amplified sequencing library. For example, such an approach can involve preparation of a standard library, enrichment for selected regions by a pull-down assay, and a secondary universal amplification step. In certain embodiments, pull-down approaches can be used in combination with ligation-based methods. In certain embodiments, a method can include biotinylated ultramer pull down with sequence specific adapter ligation (e.g., HALOPLEX PCR, Halo Genomics). For example, such an approach can involve the use of selector probes to capture restriction enzyme-digested fragments, followed by ligation of captured products to an adaptor, and universal amplification followed by sequencing. In certain embodiments, pull-down approaches can be used in combination with extension and ligation-based methods. In certain embodiments, a method can include molecular inversion probe (MIP) extension and ligation. For example, such an approach can involve the use of molecular inversion probes in combination with sequence adapters followed by universal amplification and sequencing. In certain embodiments, complementary DNA can be synthesized and sequenced without amplification.

In certain embodiments, extension and ligation approaches can be performed without a pull-down component. In certain embodiments, a method can include loci-specific forward and reverse primer hybridization, extension and ligation. Such methods can further include universal amplification or complementary DNA synthesis without amplification, followed by sequencing. Such methods can reduce or exclude background sequences during analysis, in certain embodiments.

In certain embodiments, pull-down approaches can be used with an optional amplification component or with no amplification component. In certain embodiments, a method can include a modified pull-down assay and ligation with full incorporation of capture probes without universal amplification. For example, such an approach can involve the use of modified selector probes to capture restriction enzyme-digested fragments, followed by ligation of captured products to an adaptor, optional amplification, and sequencing. In certain embodiments, a method can include a biotinylated pull-down assay with extension and ligation of adaptor sequence in combination with circular single stranded ligation. For example, such an approach can involve the use of selector probes to capture regions of interest (i.e. target sequences), extension of the probes, adaptor ligation, single stranded circular ligation, optional amplification, and sequencing. In certain embodiments, the analysis of the sequencing result can separate target sequences form background.

In some embodiments, nucleic acid is enriched for fragments from a select genomic region (e.g., chromosome) using one or more sequence-based separation methods described herein. Sequence-based separation generally is based on nucleotide sequences present in the fragments of interest (e.g., target and/or reference fragments) and substantially not present in other fragments of the sample or present in an insubstantial amount of the other fragments (e.g., 5% or less). In some embodiments, sequence-based separation can generate separated target fragments and/or separated reference fragments. Separated target fragments and/or separated reference fragments often are isolated away from the remaining fragments in the nucleic acid sample. In certain embodiments, the separated target fragments and the separated reference fragments also are isolated away from each other (e.g., isolated in separate assay compartments). In certain embodiments, the separated target fragments and the separated reference fragments are isolated together (e.g., isolated in the same assay compartment). In some embodiments, unbound fragments can be differentially removed or degraded or digested.

In some embodiments, a selective nucleic acid capture process is used to separate target and/or reference fragments away from the nucleic acid sample. Commercially available nucleic acid capture systems include, for example, Nimblegen sequence capture system (Roche NimbleGen, Madison, Wis.); Illumina BEADARRAY platform (Illumina, San Diego, Calif.); Affymetrix GENECHIP platform (Affymetrix, Santa Clara, Calif.); Agilent SureSelect Target Enrichment System (Agilent Technologies, Santa Clara, Calif.); and related platforms. Such methods typically involve hybridization of a capture oligonucleotide to a segment or all of the nucleotide sequence of a target or reference fragment and can include use of a solid phase (e.g., solid phase array) and/or a solution based platform. Capture oligonucleotides (sometimes referred to as "bait") can be selected or designed such that they preferentially hybridize to nucleic acid fragments from selected genomic regions or loci (e.g., one of chromosomes 21, 18, 13, X or Y, or a reference chromosome). In certain embodiments, a hybridization-based method (e.g., using oligonucleotide arrays) can be used to enrich for nucleic acid sequences from certain chromosomes (e.g., a potentially aneuploid chromosome, reference chromosome or other chromosome of interest) or segments of interest thereof.

Capture oligonucleotides typically comprise a nucleotide sequence capable of hybridizing or annealing to a nucleic acid fragment of interest (e.g. target fragment, reference fragment) or a portion thereof. A capture oligonucleotide may be naturally occurring or synthetic and may be DNA or RNA based. Capture oligonucleotides can allow for specific separation of, for example, a target and/or reference fragment away from other fragments in a nucleic acid sample. The term "specific" or "specificity", as used herein, refers to the binding or hybridization of one molecule to another molecule, such as an oligonucleotide for a target polynucleotide. "Specific" or "specificity" refers to the recognition, contact, and formation of a stable complex between two molecules, as compared to substantially less recognition, contact, or complex formation of either of those two molecules with other molecules. As used herein, the term "anneal" refers to the formation of a stable complex between two molecules. The terms "capture oligonucleotide", "capture oligo", "oligo", or "oligonucleotide" may be used interchangeably throughout the document, when referring to capture oligonucleotides. The following features of oligonucleotides can be applied to primers and other oligonucleotides, such as probes provided herein.

A capture oligonucleotide can be designed and synthesized using a suitable process, and may be of any length suitable for hybridizing to a nucleotide sequence of interest and performing separation and/or analysis processes described herein. Oligonucleotides may be designed based upon a nucleotide sequence of interest (e.g., target fragment sequence, reference fragment sequence). An oligonucleotide, in some embodiments, may be about 10 to about 300 nucleotides, about 10 to about 100 nucleotides, about 10 to about 70 nucleotides, about 10 to about 50 nucleotides, about 15 to about 30 nucleotides, or about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 nucleotides in length. An oligonucleotide may be composed of naturally occurring and/or non-naturally occurring nucleotides (e.g., labeled nucleotides), or a mixture thereof. Oligonucleotides suitable for use with embodiments described herein, may be synthesized and labeled using known techniques. Oligonucleotides may be chemically synthesized according to the solid phase phosphoramidite triester method first described by Beaucage and Caruthers (1981) Tetrahedron Letts. 22:1859-1862, using an automated synthesizer, and/or as described in Needham-VanDevanter et al. (1984) Nucleic Acids Res. 12:6159-6168. Purification of oligonucleotides can be effected by native acrylamide gel electrophoresis or by anion-exchange high-performance liquid chromatography (HPLC), for example, as described in Pearson and Regnier (1983) J. Chrom. 255:137-149.

All or a portion of an oligonucleotide sequence (naturally occurring or synthetic) may be substantially complementary to a target and/or reference fragment sequence or portion thereof, in some embodiments. As referred to herein, "substantially complementary" with respect to sequences refers to nucleotide sequences that will hybridize with each other. The stringency of the hybridization conditions can be altered to tolerate varying amounts of sequence mismatch.

Included are target/reference and oligonucleotide sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other.

Oligonucleotides that are substantially complimentary to a nucleic acid sequence of interest (e.g., target fragment sequence, reference fragment sequence) or portion thereof are also substantially similar to the compliment of the target nucleic acid sequence or relevant portion thereof (e.g., substantially similar to the anti-sense strand of the nucleic acid). One test for determining whether two nucleotide sequences are substantially similar is to determine the percent of identical nucleotide sequences shared. As referred to herein, "substantially similar" with respect to sequences refers to nucleotide sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more identical to each other.

Annealing conditions (e.g., hybridization conditions) can be determined and/or adjusted, depending on the characteristics of the oligonucleotides used in an assay. Oligonucleotide sequence and/or length sometimes may affect hybridization to a nucleic acid sequence of interest. Depending on the degree of mismatch between an oligonucleotide and nucleic acid of interest, low, medium or high stringency conditions may be used to effect the annealing. As used herein, the term "stringent conditions" refers to conditions for hybridization and washing. Methods for hybridization reaction temperature condition optimization are known in the art, and may be found in Current Protocols in Molecular Biology, John Wiley & Sons, N.Y., 6.3.1-6.3.6 (1989). Aqueous and non-aqueous methods are described in that reference and either can be used. Non-limiting examples of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C. Stringent hybridization temperatures can also be altered (i.e. lowered) with the addition of certain organic solvents, formamide for example. Organic solvents, like formamide, reduce the thermal stability of double-stranded polynucleotides, so that hybridization can be performed at lower temperatures, while still maintaining stringent conditions and extending the useful life of nucleic acids that may be heat labile.

As used herein, the phrase "hybridizing" or grammatical variations thereof, refers to annealing a first nucleic acid molecule to a second nucleic acid molecule under low, medium or high stringency conditions, or under nucleic acid synthesis conditions. Hybridizing can include instances where a first nucleic acid molecule anneals to a second nucleic acid molecule, where the first and second nucleic acid molecules are complementary. As used herein, "specifically hybridizes" refers to preferential hybridization under nucleic acid synthesis conditions of an oligonucleotide to a nucleic acid molecule having a sequence complementary to the oligonucleotide compared to hybridization to a nucleic acid molecule not having a complementary sequence. For example, specific hybridization includes the hybridization of a capture oligonucleotide to a target fragment sequence that is complementary to the oligonucleotide.

In some embodiments, one or more capture oligonucleotides are associated with an affinity ligand such as a member of a binding pair (e.g., biotin) or antigen that can bind to a capture agent such as avidin, streptavidin, an antibody, or a receptor. For example, a capture oligonucleotide may be biotinylated such that it can be captured onto a streptavidin-coated bead.

In some embodiments, one or more capture oligonucleotides and/or capture agents are effectively linked to a solid support or substrate. A solid support or substrate can be any physically separable solid to which a capture oligonucleotide can be directly or indirectly attached including, but not limited to, surfaces provided by microarrays and wells, and particles such as beads (e.g., paramagnetic beads, magnetic beads, microbeads, nanobeads), microparticles, and nanoparticles. Solid supports also can include, for example, chips, columns, optical fibers, wipes, filters (e.g., flat surface filters), one or more capillaries, glass and modified or functionalized glass (e.g., controlled-pore glass (CPG)), quartz, mica, diazotized membranes (paper or nylon), polyformaldehyde, cellulose, cellulose acetate, paper, ceramics, metals, metalloids, semiconductive materials, quantum dots, coated beads or particles, other chromatographic materials, magnetic particles; plastics (including acrylics, polystyrene, copolymers of styrene or other materials, polybutylene, polyurethanes, TEFLON™, polyethylene, polypropylene, polyamide, polyester, polyvinylidene difluoride (PVDF), and the like), polysaccharides, nylon or nitrocellulose, resins, silica or silica-based materials including silicon, silica gel, and modified silicon, Sephadex®, Sepharose®, carbon, metals (e.g., steel, gold, silver, aluminum, silicon and copper), inorganic glasses, conducting polymers (including polymers such as polypyrole and polyindole); micro or nanostructured surfaces such as nucleic acid tiling arrays, nanotube, nanowire, or nanoparticulate decorated surfaces; or porous surfaces or gels such as methacrylates, acrylamides, sugar polymers, cellulose, silicates, or other fibrous or stranded polymers. In some embodiments, the solid support or substrate may be coated using passive or chemically-derivatized coatings with any number of materials, including polymers, such as dextrans, acrylamides, gelatins or agarose. Beads and/or particles may be free or in connection with one another (e.g., sintered). In some embodiments, the solid phase can be a collection of particles. In some embodiments, the particles can comprise silica, and the silica may comprise silica dioxide. In some embodiments the silica can be porous, and in certain embodiments the silica can be non-porous. In some embodiments, the particles further comprise an agent that confers a paramagnetic property to the particles. In certain embodiments, the agent comprises a metal, and in certain embodiments the agent is a metal oxide, (e.g., iron or iron oxides, where the iron oxide contains a mixture of $Fe^{2+}$ and $Fe^{3+}$). The oligonucleotides may be linked to the solid support by covalent bonds or by non-covalent interactions and may be linked to the solid support directly or indirectly (e.g., via an intermediary agent such as a spacer molecule or biotin). A probe may be linked to the solid support before, during or after nucleic acid capture.

In some embodiments, nucleic acid is enriched for a particular nucleic acid fragment length, range of lengths, or lengths under or over a particular threshold or cutoff using one or more length-based separation methods. Nucleic acid fragment length typically refers to the number of nucleotides in the fragment. Nucleic acid fragment length also is sometimes referred to as nucleic acid fragment size. In some embodiments, a length-based separation method is performed without measuring lengths of individual fragments. In some embodiments, a length based separation method is performed in conjunction with a method for determining length of individual fragments. In some embodiments, length-based separation refers to a size fractionation procedure where all or part of the fractionated pool can be isolated (e.g., retained) and/or analyzed. Size fractionation procedures are known in the art (e.g., separation on an array, separation by a molecular sieve, separation by gel electrophoresis, separation by column chromatography (e.g., size-exclusion columns), and microfluidics-based approaches). In certain embodiments, length-based separation approaches can include fragment circularization, chemical treatment (e.g., formaldehyde, polyethylene glycol (PEG)), mass spectrometry and/or size-specific nucleic acid amplification, for example.

In some embodiments, nucleic acid fragments of a certain length, range of lengths, or lengths under or over a particular threshold or cutoff are separated from the sample. In some embodiments, fragments having a length under a particular threshold or cutoff (e.g., 500 bp, 400 bp, 300 bp, 200 bp, 150 bp, 100 bp) are referred to as "short" fragments and fragments having a length over a particular threshold or cutoff (e.g., 500 bp, 400 bp, 300 bp, 200 bp, 150 bp, 100 bp) are referred to as "long" fragments. In some embodiments, fragments of a certain length, range of lengths, or lengths under or over a particular threshold or cutoff are retained for analysis while fragments of a different length or range of lengths, or lengths over or under the threshold or cutoff are not retained for analysis. In some embodiments, fragments that are less than about 500 bp are retained. In some embodiments, fragments that are less than about 400 bp are retained. In some embodiments, fragments that are less than about 300 bp are retained. In some embodiments, fragments that are less than about 200 bp are retained. In some embodiments, fragments that are less than about 150 bp are retained. For example, fragments that are less than about 190 bp, 180 bp, 170 bp, 160 bp, 150 bp, 140 bp, 130 bp, 120 bp, 110 bp or 100 bp are retained. In some embodiments, fragments that are about 100 bp to about 200 bp are retained. For example, fragments that are about 190 bp, 180 bp, 170 bp, 160 bp, 150 bp, 140 bp, 130 bp, 120 bp or 110 bp are retained. In some embodiments, fragments that are in the range of about 100 bp to about 200 bp are retained. For example, fragments that are in the range of about 110 bp to about 190 bp, 130 bp to about 180 bp, 140 bp to about 170 bp, 140 bp to about 150 bp, 150 bp to about 160 bp, or 145 bp to about 155 bp are retained. In some embodiments, fragments that are about 10 bp to about 30 bp shorter than other fragments of a certain length or range of lengths are retained. In some embodiments, fragments that are about 10 bp to about 20 bp shorter than other fragments of a certain length or range of lengths are retained. In some embodiments, fragments that are about 10 bp to about 15 bp shorter than other fragments of a certain length or range of lengths are retained.

In some embodiments, nucleic acid is enriched for a particular nucleic acid fragment length, range of lengths, or lengths under or over a particular threshold or cutoff using one or more bioinformatics-based (e.g., in silico) methods. For example, nucleotide sequence reads can be obtained for nucleic acid fragments using a suitable nucleotide sequencing process. In some instances, such as when a paired-end sequencing method is used, the length of a particular fragment can be determined based on the positions of mapped sequence reads obtained from each terminus of the fragment. Sequence reads used for a particular analysis (e.g., determining the presence or absence of a genetic variation) can be enriched or filtered according to one or more selected fragment lengths or fragment length threshold values of corresponding fragments, as described in further detail herein.

Certain length-based separation methods that can be used with methods described herein sometimes employ a selective sequence tagging approach, for example. The term "sequence tagging" refers to incorporating a recognizable and distinct sequence into a nucleic acid or population of nucleic acids. The term "sequence tagging" as used herein has a different meaning than the term "sequence tag" described later herein. In such sequence tagging methods, a fragment size species (e.g., short fragments) nucleic acids are subjected to selective sequence tagging in a sample that includes long and short nucleic acids. Such methods typically involve performing a nucleic acid amplification reaction using a set of nested primers which include inner primers and outer primers. In certain embodiments, one or both of the inner can be tagged to thereby introduce a tag onto the target amplification product. The outer primers generally do not anneal to the short fragments that carry the (inner) target sequence. The inner primers can anneal to the short fragments and generate an amplification product that carries a tag and the target sequence. Typically, tagging of the long fragments is inhibited through a combination of mechanisms which include, for example, blocked extension of the inner primers by the prior annealing and extension of the outer primers. Enrichment for tagged fragments can be accomplished by any of a variety of methods, including for example, exonuclease digestion of single stranded nucleic acid and amplification of the tagged fragments using amplification primers specific for at least one tag.

Another length-based separation method that can be used with methods described herein involves subjecting a nucleic acid sample to polyethylene glycol (PEG) precipitation. Examples of methods include those described in International Patent Application Publication Nos. WO2007/140417 and WO2010/115016. This method in general entails contacting a nucleic acid sample with PEG in the presence of one or more monovalent salts under conditions sufficient to substantially precipitate large nucleic acids without substantially precipitating small (e.g., less than 300 nucleotides) nucleic acids.

Another size-based enrichment method that can be used with methods described herein involves circularization by ligation, for example, using circligase. Short nucleic acid fragments typically can be circularized with higher efficiency than long fragments. Non-circularized sequences can be separated from circularized sequences, and the enriched short fragments can be used for further analysis.

Determination of Fragment Length

In some embodiments, length is determined for one or more nucleic acid fragments. In some embodiments, length is determined for one or more target fragments, thereby identifying one or more target fragment size species. In some embodiments, length is determined for one or more target fragments and one or more reference fragments, thereby identifying one or more target fragment length species and one or more reference fragment length species. In some embodiments, fragment length is determined by measuring the length of a probe that hybridizes to the fragment, which is discussed in further detail below. Nucleic acid fragment or probe length can be determined using any method in the art suitable for determining nucleic acid fragment length, such as, for example, a mass sensitive process (e.g., mass spectrometry (e.g., matrix-assisted laser desorption ionization (MALDI) mass spectrometry and electrospray (ES) mass spectrometry), electrophoresis (e.g., capillary electrophoresis), microscopy (scanning tunneling microscopy, atomic force microscopy), measuring length using a nanopore, and sequence-based length determination (e.g., paired-end sequencing). In some embodiments, fragment or probe length can be determined without use of a separation method based on fragment charge. In some embodiments, fragment or probe length can be determined without use of an electrophoresis process. In some embodiments, fragment or probe length can be determined without use of a nucleotide sequencing process.

Mass Spectrometry

In some embodiments, mass spectrometry is used to determine nucleic acid fragment length. Mass spectrometry methods typically are used to determine the mass of a molecule, such as a nucleic acid fragment. In some embodiments, nucleic acid fragment length can be extrapolated from the mass of the fragment. In some embodiments, a predicted range of nucleic acid fragment lengths can be extrapolated from the mass of the fragment. In some embodiments, nucleic acid fragment length can be extrapolated from the mass of a probe that hybridizes to the fragment, which is described in further detail below. In some embodiments, presence of a target and/or reference nucleic acid of a given length can be verified by comparing the mass of the detected signal with the expected mass of the target and/or reference fragment. The relative signal strength, e.g., mass peak on a spectra, for a particular nucleic acid fragment and/or fragment length sometimes can indicate the relative population of the fragment species amongst other nucleic acids in the sample (see e.g., Jurinke et al. (2004) Mol. Biotechnol. 26, 147-164).

Mass spectrometry generally works by ionizing chemical compounds to generate charged molecules or molecule fragments and measuring their mass-to-charge ratios. A typical mass spectrometry procedure involves several steps, including (1) loading a sample onto the mass spectrometry instrument followed by vaporization, (2) ionization of the sample components by any one of a variety of methods (e.g., impacting with an electron beam), resulting in charged particles (ions), (3) separation of ions according to their mass-to-charge ratio in an analyzer by electromagnetic fields, (4) detection of ions (e.g., by a quantitative method), and (5) processing of the ion signal into mass spectra.

Mass spectrometry methods are well known in the art (see, e.g., Burlingame et al. Anal. Chem. 70:647R-716R (1998)), and include, for example, quadrupole mass spectrometry, ion trap mass spectrometry, time-of-flight mass spectrometry, gas chromatography mass spectrometry and tandem mass spectrometry can be used with the methods described herein. The basic processes associated with a mass spectrometry method are the generation of gas-phase ions derived from the sample, and the measurement of their mass. The movement of gas-phase ions can be precisely controlled using electromagnetic fields generated in the mass spectrometer. The movement of ions in these electromagnetic fields is proportional to the m/z (mass to charge ratio) of the ion and this forms the basis of measuring the m/z and therefore the mass of a sample. The movement of ions in these electromagnetic fields allows for the containment and focusing of the ions which accounts for the high sensitivity of mass spectrometry. During the course of m/z measurement, ions are transmitted with high efficiency to particle detectors that record the arrival of these ions. The quantity of ions at each m/z is demonstrated by peaks on a graph where the x axis is m/z and the y axis is relative abundance. Different mass spectrometers have different levels of resolution, that is, the ability to resolve peaks between ions closely related in mass. The resolution is defined as R=m/delta m, where m is the ion mass and delta m is the difference in mass between two peaks in a mass spectrum. For example, a mass spectrometer with a resolution of 1000 can resolve an ion with a m/z of 100.0 from an ion with a m/z of 100.1. Certain mass spectrometry methods can utilize various combinations of ion sources and mass analyzers which allows for flexibility in designing customized detection protocols. In some embodiments, mass spectrometers can be programmed to transmit all ions from the ion source into the mass spectrometer either sequentially or at the same time. In some embodiments, a mass spectrometer can be programmed to select ions of a particular mass for transmission into the mass spectrometer while blocking other ions.

Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Mass analyzers include, for example, a quadrupole mass filter, ion trap mass analyzer and time-of-flight mass analyzer.

The ion formation process is a starting point for mass spectrum analysis. Several ionization methods are available and the choice of ionization method depends on the sample used for analysis. For example, for the analysis of polypeptides a relatively gentle ionization procedure such as electrospray ionization (ESI) can be desirable. For ESI, a solution containing the sample is passed through a fine needle at high potential which creates a strong electrical field resulting in a fine spray of highly charged droplets that is directed into the mass spectrometer. Other ionization procedures include, for example, fast-atom bombardment (FAB) which uses a high-energy beam of neutral atoms to strike a solid sample causing desorption and ionization. Matrix-assisted laser desorption ionization (MALDI) is a method in which a laser pulse is used to strike a sample that has been crystallized in an UV-absorbing compound matrix (e.g., 2,5-dihydroxybenzoic acid, alpha-cyano-4-hydroxycinammic acid, 3-hydroxypicolinic acid (3-HPA), di-ammoniumcitrate (DAC) and combinations thereof). Other ionization procedures known in the art include, for example, plasma and glow discharge, plasma desorption ionization, resonance ionization, and secondary ionization.

A variety of mass analyzers are available that can be paired with different ion sources. Different mass analyzers have different advantages as known in the art and as described herein. The mass spectrometer and methods chosen for detection depends on the particular assay, for example, a more sensitive mass analyzer can be used when a small amount of ions are generated for detection. Several types of mass analyzers and mass spectrometry methods are described below.

Ion mobility mass (IM) spectrometry is a gas-phase separation method. IM separates gas-phase ions based on their collision cross-section and can be coupled with time-of-flight (TOF) mass spectrometry. IM-MS is discussed in more detail by Verbeck et al. in the *Journal of Biomolecular Techniques* (Vol. 13, Issue 2, 56-61).

Quadrupole mass spectrometry utilizes a quadrupole mass filter or analyzer. This type of mass analyzer is composed of four rods arranged as two sets of two electrically connected rods. A combination of rf and dc voltages are applied to each pair of rods which produces fields that cause an oscillating movement of the ions as they move from the beginning of the mass filter to the end. The result of these fields is the production of a high-pass mass filter in one pair of rods and a low-pass filter in the other pair of rods. Overlap between the high-pass and low-pass filter leaves a defined m/z that can pass both filters and traverse the length of the quadrupole. This m/z is selected and remains stable in the quadrupole mass filter while all other m/z have unstable trajectories and do not remain in the mass filter. A mass spectrum results by ramping the applied fields such that an increasing m/z is selected to pass through the mass filter and reach the detector. In addition, quadrupoles can also be set up to contain and transmit ions of all m/z by applying a rf-only field. This allows quadrupoles to function as a lens or focusing system in regions of the mass spectrometer where ion transmission is needed without mass filtering.

A quadrupole mass analyzer, as well as the other mass analyzers described herein, can be programmed to analyze a defined m/z or mass range. Since the desired mass range of nucleic acid fragment is known, in some instances, a mass spectrometer can be programmed to transmit ions of the projected correct mass range while excluding ions of a higher or lower mass range. The ability to select a mass range can decrease the background noise in the assay and thus increase the signal-to-noise ratio. Thus, in some instances, a mass spectrometer can accomplish a separation step as well as detection and identification of certain mass-distinguishable nucleic acid fragments.

Ion trap mass spectrometry utilizes an ion trap mass analyzer. Typically, fields are applied such that ions of all m/z are initially trapped and oscillate in the mass analyzer. Ions enter the ion trap from the ion source through a focusing device such as an octapole lens system. Ion trapping takes place in the trapping region before excitation and ejection through an electrode to the detector. Mass analysis can be accomplished by sequentially applying voltages that increase the amplitude of the oscillations in a way that ejects ions of increasing m/z out of the trap and into the detector. In contrast to quadrupole mass spectrometry, all ions are retained in the fields of the mass analyzer except those with the selected m/z. Control of the number of ions can be accomplished by varying the time over which ions are injected into the trap.

Time-of-flight mass spectrometry utilizes a time-of-flight mass analyzer. Typically, an ion is first given a fixed amount of kinetic energy by acceleration in an electric field (generated by high voltage). Following acceleration, the ion enters a field-free or "drift" region where it travels at a velocity that is inversely proportional to its m/z. Therefore, ions with low m/z travel more rapidly than ions with high m/z. The time required for ions to travel the length of the field-free region is measured and used to calculate the m/z of the ion.

Gas chromatography mass spectrometry often can a target in real-time. The gas chromatography (GC) portion of the system separates the chemical mixture into pulses of analyte and the mass spectrometer (MS) identifies and quantifies the analyte.

Tandem mass spectrometry can utilize combinations of the mass analyzers described above. Tandem mass spectrometers can use a first mass analyzer to separate ions according to their m/z in order to isolate an ion of interest for further analysis. The isolated ion of interest is then broken into fragment ions (called collisionally activated dissociation or collisionally induced dissociation) and the fragment ions are analyzed by the second mass analyzer. These types of tandem mass spectrometer systems are called tandem in space systems because the two mass analyzers are separated in space, usually by a collision cell. Tandem mass spectrometer systems also include tandem in time systems where one mass analyzer is used, however the mass analyzer is used sequentially to isolate an ion, induce fragmentation, and then perform mass analysis.

Mass spectrometers in the tandem in space category have more than one mass analyzer. For example, a tandem quadrupole mass spectrometer system can have a first quadrupole mass filter, followed by a collision cell, followed by a second quadrupole mass filter and then the detector. Another arrangement is to use a quadrupole mass filter for the first mass analyzer and a time-of-flight mass analyzer for the second mass analyzer with a collision cell separating the two mass analyzers. Other tandem systems are known in the art including reflectron-time-of-flight, tandem sector and sector-quadrupole mass spectrometry.

Mass spectrometers in the tandem in time category have one mass analyzer that performs different functions at different times. For example, an ion trap mass spectrometer can be used to trap ions of all m/z. A series of rf scan functions are applied which ejects ions of all m/z from the trap except the m/z of ions of interest. After the m/z of interest has been isolated, an rf pulse is applied to produce collisions with gas molecules in the trap to induce fragmentation of the ions. Then the m/z values of the fragmented ions are measured by the mass analyzer. Ion cyclotron resonance instruments, also known as Fourier transform mass spectrometers, are an example of tandem-in-time systems.

Several types of tandem mass spectrometry experiments can be performed by controlling the ions that are selected in each stage of the experiment. The different types of experiments utilize different modes of operation, sometimes called "scans," of the mass analyzers. In a first example, called a mass spectrum scan, the first mass analyzer and the collision cell transmit all ions for mass analysis into the second mass analyzer. In a second example, called a product ion scan, the ions of interest are mass-selected in the first mass analyzer and then fragmented in the collision cell. The ions formed are then mass analyzed by scanning the second mass analyzer. In a third example, called a precursor ion scan, the first mass analyzer is scanned to sequentially transmit the mass analyzed ions into the collision cell for fragmentation. The second mass analyzer mass-selects the product ion of interest for transmission to the detector. Therefore, the detector signal is the result of all precursor ions that can be fragmented into a common product ion. Other experimental formats include neutral loss scans where a constant mass difference is accounted for in the mass scans.

For quantification, controls may be used which can provide a signal in relation to the amount of the nucleic acid fragment, for example, that is present or is introduced. A control to allow conversion of relative mass signals into absolute quantities can be accomplished by addition of a known quantity of a mass tag or mass label to each sample before detection of the nucleic acid fragments. See for example, Ding and Cantor (2003) PNAS USA. March 18; 100(6):3059-64. Any mass tag that does not interfere with detection of the fragments can be used for normalizing the mass signal. Such standards typically have separation properties that are different from those of any of the molecular tags in the sample, and could have the same or different mass signatures.

A separation step sometimes can be used to remove salts, enzymes, or other buffer components from the nucleic acid sample. Several methods well known in the art, such as chromatography, gel electrophoresis, or precipitation, can be used to clean up the sample. For example, size exclusion chromatography or affinity chromatography can be used to remove salt from a sample. The choice of separation method can depend on the amount of a sample. For example, when small amounts of sample are available or a miniaturized apparatus is used, a micro-affinity chromatography separation step can be used. In addition, whether a separation step is desired, and the choice of separation method, can depend on the detection method used. Salts sometimes can absorb energy from the laser in matrix-assisted laser desorption/ionization and result in lower ionization efficiency. Thus, the efficiency of matrix-assisted laser desorption/ionization and electrospray ionization sometimes can be improved by removing salts from a sample.

Electrophoresis

In some embodiments, electrophoresis is used to determine nucleic acid fragment length. In some embodiments, electrophoresis is not used to determine nucleic acid fragment length. In some embodiments, length of a corresponding probe (e.g., a corresponding trimmed probe described herein) is determined using electrophoresis. Electrophoresis also can be used, in some embodiments, as a length-based separation method as described herein. Any electrophoresis method known in the art, whereby nucleic acids are separated by length, can be used in conjunction with the methods provided herein, which include, but are not limited to, standard electrophoretic techniques and specialized electrophoretic techniques, such as, for example capillary electrophoresis. Examples of methods for separating nucleic acid and measuring nucleic acid fragment length using standard electrophoretic techniques can be found in the art. A non-limiting example is presented herein. After running a nucleic acid sample in an agarose or polyacrylamide gel, the gel may be labeled (e.g., stained) with ethidium bromide (see, Sambrook and Russell, Molecular Cloning: A Laboratory Manual 3d ed., 2001). The presence of a band of the same size as a standard control is an indication of the presence of a particular nucleic acid sequence length, the amount of which may then be compared to the control based on the intensity of the band, thus detecting and quantifying the nucleic acid sequence length of interest.

In some embodiments, capillary electrophoresis is used to separate, identify and sometimes quantify nucleic acid fragments. Capillary electrophoresis (CE) encompasses a family of related separation techniques that use narrow-bore fused-silica capillaries to separate a complex array of large and small molecules, such as, for example, nucleic acids of varying length. High electric field strengths can be used to separate nucleic acid molecules based on differences in charge, size and hydrophobicity. Sample introduction is accomplished by immersing the end of the capillary into a sample vial and applying pressure, vacuum or voltage. Depending on the types of capillary and electrolytes used, the technology of CE can be segmented into several separation techniques, any of which can be adapted to the methods provided herein. Non-limiting examples of these include Capillary Zone Electrophoresis (CZE), also known as free-solution CE (FSCE), Capillary Isoelectric Focusing (CIEF), Isotachophoresis (ITP), Electrokinetic Chromatography (EKC), Micellar Electrokinetic Capillary Chromatography (MECC OR MEKC), Micro Emulsion Electrokinetic Chromatography (MEEKC), Non-Aqueous Capillary Electrophoresis (NACE), and Capillary Electrochromatography (CEC).

Any device, instrument or machine capable of performing capillary electrophoresis can be used in conjunction with the methods provided herein. In general, a capillary electrophoresis system's main components are a sample vial, source and destination vials, a capillary, electrodes, a high-voltage power supply, a detector, and a data output and handling device. The source vial, destination vial and capillary are filled with an electrolyte such as an aqueous buffer solution. To introduce the sample, the capillary inlet is placed into a vial containing the sample and then returned to the source vial (sample is introduced into the capillary via capillary action, pressure, or siphoning). The migration of the analytes (i.e. nucleic acids) is then initiated by an electric field that is applied between the source and destination vials and is supplied to the electrodes by the high-voltage power supply. Ions, positive or negative, are pulled through the capillary in the same direction by electroosmotic flow. The analytes (i.e. nucleic acids) separate as they migrate due to their electrophoretic mobility and are detected near the outlet end of the capillary. The output of the detector is sent to a data output and handling device such as an integrator or computer. The data is then displayed as an electropherogram, which can report detector response as a function of time. Separated nucleic acids can appear as peaks with different migration times in an electropherogram.

Separation by capillary electrophoresis can be detected by several detection devices. The majority of commercial systems use UV or UV-Vis absorbance as their primary mode of detection. In these systems, a section of the capillary itself is used as the detection cell. The use of on-tube detection enables detection of separated analytes with no loss of resolution. In general, capillaries used in capillary electrophoresis can be coated with a polymer for increased stability. The portion of the capillary used for UV detection is often optically transparent. The path length of the detection cell in capillary electrophoresis (~50 micrometers) is far less than that of a traditional UV cell (~1 cm). According to the Beer-Lambert law, the sensitivity of the detector is proportional to the path length of the cell. To improve the sensitivity, the path length can be increased, though this can result in a loss of resolution. The capillary tube itself can be expanded at the detection point, creating a "bubble cell" with a longer path length or additional tubing can be added at the detection point. Both of these methods, however, may decrease the resolution of the separation.

Fluorescence detection also can be used in capillary electrophoresis for samples that naturally fluoresce or are chemically modified to contain fluorescent tags, such as, for example, labeled nucleic acid fragments or probes described herein. This mode of detection offers high sensitivity and improved selectivity for these samples. The method requires that the light beam be focused on the capillary. Laser-induced fluorescence can be been used in CE systems with detection limits as low as 10-18 to 10-21 mol. The sensitivity of the technique is attributed to the high intensity of the incident light and the ability to accurately focus the light on the capillary.

Several capillary electrophoresis machines are known in the art and can be used in conjunction with the methods provided herein. These include, but are not limited to, CALIPER LAB CHIP GX (Caliper Life Sciences, Mountain View, Calif.), P/ACE 2000 Series (Beckman Coulter, Brea, Calif.), HP G1600A CE (Hewlett-Packard, Palo Alto, Calif.), AGILENT 7100 CE (Agilent Technologies, Santa Clara, Calif.), and ABI PRISM Genetic Analyzer (Applied Biosystems, Carlsbad, Calif.).

Microscopy

In some embodiments, nucleic acid fragment length is determined using an imaging-based method, such as a microscopy method. In some embodiments, length of a corresponding probe (e.g., a corresponding trimmed probe described herein) is determined using an imaging-based method. In some embodiments, fragment length can be determined by microscopic visualization of single nucleic acid fragments (see e.g., U.S. Pat. No. 5,720,928). In some embodiments, nucleic acid fragments are fixed to a surface (e.g., modified glass surface) in an elongated state, stained and visualized microscopically. Images of the fragments can be collected and processed (e.g., measured for length). In some embodiments, imaging and image analysis steps can be automated. Methods for directly visualizing nucleic acid fragments using microscopy are known in the art (see e.g., Lai et al. (1999) Nat Genet. 23(3):309-13; Aston et al. (1999) Trends Biotechnol. 17(7):297-302; Aston et al. (1999) Methods Enzymol. 303:55-73; Jing et al. (1998) Proc Natl Acad Sci USA. 95(14):8046-51; and U.S. Pat. No. 5,720,928). Other microscopy methods that can be used with the methods described herein include, without limitation, scanning tunneling microscopy (STM), atomic force microscopy (ATM), scanning force microscopy (SFM), photon scanning microscopy (PSTM), scanning tunneling potentiometry (STP), magnetic force microscopy (MFM), scanning probe microscopy, scanning voltage microscopy, photoconductive atomic force microscopy, electrochemical scanning tunneling microscopy, electron microscopy, spin polarized scanning tunneling microscopy (SPSTM), scanning thermal microscopy, scanning joule expansion microscopy, photothermal microspectroscopy, and the like.

In some embodiments, scanning tunneling microscopy (STM) can be used to determine nucleic acid fragment length. STM methods often can generate atomic-level images of molecules, such as nucleic acid fragments. STM can be performed, for example, in air, water, ultra-high vacuum, various other liquid or gas ambients, and can be performed at temperatures ranging from near zero Kelvin to a few hundred degrees Celsius, for example. The components of an STM system typically include scanning tip, piezoelectric controlled height and x, y scanner, coarse sample-to-tip control, vibration isolation system, and computer. STM methods are generally based on the concept of quantum tunneling. For example, when a conducting tip is brought close to the surface of a molecule (e.g., nucleic acid fragment), a bias (i.e., voltage difference) applied between the two can allow electrons to tunnel through the vacuum between them. The resulting tunneling current is a function of tip position, applied voltage, and the local density of states (LDOS) of the sample. Information is acquired by monitoring the current as the tip's position scans across the surface, and can be displayed in image form. If the tip is moved across the sample in the x-y plane, the changes in surface height and density of states cause changes in current. These changes can be mapped in images. The change in current with respect to position sometimes can be measured itself, or the height, z, of the tip corresponding to a constant current can be measured. These two modes often are referred to as constant height mode and constant current mode, respectively.

In some embodiments, atomic force microscopy (AFM) can be used to determine nucleic acid fragment length. AFM generally is a high-resolution type of nanoscale microscopy. Information about an object (e.g., nucleic acid fragment) typically is gathered by "feeling" the surface with a mechanical probe. Piezoelectric elements that facilitate tiny but accurate and precise movements on electronic command can facilitate very precise scanning. In some variations, electric potentials can be scanned using conducting cantilevers. The components of an AFM system typically include a cantilever with a sharp tip (i.e., probe) at its end that is used to scan the surface of a specimen (e.g., nucleic acid fragment). The cantilever typically is silicon or silicon nitride with a tip radius of curvature on the order of nanometers. When the tip is brought into proximity of a sample surface, forces between the tip and the sample lead to a deflection of the cantilever according to Hooke's law. Depending on the situation, forces that are measured in AFM include, for example, mechanical contact force, van der Waals forces, capillary forces, chemical bonding, electrostatic forces, magnetic forces, Casimir forces, solvation forces, and the like. Typically, the deflection is measured using a laser spot reflected from the top surface of the cantilever into an array of photodiodes. Other methods that are used include optical interferometry, capacitive sensing or piezoresistive AFM cantilevers.

Nanopore

In some embodiments, nucleic acid fragment length is determined using a nanopore. In some embodiments, length of a corresponding probe (e.g., a corresponding trimmed probe described herein) is determined using a nanopore. A nanopore is a small hole or channel, typically of the order of 1 nanometer in diameter. Certain transmembrane cellular proteins can act as nanopores (e.g., alpha-hemolysin). In some embodiments, nanopores can be synthesized (e.g., using a silicon platform). Immersion of a nanopore in a conducting fluid and application of a potential across it results in a slight electrical current due to conduction of ions through the nanopore. The amount of current which flows is sensitive to the size of the nanopore. As a nucleic acid fragment passes through a nanopore, the nucleic acid molecule obstructs the nanopore to a certain degree and generates a change to the current. The duration of current change as the nucleic acid fragment passes through the nanopore can be measured. In some embodiments, nucleic acid fragment length can be determined based on this measurement.

In some embodiments, nucleic acid fragment length may be determined as a function of time. Longer nucleic acid fragments sometimes may take relatively more time to pass through a nanopore and shorter nucleic acid fragments sometimes may take relatively less time to pass through a nanopore. Thus, relative length of a fragment can be determined based on nanopore transit time, in some embodiments. In some embodiments, approximate or absolute fragment length can be determined by comparing nanopore transit time of target fragments and/or reference fragments to transit times for a set of standards (i.e., with known lengths).

Probes

In some embodiments, fragment length is determined using one or more probes. In some embodiments, probes are designed such that they each hybridize to a nucleic acid of interest in a sample. For example, a probe may comprise a polynucleotide sequence that is complementary to a nucleic acid of interest or may comprise a series of monomers that can bind to a nucleic acid of interest. Probes may be any length suitable to hybridize (e.g., completely hybridize) to one or more nucleic acid fragments of interest. For example, probes may be of any length which spans or extends beyond the length of a nucleic acid fragment to which it hybridizes. Probes may be about 100 bp or more in length. For example, probes may be at least about 200, 300, 400, 500, 600, 700, 800, 900 or 1000 bp in length.

In some embodiments, probes may comprise a polynucleotide sequence that is complementary to a nucleic acid of interest and one or more polynucleotide sequences that are not complementary to a nucleic acid of interest (i.e., non-complementary sequences). Non-complementary sequences may reside, for example, at the 5' and/or 3' end of a probe. In some embodiments, non-complementary sequences may comprise nucleotide sequences that do not exist in the organism of interest and/or sequences that are not capable of hybridizing to any sequence in the human genome. For example, non-complementary sequences may be derived from any non-human genome known in the art, such as, for example, non-mammalian animal genomes, plant genomes, fungal genomes, bacterial genomes, or viral genomes. In some embodiments, a non-complementary sequence is from the PhiX 174 genome. In some embodiments, a non-complementary sequence may comprise modified or synthetic nucleotides that are not capable of hybridizing to a complementary nucleotide.

Probes may be designed and synthesized according to methods known in the art and described herein for oligonucleotides (e.g., capture oligonucleotides). Probes also may include any of the properties known in the art and described herein for oligonucleotides. Probes herein may be designed such that they comprise nucleotides (e.g., adenine (A), thymine (T), cytosine (C), guanine (G) and uracil (U)), modified nucleotides (e.g., pseudouridine, dihydrouridine, inosine (I), and 7-methylguanosine), synthetic nucleotides, degenerate bases (e.g., 6H,8H-3,4-dihydropyrimido[4,5-c][1,2]oxazin-7-one (P), 2-amino-6-methoxyaminopurine (K), N6-methoxyadenine (Z), and hypoxanthine (I)), universal bases and/or monomers other than nucleotides, modified nucleotides or synthetic nucleotides, or combinations thereof and generally are designed such that they initially have longer lengths than the fragments to which they hybridize.

In some embodiments, a probe comprises a plurality of monomers that are capable of hybridizing to any one of naturally occurring or modified versions of nucleotides such as adenine (A), thymine (T), cytosine (C), guanine (G) and uracil (U). In some embodiments, a probe comprises a plurality of monomers that are capable of hybridizing to at least three of adenine, thymine, cytosine, and guanine. For example, a probe may include a species of monomer that is capable of hybridizing to A, T and C; A, T and G; G, C and T; or G, C and A. In some embodiments, a probe comprises a plurality of monomers that are capable of hybridizing to all of adenine, thymine, cytosine, and guanine. For example, a probe may include a species of monomer that is capable of hybridizing to all of A, T, C and G. In some embodiments, hybridization conditions (e.g., stringency) can be adjusted according to methods described herein, for example, to facilitate hybridization of certain monomer species to various nucleotide species. In some embodiments, the monomers include nucleotides. In some embodiments, the monomers include naturally occurring nucleotides. In some embodiments, the monomers include modified nucleotides.

In some embodiments, the monomers of a probe include inosine. Inosine is a nucleotide commonly found in tRNAs and is capable, in some instances, of hybridizing to A, T and C. Example 9 herein describes a method that utilizes poly-inosine probes for the determination of nucleic acid fragment size. In some embodiments, polyinosine probes are hybridized to the nucleic acid fragments under low-stringent or non-stringent hybridization conditions (e.g., such as low temperature and/or high salt compared to stringent hybridization conditions described herein). In some embodiments, nucleic acid fragments are treated with sodium bisulfite, which causes deamination of unmethylated cytosine residues in the fragments to form uracil residues. In some embodiments, nucleic acid fragments treated with sodium bisulfite are amplified (e.g., PCR amplified) prior to sodium bisulfite treatment. In some embodiments, the nucleic acid fragments are ligated to a sequence comprising a universal amplification primer site having no cytosine residues. A complementary second strand can then be generated, for example, using a universal amplification primer and an extension reaction. Typically, the uracil residues in the first strand generate complementary adenine residues in the second strand. Thus, a second strand having no guanine residues can be generated. Such guanine-free complementary second strands, in some instances, can hybridize to poly-inosine probes under stringent hybridization conditions.

In some embodiments, the monomers of a probe include universal base monomers. Universal base monomers typically are nucleobase analogs or synthetic monomers that can hybridize non-selectively to each of the native bases (e.g., A, G, C, T). Thus, a probe comprising universal base monomers sometimes can hybridize to a nucleic acid fragment regardless of nucleotide sequence. Universal bases can include, without limitation, 3-nitropyrrole, 4-nitroindole, 5-nitroindole, 6-nitroindole, 3-methyl 7-propynyl isocarbostyril (PIM), 3-methyl isocarbostyril (MICS), and 5-methyl isocarbostyril (5MICS) (see e.g., Nichols et al. (1994) Nature 369, 492-493; Bergstrom et al. (1995) J. Am. Chem. Soc. 117, 1201-1209; Loakes and Brown (1994) Nucleic Acids Res. 22, 4039-4043; Lin and Brown (1992) Nucleic Acids Res. 20, 5149-5152; Lin and Brown (1989) Nucleic Acids Res. 17, 10383; Brown and Lin (1991) Carbohydrate Research 216, 129-139; Berger et al. (2000) Nucleic Acids Res. 28(15): 2911-2914).

In some embodiments, the monomers of a probe include non-nucleotide monomers. In some embodiments, the monomers include subunits of a synthetic polymer. In some embodiments, the monomers include pyrrolidone. Pyrrolidone is a monomer of the synthetic polymer polypyrrolidone and is capable, in some instances, of hybridizing to all of A, T, G and C.

In some embodiments, a method for determining fragment length includes the step of contacting under annealing conditions nucleic acid fragments (e.g., target and/or reference fragments) with a plurality of probes that can anneal to the fragments, thereby generating fragment-probe species such as, for example, target-probe species and reference-probe species. Probes and/or hybridization conditions (e.g., stringency) can be optimized to favor complete or substantially complete fragment binding (e.g., high stringency). Complete or substantially complete fragment-probe hybridizations generally include duplexes where the fragment does not comprise unhybridized portions and the probe may comprise unhybridized portions, as described in further detail below.

Figure 12:
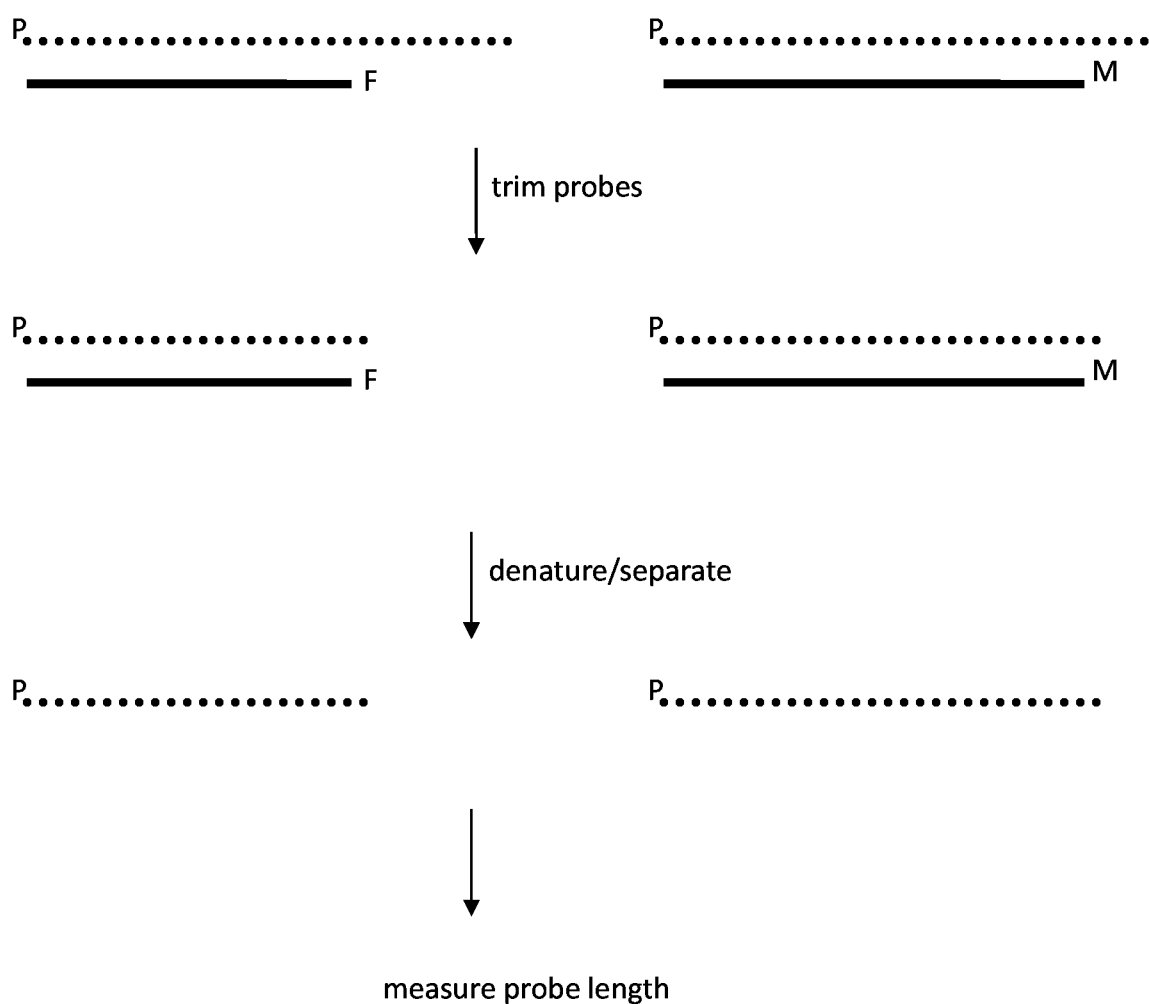
FIG. 12 shows a method for determining nucleic acid fragment length, which includes the steps of 1) hybridization of probe (P; dotted line) to fragment (solid line), 2) trimming of the probe, and 3) measuring probe length. Fragment size determination is shown for a fetal-derived fragment (F) and a maternally-derived fragment (M).

In some embodiments, such as when the probe length is longer than the fragment length, the target-probe species and/or reference-probe species may each comprise unhybridized probe portions (i.e., single stranded probe portions; see e.g., FIG. 12). Unhybridized probe portions may be at either end of the probe (e.g., 3' or 5' end of a probe) or at both ends of the probe (i.e., 3' and 5' ends of a probe) and may comprise any number of monomers. In some embodiments, unhybridized probe portions may comprise about 1 to about 500 monomers. For example, unhybridized probe portions may comprise about 5, 10, 20, 30, 40, 50, 100, 200, 300 or 400 monomers.

In some embodiments, unhybridized probe portions may be removed from the target-probe species and/or reference-probe species, thereby generating trimmed probes. Removal of unhybridized probe portions may be achieved by any method known in the art for cleaving and/or digesting a polymer, such as, for example, a method for cleaving or digesting a single stranded nucleic acid. Unhybridized probe portions may be removed from the 5' end of the probe and/or the 3' end of the probe. Such methods may comprise the use of chemical and/or enzymatic cleavage or digestion. In some embodiments, an enzyme capable of cleaving phosphodiester bonds between nucleotide subunits of a nucleic acid is used for removing the unhybridized probe portions. Such enzymes may include, without limitation, nucleases (e.g., DNAse I, RNAse I), endonucleases (e.g., mung bean nuclease, S1 nuclease, and the like), restriction nucleases, exonucleases (e.g., Exonuclease I, Exonuclease III, Exonuclease T, T7 Exonuclease, Lambda Exonuclease, and the like), phosphodiesterases (e.g., Phosphodiesterase II, calf spleen phosphodiesterase, snake venom phosphodiesterase, and the like), deoxyribonucleases (DNAse), ribonucleases (RNAse), flap endonucleases, 5' nucleases, 3' nucleases, 3'-5' exonucleases, 5'-3' exonucleases and the like, or combinations thereof. Trimmed probes generally are of the same or substantially the same length as the fragment to which they hybridize. Thus, determining the length of a trimmed probe herein can provide a measurement of the corresponding nucleic acid fragment length. Trimmed probe length can be measured using any of the methods known in the art or described herein for determining nucleic acid fragment length. In some embodiments, probes may contain a detectable molecule or entity to facilitate detection and/or length determination (e.g., a fluorophore, radioisotope, colorimetric agent, particle, enzyme, and the like). Trimmed probe length may be assessed with or without separating products of unhybridized portions after they are removed.

In some embodiments, trimmed probes are dissociated (i.e., separated) from their corresponding nucleic acid fragments. Probes may be separated from their corresponding nucleic acid fragments using any method known in the art, including, but not limited to, heat denaturation. Trimmed probes can be distinguished from corresponding nucleic acid fragments by a method known in the art or described herein for labeling and/or isolating a species of molecule in a mixture. For example, a probe and/or nucleic acid fragment may comprise a detectable property such that a probe is distinguishable from the nucleic acid to which it hybridizes. Non-limiting examples of detectable properties include, optical properties, electrical properties, magnetic properties, chemical properties, and time and/or speed through an opening of known size. In some embodiments, probes and sample nucleic acid fragments are physically separated from each other. Separation can be accomplished, for example, using capture ligands, such as biotin or other affinity ligands, and capture agents, such as avidin, streptavidin, an antibody, or a receptor. A probe or nucleic acid fragment can contain a capture ligand having specific binding activity for a capture agent. For example, fragments from a nucleic acid sample can be biotinylated or attached to an affinity ligand using methods well known in the art and separated away from the probes using a pull-down assay with steptavidin-coated beads, for example. In some embodiments, a capture ligand and capture agent or any other moiety (e.g., mass tag) can be used to add mass to the nucleic acid fragments such that they can be excluded from the mass range of the probes detected in a mass spectrometer. In some embodiments, mass is added to the probes, by way of the monomers themselves and/or addition of a mass tag, to shift the mass range away from the mass range for the nucleic acid fragments.

Nucleic Acid Library

In some embodiments a nucleic acid library is a plurality of polynucleotide molecules (e.g., a sample of nucleic acids) that are prepared, assemble and/or modified for a specific process, non-limiting examples of which include immobilization on a solid phase (e.g., a solid support, e.g., a flow cell, a bead), enrichment, amplification, cloning, detection and/or for nucleic acid sequencing. In certain embodiments, a nucleic acid library is prepared prior to or during a sequencing process. A nucleic acid library (e.g., sequencing library) can be prepared by a suitable method as known in the art. A nucleic acid library can be prepared by a targeted or a non-targeted preparation process.

In some embodiments a library of nucleic acids is modified to comprise a chemical moiety (e.g., a functional group) configured for immobilization of nucleic acids to a solid support. In some embodiments a library of nucleic acids is modified to comprise a biomolecule (e.g., a functional group) and/or member of a binding pair configured for immobilization of the library to a solid support, non-limiting examples of which include thyroxin-binding globulin, steroid-binding proteins, antibodies, antigens, haptens, enzymes, lectins, nucleic acids, repressors, protein A, protein G, avidin, streptavidin, biotin, complement component C1q, nucleic acid-binding proteins, receptors, carbohydrates, oligonucleotides, polynucleotides, complementary nucleic acid sequences, the like and combinations thereof. Some examples of specific binding pairs include, without limitation: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; an oligonucleotide or polynucleotide and its corresponding complement; the like or combinations thereof.

In some embodiments a library of nucleic acids is modified to comprise one or more polynucleotides of known composition, non-limiting examples of which include an identifier (e.g., a tag, an indexing tag), a capture sequence, a label, an adapter, a restriction enzyme site, a promoter, an enhancer, an origin of replication, a stem loop, a complimentary sequence (e.g., a primer binding site, an annealing site), a suitable integration site (e.g., a transposon, a viral integration site), a modified nucleotide, the like or combinations thereof. Polynucleotides of known sequence can be added at a suitable position, for example on the 5' end, 3' end or within a nucleic acid sequence. Polynucleotides of known sequence can be the same or different sequences. In some embodiments a polynucleotide of known sequence is configured to hybridize to one or more oligonucleotides immobilized on a surface (e.g., a surface in flow cell). For example, a nucleic acid molecule comprising a 5' known sequence may hybridize to a first plurality of oligonucleotides while the 3' known sequence may hybridize to a second plurality of oligonucleotides. In some embodiments a library of nucleic acid can comprise chromosome-specific tags, capture sequences, labels and/or adaptors. In some embodiments a library of nucleic acids comprise one or more detectable labels. In some embodiments one or more detectable labels may be incorporated into a nucleic acid library at a 5' end, at a 3' end, and/or at any nucleotide position within a nucleic acid in the library. In some embodiments a library of nucleic acids comprises hybridized oligonucleotides. In certain embodiments hybridized oligonucleotides are labeled probes. In some embodiments a library of nucleic acids comprises hybridized oligonucleotide probes prior to immobilization on a solid phase.

In some embodiments a polynucleotide of known sequence comprises a universal sequence. A universal sequence is a specific nucleotide acid sequence that is integrated into two or more nucleic acid molecules or two or more subsets of nucleic acid molecules where the universal sequence is the same for all molecules or subsets of molecules that it is integrated into. A universal sequence is often designed to hybridize to and/or amplify a plurality of different sequences using a single universal primer that is complementary to a universal sequence. In some embodiments two (e.g., a pair) or more universal sequences and/or universal primers are used. A universal primer often comprises a universal sequence. In some embodiments adapters (e.g., universal adapters) comprise universal sequences. In some embodiments one or more universal sequences are used to capture, identify and/or detect multiple species or subsets of nucleic acids.

In certain embodiments of preparing a nucleic acid library, (e.g., in certain sequencing by synthesis procedures), nucleic acids are size selected and/or fragmented into lengths of several hundred base pairs, or less (e.g., in preparation for library generation). In some embodiments, library preparation is performed without fragmentation (e.g., when using ccfDNA).

In certain embodiments, a ligation-based library preparation method is used (e.g., ILLUMINA TRUSEQ, Illumina, San Diego Calif.). Ligation-based library preparation methods often make use of an adaptor (e.g., a methylated adaptor) design which can incorporate an index sequence at the initial ligation step and often can be used to prepare samples for single-read sequencing, paired-end sequencing and multiplexed sequencing. For example, sometimes nucleic acids (e.g., fragmented nucleic acids or ccfDNA) are end repaired by a fill-in reaction, an exonuclease reaction or a combination thereof. In some embodiments the resulting blunt-end repaired nucleic acid can then be extended by a single nucleotide, which is complementary to a single nucleotide overhang on the 3' end of an adapter/primer. Any nucleotide can be used for the extension/overhang nucleotides. In some embodiments nucleic acid library preparation comprises ligating an adapter oligonucleotide. Adapter oligonucleotides are often complementary to flow-cell anchors, and sometimes are utilized to immobilize a nucleic acid library to a solid support, such as the inside surface of a flow cell, for example. In some embodiments, an adapter oligonucleotide comprises an identifier, one or more sequencing primer hybridization sites (e.g., sequences complementary to universal sequencing primers, single end sequencing primers, paired end sequencing primers, multiplexed sequencing primers, and the like), or combinations thereof (e.g., adapter/sequencing, adapter/identifier, adapter/identifier/sequencing).

An identifier can be a suitable detectable label incorporated into or attached to a nucleic acid (e.g., a polynucleotide) that allows detection and/or identification of nucleic acids that comprise the identifier. In some embodiments an identifier is incorporated into or attached to a nucleic acid during a sequencing method (e.g., by a polymerase). Non-limiting examples of identifiers include nucleic acid tags, nucleic acid indexes or barcodes, a radiolabel (e.g., an isotope), metallic label, a fluorescent label, a chemiluminescent label, a phosphorescent label, a fluorophore quencher, a dye, a protein (e.g., an enzyme, an antibody or part thereof, a linker, a member of a binding pair), the like or combinations thereof. In some embodiments an identifier (e.g., a nucleic acid index or barcode) is a unique, known and/or identifiable sequence of nucleotides or nucleotide analogues. In some embodiments identifiers are six or more contiguous nucleotides. A multitude of fluorophores are available with a variety of different excitation and emission spectra. Any suitable type and/or number of fluorophores can be used as an identifier. In some embodiments 1 or more, 2 or more, 3 or more, 4 or more, 5 or more, 6 or more, 7 or more, 8 or more, 9 or more, 10 or more, 20 or more, 30 or more or 50 or more different identifiers are utilized in a method described herein (e.g., a nucleic acid detection and/or sequencing method). In some embodiments, one or two types of identifiers (e.g., fluorescent labels) are linked to each nucleic acid in a library. Detection and/or quantification of an identifier can be performed by a suitable method, apparatus or machine, non-limiting examples of which include flow cytometry, quantitative polymerase chain reaction (qPCR), gel electrophoresis, a luminometer, a fluorometer, a spectrophotometer, a suitable genechip or microarray analysis, Western blot, mass spectrometry, chromatography, cytofluorimetric analysis, fluorescence microscopy, a suitable fluorescence or digital imaging method, confocal laser scanning microscopy, laser scanning cytometry, affinity chromatography, manual batch mode separation, electric field suspension, a suitable nucleic acid sequencing method and/or nucleic acid sequencing apparatus, the like and combinations thereof.

In some embodiments, a transposon-based library preparation method is used (e.g., EPICENTRE NEXTERA, Epicentre, Madison Wis.). Transposon-based methods typically use in vitro transposition to simultaneously fragment and tag DNA in a single-tube reaction (often allowing incorporation of platform-specific tags and optional barcodes), and prepare sequencer-ready libraries.

In some embodiments a nucleic acid library or parts thereof are amplified (e.g., amplified by a PCR-based method). In some embodiments a sequencing method comprises amplification of a nucleic acid library. A nucleic acid library can be amplified prior to or after immobilization on a solid support (e.g., a solid support in a flow cell). Nucleic acid amplification includes the process of amplifying or increasing the numbers of a nucleic acid template and/or of a complement thereof that are present (e.g., in a nucleic acid library), by producing one or more copies of the template and/or its complement. Amplification can be carried out by a suitable method. A nucleic acid library can be amplified by a thermocycling method or by an isothermal amplification method. In some embodiments a rolling circle amplification method is used. In some embodiments amplification takes place on a solid support (e.g., within a flow cell) where a nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support.

In some embodiments solid phase amplification comprises a nucleic acid amplification reaction comprising only one species of oligonucleotide primer immobilized to a surface. In certain embodiments solid phase amplification comprises a plurality of different immobilized oligonucleotide primer species. In some embodiments solid phase amplification may comprise a nucleic acid amplification reaction comprising one species of oligonucleotide primer immobilized on a solid surface and a second different oligonucleotide primer species in solution. Multiple different species of immobilized or solution based primers can be used. Non-limiting examples of solid phase nucleic acid amplification reactions include interfacial amplification, bridge amplification, emulsion PCR, WildFire amplification (e.g., US patent publication US20130012399), the like or combinations thereof.

Sequencing

In some embodiments, nucleic acids (e.g., nucleic acid fragments, sample nucleic acid, cell-free nucleic acid) may be sequenced. In some embodiments, a full or substantially full sequence is obtained and sometimes a partial sequence is obtained. In some embodiments, a nucleic acid is not sequenced, and the sequence of a nucleic acid is not determined by a sequencing method, when performing a method described herein. In some embodiments, fragment length is determined using a sequencing method. In some embodiments, fragment length is determined without use of a sequencing method. Sequencing, mapping and related analytical methods are described herein and are known in the art (e.g., United States Patent Application Publication US2009/0029377, incorporated by reference). Certain aspects of such processes are described hereafter.

In some embodiments, fragment length is determined using a sequencing method. In some embodiments, fragment length is determined using a paired-end sequencing platform. Such platforms involve sequencing of both ends of a nucleic acid fragment. Generally, the sequences corresponding to both ends of the fragment can be mapped to a reference genome (e.g., a reference human genome). In certain embodiments, both ends are sequenced at a read length that is sufficient to map, individually for each fragment end, to a reference genome. Examples of paired-end sequence read lengths are described below. In certain embodiments, all or a portion of the sequence reads can be mapped to a reference genome without mismatch. In some embodiments, each read is mapped independently. In some embodiments, information from both sequence reads (i.e., from each end) is factored in the mapping process. The length of a fragment can be determined, for example, by calculating the difference between genomic coordinates assigned to each mapped paired-end read.

In some embodiments, fragment length can be determined using a sequencing process whereby a complete, or substantially complete, nucleotide sequence is obtained for the fragment. Such sequencing processes include platforms that generate relatively long read lengths (e.g., Roche 454, Ion Torrent, single molecule (Pacific Biosciences), real-time SMRT technology, and the like).

In some embodiments some or all nucleic acids in a sample are enriched and/or amplified (e.g., non-specifically, e.g., by a PCR based method) prior to or during sequencing. In certain embodiments specific nucleic acid portions or subsets in a sample are enriched and/or amplified prior to or during sequencing. In some embodiments, a portion or subset of a pre-selected pool of nucleic acids is sequenced randomly. In some embodiments, nucleic acids in a sample are not enriched and/or amplified prior to or during sequencing.

As used herein, "reads" (i.e., "a read", "a sequence read") are short nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads).

The length of a sequence read is often associated with the particular sequencing technology.

High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, sequence reads are of a mean, median, average or absolute length of about 15 bp to about 900 bp long. In certain embodiments sequence reads are of a mean, median, average or absolute length about 1000 bp or more.

In some embodiments the nominal, average, mean or absolute length of single-end reads sometimes is about 1 nucleotide to about 500 contiguous nucleotides, about 15 contiguous nucleotides to about 50 contiguous nucleotides, about 30 contiguous nucleotides to about 40 contiguous nucleotides, and sometimes about 35 contiguous nucleotides or about 36 contiguous nucleotides. In certain embodiments the nominal, average, mean or absolute length of single-end reads is about 20 to about 30 bases, or about 24 to about 28 bases in length. In certain embodiments the nominal, average, mean or absolute length of single-end reads is about 1, 2, 3, 4, 5, 6, 7, 8, 9, 10, 11, 12, 13, 14, 15, 16, 17, 18, 19, 21, 22, 23, 24, 25, 26, 27, 28, 29, 30, 31, 32, 33, 34, 35, 36, 37, 38, 39, 40, 41, 42, 43, 44, 45, 46, 47, 48 or 49 bases in length.

In certain embodiments, the nominal, average, mean or absolute length of the paired-end reads sometimes is about 10 contiguous nucleotides to about 25 contiguous nucleotides (e.g., about 10, 11, 12, 13, 14, 15, 16, 17, 18, 19, 20, 21, 22, 23, 24 or 25 nucleotides in length), about 15 contiguous nucleotides to about 20 contiguous nucleotides, and sometimes is about 17 contiguous nucleotides, about 18 contiguous nucleotides, about 20 contiguous nucleotides, about 25 contiguous nucleotides, about 36 contiguous nucleotides or about 45 contiguous nucleotides.

Reads generally are representations of nucleotide sequences in a physical nucleic acid. For example, in a read containing an ATGC depiction of a sequence, "A" represents an adenine nucleotide, "T" represents a thymine nucleotide, "G" represents a guanine nucleotide and "C" represents a cytosine nucleotide, in a physical nucleic acid. Sequence reads obtained from the blood of a pregnant female can be reads from a mixture of fetal and maternal nucleic acid. A mixture of relatively short reads can be transformed by processes described herein into a representation of a genomic nucleic acid present in the pregnant female and/or in the fetus. A mixture of relatively short reads can be transformed into a representation of a copy number variation (e.g., a maternal and/or fetal copy number variation), genetic variation or an aneuploidy, for example. Reads of a mixture of maternal and fetal nucleic acid can be transformed into a representation of a composite chromosome or a segment thereof comprising features of one or both maternal and fetal chromosomes. In certain embodiments, "obtaining" nucleic acid sequence reads of a sample from a subject and/or "obtaining" nucleic acid sequence reads of a biological specimen from one or more reference persons can involve directly sequencing nucleic acid to obtain the sequence information. In some embodiments, "obtaining" can involve receiving sequence information obtained directly from a nucleic acid by another.

In some embodiments, a fraction of the genome is sequenced, which sometimes is expressed in the amount of the genome covered by the determined nucleotide sequences (e.g., "fold" coverage less than 1). When a genome is sequenced with about 1-fold coverage, roughly 100% of the nucleotide sequence of the genome is represented by reads. A genome also can be sequenced with redundancy, where a given region of the genome can be covered by two or more reads or overlapping reads (e.g., "fold" coverage greater than 1). In some embodiments, a genome is sequenced with about 0.01-fold to about 100-fold coverage, about 0.2-fold to 20-fold coverage, or about 0.2-fold to about 1-fold coverage (e.g., about 0.02-, 0.03-, 0.04-, 0.05-, 0.06-, 0.07-, 0.08, 0.09-, 0.1-, 0.2-, 0.3-, 0.4-, 0.5-, 0.6-, 0.7-, 0.8-, 0.9-, 1-, 2-, 3-, 4-, 5-, 6-, 7-, 8-, 9-, 10-, 15-, 20-, 30-, 40-, 50-, 60-, 70-, 80-, 90-fold coverage).

In some embodiments, genome coverage or sequence coverage is proportional to overall sequence read count. For example, assays that generate and/or analyze higher amounts of sequence read counts typically are associated with higher levels of sequence coverage. Assays that generate and/or analyze fewer sequence read counts typically are associated with lower levels of sequence coverage. In some embodiments, sequence coverage and/or sequence read count can be reduced without significantly decreasing the accuracy (e.g., sensitivity and/or specificity) of a method described herein. A significant decrease in accuracy can be a decrease in accuracy of about 1% to about 20% compared to a method that does not use a reduced sequence read count. For example, a significant decrease in accuracy can be about a 2%, 3%, 4%, 5%, 6%, 7%, 8%, 9%, 10%, 15% or more decrease. In some embodiments, sequence coverage and/or sequence read count is reduced by about 50% or more. For example, sequence coverage and/or sequence read count can be reduced by about 55%, 60%, 65%, 70%, 75%, 80%, 85%, 90%, 95% or more. In some embodiments, sequence coverage and/or sequence read count is reduced by about 60% to about 85%. For example, sequence coverage and/or sequence read count can be reduced by about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83% or 84%. In some embodiments, sequence coverage and/or sequence read count can be reduced by removing certain sequence reads. In some instances, sequence reads from fragments longer than a particular length (e.g., fragments longer than about 160 bases) are removed.

In some embodiments, a subset of reads is selected for analysis and sometimes a certain portion of reads is removed from analysis. Selection of a subset of reads can, in certain instances, enrich for a species of nucleic acid (e.g., fetal nucleic acid). Enrichment of reads from fetal nucleic acid, for example, often increases the accuracy of a method described herein (e.g., fetal aneuploidy detection). However, selection and removal of reads from an analysis often decreases the accuracy of a method described herein (e.g., due to increased variance). Thus, without being limited by theory, there generally is a tradeoff between increased accuracy associated with fetal read enrichment and decreased accuracy associated with a reduced amount of reads in methods comprising selection and/or removal of reads (e.g., from fragments in a particular size range). In some embodiments, a method comprises selecting a subset of reads enriched for reads from fetal nucleic acid without significantly decreasing the accuracy of the method. Despite this apparent tradeoff, it has been determined, as described herein, that utilizing a subset of nucleotide sequence reads (e.g., reads from relatively short fragments), can improve or maintain the accuracy of fetal genetic analyses. For example, in certain embodiments, about 80% or more of nucleotide sequence reads can be discarded while maintaining sensitivity and specificity values that are similar to values for a comparable method that does not discard such nucleotide sequence reads.

In certain embodiments, a subset of nucleic acid fragments is selected prior to sequencing. In certain embodiments, hybridization-based techniques (e.g., using oligonucleotide arrays) can be used to first select for nucleic acid sequences from certain chromosomes (e.g., sex chromosomes and/or a potentially aneuploid chromosome and other chromosome(s) not involved in the aneuploidy tested). In some embodiments, nucleic acid can be fractionated by size (e.g., by gel electrophoresis, size exclusion chromatography or by microfluidics-based approach) and in certain instances, fetal nucleic acid can be enriched by selecting for nucleic acid having a lower molecular weight (e.g., less than 300 base pairs, less than 200 base pairs, less than 150 base pairs, less than 100 base pairs). In some embodiments, fetal nucleic acid can be enriched by suppressing maternal background nucleic acid, such as by the addition of formaldehyde. In some embodiments, a portion or subset of a pre-selected set of nucleic acid fragments is sequenced randomly. In some embodiments, the nucleic acid is amplified prior to sequencing. In some embodiments, a portion or subset of the nucleic acid is amplified prior to sequencing.

In some embodiments, one nucleic acid sample from one individual is sequenced. In certain embodiments, nucleic acids from each of two or more samples are sequenced, where samples are from one individual or from different individuals. In certain embodiments, nucleic acid samples from two or more biological samples are pooled, where each biological sample is from one individual or two or more individuals and the pool is sequenced. In the latter embodiments, a nucleic acid sample from each biological sample often is identified by one or more unique identifiers or identification tags.

In some embodiments a sequencing method utilizes identifiers that allow multiplexing of sequence reactions in a sequencing process. The greater the number of unique identifiers, the greater the number of samples and/or chromosomes for detection, for example, that can be multiplexed in a sequencing process. A sequencing process can be performed using any suitable number of unique identifiers (e.g., 4, 8, 12, 24, 48, 96, or more).

A sequencing process sometimes makes use of a solid phase, and sometimes the solid phase comprises a flow cell on which nucleic acid from a library can be attached and reagents can be flowed and contacted with the attached nucleic acid. A flow cell sometimes includes flow cell lanes, and use of identifiers can facilitate analyzing a number of samples in each lane. A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs. In some embodiments the number of samples analyzed in a given flow cell lane are dependent on the number of unique identifiers utilized during library preparation and/ or probe design, single flow cell lane. Multiplexing using 12 identifiers, for example, allows simultaneous analysis of 96 samples (e.g., equal to the number of wells in a 96 well microwell plate) in an 8 lane flow cell. Similarly, multiplexing using 48 identifiers, for example, allows simultaneous analysis of 384 samples (e.g., equal to the number of wells in a 384 well microwell plate) in an 8 lane flow cell. Non-limiting examples of commercially available multiplex sequencing kits include Illumina's multiplexing sample preparation oligonucleotide kit and multiplexing sequencing primers and PhiX control kit (e.g., Illumina's catalog numbers PE-400-1001 and PE-400-1002, respectively).

Any suitable method of sequencing nucleic acids can be used, non-limiting examples of which include Maxim & Gilbert, chain-termination methods, sequencing by synthesis, sequencing by ligation, sequencing by mass spectrometry, microscopy-based techniques, the like or combinations thereof. In some embodiments, a first generation technology, such as, for example, Sanger sequencing methods including automated Sanger sequencing methods, including microfluidic Sanger sequencing, can be used in a method provided herein. In some embodiments sequencing technologies that include the use of nucleic acid imaging technologies (e.g. transmission electron microscopy (TEM) and atomic force microscopy (AFM)), can be used. In some embodiments, a high-throughput sequencing method is used. High-throughput sequencing methods generally involve clonally amplified DNA templates or single DNA molecules that are sequenced in a massively parallel fashion, sometimes within a flow cell. Next generation (e.g., 2nd and 3rd generation) sequencing techniques capable of sequencing DNA in a massively parallel fashion can be used for methods described herein and are collectively referred to herein as "massively parallel sequencing" (MPS). In some embodiments MPS sequencing methods utilize a targeted approach, where specific chromosomes, genes or regions of interest are sequences. In certain embodiments a non-targeted approach is used where most or all nucleic acids in a sample are sequenced, amplified and/or captured randomly.

In some embodiments a targeted enrichment, amplification and/or sequencing approach is used. A targeted approach often isolates, selects and/or enriches a subset of nucleic acids in a sample for further processing by use of sequence-specific oligonucleotides. In some embodiments a library of sequence-specific oligonucleotides are utilized to target (e.g., hybridize to) one or more sets of nucleic acids in a sample. Sequence-specific oligonucleotides and/or primers are often selective for particular sequences (e.g., unique nucleic acid sequences) present in one or more chromosomes, genes, exons, introns, and/or regulatory regions of interest. Any suitable method or combination of methods can be used for enrichment, amplification and/or sequencing of one or more subsets of targeted nucleic acids. In some embodiments targeted sequences are isolated and/or enriched by capture to a solid phase (e.g., a flow cell, a bead) using one or more sequence-specific anchors. In some embodiments targeted sequences are enriched and/or amplified by a polymerase-based method (e.g., a PCR-based method, by any suitable polymerase based extension) using sequence-specific primers and/or primer sets. Sequence specific anchors often can be used as sequence-specific primers.

MPS sequencing sometimes makes use of sequencing by synthesis and certain imaging processes. A nucleic acid sequencing technology that may be used in a method described herein is sequencing-by-synthesis and reversible terminator-based sequencing (e.g. Illumina's Genome Analyzer; Genome Analyzer II; HISEQ 2000; HISEQ 2500 (Illumina, San Diego Calif.)). With this technology, millions of nucleic acid (e.g. DNA) fragments can be sequenced in parallel. In one example of this type of sequencing technology, a flow cell is used which contains an optically transparent slide with 8 individual lanes on the surfaces of which are bound oligonucleotide anchors (e.g., adaptor primers). A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs.

Sequencing by synthesis, in some embodiments, comprises iteratively adding (e.g., by covalent addition) a nucleotide to a primer or preexisting nucleic acid strand in a template directed manner. Each iterative addition of a nucleotide is detected and the process is repeated multiple times until a sequence of a nucleic acid strand is obtained. The length of a sequence obtained depends, in part, on the number of addition and detection steps that are performed. In some embodiments of sequencing by synthesis, one, two, three or more nucleotides of the same type (e.g., A, G, C or T) are added and detected in a round of nucleotide addition. Nucleotides can be added by any suitable method (e.g., enzymatically or chemically). For example, in some embodiments a polymerase or a ligase adds a nucleotide to a primer or to a preexisting nucleic acid strand in a template directed manner. In some embodiments of sequencing by synthesis, different types of nucleotides, nucleotide analogues and/or identifiers are used. In some embodiments reversible terminators and/or removable (e.g., cleavable) identifiers are used. In some embodiments fluorescent labeled nucleotides and/or nucleotide analogues are used. In certain embodiments sequencing by synthesis comprises a cleavage (e.g., cleavage and removal of an identifier) and/or a washing step. In some embodiments the addition of one or more nucleotides is detected by a suitable method described herein or known in the art, non-limiting examples of which include any suitable imaging apparatus or machine, a suitable camera, a digital camera, a CCD (Charge Couple Device) based imaging apparatus (e.g., a CCD camera), a CMOS (Complementary Metal Oxide Silicon) based imaging apparatus (e.g., a CMOS camera), a photo diode (e.g., a photomultiplier tube), electron microscopy, a field-effect transistor (e.g., a DNA field-effect transistor), an ISFET ion sensor (e.g., a CHEMFET sensor), the like or combinations thereof. Other sequencing methods that may be used to conduct methods herein include digital PCR and sequencing by hybridization.

Other sequencing methods that may be used to conduct methods herein include digital PCR and sequencing by hybridization. Digital polymerase chain reaction (digital PCR or dPCR) can be used to directly identify and quantify nucleic acids in a sample. Digital PCR can be performed in an emulsion, in some embodiments. For example, individual nucleic acids are separated, e.g., in a microfluidic chamber device, and each nucleic acid is individually amplified by PCR. Nucleic acids can be separated such that there is no more than one nucleic acid per well. In some embodiments, different probes can be used to distinguish various alleles (e.g. fetal alleles and maternal alleles). Alleles can be enumerated to determine copy number.

In certain embodiments, sequencing by hybridization can be used. The method involves contacting a plurality of polynucleotide sequences with a plurality of polynucleotide probes, where each of the plurality of polynucleotide probes can be optionally tethered to a substrate. The substrate can be a flat surface with an array of known nucleotide sequences, in some embodiments. The pattern of hybridization to the array can be used to determine the polynucleotide sequences present in the sample. In some embodiments, each probe is tethered to a bead, e.g., a magnetic bead or the like. Hybridization to the beads can be identified and used to identify the plurality of polynucleotide sequences within the sample.

In some embodiments, nanopore sequencing can be used in a method described herein. Nanopore sequencing is a single-molecule sequencing technology whereby a single nucleic acid molecule (e.g. DNA) is sequenced directly as it passes through a nanopore.

A suitable MPS method, system or technology platform for conducting methods described herein can be used to obtain nucleic acid sequencing reads. Non-limiting examples of MPS platforms include Illumina/Solex/HiSeq (e.g., Illumina's Genome Analyzer; Genome Analyzer II; HISEQ 2000; HISEQ), SOLiD, Roche/454, PACBIO and/or SMRT, Helicos True Single Molecule Sequencing, Ion Torrent and Ion semiconductor-based sequencing (e.g., as developed by Life Technologies), WildFire, 5500, 5500xl W and/or 5500xl W Genetic Analyzer based technologies (e.g., as developed and sold by Life Technologies, US patent publication no. US20130012399); Polony sequencing, Pyrosequencing, Massively Parallel Signature Sequencing (MPSS), RNA polymerase (RNAP) sequencing, LaserGen systems and methods, Nanopore-based platforms, chemical-sensitive field effect transistor (CHEMFET) array, electron microscopy-based sequencing (e.g., as developed by ZS Genetics, Halcyon Molecular), nanoball sequencing, In some embodiments, chromosome-specific sequencing is performed. In some embodiments, chromosome-specific sequencing is performed utilizing DANSR (digital analysis of selected regions). Digital analysis of selected regions enables simultaneous quantification of hundreds of loci by cfDNA-dependent catenation of two locus-specific oligonucleotides via an intervening 'bridge' oligonucleotide to form a PCR template. In some embodiments, chromosome-specific sequencing is performed by generating a library enriched in chromosome-specific sequences. In some embodiments, sequence reads are obtained only for a selected set of chromosomes. In some embodiments, sequence reads are obtained only for chromosomes 21, 18 and 13.

Mapping Reads

Sequence reads can be mapped and the number of reads mapping to a specified nucleic acid region (e.g., a chromosome, portion or segment thereof) are referred to as counts. Any suitable mapping method (e.g., process, algorithm, program, software, module, the like or combination thereof) can be used. Certain aspects of mapping processes are described hereafter.

Mapping nucleotide sequence reads (i.e., sequence information from a fragment whose physical genomic position is unknown) can be performed in a number of ways, and often comprises alignment of the obtained sequence reads with a matching sequence in a reference genome. In such alignments, sequence reads generally are aligned to a reference sequence and those that align are designated as being "mapped", "a mapped sequence read" or "a mapped read". In certain embodiments, a mapped sequence read is referred to as a "hit" or "count". In some embodiments, mapped sequence reads are grouped together according to various parameters and assigned to particular portions, which are discussed in further detail below.

As used herein, the terms "aligned", "alignment", or "aligning" refer to two or more nucleic acid sequences that can be identified as a match (e.g., 100% identity) or partial match. Alignments can be done manually or by a computer (e.g., a software, program, module, or algorithm), non-limiting examples of which include the Efficient Local Alignment of Nucleotide Data (ELAND) computer program distributed as part of the Illumina Genomics Analysis pipeline. Alignment of a sequence read can be a 100% sequence match. In some cases, an alignment is less than a 100% sequence match (i.e., non-perfect match, partial match, partial alignment). In some embodiments an alignment is about a 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76% or 75% match. In some embodiments, an alignment comprises a mismatch. In some embodiments, an alignment comprises 1, 2, 3, 4 or 5 mismatches. Two or more sequences can be aligned using either strand. In certain embodiments a nucleic acid sequence is aligned with the reverse complement of another nucleic acid sequence.

Various computational methods can be used to map each sequence read to a portion. Non-limiting examples of computer algorithms that can be used to align sequences include, without limitation, BLAST, BLITZ, FASTA, BOWTIE 1, BOWTIE 2, ELAND, MAQ, PROBEMATCH, SOAP or SEQMAP, or variations thereof or combinations thereof. In some embodiments, sequence reads can be aligned with sequences in a reference genome. In some embodiments, the sequence reads can be found and/or aligned with sequences in nucleic acid databases known in the art including, for example, GenBank, dbEST, dbSTS, EMBL (European Molecular Biology Laboratory) and DDBJ (DNA Databank of Japan). BLAST or similar tools can be used to search the identified sequences against a sequence database. Search hits can then be used to sort the identified sequences into appropriate portions (described hereafter), for example.

In some embodiments, a read may uniquely or non-uniquely map to portions in a reference genome. A read is considered as "uniquely mapped" if it aligns with a single sequence in the reference genome. A read is considered as "non-uniquely mapped" if it aligns with two or more sequences in the reference genome. In some embodiments, non-uniquely mapped reads are eliminated from further analysis (e.g. quantification). A certain, small degree of mismatch (0-1) may be allowed to account for single nucleotide polymorphisms that may exist between the reference genome and the reads from individual samples being mapped, in certain embodiments.

In some embodiments, no degree of mismatch is allowed for a read mapped to a reference sequence.

As used herein, the term "reference genome" can refer to any particular known, sequenced or characterized genome, whether partial or complete, of any organism or virus which may be used to reference identified sequences from a subject. For example, a reference genome used for human subjects as well as many other organisms can be found at the National Center for Biotechnology Information at www.ncbi.nlm.nih.gov. A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. In some embodiments, a reference genome comprises sequences assigned to chromosomes.

In certain embodiments, where a sample nucleic acid is from a pregnant female, a reference sequence sometimes is not from the fetus, the mother of the fetus or the father of the fetus, and is referred to herein as an "external reference." A maternal reference may be prepared and used in some embodiments. When a reference from the pregnant female is prepared ("maternal reference sequence") based on an external reference, reads from DNA of the pregnant female that contains substantially no fetal DNA often are mapped to the external reference sequence and assembled.

In certain embodiments the external reference is from DNA of an individual having substantially the same ethnicity as the pregnant female. A maternal reference sequence may not completely cover the maternal genomic DNA (e.g., it may cover about 50%, 60%, 70%, 80%, 90% or more of the maternal genomic DNA), and the maternal reference may not perfectly match the maternal genomic DNA sequence (e.g., the maternal reference sequence may include multiple mismatches).

In certain embodiments, mappability is assessed for a genomic region (e.g., portion, genomic portion, portion). Mappability is the ability to unambiguously align a nucleotide sequence read to a portion of a reference genome, typically up to a specified number of mismatches, including, for example, 0, 1, 2 or more mismatches. For a given genomic region, the expected mappability can be estimated using a sliding-window approach of a preset read length and averaging the resulting read-level mappability values. Genomic regions comprising stretches of unique nucleotide sequence sometimes have a high mappability value.

Portions

In some embodiments, mapped sequence reads (i.e. sequence tags) are grouped together according to various parameters and assigned to particular portions (e.g., portions of a reference genome). Often, individual mapped sequence reads can be used to identify a portion (e.g., the presence, absence or amount of a portion) present in a sample. In some embodiments, the amount of a portion is indicative of the amount of a larger sequence (e.g. a chromosome) in the sample. The term "portion" can also be referred to herein as a "genomic section", "bin", "region", "partition", "portion of a reference genome", "portion of a chromosome" or "genomic portion." In some embodiments a portion is an entire chromosome, a segment of a chromosome, a segment of a reference genome, a segment spanning multiple chromosome, multiple chromosome segments, and/or combinations thereof. In some embodiments, a portion is predefined based on specific parameters (e.g., indicators). In some embodiments, a portion is arbitrarily or non-arbitrarily defined based on partitioning of a genome (e.g., partitioned by size, GC content, contiguous regions, contiguous regions of an arbitrarily defined size, and the like). In some embodiments portions are chosen from discrete genomic bins, genomic bins having sequential sequences of predetermined length, variable-size bins, point-based views of a smoothed coverage map, and/or a combination thereof.

In some embodiments, a portion is delineated based on one or more parameters which include, for example, length or a particular feature or features of the sequence. Portions can be selected, filtered and/or removed from consideration using any suitable criteria know in the art or described herein. In some embodiments, a portion is based on a particular length of genomic sequence. In some embodiments, a method can include analysis of multiple mapped sequence reads to a plurality of portions. Portions can be approximately the same length or portions can be different lengths. In some embodiments, portions are of about equal length. In some embodiments portions of different lengths are adjusted or weighted. In some embodiments a portion is about 10 kilobases (kb) to about 20 kb, about 10 kb to about 100 kb, about 20 kb to about 80 kb, about 30 kb to about 70 kb, about 40 kb to about 60 kb. In some embodiments a portion is about 10 kb, 20 kb, 30 kb, 40 kb, 50 kb or about 60 kb in length. A portion is not limited to contiguous runs of sequence. Thus, portions can be made up of contiguous and/or non-contiguous sequences. A portion is not limited to a single chromosome. In some embodiments, a portion includes all or part of one chromosome or all or part of two or more chromosomes. In some embodiments, portions may span one, two, or more entire chromosomes. In addition, portions may span jointed or disjointed regions of multiple chromosomes.

In some embodiments, portions can be particular chromosome segments in a chromosome of interest, such as, for example, a chromosome where a genetic variation is assessed (e.g. an aneuploidy of chromosomes 13, 18 and/or 21 or a sex chromosome). A portion can also be a pathogenic genome (e.g. bacterial, fungal or viral) or fragment thereof. Portions can be genes, gene fragments, regulatory sequences, introns, exons, and the like.

In some embodiments, a genome (e.g. human genome) is partitioned into portions based on information content of particular regions. In some embodiments, partitioning a genome may eliminate similar regions (e.g., identical or homologous regions or sequences) across the genome and only keep unique regions. Regions removed during partitioning may be within a single chromosome or may span multiple chromosomes. In some embodiments a partitioned genome is trimmed down and optimized for faster alignment, often allowing for focus on uniquely identifiable sequences.

In some embodiments, partitioning may down weight similar regions. A process for down weighting a portion is discussed in further detail below.

In some embodiments, partitioning of a genome into regions transcending chromosomes may be based on information gain produced in the context of classification. For example, information content may be quantified using a p-value profile measuring the significance of particular genomic locations for distinguishing between groups of confirmed normal and abnormal subjects (e.g. euploid and trisomy subjects, respectively). In some embodiments, partitioning of a genome into regions transcending chromosomes may be based on any other criterion, such as, for example, speed/convenience while aligning tags, GC content (e.g., high or low GC content), uniformity of GC content, other measures of sequence content (e.g. fraction of individual nucleotides, fraction of pyrimidines or purines, fraction of natural vs. non-natural nucleic acids, fraction of methylated nucleotides, and CpG content), methylation state, duplex melting temperature, amenability to sequencing or PCR, uncertainty value assigned to individual portions of a reference genome, and/or a targeted search for particular features.

A "segment" of a chromosome generally is part of a chromosome, and typically is a different part of a chromosome than a portion. A segment of a chromosome sometimes is in a different region of a chromosome than a portion, sometimes does not share a polynucleotide with a portion, and sometimes includes a polynucleotide that is in a portion. A segment of a chromosome often contains a larger number of nucleotides than a portion (e.g., a segment sometimes includes a portion), and sometimes a segment of a chromosome contains a smaller number of nucleotides than a portion (e.g., a segment sometimes is within a portion).

Filtering and/or Selecting Portions

Portions sometimes are processed (e.g., normalized, filtered, selected, the like, or combinations thereof) according to one or more features, parameters, criteria and/or methods described herein or known in the art. Portions can be processed by any suitable method and according to any suitable parameter. Non-limiting examples of features and/or parameters that can be used to filter and/or select portions include counts, coverage, mappability, variability, a level of uncertainty, guanine-cytosine (GC) content, CCF fragment length and/or read length (e.g., a fragment length ratio (FLR), a fetal ratio statistic (FRS)), DNaseI-sensitivity, methylation state, acetylation, histone distribution, chromatin structure, the like or combinations thereof. Portions can be filtered and/or selected according to any suitable feature or parameter that correlates with a feature or parameter listed or described herein. Portions can be filtered and/or selected according to features or parameters that are specific to a portion (e.g., as determined for a single portion according to multiple samples) and/or features or parameters that are specific to a sample (e.g., as determined for multiple portions within a sample). In some embodiments portions are filtered and/or removed according to relatively low mappability, relatively high variability, a high level of uncertainty, relatively long CCF fragment lengths (e.g., low FRS, low FLR), relatively large fraction of repetitive sequences, high GC content, low GC content, low counts, zero counts, high counts, the like, or combinations thereof. In some embodiments portions (e.g., a subset of portions) are selected according to suitable level of mappability, variability, level of uncertainty, fraction of repetitive sequences, count, GC content, the like, or combinations thereof. In some embodiments portions (e.g., a subset of portions) are selected according to relatively short CCF fragment lengths (e.g., high FRS, high FLR). Counts and/or reads mapped to portions are sometimes processed (e.g., normalized) prior to and/or after filtering or selecting portions (e.g., a subset of portions). In some embodiments counts and/or reads mapped to portions are not processed prior to and/or after filtering or selecting portions (e.g., a subset of portions).

Sequence reads from any suitable number of samples can be utilized to identify a subset of portions that meet one or more criteria, parameters and/or features described herein. Sequence reads from a group of samples from multiple pregnant females sometimes are utilized. One or more samples from each of the multiple pregnant females can be addressed (e.g., 1 to about 20 samples from each pregnant female (e.g., about 2, 3, 4, 5, 6, 7, 8, 9, 10, 11, 12, 13, 14, 15, 16, 17, 18 or 19 samples)), and a suitable number of pregnant females may be addressed (e.g., about 2 to about 10,000 pregnant females (e.g., about 10, 20, 30, 40, 50, 60, 70, 80, 90, 100, 150, 200, 250, 300, 350, 400, 500, 600, 700, 800, 900, 1000, 2000, 3000, 4000, 5000, 6000, 7000, 8000, 9000 pregnant females)). In some embodiments, sequence reads from the same test sample(s) from the same pregnant female are mapped to portions in the reference genome and are used to generate the subset of portions.

It has been observed that circulating cell free nucleic acid fragments (CCF fragments) obtained from a pregnant female generally comprise nucleic acid fragments originating from fetal cells (i.e., fetal fragments) and nucleic acid fragments originating from maternal cells (i.e., maternal fragments). Sequence reads derived from CCF fragments originating from a fetus are referred to herein as "fetal reads." Sequence reads derived from CCF fragments originating from the genome of a pregnant female (e.g., a mother) bearing a fetus are referred to herein as "maternal reads." CCF fragments from which fetal reads are obtained are referred to herein as fetal templates and CCF fragments from which maternal reads are obtained are referred herein to as maternal templates.

It also has been observed that in CCF fragments, fetal fragments generally are relatively short (e.g., about 200 base pairs in length or less) and that maternal fragments include such relatively short fragments and relatively longer fragments. A subset of portions to which are mapped a significant amount of reads from relatively short fragments can be selected and/or identified. Without being limited by theory, it is expected that reads mapped to such portions are enriched for fetal reads, which can improve the accuracy of a fetal genetic analysis (e.g., detecting the presence or absence of a fetal genetic variation (e.g., fetal chromosome aneuploidy (e.g., T21, T18 and/or T13))).

A significant number of reads often are not considered, however, when a fetal genetic analysis is based on a subset of reads. Selection of a subset of reads mapped to a selected subset of portions, and removal of reads in non-selected portions, for a fetal genetic analysis can decrease the accuracy of the genetic analysis, due to increased variance for example. In some embodiments, about 30% to about 70% (e.g., about 35%, 40%, 45%, 50%, 55%, 60%, or 65%) of sequencing reads obtained from a subject or sample map are removed from consideration upon selection of a subset of portions for a fetal genetic analysis. In certain embodiments about 30% to about 70% (e.g., about 35%, 40%, 45%, 50%, 55%, 60%, or 65%) of sequencing reads obtained from a subject or sample map to a subset of portions utilized for a fetal genetic analysis.

Thus, without being limited by theory, there generally is a tradeoff between increased accuracy associated with fetal read enrichment and decreased accuracy associated with a reduced amount of read data (e.g., removal of portions and/or reads) for a fetal genetic analysis. In some embodiments, a method comprises selecting a subset of portions enriched for reads from fetal nucleic acid (e.g., fetal reads) which improves, or does not significantly decrease, the accuracy of a fetal genetic analysis. Despite this apparent tradeoff, it has been determined, as described herein, that utilizing a subset of portions, to which are mapped a significant amount of reads from relatively short fragments, can improve the accuracy of fetal genetic analyses.

In some embodiments a subset of portions are selected according to reads from CCF fragments where the reads mapped to a portion have a length less than a selected fragment length. Sometimes a subset of portions are selected by filtering portions that do not meet this criteria. In certain embodiments, a subset of portions are selected according to the amount of reads derived from relatively short CCF fragments (e.g., about 200 base pairs or less) that map to a portion. Any suitable method can be utilized to identify and/or select portions to which a significant amount of reads from CCF fragments having a length less than a selected fragment length (e.g., a first selected fragment length) are mapped. CCF fragments having a length less than a selected fragment length often are relatively short CCF fragments, and sometimes the selected fragment length is about 200 base pairs or less (e.g., CCF fragments that are about 190, 180, 170, 160, 150, 140, 130, 120, 110, 100, 90, or 80 bases in length). The length of a CCF fragment can be determined (e.g., deduced or inferred) by mapping two or more reads derived from the fragment (e.g., a paired-end read) to a reference genome. For paired-end reads derived from a CCF fragment, for example, reads can be mapped to a reference genome, the length of the genomic sequence between the mapped reads can be determined, and the total of the two read lengths and the length of the genomic sequence between the reads is equal to the length of the CCF fragment.

The length of a CCF fragment template sometimes is determined directly from the length of a read derived from the fragment (e.g., single-end read).

In some embodiments, a subset of portions, to which a significant amount of reads from CCF fragments having a length less than a selected fragment length, is selected and/or identified according to whether the amount of mapped reads from CCF fragments having a length less than a first selected fragment length is greater than the amount of mapped reads from CCF fragments having a length less than a second selected fragment length. In certain embodiments, a subset of portions, to which a significant amount of reads from CCF fragments having a length less than a selected fragment length, is selected and/or identified according to whether the amount of mapped reads from CCF fragments having a length less than a first selected fragment length for a portion is greater than the average, mean or median amount of mapped reads from CCF fragments having a length less than a second selected fragment length for portions analyzed. In some embodiments, a subset of portions, to which a significant amount of reads from CCF fragments having a length less than a selected fragment length, is selected and/or identified based on a fragment length ratio (FLR) determined for each portion. A "fragment length ratio" also is referred to herein as a fetal ratio statistic (FRS).

In certain embodiments, a FLR is determined, in part, according to the amount of reads mapped to a portion from CCF fragments having a length less than a selected fragment length. In some embodiments, a FLR value often is a ratio of X to Y, where X is the amount of reads derived from CCF fragments having a length less than a first selected fragment length, and Y is the amount of reads derived from CCF fragments having a length less than a second selected fragment length. A first selected fragment length often is selected independent of a second selected fragment length, and visa versa, and the second selected fragment length typically is larger than the first selected fragment length. A first selected fragment length can be from about 200 bases or less to about 30 bases or less. In some embodiments, a first selected fragment length is about 200, 190, 180, 170, 160, 155, 150, 145, 140, 135, 130, 125, 120, 115, 110, 105, 100, 95, 90, 85, 80, 75, 70, 65, 60, 55 or 50 bases. In some embodiments, a first selected fragment length is about 170 to about 130 bases, and sometimes is about 160 to about 140 bases. In some embodiments, a second selected fragment length is about 2000 bases to about 200 bases. In certain embodiments a second selected fragment length is about 1000, 950, 800, 850, 800, 750, 700, 650, 600, 550, 500, 450, 400, 350, 300, 250 bases. In some embodiments the first selected fragment length is about 140 to about 160 bases (e.g., about 150 bases) and the second selected fragment length is about 500 to about 700 bases (e.g., about 600 bases). In some embodiments the first selected fragment length is about 150 bases and the second selected fragment length is about 600 bases.

In some embodiments a FLR is an average, mean or median of multiple FLR values. For example, sometimes a FLR for a given portion is an average, mean or median of FLR values for (i) two or more test samples, (ii) two or more subjects, or (iii) two or more test samples and two or more subjects. In certain embodiments an average, mean or median FLR is derived from FLR values for two or more portions of a genome, chromosome, or segment thereof. In some embodiments an average, mean or median FLR is associated with an uncertainty (e.g., standard deviation, median absolute deviation).

In some embodiments, a subset of portions is selected and/or identified according to one or more FLR values (e.g., a comparison of one or more FLR values). In certain embodiments a subset of portions is selected and/or identified according to a FLR and a threshold (e.g., a comparison of a FLR and a threshold). In certain embodiments an average, mean or median FLR derived from a given portion is compared to an average, mean or median FLR derived from two or more portions of a genome, chromosome, or segment thereof. For example, sometimes an average FLR for a given portion is compared to a median FLR for a given portion. In certain embodiments a portion is selected and/or identified according to an average, mean or median FLR determined for a portion and an average, mean or median FLR determined for a collection of portions (e.g., portion from a genome, chromosome, or segment thereof). In some embodiments, an average FLR for a portion is below a certain threshold determined according to a median FLR and the portion is removed from consideration (e.g., in a fetal genetic analysis). In some embodiments, an average, mean or median FLR for a portion is above a certain threshold determined according to an average, mean or median FLR for a genome, chromosome, or segment thereof, and the portion is selected and/or added to a subset of portions for consideration (e.g., when determining the presence or absence of a genetic variation). In some embodiments, a FLR for a portion is equal to or greater than about 0.15 to about 0.30 (e.g., about 0.16, 0.17, 0.18, 0.19, 0.20, 0.21, 0.21, 0.22, 0.23, 0.24, 0.25, 0.26, 0.27, 0.28, 0.29) and the portion is selected for consideration (e.g., added to or incorporated into a subset of portions for a fetal genetic analysis). In some embodiments, a FLR for a portion is equal to or less than about 0.20 to about 0.10 (e.g., about 0.19, 0.18, 0.17, 0.16, 0.15, 0.14, 0.13, 0.12, 0.11) and the portion is removed from consideration (e.g., filtered).

Portions in a subset sometimes are selected and/or identified according to, in part, whether a significant amount of reads from CCF fragments having a length less than a selected fragment length are mapped to a portion (e.g., according to a FLR). In some embodiments, portions in a subset may be selected and/or identified according to one or more characteristics or criteria in addition to the amount of sequence reads mapped from fragment lengths less than a selected fragment length. In some embodiments, a subset of portions are selected and/or identified according to whether a significant amount of reads from CCF fragments having a length less than a selected fragment length are mapped to a portion (e.g., according to a FLR) and one or more other features. Non-limiting examples of other features include the number of exons in, and/or GC content of, a genome, chromosome or segment thereof, and/or one or more of the portions. Accordingly, sometimes portions selected and/or identified according to whether a significant amount of reads from CCF fragments having a length less than a selected fragment length are mapped to a portion (e.g., according to a FLR) for a subset, are further selected or removed according to GC content of the portion and/or the number of exons in the portion. In some embodiments, a portion is not selected or removed from consideration (e.g., filtered) if GC content and/or the number of exons in the portion does not correlate with a FLR for the portion.

In some embodiments a subset of portions consist of, consist essentially of, or comprise portions that meet one or more particular criteria described herein (e.g., portions are characterized by a FLR equal to or greater than a certain value). In certain embodiments portions that do not meet a criterion are included in a subset of portions that meet the criterion, for example, to increase accuracy of a fetal genetic analysis. In certain embodiments, in a subset of portions that "consists essentially of" portions selected according to a criterion (e.g., a FLR equal to or greater than a certain value), about 90% or more (e.g., about 91%, 91%, 93%, 94%, 95%, 96%, 97%, 98%, 99% or more) of the portions meet the criterion and about 10% or fewer (e.g., about 9%, 8%, 7%, 6%, 5%, 4%, 3%, 2%, about 1% or fewer) of the portions do not meet the criterion.

Portions can be selected and/or filtered by any suitable method. In some embodiments portions are selected according to visual inspection of data, graphs, plots and/or charts. In certain embodiments portions are selected and/or filtered (e.g., in part) by a system or a machine comprising one or more microprocessors and memory. In some embodiments portions are selected and/or filtered (e.g., in part) by a non-transitory computer-readable storage medium with an executable program stored thereon, where the program instructs a microprocessor to perform the selecting and/or filtering.

A subset of portions selected by methods described herein can be utilized for a fetal genetic analysis in different manners. In certain embodiments reads derived from a sample are utilized in a mapping process using a pre-selected subset of portions described herein, and not using all or most of the portions in a reference genome. Those reads that map to the pre-selected subset of portions often are utilized in further steps of a fetal genetic analysis, and reads that do not map to the pre-selected subset of portions often are not utilized in further steps of a fetal genetic analysis (e.g., reads that do not map are removed or filtered).

In some embodiments sequence reads derived from a sample are mapped to all or most portions of a reference genome and a pre-selected subset of portions described herein are thereafter selected. Reads from a selected subset of portions often are utilized in further steps of a fetal genetic analysis. In the latter embodiments, reads from portions not selected are often not utilized in further steps of a fetal genetic analysis (e.g., reads in the non-selected portions are removed or filtered).

Counts

Sequence reads that are mapped or partitioned based on a selected feature or variable can be quantified to determine the number of reads that are mapped to one or more portions (e.g., portion of a reference genome), in some embodiments. In certain embodiments the quantity of sequence reads that are mapped to a portion are termed counts (e.g., a count). Often a count is associated with a portion. In certain embodiments counts for two or more portions (e.g., a set of portions) are mathematically manipulated (e.g., averaged, added, normalized, the like or a combination thereof). In some embodiments a count is determined from some or all of the sequence reads mapped to (i.e., associated with) a portion. In certain embodiments, a count is determined from a pre-defined subset of mapped sequence reads. Pre-defined subsets of mapped sequence reads can be defined or selected utilizing any suitable feature or variable. In some embodiments, pre-defined subsets of mapped sequence reads can include from 1 to n sequence reads, where n represents a number equal to the sum of all sequence reads generated from a test subject or reference subject sample.

In certain embodiments a count is derived from sequence reads that are processed or manipulated by a suitable method, operation or mathematical process known in the art. A count (e.g., counts) can be determined by a suitable method, operation or mathematical process. In certain embodiments a count is derived from sequence reads associated with a portion where some or all of the sequence reads are weighted, removed, filtered, normalized, adjusted, averaged, derived as a mean, added, or subtracted or processed by a combination thereof. In some embodiments, a count is derived from raw sequence reads and or filtered sequence reads. In certain embodiments a count value is determined by a mathematical process. In certain embodiments a count value is an average, mean or sum of sequence reads mapped to a portion. Often a count is a mean number of counts. In some embodiments, a count is associated with an uncertainty value.

In some embodiments, counts can be manipulated or transformed (e.g., normalized, combined, added, filtered, selected, averaged, derived as a mean, the like, or a combination thereof). In some embodiments, counts can be transformed to produce normalized counts. Counts can be processed (e.g., normalized) by a method known in the art and/or as described herein (e.g., portion-wise normalization, normalization by GC content, linear and nonlinear least squares regression, GC LOESS, LOWESS, PERUN, RM, GCRM, cQn and/or combinations thereof).

Counts (e.g., raw, filtered and/or normalized counts) can be processed and normalized to one or more levels. Levels and profiles are described in greater detail hereafter. In certain embodiments counts can be processed and/or normalized to a reference level. Reference levels are addressed later herein. Counts processed according to a level (e.g., processed counts) can be associated with an uncertainty value (e.g., a calculated variance, an error, standard deviation, Z-score, p-value, mean absolute deviation, etc.). In some embodiments an uncertainty value defines a range above and below a level. A value for deviation can be used in place of an uncertainty value, and non-limiting examples of measures of deviation include standard deviation, average absolute deviation, median absolute deviation, standard score (e.g., Z-score, Z-score, normal score, standardized variable) and the like.

Counts are often obtained from a nucleic acid sample from a pregnant female bearing a fetus. Counts of nucleic acid sequence reads mapped to one or more portions often are counts representative of both the fetus and the mother of the fetus (e.g., a pregnant female subject). In certain embodiments some of the counts mapped to a portion are from a fetal genome and some of the counts mapped to the same portion are from a maternal genome.

Data Processing and Normalization

Mapped sequence reads that have been counted are referred to herein as raw data, since the data represents unmanipulated counts (e.g., raw counts). In some embodiments, sequence read data in a data set can be processed further (e.g., mathematically and/or statistically manipulated) and/or displayed to facilitate providing an outcome. In certain embodiments, data sets, including larger data sets, may benefit from pre-processing to facilitate further analysis. Pre-processing of data sets sometimes involves removal of redundant and/or uninformative portions or portions of a reference genome (e.g., portions of a reference genome with uninformative data, redundant mapped reads, portions with zero median counts, over represented or under represented sequences). Without being limited by theory, data processing and/or preprocessing may (i) remove noisy data, (ii) remove uninformative data, (iii) remove redundant data, (iv) reduce the complexity of larger data sets, and/or (v) facilitate transformation of the data from one form into one or more other forms. The terms "pre-processing" and "processing" when utilized with respect to data or data sets are collectively referred to herein as "processing". Processing can render data more amenable to further analysis, and can generate an outcome in some embodiments. In some embodiments one or more or all processing methods (e.g., normalization methods, portion filtering, mapping, validation, the like or combinations thereof) are performed by a processor, a microprocessor, a computer, in conjunction with memory and/or by a microprocessor controlled machine.

The term "noisy data" as used herein refers to (a) data that has a significant variance between data points when analyzed or plotted, (b) data that has a significant standard deviation (e.g., greater than 3 standard deviations), (c) data that has a significant standard error of the mean, the like, and combinations of the foregoing. Noisy data sometimes occurs due to the quantity and/or quality of starting material (e.g., nucleic acid sample), and sometimes occurs as part of processes for preparing or replicating DNA used to generate sequence reads. In certain embodiments, noise results from certain sequences being over represented when prepared using PCR-based methods. Methods described herein can reduce or eliminate the contribution of noisy data, and therefore reduce the effect of noisy data on the provided outcome.

The terms "uninformative data", "uninformative portions of a reference genome", and "uninformative portions" as used herein refer to portions, or data derived therefrom, having a numerical value that is significantly different from a predetermined threshold value or falls outside a predetermined cutoff range of values. The terms "threshold" and "threshold value" herein refer to any number that is calculated using a qualifying data set and serves as a limit of diagnosis of a genetic variation (e.g. a copy number variation, an aneuploidy, a chromosomal aberration, and the like). In certain embodiments a threshold is exceeded by results obtained by methods described herein and a subject is diagnosed with a genetic variation (e.g. trisomy 21). A threshold value or range of values often is calculated by mathematically and/or statistically manipulating sequence read data (e.g., from a reference and/or subject), in some embodiments, and in certain embodiments, sequence read data manipulated to generate a threshold value or range of values is sequence read data (e.g., from a reference and/or subject). In some embodiments, an uncertainty value is determined. An uncertainty value generally is a measure of variance or error and can be any suitable measure of variance or error. In some embodiments an uncertainty value is a standard deviation, standard error, calculated variance, p-value, or mean absolute deviation (MAD). In some embodiments an uncertainty value can be calculated according to a formula in Example 4.

Any suitable procedure can be utilized for processing data sets described herein. Non-limiting examples of procedures suitable for use for processing data sets include filtering, normalizing, weighting, monitoring peak heights, monitoring peak areas, monitoring peak edges, determining area ratios, mathematical processing of data, statistical processing of data, application of statistical algorithms, analysis with fixed variables, analysis with optimized variables, plotting data to identify patterns or trends for additional processing, the like and combinations of the foregoing. In some embodiments, data sets are processed based on various features (e.g., GC content, redundant mapped reads, centromere regions, telomere regions, the like and combinations thereof) and/or variables (e.g., fetal gender, maternal age, maternal ploidy, percent contribution of fetal nucleic acid, the like or combinations thereof). In certain embodiments, processing data sets as described herein can reduce the complexity and/or dimensionality of large and/or complex data sets. A non-limiting example of a complex data set includes sequence read data generated from one or more test subjects and a plurality of reference subjects of different ages and ethnic backgrounds. In some embodiments, data sets can include from thousands to millions of sequence reads for each test and/or reference subject.

Data processing can be performed in any number of steps, in certain embodiments. For example, data may be processed using only a single processing procedure in some embodiments, and in certain embodiments data may be processed using 1 or more, 5 or more, 10 or more or 20 or more processing steps (e.g., 1 or more processing steps, 2 or more processing steps, 3 or more processing steps, 4 or more processing steps, 5 or more processing steps, 6 or more processing steps, 7 or more processing steps, 8 or more processing steps, 9 or more processing steps, 10 or more processing steps, 11 or more processing steps, 12 or more processing steps, 13 or more processing steps, 14 or more processing steps, 15 or more processing steps, 16 or more processing steps, 17 or more processing steps, 18 or more processing steps, 19 or more processing steps, or 20 or more processing steps). In some embodiments, processing steps may be the same step repeated two or more times (e.g., filtering two or more times, normalizing two or more times), and in certain embodiments, processing steps may be two or more different processing steps (e.g., filtering, normalizing; normalizing, monitoring peak heights and edges; filtering, normalizing, normalizing to a reference, statistical manipulation to determine p-values, and the like), carried out simultaneously or sequentially. In some embodiments, any suitable number and/or combination of the same or different processing steps can be utilized to process sequence read data to facilitate providing an outcome. In certain embodiments, processing data sets by the criteria described herein may reduce the complexity and/or dimensionality of a data set.

In some embodiments, one or more processing steps can comprise one or more filtering steps. The term "filtering" as used herein refers to removing portions or portions of a reference genome from consideration. Portions of a reference genome can be selected for removal based on any suitable criteria, including but not limited to redundant data (e.g., redundant or overlapping mapped reads), non-informative data (e.g., portions of a reference genome with zero median counts), portions of a reference genome with over represented or under represented sequences, noisy data, the like, or combinations of the foregoing. A filtering process often involves removing one or more portions of a reference genome from consideration and subtracting the counts in the one or more portions of a reference genome selected for removal from the counted or summed counts for the portions of a reference genome, chromosome or chromosomes, or genome under consideration. In some embodiments, portions of a reference genome can be removed successively (e.g., one at a time to allow evaluation of the effect of removal of each individual portion), and in certain embodiments all portions of a reference genome marked for removal can be removed at the same time. In some embodiments, portions of a reference genome characterized by a variance above or below a certain level are removed, which sometimes is referred to herein as filtering "noisy" portions of a reference genome. In certain embodiments, a filtering process comprises obtaining data points from a data set that deviate from the mean profile level of a portion, a chromosome, or segment of a chromosome by a predetermined multiple of the profile variance, and in certain embodiments, a filtering process comprises removing data points from a data set that do not deviate from the mean profile level of a portion, a chromosome or segment of a chromosome by a predetermined multiple of the profile variance. In some embodiments, a filtering process is utilized to reduce the number of candidate portions of a reference genome analyzed for the presence or absence of a genetic variation. Reducing the number of candidate portions of a reference genome analyzed for the presence or absence of a genetic variation (e.g., micro-deletion, micro-duplication) often reduces the complexity and/or dimensionality of a data set, and sometimes increases the speed of searching for and/or identifying genetic variations and/or genetic aberrations by two or more orders of magnitude.

In some embodiments one or more processing steps can comprise one or more normalization steps. Normalization can be performed by a suitable method described herein or known in the art. In certain embodiments normalization comprises adjusting values measured on different scales to a notionally common scale. In certain embodiments normalization comprises a sophisticated mathematical adjustment to bring probability distributions of adjusted values into alignment. In some embodiments normalization comprises aligning distributions to a normal distribution. In certain embodiments normalization comprises mathematical adjustments that allow comparison of corresponding normalized values for different datasets in a way that eliminates the effects of certain gross influences (e.g., error and anomalies). In certain embodiments normalization comprises scaling. Normalization sometimes comprises division of one or more data sets by a predetermined variable or formula. Non-limiting examples of normalization methods include portion-wise normalization, normalization by GC content, linear and nonlinear least squares regression, LOESS, GC LOESS, LOWESS (locally weighted scatterplot smoothing), PERUN, repeat masking (RM), GC-normalization and repeat masking (GCRM), conditional quantile normalization (cQn) and/or combinations thereof. In some embodiments, the determination of a presence or absence of a genetic variation (e.g., an aneuploidy) utilizes a normalization method (e.g., portion-wise normalization, normalization by GC content, linear and nonlinear least squares regression, LOESS, GC LOESS, LOWESS (locally weighted scatterplot smoothing), PERUN, repeat masking (RM), GC-normalization and repeat masking (GCRM), cQn, a normalization method known in the art and/or a combination thereof). In some embodiments counts are normalized.

For example, LOESS is a regression modeling method known in the art that combines multiple regression models in a k-nearest-neighbor-based meta-model. LOESS is sometimes referred to as a locally weighted polynomial regression. GC LOESS, in some embodiments, applies an LOESS model to the relationship between fragment count (e.g., sequence reads, counts) and GC composition for portions of a reference genome. Plotting a smooth curve through a set of data points using LOESS is sometimes called an LOESS curve, particularly when each smoothed value is given by a weighted quadratic least squares regression over the span of values of the y-axis scattergram criterion variable. For each point in a data set, the LOESS method fits a low-degree polynomial to a subset of the data, with explanatory variable values near the point whose response is being estimated. The polynomial is fitted using weighted least squares, giving more weight to points near the point whose response is being estimated and less weight to points further away. The value of the regression function for a point is then obtained by evaluating the local polynomial using the explanatory variable values for that data point. The LOESS fit is sometimes considered complete after regression function values have been computed for each of the data points. Many of the details of this method, such as the degree of the polynomial model and the weights, are flexible.

Any suitable number of normalizations can be used. In some embodiments, data sets can be normalized 1 or more, 5 or more, 10 or more or even 20 or more times. Data sets can be normalized to values (e.g., normalizing value) representative of any suitable feature or variable (e.g., sample data, reference data, or both). Non-limiting examples of types of data normalizations that can be used include normalizing raw count data for one or more selected test or reference portions to the total number of counts mapped to the chromosome or the entire genome on which the selected portion or sections are mapped; normalizing raw count data for one or more selected portions to a median reference count for one or more portions or the chromosome on which a selected portion or segments is mapped; normalizing raw count data to previously normalized data or derivatives thereof; and normalizing previously normalized data to one or more other predetermined normalization variables. Normalizing a data set sometimes has the effect of isolating statistical error, depending on the feature or property selected as the predetermined normalization variable. Normalizing a data set sometimes also allows comparison of data characteristics of data having different scales, by bringing the data to a common scale (e.g., predetermined normalization variable). In some embodiments, one or more normalizations to a statistically derived value can be utilized to minimize data differences and diminish the importance of outlying data. Normalizing portions, or portions of a reference genome, with respect to a normalizing value sometimes is referred to as "portion-wise normalization".

In certain embodiments, a processing step comprising normalization includes normalizing to a static window, and in some embodiments, a processing step comprising normalization includes normalizing to a moving or sliding window. The term "window" as used herein refers to one or more portions chosen for analysis, and sometimes used as a reference for comparison (e.g., used for normalization and/or other mathematical or statistical manipulation). The term "normalizing to a static window" as used herein refers to a normalization process using one or more portions selected for comparison between a test subject and reference subject data set. In some embodiments the selected portions are utilized to generate a profile. A static window generally includes a predetermined set of portions that do not change during manipulations and/or analysis. The terms "normalizing to a moving window" and "normalizing to a sliding window" as used herein refer to normalizations performed to portions localized to the genomic region (e.g., immediate genetic surrounding, adjacent portion or sections, and the like) of a selected test portion, where one or more selected test portions are normalized to portions immediately surrounding the selected test portion. In certain embodiments, the selected portions are utilized to generate a profile. A sliding or moving window normalization often includes repeatedly moving or sliding to an adjacent test portion, and normalizing the newly selected test portion to portions immediately surrounding or adjacent to the newly selected test portion, where adjacent windows have one or more portions in common. In certain embodiments, a plurality of selected test portions and/or chromosomes can be analyzed by a sliding window process.

In some embodiments, normalizing to a sliding or moving window can generate one or more values, where each value represents normalization to a different set of reference portions selected from different regions of a genome (e.g., chromosome). In certain embodiments, the one or more values generated are cumulative sums (e.g., a numerical estimate of the integral of the normalized count profile over the selected portion, domain (e.g., part of chromosome), or chromosome). The values generated by the sliding or moving window process can be used to generate a profile and facilitate arriving at an outcome. In some embodiments, cumulative sums of one or more portions can be displayed as a function of genomic position. Moving or sliding window analysis sometimes is used to analyze a genome for the presence or absence of micro-deletions and/or micro-insertions. In certain embodiments, displaying cumulative sums of one or more portions is used to identify the presence or absence of regions of genetic variation (e.g., micro-deletions, micro-duplications). In some embodiments, moving or sliding window analysis is used to identify genomic regions containing micro-deletions and in certain embodiments, moving or sliding window analysis is used to identify genomic regions containing micro-duplications.

A particularly useful normalization methodology for reducing error associated with nucleic acid indicators is referred to herein as Parameterized Error Removal and Unbiased Normalization (PERUN) described herein and for example, in U.S. patent application Ser. No. 13/669,136 and international patent application no. PCT/US12/59123 (WO2013/052913) the entire content of which is incorporated herein by reference, including all text, tables, equations and drawings. PERUN methodology can be applied to a variety of nucleic acid indicators (e.g., nucleic acid sequence reads) for the purpose of reducing effects of error that confound predictions based on such indicators.

For example, PERUN methodology can be applied to nucleic acid sequence reads from a sample and reduce the effects of error that can impair genomic section level determinations. Such an application is useful for using nucleic acid sequence reads to determine the presence or absence of a genetic variation in a subject manifested as a varying level of a nucleotide sequence (e.g., a portion, a genomic section level). Non-limiting examples of variations in portions are chromosome aneuploidies (e.g., trisomy 21, trisomy 18, trisomy 13) and presence or absence of a sex chromosome (e.g., XX in females versus XY in males). A trisomy of an autosome (e.g., a chromosome other than a sex chromosome) can be referred to as an affected autosome. Other non-limiting examples of variations in genomic section levels include microdeletions, microinsertions, duplications and mosaicism.

In certain applications, PERUN methodology can reduce experimental bias by normalizing nucleic acid indicators for particular genomic groups, the latter of which are referred to as portions. Portions include a suitable collection of nucleic acid indicators, a non-limiting example of which includes a length of contiguous nucleotides, which is referred to herein as a genomic section or portion of a reference genome. Bins can include other nucleic acid indicators as described herein. In such applications, PERUN methodology generally normalizes nucleic acid indicators at particular bins across a number of samples in three dimensions.

In certain applications, PERUN methodology can reduce experimental and/or systematic bias by normalizing nucleic acid indicators (e.g., counts, reads) mapped to particular segments (e.g., portions) of a reference genome. In such applications, PERUN methodology generally normalizes counts of nucleic acid reads at particular portions of a reference genome across a number of samples in three dimensions. A detailed description of PERUN and applications thereof is provided in the Examples section herein, in international patent application no. PCT/US12/59123 (WO2013/052913) and U.S. patent application publication no. US20130085681, the entire content of which is incorporated herein by reference, including all text, tables, equations and drawings.

In certain embodiments, PERUN methodology includes calculating a genomic section level for portions of a reference genome from (a) sequence read counts mapped to a portion of a reference genome for a test sample, (b) experimental bias (e.g., GC bias) for the test sample, and (c) one or more fit parameters (e.g., estimates of fit) for a fitted relationship between (i) experimental bias for a portion of a reference genome to which sequence reads are mapped and (ii) counts of sequence reads mapped to the portion. Experimental bias for each of the portions of a reference genome can be determined across multiple samples according to a fitted relationship for each sample between (i) the counts of sequence reads mapped to each of the portions of a reference genome, and (ii) a mapping feature for each of the portions of a reference genome. This fitted relationship for each sample can be assembled for multiple samples in three dimensions. The assembly can be ordered according to the experimental bias in certain embodiments, although PERUN methodology may be practiced without ordering the assembly according to the experimental bias. The fitted relationship for each sample and the fitted relationship for each portion of the reference genome can be fitted independently to a linear function or non-linear function by a suitable fitting method (e.g., a fitting model) known in the art. Non-limiting examples of a suitable model that can be used to fit a relationship include a linear regression model, simple regression model, ordinary least squares regression model, multiple regression model, general multiple regression model, polynomial regression model, general linear model, generalized linear model, discrete choice regression model, logistic regression model, multinomial logit model, mixed logit model, probit model, multinomial probit model, ordered logit model, ordered probit model, Poisson model, multivariate response regression model, multilevel model, fixed effects model, random effects model, mixed model, nonlinear regression model, nonparametric model, semiparametric model, robust model, quantile model, isotonic model, principal components model, least angle model, local model, segmented model, and errors-in-variables model.

In some embodiments, a relationship is a geometric and/or graphical relationship. The terms "relationship" and "relation", as used herein, are synonymous. In some embodiments a relationship is a mathematical relationship. In some embodiments, a relationship is plotted. In some embodiments a relationship is a linear relationship. In certain embodiments a relationship is a non-linear relationship. In certain embodiments a relationship is a regression (e.g., a regression line). A regression can be a linear regression or a non-linear regression. A relationship can be expressed by a mathematical equation. Often a relationship is defined, in part, by one or more constants and/or one or more variables. A relationship can be generated by a method known in the art. A relationship in two dimensions can be generated for one or more samples, in certain embodiments, and a variable probative of error, or possibly probative of error, can be selected for one or more of the dimensions. A relationship can be generated, for example, using graphing software known in the art that plots a graph using values of two or more variables provided by a user. A relationship can be fitted using a method known in the art (e.g., by performing a regression, a regression analysis, e.g., by a suitable regression program, e.g., software). Certain relationships can be fitted by linear regression, and the linear regression can generate a slope value and intercept value. Certain relationships sometimes are not linear and can be fitted by a non-linear function, such as a parabolic, hyperbolic or exponential function (e.g., a quadratic function), for example.

In PERUN methodology, one or more of the fitted relationships may be linear. For an analysis of cell-free circulating nucleic acid from pregnant females, where the experimental bias is GC bias and the mapping feature is GC content, a fitted relationship for a sample between the (i) the counts of sequence reads mapped to each portion, and (ii) GC content for each of the portions of a reference genome, can be linear. For the latter fitted relationship, the slope pertains to GC bias, and a GC bias coefficient can be determined for each sample when the fitted relationships are assembled across multiple samples. In such embodiments, the fitted relationship for multiple samples and a portion between (i) GC bias coefficient for the portion, and (ii) counts of sequence reads mapped to portion, also can be linear. An intercept and slope can be obtained from the latter fitted relationship. In such applications, the slope addresses sample-specific bias based on GC-content and the intercept addresses a portion-specific attenuation pattern common to all samples. PERUN methodology can significantly reduce such sample-specific bias and portion-specific attenuation when calculating genomic section levels for providing an outcome (e.g., presence or absence of genetic variation; determination of fetal sex).

In some embodiments PERUN normalization makes use of fitting to a linear function and is described by Equation A, Equation B or a derivation thereof.

Equation A:

$$M = LI + GS \quad (A)$$

Equation B:

$$L = (M - GS)/I \quad (B)$$

In some embodiments L is a PERUN normalized level or profile. In some embodiments L is the desired output from the PERUN normalization procedure. In certain embodiments L is portion-specific. In some embodiments L is determined according to multiple portions of a reference genome and represents a PERUN normalized level of a genome, chromosome, portions or segment thereof. The level L is often used for further analyses (e.g., to determine Z-values, maternal deletions/duplications, fetal microdeletions/microduplications, fetal gender, sex aneuploidies, and so on). The method of normalizing according to Equation B is named Parameterized Error Removal and Unbiased Normalization (PERUN).

In some embodiments G is a GC bias coefficient measured using a linear model, LOESS, or any equivalent approach. In some embodiments G is a slope. In some embodiments the GC bias coefficient G is evaluated as the slope of the regression for counts M (e.g., raw counts) for portion i and the GC content of portion i determined from a reference genome. In some embodiments G represents secondary information, extracted from M and determined according to a relationship. In some embodiments G represents a relationship for a set of portion-specific counts and a set of portion-specific GC content values for a sample (e.g., a test sample). In some embodiments portion-specific GC content is derived from a reference genome. In some embodiments portion-specific GC content is derived from observed or measured GC content (e.g., measured from the sample). A GC bias coefficient often is determined for each sample in a group of samples and generally is determined for a test sample. A GC bias coefficient often is sample specific. In some embodiments a GC bias coefficient is a constant. In certain embodiments a GC bias coefficient, once derived for a sample, does not change.

In some embodiments I is an intercept and S is a slope derived from a linear relationship. In some embodiments the relationship from which I and S are derived is different than the relationship from which G is derived. In some embodiments the relationship from which I and S are derived is fixed for a given experimental setup. In some embodiments I and S are derived from a linear relationship according to counts (e.g., raw counts) and a GC bias coefficient according to multiple samples. In some embodiments I and S are derived independently of the test sample. In some embodiments I and S are derived from multiple samples. I and S often are portion-specific. In some embodiments, I and S are determined with the assumption that L=1 for all portions of a reference genome in euploid samples. In some embodiments a linear relationship is determined for euploid samples and I and S values specific for a selected portion (assuming L=1) are determined. In certain embodiments the same procedure is applied to all portions of a reference genome in a human genome and a set of intercepts/and slopes S is determined for every portion.

In some embodiments a cross-validation approach is applied. Cross-validation, sometimes is referred to as rotation estimation. In some embodiments a cross-validation approach is applied to assess how accurately a predictive model (e.g., such as PERUN) will perform in practice using a test sample. In some embodiments one round of cross-validation comprises partitioning a sample of data into complementary subsets, performing a cross validation analysis on one subset (e.g., sometimes referred to as a training set), and validating the analysis using another subset (e.g., sometimes called a validation set or test set). In certain embodiments, multiple rounds of cross-validation are performed using different partitions and/or different subsets). Non-limiting examples of cross-validation approaches include leave-one-out, sliding edges, K-fold, 2-fold, repeat random sub-sampling, the like or combinations thereof. In some embodiments a cross-validation randomly selects a work set containing 90% of a set of samples comprising known euploid fetuses and uses that subset to train a model. In certain embodiments, the random selection is repeated 100 times, yielding a set of 100 slopes and 100 intercepts for every portion.

In some embodiments the value of M is a measured value derived from a test sample. In some embodiments M is measured raw counts for a portion. In some embodiments, where the values I and S are available for a portion, measurement M is determined from a test sample and is used to determine the PERUN normalized level L for a genome, chromosome, segment or portion thereof according to Equation B Thus, application of PERUN methodology to sequence reads across multiple samples in parallel can significantly reduce error caused by (i) sample-specific experimental bias (e.g., GC bias) and (ii) portion-specific attenuation common to samples. Other methods in which each of these two sources of error are addressed separately or serially often are not able to reduce these as effectively as PERUN methodology. Without being limited by theory, it is expected that PERUN methodology reduces error more effectively in part because its generally additive processes do not magnify spread as much as generally multiplicative processes utilized in other normalization approaches (e.g., GC-LOESS).

Additional normalization and statistical techniques may be utilized in combination with PERUN methodology. An additional process can be applied before, after and/or during employment of PERUN methodology. Non-limiting examples of processes that can be used in combination with PERUN methodology are described hereafter.

In some embodiments, a secondary normalization or adjustment of a genomic section level for GC content can be utilized in conjunction with PERUN methodology. A suitable GC content adjustment or normalization procedure can be utilized (e.g., GC-LOESS, GCRM). In certain embodiments, a particular sample can be selected and/or identified for application of an additional GC normalization process. For example, application of PERUN methodology can determine GC bias for each sample, and a sample associated with a GC bias above a certain threshold can be selected for an additional GC normalization process. In such embodiments, a predetermined threshold level can be used to select such samples for additional GC normalization.

In certain embodiments, a portion filtering or weighting process can be utilized in conjunction with PERUN methodology. A suitable portion filtering or weighting process can be utilized, non-limiting examples are described herein, in international patent application no. PCT/US12/59123 (WO2013/052913) and U.S. patent application publication no. US20130085681, the entire content of which is incorporated herein by reference, including all text, tables, equations and drawings. In some embodiments, a normalization technique that reduces error associated with maternal insertions, duplications and/or deletions (e.g., maternal and/or fetal copy number variations), is utilized in conjunction with PERUN methodology.

Genomic section levels calculated by PERUN methodology can be utilized directly for providing an outcome. In some embodiments, genomic section levels can be utilized directly to provide an outcome for samples in which fetal fraction is about 2% to about 6% or greater (e.g., fetal fraction of about 4% or greater). Genomic section levels calculated by PERUN methodology sometimes are further processed for the provision of an outcome. In some embodiments, calculated genomic section levels are standardized. In certain embodiments, the sum, mean or median of calculated genomic section levels for a test portion (e.g., chromosome 21) can be divided by the sum, mean or median of calculated genomic section levels for portions other than the test portion (e.g., autosomes other than chromosome 21), to generate an experimental genomic section level. An experimental genomic section level or a raw genomic section level can be used as part of a standardization analysis, such as calculation of a Z-score or Z-score. A Z-score can be generated for a sample by subtracting an expected genomic section level from an experimental genomic section level or raw genomic section level and the resulting value may be divided by a standard deviation for the samples. Resulting Z-scores can be distributed for different samples and analyzed, or can be related to other variables, such as fetal fraction and others, and analyzed, to provide an outcome, in certain embodiments.

As noted herein, PERUN methodology is not limited to normalization according to GC bias and GC content per se, and can be used to reduce error associated with other sources of error. A non-limiting example of a source of non-GC content bias is mappability. When normalization parameters other than GC bias and content are addressed, one or more of the fitted relationships may be non-linear (e.g., hyperbolic, exponential). Where experimental bias is determined from a non-linear relationship, for example, an experimental bias curvature estimation may be analyzed in some embodiments.

PERUN methodology can be applied to a variety of nucleic acid indicators. Non-limiting examples of nucleic acid indicators are nucleic acid sequence reads and nucleic acid levels at a particular location on a microarray. Non-limiting examples of sequence reads include those obtained from cell-free circulating DNA, cell-free circulating RNA, cellular DNA and cellular RNA. PERUN methodology can be applied to sequence reads mapped to suitable reference sequences, such as genomic reference DNA, cellular reference RNA (e.g., transcriptome), and portions thereof (e.g., part(s) of a genomic complement of DNA or RNA transcriptome, part(s) of a chromosome).

Thus, in certain embodiments, cellular nucleic acid (e.g., DNA or RNA) can serve as a nucleic acid indicator. Cellular nucleic acid reads mapped to reference genome portions can be normalized using PERUN methodology. Cellular nucleic acid bound to a particular protein sometimes are referred to chromatin immunoprecipitation (ChIP) processes. ChIP-enriched nucleic acid is a nucleic acid in association with cellular protein, such as DNA or RNA for example. Reads of ChIP-enriched nucleic acid can be obtained using technology known in the art. Reads of ChIP-enriched nucleic acid can be mapped to one or more portions of a reference genome, and results can be normalized using PERUN methodology for providing an outcome.

In certain embodiments, cellular RNA can serve as nucleic acid indicators. Cellular RNA reads can be mapped to reference RNA portions and normalized using PERUN methodology for providing an outcome. Known sequences for cellular RNA, referred to as a transcriptome, or a segment thereof, can be used as a reference to which RNA reads from a sample can be mapped. Reads of sample RNA can be obtained using technology known in the art. Results of RNA reads mapped to a reference can be normalized using PERUN methodology for providing an outcome.

In some embodiments, microarray nucleic acid levels can serve as nucleic acid indicators. Nucleic acid levels across samples for a particular address, or hybridizing nucleic acid, on an array can be analyzed using PERUN methodology, thereby normalizing nucleic acid indicators provided by microarray analysis. In this manner, a particular address or hybridizing nucleic acid on a microarray is analogous to a portion for mapped nucleic acid sequence reads, and PERUN methodology can be used to normalize microarray data to provide an improved outcome.

In some embodiments, a processing step comprises a weighting. The terms "weighted", "weighting" or "weight function" or grammatical derivatives or equivalents thereof, as used herein, refer to a mathematical manipulation of a portion or all of a data set sometimes utilized to alter the influence of certain data set features or variables with respect to other data set features or variables (e.g., increase or decrease the significance and/or contribution of data contained in one or more portions or portions of a reference genome, based on the quality or usefulness of the data in the selected portion or portions of a reference genome). A weighting function can be used to increase the influence of data with a relatively small measurement variance, and/or to decrease the influence of data with a relatively large measurement variance, in some embodiments. For example, portions of a reference genome with under represented or low quality sequence data can be "down weighted" to minimize the influence on a data set, whereas selected portions of a reference genome can be "up weighted" to increase the influence on a data set. A non-limiting example of a weighting function is [1/(standard deviation)$^2$]. A weighting step sometimes is performed in a manner substantially similar to a normalizing step. In some embodiments, a data set is divided by a predetermined variable (e.g., weighting variable). A predetermined variable (e.g., minimized target function, Phi) often is selected to weigh different parts of a data set differently (e.g., increase the influence of certain data types while decreasing the influence of other data types).

In certain embodiments, a processing step can comprise one or more mathematical and/or statistical manipulations. Any suitable mathematical and/or statistical manipulation, alone or in combination, may be used to analyze and/or manipulate a data set described herein. Any suitable number of mathematical and/or statistical manipulations can be used. In some embodiments, a data set can be mathematically and/or statistically manipulated 1 or more, 5 or more, 10 or more or 20 or more times. Non-limiting examples of mathematical and statistical manipulations that can be used include addition, subtraction, multiplication, division, algebraic functions, least squares estimators, curve fitting, differential equations, rational polynomials, double polynomials, orthogonal polynomials, z-scores, p-values, chi values, phi values, analysis of peak levels, determination of peak edge locations, calculation of peak area ratios, analysis of median chromosomal level, calculation of mean absolute deviation, sum of squared residuals, mean, standard deviation, standard error, the like or combinations thereof. A mathematical and/or statistical manipulation can be performed on all or a portion of sequence read data, or processed products thereof. Non-limiting examples of data set variables or features that can be statistically manipulated include raw counts, filtered counts, normalized counts, peak heights, peak widths, peak areas, peak edges, lateral tolerances, P-values, median levels, mean levels, count distribution within a genomic region, relative representation of nucleic acid species, the like or combinations thereof.

In some embodiments, a processing step can comprise the use of one or more statistical algorithms. Any suitable statistical algorithm, alone or in combination, may be used to analyze and/or manipulate a data set described herein. Any suitable number of statistical algorithms can be used. In some embodiments, a data set can be analyzed using 1 or more, 5 or more, 10 or more or 20 or more statistical algorithms. Non-limiting examples of statistical algorithms suitable for use with methods described herein include decision trees, counternulls, multiple comparisons, omnibus test, Behrens-Fisher problem, bootstrapping, Fisher's method for combining independent tests of significance, null hypothesis, type I error, type II error, exact test, one-sample Z test, two-sample Z test, one-sample t-test, paired t-test, two-sample pooled t-test having equal variances, two-sample unpooled t-test having unequal variances, one-proportion z-test, two-proportion z-test pooled, two-proportion z-test unpooled, one-sample chi-square test, two-sample F test for equality of variances, confidence interval, credible interval, significance, meta analysis, simple linear regression, robust linear regression, the like or combinations of the foregoing. Non-limiting examples of data set variables or features that can be analyzed using statistical algorithms include raw counts, filtered counts, normalized counts, peak heights, peak widths, peak edges, lateral tolerances, P-values, median levels, mean levels, count distribution within a genomic region, relative representation of nucleic acid species, the like or combinations thereof.

In certain embodiments, a data set can be analyzed by utilizing multiple (e.g., 2 or more) statistical algorithms (e.g., least squares regression, principle component analysis, linear discriminant analysis, quadratic discriminant analysis, bagging, neural networks, support vector machine models, random forests, classification tree models, K-nearest neighbors, logistic regression and/or loss smoothing) and/or mathematical and/or statistical manipulations (e.g., referred to herein as manipulations). The use of multiple manipulations can generate an N-dimensional space that can be used to provide an outcome, in some embodiments. In certain embodiments, analysis of a data set by utilizing multiple manipulations can reduce the complexity and/or dimensionality of the data set. For example, the use of multiple manipulations on a reference data set can generate an N-dimensional space (e.g., probability plot) that can be used to represent the presence or absence of a genetic variation, depending on the genetic status of the reference samples (e.g., positive or negative for a selected genetic variation). Analysis of test samples using a substantially similar set of manipulations can be used to generate an N-dimensional point for each of the test samples. The complexity and/or dimensionality of a test subject data set sometimes is reduced to a single value or N-dimensional point that can be readily compared to the N-dimensional space generated from the reference data. Test sample data that fall within the N-dimensional space populated by the reference subject data are indicative of a genetic status substantially similar to that of the reference subjects. Test sample data that fall outside of the N-dimensional space populated by the reference subject data are indicative of a genetic status substantially dissimilar to that of the reference subjects. In some embodiments, references are euploid or do not otherwise have a genetic variation or medical condition.

After data sets have been counted, optionally filtered and normalized, the processed data sets can be further manipulated by one or more filtering and/or normalizing procedures, in some embodiments. A data set that has been further manipulated by one or more filtering and/or normalizing procedures can be used to generate a profile, in certain embodiments. The one or more filtering and/or normalizing procedures sometimes can reduce data set complexity and/or dimensionality, in some embodiments. An outcome can be provided based on a data set of reduced complexity and/or dimensionality.

In some embodiments portions may be filtered according to a measure of error (e.g., standard deviation, standard error, calculated variance, p-value, mean absolute error (MAE), average absolute deviation and/or mean absolute deviation (MAD). In certain embodiments a measure of error refers to count variability. In some embodiments portions are filtered according to count variability. In certain embodiments count variability is a measure of error determined for counts mapped to a portion (i.e., portion) of a reference genome for multiple samples (e.g., multiple sample obtained from multiple subjects, e.g., 50 or more, 100 or more, 500 or more 1000 or more, 5000 or more or 10,000 or more subjects). In some embodiments portions with a count variability above a pre-determined upper range are filtered (e.g., excluded from consideration). In some embodiments a pre-determined upper range is a MAD value equal to or greater than about 50, about 52, about 54, about 56, about 58, about 60, about 62, about 64, about 66, about 68, about 70, about 72, about 74 or equal to or greater than about 76. In some embodiments portions with a count variability below a pre-determined lower range are filtered (e.g., excluded from consideration). In some embodiments a pre-determined lower range is a MAD value equal to or less than about 40, about 35, about 30, about 25, about 20, about 15, about 10, about 5, about 1, or equal to or less than about 0. In some embodiments portions with a count variability outside a pre-determined range are filtered (e.g., excluded from consideration). In some embodiments a pre-determined range is a MAD value greater than zero and less than about 76, less than about 74, less than about 73, less than about 72, less than about 71, less than about 70, less than about 69, less than about 68, less than about 67, less than about 66, less than about 65, less than about 64, less than about 62, less than about 60, less than about 58, less than about 56, less than about 54, less than about 52 or less than about 50. In some embodiments a pre-determined range is a MAD value greater than zero and less than about 67.7. In some embodiments portions with a count variability within a pre-determined range are selected (e.g., used for determining the presence or absence of a genetic variation).

In some embodiments the count variability of portions represent a distribution (e.g., a normal distribution). In some embodiments portions are selected within a quantile of the distribution. In some embodiments portions within a quantile equal to or less than about 99.9%, 99.8%, 99.7%, 99.6%, 99.5%, 99.4%, 99.3%, 99.2%, 99.1%, 99.0%, 98.9%, 98.8%, 98.7%, 98.6%, 98.5%, 98.4%, 98.3%, 98.2%, 98.1%, 98.0%, 97%, 96%, 95%, 94%, 93%, 92%, 91%, 90%, 85%, 80%, or equal to or less than a quantile of about 75% for the distribution are selected. In some embodiments portions within a 99% quantile of the distribution of count variability are selected. In some embodiments portions with a MAD>0 and a MAD<67.725 a within the 99% quantile and are selected, resulting in the identification of a set of stable portions of a reference genome.

Non-limiting examples of portion filtering with respect to PERUN is provided herein and in international patent application no. PCT/US12/59123 (WO2013/052913) the entire content of which is incorporated herein by reference, including all text, tables, equations and drawings. Portions may be filtered based on, or based on part on, a measure of error. A measure of error comprising absolute values of deviation, such as an R-factor, can be used for portion removal or weighting in certain embodiments. An R-factor, in some embodiments, is defined as the sum of the absolute deviations of the predicted count values from the actual measurements divided by the predicted count values from the actual measurements (e.g., Equation B herein). While a measure of error comprising absolute values of deviation may be used, a suitable measure of error may be alternatively employed. In certain embodiments, a measure of error not comprising absolute values of deviation, such as a dispersion based on squares, may be utilized. In some embodiments, portions are filtered or weighted according to a measure of mappability (e.g., a mappability score). A portion sometimes is filtered or weighted according to a relatively low number of sequence reads mapped to the portion (e.g., 0, 1, 2, 3, 4, 5 reads mapped to the portion). Portions can be filtered or weighted according to the type of analysis being performed. For example, for chromosome 13, 18 and/or 21 aneuploidy analysis, sex chromosomes may be filtered, and only autosomes, or a subset of autosomes, may be analyzed. For fetal gender determination, autosomes may be filtered, and only sex chromosomes (X and Y), or one of the sex chromosomes (X or Y), may be analyzed.

In particular embodiments, the following filtering process may be employed. The same set of portions (e.g., portions of a reference genome) within a given chromosome (e.g., chromosome 21) are selected and the number of reads in affected and unaffected samples are compared. The gap relates trisomy 21 and euploid samples and it involves a set of portions covering most of chromosome 21. The set of portions is the same between euploid and T21 samples. The distinction between a set of portions and a single section is not crucial, as a portion can be defined. The same genomic region is compared in different patients. This process can be utilized for a trisomy analysis, such as for T13 or T18 in addition to, or instead of, T21.

After data sets have been counted, optionally filtered and normalized, the processed data sets can be manipulated by weighting, in some embodiments. One or more portions can be selected for weighting to reduce the influence of data (e.g., noisy data, uninformative data) contained in the selected portions, in certain embodiments, and in some embodiments, one or more portions can be selected for weighting to enhance or augment the influence of data (e.g., data with small measured variance) contained in the selected portions. In some embodiments, a data set is weighted utilizing a single weighting function that decreases the influence of data with large variances and increases the influence of data with small variances. A weighting function sometimes is used to reduce the influence of data with large variances and augment the influence of data with small variances (e.g., $[1/(\text{standard deviation})^2]$). In some embodiments, a profile plot of processed data further manipulated by weighting is generated to facilitate classification and/or providing an outcome. An outcome can be provided based on a profile plot of weighted data Filtering or weighting of portions can be performed at one or more suitable points in an analysis. For example, portions may be filtered or weighted before or after sequence reads are mapped to portions of a reference genome. Portions may be filtered or weighted before or after an experimental bias for individual genome portions is determined in some embodiments. In certain embodiments, portions may be filtered or weighted before or after genomic section levels are calculated.

After data sets have been counted, optionally filtered, normalized, and optionally weighted, the processed data sets can be manipulated by one or more mathematical and/or statistical (e.g., statistical functions or statistical algorithm) manipulations, in some embodiments. In certain embodiments, processed data sets can be further manipulated by calculating Z-scores for one or more selected portions, chromosomes, or portions of chromosomes. In some embodiments, processed data sets can be further manipulated by calculating P-values. One embodiment of an equation for calculating a Z-score and a p-value is presented in Equation 1 (Example 2). In certain embodiments, mathematical and/or statistical manipulations include one or more assumptions pertaining to ploidy and/or fetal fraction. In some embodiments, a profile plot of processed data further manipulated by one or more statistical and/or mathematical manipulations is generated to facilitate classification and/or providing an outcome. An outcome can be provided based on a profile plot of statistically and/or mathematically manipulated data. An outcome provided based on a profile plot of statistically and/or mathematically manipulated data often includes one or more assumptions pertaining to ploidy and/or fetal fraction.

In certain embodiments, multiple manipulations are performed on processed data sets to generate an N-dimensional space and/or N-dimensional point, after data sets have been counted, optionally filtered and normalized. An outcome can be provided based on a profile plot of data sets analyzed in N-dimensions.

In some embodiments, data sets are processed utilizing one or more peak level analysis, peak width analysis, peak edge location analysis, peak lateral tolerances, the like, derivations thereof, or combinations of the foregoing, as part of or after data sets have processed and/or manipulated. In some embodiments, a profile plot of data processed utilizing one or more peak level analysis, peak width analysis, peak edge location analysis, peak lateral tolerances, the like, derivations thereof, or combinations of the foregoing is generated to facilitate classification and/or providing an outcome. An outcome can be provided based on a profile plot of data that has been processed utilizing one or more peak level analysis, peak width analysis, peak edge location analysis, peak lateral tolerances, the like, derivations thereof, or combinations of the foregoing.

In some embodiments, the use of one or more reference samples that are substantially free of a genetic variation in question can be used to generate a reference median count profile, which may result in a predetermined value representative of the absence of the genetic variation, and often deviates from a predetermined value in areas corresponding to the genomic location in which the genetic variation is located in the test subject, if the test subject possessed the genetic variation.

In test subjects at risk for, or suffering from a medical condition associated with a genetic variation, the numerical value for the selected portion or sections is expected to vary significantly from the predetermined value for non-affected genomic locations. In certain embodiments, the use of one or more reference samples known to carry the genetic variation in question can be used to generate a reference median count profile, which may result in a predetermined value representative of the presence of the genetic variation, and often deviates from a predetermined value in areas corresponding to the genomic location in which a test subject does not carry the genetic variation. In test subjects not at risk for, or suffering from a medical condition associated with a genetic variation, the numerical value for the selected portion or sections is expected to vary significantly from the predetermined value for affected genomic locations.

In some embodiments, analysis and processing of data can include the use of one or more assumptions. A suitable number or type of assumptions can be utilized to analyze or process a data set. Non-limiting examples of assumptions that can be used for data processing and/or analysis include maternal ploidy, fetal contribution, prevalence of certain sequences in a reference population, ethnic background, prevalence of a selected medical condition in related family members, parallelism between raw count profiles from different patients and/or runs after GC-normalization and repeat masking (e.g., GCRM), identical matches represent PCR artifacts (e.g., identical base position), assumptions inherent in a fetal quantifier assay (e.g., FQA), assumptions regarding twins (e.g., if 2 twins and only 1 is affected the effective fetal fraction is only 50% of the total measured fetal fraction (similarly for triplets, quadruplets and the like)), fetal cell free DNA (e.g., cfDNA) uniformly covers the entire genome, the like and combinations thereof.

In those instances where the quality and/or depth of mapped sequence reads does not permit an outcome prediction of the presence or absence of a genetic variation at a desired confidence level (e.g., 95% or higher confidence level), based on the normalized count profiles, one or more additional mathematical manipulation algorithms and/or statistical prediction algorithms, can be utilized to generate additional numerical values useful for data analysis and/or providing an outcome. The term "normalized count profile" as used herein refers to a profile generated using normalized counts. Examples of methods that can be used to generate normalized counts and normalized count profiles are described herein. As noted, mapped sequence reads that have been counted can be normalized with respect to test sample counts or reference sample counts. In some embodiments, a normalized count profile can be presented as a plot.

Profiles

In some embodiments, a processing step can comprise generating one or more profiles (e.g., profile plot) from various aspects of a data set or derivation thereof (e.g., product of one or more mathematical and/or statistical data processing steps known in the art and/or described herein). The term "profile" as used herein refers to a product of a mathematical and/or statistical manipulation of data that can facilitate identification of patterns and/or correlations in large quantities of data. A "profile" often includes values resulting from one or more manipulations of data or data sets, based on one or more criteria. A profile often includes multiple data points. Any suitable number of data points may be included in a profile depending on the nature and/or complexity of a data set. In certain embodiments, profiles may include 2 or more data points, 3 or more data points, 5 or more data points, 10 or more data points, 24 or more data points, 25 or more data points, 50 or more data points, 100 or more data points, 500 or more data points, 1000 or more data points, 5000 or more data points, 10,000 or more data points, or 100,000 or more data points.

In some embodiments, a profile is representative of the entirety of a data set, and in certain embodiments, a profile is representative of a part or subset of a data set. That is, a profile sometimes includes or is generated from data points representative of data that has not been filtered to remove any data, and sometimes a profile includes or is generated from data points representative of data that has been filtered to remove unwanted data. In some embodiments, a data point in a profile represents the results of data manipulation for a portion. In certain embodiments, a data point in a profile includes results of data manipulation for groups of portions. In some embodiments, groups of portions may be adjacent to one another, and in certain embodiments, groups of portions may be from different parts of a chromosome or genome.

Data points in a profile derived from a data set can be representative of any suitable data categorization. Non-limiting examples of categories into which data can be grouped to generate profile data points include: portions based on size, portions based on sequence features (e.g., GC content, AT content, position on a chromosome (e.g., short arm, long arm, centromere, telomere), and the like), levels of expression, chromosome, the like or combinations thereof. In some embodiments, a profile may be generated from data points obtained from another profile (e.g., normalized data profile renormalized to a different normalizing value to generate a renormalized data profile). In certain embodiments, a profile generated from data points obtained from another profile reduces the number of data points and/or complexity of the data set. Reducing the number of data points and/or complexity of a data set often facilitates interpretation of data and/or facilitates providing an outcome.

A profile (e.g., a genomic profile, a chromosome profile, a profile of a segment of a chromosome) often is a collection of normalized or non-normalized counts for two or more portions. A profile often includes at least one level (e.g., a genomic section level), and often comprises two or more levels (e.g., a profile often has multiple levels). A level generally is for a set of portions having about the same counts or normalized counts. Levels are described in greater detail herein. In certain embodiments, a profile comprises one or more portions, which portions can be weighted, removed, filtered, normalized, adjusted, averaged, derived as a mean, added, subtracted, processed or transformed by any combination thereof. A profile often comprises normalized counts mapped to portions defining two or more levels, where the counts are further normalized according to one of the levels by a suitable method. Often counts of a profile (e.g., a profile level) are associated with an uncertainty value.

A profile comprising one or more levels is sometimes padded (e.g., hole padding). Padding (e.g., hole padding) refers to a process of identifying and adjusting levels in a profile that are due to maternal microdeletions or maternal duplications (e.g., copy number variations). In some embodiments levels are padded that are due to fetal microduplications or fetal microdeletions. Microduplications or microdeletions in a profile can, in some embodiments, artificially raise or lower the overall level of a profile (e.g., a profile of a chromosome) leading to false positive or false negative determinations of a chromosome aneuploidy (e.g., a trisomy). In some embodiments levels in a profile that are due to microduplications and/or deletions are identified and adjusted (e.g., padded and/or removed) by a process sometimes referred to as padding or hole padding. In certain embodiments a profile comprises one or more first levels that are significantly different than a second level within the profile, each of the one or more first levels comprise a maternal copy number variation, fetal copy number variation, or a maternal copy number variation and a fetal copy number variation and one or more of the first levels are adjusted.

A profile comprising one or more levels can include a first level and a second level. In some embodiments a first level is different (e.g., significantly different) than a second level. In some embodiments a first level comprises a first set of portions, a second level comprises a second set of portions and the first set of portions is not a subset of the second set of portions. In certain embodiments, a first set of portions is different than a second set of portions from which a first and second level are determined. In some embodiments a profile can have multiple first levels that are different (e.g., significantly different, e.g., have a significantly different value) than a second level within the profile. In some embodiments a profile comprises one or more first levels that are significantly different than a second level within the profile and one or more of the first levels are adjusted. In some embodiments a profile comprises one or more first levels that are significantly different than a second level within the profile, each of the one or more first levels comprise a maternal copy number variation, fetal copy number variation, or a maternal copy number variation and a fetal copy number variation and one or more of the first levels are adjusted. In some embodiments a first level within a profile is removed from the profile or adjusted (e.g., padded). A profile can comprise multiple levels that include one or more first levels significantly different than one or more second levels and often the majority of levels in a profile are second levels, which second levels are about equal to one another. In some embodiments greater than 50%, greater than 60%, greater than 70%, greater than 80%, greater than 90% or greater than 95% of the levels in a profile are second levels.

A profile sometimes is displayed as a plot. For example, one or more levels representing counts (e.g., normalized counts) of portions can be plotted and visualized. Non-limiting examples of profile plots that can be generated include raw count (e.g., raw count profile or raw profile), normalized count, portion-weighted, z-score, p-value, area ratio versus fitted ploidy, median level versus ratio between fitted and measured fetal fraction, principle components, the like, or combinations thereof. Profile plots allow visualization of the manipulated data, in some embodiments. In certain embodiments, a profile plot can be utilized to provide an outcome (e.g., area ratio versus fitted ploidy, median level versus ratio between fitted and measured fetal fraction, principle components). The terms "raw count profile plot" or "raw profile plot" as used herein refer to a plot of counts in each portion in a region normalized to total counts in a region (e.g., genome, portion, chromosome, chromosome portions of a reference genome or a segment of a chromosome). In some embodiments, a profile can be generated using a static window process, and in certain embodiments, a profile can be generated using a sliding window process.

A profile generated for a test subject sometimes is compared to a profile generated for one or more reference subjects, to facilitate interpretation of mathematical and/or statistical manipulations of a data set and/or to provide an outcome. In some embodiments, a profile is generated based on one or more starting assumptions (e.g., maternal contribution of nucleic acid (e.g., maternal fraction), fetal contribution of nucleic acid (e.g., fetal fraction), ploidy of reference sample, the like or combinations thereof). In certain embodiments, a test profile often centers around a predetermined value representative of the absence of a genetic variation, and often deviates from a predetermined value in areas corresponding to the genomic location in which the genetic variation is located in the test subject, if the test subject possessed the genetic variation. In test subjects at risk for, or suffering from a medical condition associated with a genetic variation, the numerical value for a selected portion is expected to vary significantly from the predetermined value for non-affected genomic locations. Depending on starting assumptions (e.g., fixed ploidy or optimized ploidy, fixed fetal fraction or optimized fetal fraction or combinations thereof) the predetermined threshold or cutoff value or threshold range of values indicative of the presence or absence of a genetic variation can vary while still providing an outcome useful for determining the presence or absence of a genetic variation. In some embodiments, a profile is indicative of and/or representative of a phenotype.

By way of a non-limiting example, normalized sample and/or reference count profiles can be obtained from raw sequence read data by (a) calculating reference median counts for selected chromosomes, portions or segments thereof from a set of references known not to carry a genetic variation, (b) removal of uninformative portions from the reference sample raw counts (e.g., filtering); (c) normalizing the reference counts for all remaining portions of a reference genome to the total residual number of counts (e.g., sum of remaining counts after removal of uninformative portions of a reference genome) for the reference sample selected chromosome or selected genomic location, thereby generating a normalized reference subject profile; (d) removing the corresponding portions from the test subject sample; and (e) normalizing the remaining test subject counts for one or more selected genomic locations to the sum of the residual reference median counts for the chromosome or chromosomes containing the selected genomic locations, thereby generating a normalized test subject profile. In certain embodiments, an additional normalizing step with respect to the entire genome, reduced by the filtered portions in (b), can be included between (c) and (d).

A data set profile can be generated by one or more manipulations of counted mapped sequence read data. Some embodiments include the following. Sequence reads are mapped and the number of counts (i.e. sequence tags) mapping to each genomic portion are determined (e.g., counted). A raw count profile is generated from the mapped sequence reads that are counted. An outcome is provided by comparing a raw count profile from a test subject to a reference median count profile for chromosomes, portions or segments thereof from a set of reference subjects known not to possess a genetic variation, in certain embodiments.

In some embodiments, sequence read data is optionally filtered to remove noisy data or uninformative portions. After filtering, the remaining counts typically are summed to generate a filtered data set. A filtered count profile is generated from a filtered data set, in certain embodiments.

After sequence read data have been counted and optionally filtered, data sets can be normalized to generate levels or profiles. A data set can be normalized by normalizing one or more selected portions to a suitable normalizing reference value. In some embodiments, a normalizing reference value is representative of the total counts for the chromosome or chromosomes from which portions are selected. In certain embodiments, a normalizing reference value is representative of one or more corresponding portions, portions of chromosomes or chromosomes from a reference data set prepared from a set of reference subjects known not to possess a genetic variation. In some embodiments, a normalizing reference value is representative of one or more corresponding portions, portions of chromosomes or chromosomes from a test subject data set prepared from a test subject being analyzed for the presence or absence of a genetic variation. In certain embodiments, the normalizing process is performed utilizing a static window approach, and in some embodiments the normalizing process is performed utilizing a moving or sliding window approach. In certain embodiments, a profile comprising normalized counts is generated to facilitate classification and/or providing an outcome. An outcome can be provided based on a plot of a profile comprising normalized counts (e.g., using a plot of such a profile).

Levels

In some embodiments, a value (e.g., a number, a quantitative value) is ascribed to a level. A level can be determined by a suitable method, operation or mathematical process (e.g., a processed level). A level often is, or is derived from, counts (e.g., normalized counts) for a set of portions. In some embodiments a level of a portion is substantially equal to the total number of counts mapped to a portion (e.g., counts, normalized counts). Often a level is determined from counts that are processed, transformed or manipulated by a suitable method, operation or mathematical process known in the art. In some embodiments a level is derived from counts that are processed and non-limiting examples of processed counts include weighted, removed, filtered, normalized, adjusted, averaged, derived as a mean (e.g., mean level), added, subtracted, transformed counts or combination thereof. In some embodiments a level comprises counts that are normalized (e.g., normalized counts of portions). A level can be for counts normalized by a suitable process, non-limiting examples of which include portion-wise normalization, normalization by GC content, linear and nonlinear least squares regression, GC LOESS, LOWESS, PERUN, RM, GCRM, cQn, the like and/or combinations thereof. A level can comprise normalized counts or relative amounts of counts. In some embodiments a level is for counts or normalized counts of two or more portions that are averaged and the level is referred to as an average level. In some embodiments a level is for a set of portions having a mean count or mean of normalized counts which is referred to as a mean level. In some embodiments a level is derived for portions that comprise raw and/or filtered counts. In some embodiments, a level is based on counts that are raw. In some embodiments a level is associated with an uncertainty value (e.g., a standard deviation, a MAD). In some embodiments a level is represented by a Z-score or p-value.

A level for one or more portions is synonymous with a "genomic section level" herein. The term "level" as used herein is sometimes synonymous with the term "elevation". A determination of the meaning of the term "level" can be determined from the context in which it is used. For example, the term "level", when used in the context of genomic sections, profiles, reads and/or counts often means an elevation. The term "level", when used in the context of a substance or composition (e.g., level of RNA, plexing level) often refers to an amount. The term "level", when used in the context of uncertainty (e.g., level of error, level of confidence, level of deviation, level of uncertainty) often refers to an amount.

Normalized or non-normalized counts for two or more levels (e.g., two or more levels in a profile) can sometimes be mathematically manipulated (e.g., added, multiplied, averaged, normalized, the like or combination thereof) according to levels. For example, normalized or non-normalized counts for two or more levels can be normalized according to one, some or all of the levels in a profile. In some embodiments normalized or non-normalized counts of all levels in a profile are normalized according to one level in the profile. In some embodiments normalized or non-normalized counts of a first level in a profile are normalized according to normalized or non-normalized counts of a second level in the profile.

Non-limiting examples of a level (e.g., a first level, a second level) are a level for a set of portions comprising processed counts, a level for a set of portions comprising a mean, median or average of counts, a level for a set of portions comprising normalized counts, the like or any combination thereof. In some embodiments, a first level and a second level in a profile are derived from counts of portions mapped to the same chromosome. In some embodiments, a first level and a second level in a profile are derived from counts of portions mapped to different chromosomes.

In some embodiments a level is determined from normalized or non-normalized counts mapped to one or more portions. In some embodiments, a level is determined from normalized or non-normalized counts mapped to two or more portions, where the normalized counts for each portion often are about the same. There can be variation in counts (e.g., normalized counts) in a set of portions for a level. In a set of portions for a level there can be one or more portions having counts that are significantly different than in other portions of the set (e.g., peaks and/or dips). Any suitable number of normalized or non-normalized counts associated with any suitable number of portions can define a level.

In some embodiments one or more levels can be determined from normalized or non-normalized counts of all or some of the portions of a genome. Often a level can be determined from all or some of the normalized or non-normalized counts of a chromosome, or segment thereof. In some embodiments, two or more counts derived from two or more portions (e.g., a set of portions) determine a level. In some embodiments two or more counts (e.g., counts from two or more portions) determine a level. In some embodiments, counts from 2 to about 100,000 portions determine a level. In some embodiments, counts from 2 to about 50,000, 2 to about 40,000, 2 to about 30,000, 2 to about 20,000, 2 to about 10,000, 2 to about 5000, 2 to about 2500, 2 to about 1250, 2 to about 1000, 2 to about 500, 2 to about 250, 2 to about 100 or 2 to about 60 portions determine a level. In some embodiments counts from about 10 to about 50 portions determine a level. In some embodiments counts from about 20 to about 40 or more portions determine a level. In some embodiments, a level comprises counts from about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60 or more portions. In some embodiments, a level corresponds to a set of portions (e.g., a set of portions of a reference genome, a set of portions of a chromosome or a set of portions of a segment of a chromosome).

In some embodiments, a level is determined for normalized or non-normalized counts of portions that are contiguous. In some embodiments portions (e.g., a set of portions) that are contiguous represent neighboring segments of a genome or neighboring segments of a chromosome or gene. For example, two or more contiguous portions, when aligned by merging the portions end to end, can represent a sequence assembly of a DNA sequence longer than each portion. For example two or more contiguous portions can represent of an intact genome, chromosome, gene, intron, exon or segment thereof. In some embodiments a level is determined from a collection (e.g., a set) of contiguous portions and/or non-contiguous portions.

Different Levels

In some embodiments, a profile of normalized counts comprises a level (e.g., a first level) significantly different than another level (e.g., a second level) within the profile. A first level may be higher or lower than a second level. In some embodiments, a first level is for a set of portions comprising one or more reads comprising a copy number variation (e.g., a maternal copy number variation, fetal copy number variation, or a maternal copy number variation and a fetal copy number variation) and the second level is for a set of portions comprising reads having substantially no copy number variation. In some embodiments, significantly different refers to an observable difference. In some embodiments significantly different refers to statistically different or a statistically significant difference. A statistically significant difference is sometimes a statistical assessment of an observed difference. A statistically significant difference can be assessed by a suitable method in the art. Any suitable threshold or range can be used to determine that two levels are significantly different. In certain embodiments two levels (e.g., mean levels) that differ by about 0.01 percent or more (e.g., 0.01 percent of one or either of the level values) are significantly different. In some embodiments two levels (e.g., mean levels) that differ by about 0.1 percent or more are significantly different. In certain embodiments, two levels (e.g., mean levels) that differ by about 0.5 percent or more are significantly different. In some embodiments two levels (e.g., mean levels) that differ by about 0.5, 0.75, 1, 1.5, 2, 2.5, 3, 3.5, 4, 4.5, 5, 5.5, 6, 6.5, 7, 7.5, 8, 8.5, 9, 9.5 or more than about 10% are significantly different. In some embodiments two levels (e.g., mean levels) are significantly different and there is no overlap in either level and/or no overlap in a range defined by an uncertainty value calculated for one or both levels. In certain embodiments the uncertainty value is a standard deviation expressed as sigma. In some embodiments two levels (e.g., mean levels) are significantly different and they differ by about 1 or more times the uncertainty value (e.g., 1 sigma). In some embodiments two levels (e.g., mean levels) are significantly different and they differ by about 2 or more times the uncertainty value (e.g., 2 sigma), about 3 or more, about 4 or more, about 5 or more, about 6 or more, about 7 or more, about 8 or more, about 9 or more, or about 10 or more times the uncertainty value. In some embodiments two levels (e.g., mean levels) are significantly different when they differ by about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 times the uncertainty value or more. In some embodiments, the confidence level increases as the difference between two levels increases. In certain embodiments, the confidence level decreases as the difference between two levels decreases and/or as the uncertainty value increases. For example, sometimes the confidence level increases with the ratio of the difference between levels and the standard deviation (e.g., MADs).

One or more prediction algorithms may be used to determine significance or give meaning to the detection data collected under variable conditions that may be weighed independently of or dependently on each other. The term "variable" as used herein refers to a factor, quantity, or function of an algorithm that has a value or set of values.

In some embodiments, a first set of portions often includes portions that are different than (e.g., non-overlapping with) a second set of portions. For example, sometimes a first level of normalized counts is significantly different than a second level of normalized counts in a profile, and the first level is for a first set of portions, the second level is for a second set of portions and the portions do not overlap in the first set and second set of portions. In certain embodiments, a first set of portions is not a subset of a second set of portions from which a first level and second level are determined, respectively. In some embodiments a first set of portions is different and/or distinct from a second set of portions from which a first level and second level are determined, respectively.

In some embodiments a first set of portions is a subset of a second set of portions in a profile. For example, sometimes a second level of normalized counts for a second set of portions in a profile comprises normalized counts of a first set of portions for a first level in the profile and the first set of portions is a subset of the second set of portions in the profile. In some embodiments an average, mean or median level is derived from a second level where the second level comprises a first level. In some embodiments, a second level comprises a second set of portions representing an entire chromosome and a first level comprises a first set of portions where the first set is a subset of the second set of portions and the first level represents a maternal copy number variation, fetal copy number variation, or a maternal copy number variation and a fetal copy number variation that is present in the chromosome.

In some embodiments, a value of a second level is closer to the mean, average or median value of a count profile for a chromosome, or segment thereof, than the first level. In some embodiments, a second level is a mean level of a chromosome, a portion of a chromosome or a segment thereof. In some embodiments, a first level is significantly different from a predominant level (e.g., a second level) representing a chromosome, or segment thereof. A profile may include multiple first levels that significantly differ from a second level, and each first level independently can be higher or lower than the second level. In some embodiments, a first level and a second level are derived from the same chromosome and the first level is higher or lower than the second level, and the second level is the predominant level of the chromosome. In some embodiments, a first level and a second level are derived from the same chromosome, a first level is indicative of a copy number variation (e.g., a maternal and/or fetal copy number variation, deletion, insertion, duplication) and a second level is a mean level or predominant level of portions for a chromosome, or segment thereof.

In certain embodiments, a read in a second set of portions for a second level substantially does not include a genetic variation (e.g., a copy number variation, a maternal and/or fetal copy number variation). Often, a second set of portions for a second level includes some variability (e.g., variability in level, variability in counts for portions). In some embodiments, one or more portions in a set of portions for a level associated with substantially no copy number variation include one or more reads having a copy number variation present in a maternal and/or fetal genome. For example, sometimes a set of portions include a copy number variation that is present in a small segment of a chromosome (e.g., less than 10 portions) and the set of portions is for a level associated with substantially no copy number variation. Thus a set of portions that include substantially no copy number variation still can include a copy number variation that is present in less than about 10, 9, 8, 7, 6, 5, 4, 3, 2 or 1 portions of a level.

In some embodiments a first level is for a first set of portions and a second level is for a second set of portions and the first set of portions and second set of portions are contiguous (e.g., adjacent with respect to the nucleic acid sequence of a chromosome or segment thereof). In some embodiments the first set of portions and second set of portions are not contiguous.

Relatively short sequence reads from a mixture of fetal and maternal nucleic acid can be utilized to provide counts which can be transformed into a level and/or a profile. Counts, levels and profiles can be depicted in electronic or tangible form and can be visualized. Counts mapped to portions (e.g., represented as levels and/or profiles) can provide a visual representation of a fetal and/or a maternal genome, chromosome, or a portion or a segment of a chromosome that is present in a fetus and/or pregnant female.

Reference Level and Normalized Reference Value

In some embodiments a profile comprises a reference level (e.g., a level used as a reference). Often a profile of normalized counts provides a reference level from which expected levels and expected ranges are determined (see discussion below on expected levels and ranges). A reference level often is for normalized counts of portions comprising mapped reads from both a mother and a fetus. A reference level is often the sum of normalized counts of mapped reads from a fetus and a mother (e.g., a pregnant female). In some embodiments a reference level is for portions comprising mapped reads from a euploid mother and/or a euploid fetus. In some embodiments a reference level is for portions comprising mapped reads having a fetal and/or maternal genetic variation (e.g., an aneuploidy (e.g., a trisomy), a copy number variation, a microduplication, a microdeletion, an insertion). In some embodiments a reference level is for portions that include substantially no maternal and/or fetal genetic variations (e.g., an aneuploidy (e.g., a trisomy), a copy number variation, a microduplication, a microdeletion, an insertion). In some embodiments a second level is used as a reference level. In certain embodiments a profile comprises a first level of normalized counts and a second level of normalized counts, the first level is significantly different from the second level and the second level is the reference level. In certain embodiments a profile comprises a first level of normalized counts for a first set of portions, a second level of normalized counts for a second set of portions, the first set of portions includes mapped reads having a maternal and/or fetal copy number variation, the second set of portions comprises mapped reads having substantially no maternal copy number variation and/or fetal copy number variation, and the second level is a reference level.

In some embodiments counts mapped to portions for one or more levels of a profile are normalized according to counts of a reference level. In some embodiments, normalizing counts of a level according to counts of a reference level comprise dividing counts of a level by counts of a reference level or a multiple or fraction thereof. Counts normalized according to counts of a reference level often have been normalized according to another process (e.g., PERUN) and counts of a reference level also often have been normalized (e.g., by PERUN). In some embodiments the counts of a level are normalized according to counts of a reference level and the counts of the reference level are scalable to a suitable value either prior to or after normalizing. The process of scaling the counts of a reference level can comprise any suitable constant (i.e., number) and any suitable mathematical manipulation may be applied to the counts of a reference level.

A normalized reference value (NRV) is often determined according to the normalized counts of a reference level. Determining an NRV can comprise any suitable normalization process (e.g., mathematical manipulation) applied to the counts of a reference level where the same normalization process is used to normalize the counts of other levels within the same profile. Determining an NRV often comprises dividing a reference level by itself. Determining an NRV often comprises dividing a reference level by a multiple of itself. Determining an NRV often comprises dividing a reference level by the sum or difference of the reference level and a constant (e.g., any number).

An NRV is sometimes referred to as a null value. An NRV can be any suitable value. In some embodiments, an NRV is any value other than zero. In some embodiments an NRV is a whole number. In some embodiments an NRV is a positive integer. In some embodiments, an NRV is 1, 10, 100 or 1000. Often, an NRV is equal to 1. In some embodiments an NRV is equal to zero. The counts of a reference level can be normalized to any suitable NRV. In some embodiments, the counts of a reference level are normalized to an NRV of zero. Often the counts of a reference level are normalized to an NRV of 1.

Expected Levels

An expected level is sometimes a pre-defined level (e.g., a theoretical level, predicted level). An "expected level" is sometimes referred to herein as a "predetermined level value". In some embodiments, an expected level is a predicted value for a level of normalized counts for a set of portions that include a copy number variation. In certain embodiments, an expected level is determined for a set of portions that include substantially no copy number variation. An expected level can be determined for a chromosome ploidy (e.g., 0, 1, 2 (i.e., diploid), 3 or 4 chromosomes) or a microploidy (homozygous or heterozygous deletion, duplication, insertion or absence thereof). Often an expected level is determined for a maternal microploidy (e.g., a maternal and/or fetal copy number variation).

An expected level for a genetic variation or a copy number variation can be determined by any suitable manner. Often an expected level is determined by a suitable mathematical manipulation of a level (e.g., counts mapped to a set of portions for a level). In some embodiments an expected level is determined by utilizing a constant sometimes referred to as an expected level constant. An expected level for a copy number variation is sometimes calculated by multiplying a reference level, normalized counts of a reference level or an NRV by an expected level constant, adding an expected level constant, subtracting an expected level constant, dividing by an expected level constant, or by a combination thereof. Often an expected level (e.g., an expected level of a maternal and/or fetal copy number variation) determined for the same subject, sample or test group is determined according to the same reference level or NRV.

Often an expected level is determined by multiplying a reference level, normalized counts of a reference level or an NRV by an expected level constant where the reference level, normalized counts of a reference level or NRV is not equal to zero. In some embodiments an expected level is determined by adding an expected level constant to reference level, normalized counts of a reference level or an NRV that is equal to zero. In some embodiments, an expected level, normalized counts of a reference level, NRV and expected level constant are scalable. The process of scaling can comprise any suitable constant (i.e., number) and any suitable mathematical manipulation where the same scaling process is applied to all values under consideration.

Expected Level Constant

An expected level constant can be determined by a suitable method. In some embodiments an expected level constant is arbitrarily determined. Often an expected level constant is determined empirically. In some embodiments an expected level constant is determined according to a mathematical manipulation. In some embodiments an expected level constant is determined according to a reference (e.g., a reference genome, a reference sample, reference test data). In some embodiments, an expected level constant is predetermined for a level representative of the presence or absence of a genetic variation or copy number variation (e.g., a duplication, insertion or deletion). In some embodiments, an expected level constant is predetermined for a level representative of the presence or absence of a maternal copy number variation, fetal copy number variation, or a maternal copy number variation and a fetal copy number variation. An expected level constant for a copy number variation can be any suitable constant or set of constants.

In some embodiments, the expected level constant for a homozygous duplication (e.g., a homozygous duplication) can be from about 1.6 to about 2.4, from about 1.7 to about 2.3, from about 1.8 to about 2.2, or from about 1.9 to about 2.1. In some embodiments the expected level constant for a homozygous duplication is about 1.6, 1.7, 1.8, 1.9, 2.0, 2.1, 2.2, 2.3 or about 2.4. Often the expected level constant for a homozygous duplication is about 1.90, 1.92, 1.94, 1.96, 1.98, 2.0, 2.02, 2.04, 2.06, 2.08 or about 2.10. Often the expected level constant for a homozygous duplication is about 2.

In some embodiments, the expected level constant for a heterozygous duplication (e.g., a homozygous duplication) is from about 1.2 to about 1.8, from about 1.3 to about 1.7, or from about 1.4 to about 1.6. In some embodiments the expected level constant for a heterozygous duplication is about 1.2, 1.3, 1.4, 1.5, 1.6, 1.7 or about 1.8. Often the expected level constant for a heterozygous duplication is about 1.40, 1.42, 1.44, 1.46, 1.48, 1.5, 1.52, 1.54, 1.56, 1.58 or about 1.60. In some embodiments, the expected level constant for a heterozygous duplication is about 1.5.

In some embodiments, the expected level constant for the absence of a copy number variation (e.g., the absence of a maternal copy number variation and/or fetal copy number variation) is from about 1.3 to about 0.7, from about 1.2 to about 0.8, or from about 1.1 to about 0.9. In some embodiments the expected level constant for the absence of a copy number variation is about 1.3, 1.2, 1.1, 1.0, 0.9, 0.8 or about 0.7. Often the expected level constant for the absence of a copy number variation is about 1.09, 1.08, 1.06, 1.04, 1.02, 1.0, 0.98, 0.96, 0.94, or about 0.92. In some embodiments, the expected level constant for the absence of a copy number variation is about 1.

In some embodiments, the expected level constant for a heterozygous deletion (e.g., a maternal, fetal, or a maternal and a fetal heterozygous deletion) is from about 0.2 to about 0.8, from about 0.3 to about 0.7, or from about 0.4 to about 0.6. In some embodiments the expected level constant for a heterozygous deletion is about 0.2, 0.3, 0.4, 0.5, 0.6, 0.7 or about 0.8. Often the expected level constant for a heterozygous deletion is about 0.40, 0.42, 0.44, 0.46, 0.48, 0.5, 0.52, 0.54, 0.56, 0.58 or about 0.60. In some embodiments, the expected level constant for a heterozygous deletion is about 0.5.

In some embodiments, the expected level constant for a homozygous deletion (e.g., a homozygous deletion) can be from about −0.4 to about 0.4, from about −0.3 to about 0.3, from about −0.2 to about 0.2, or from about −0.1 to about 0.1. In some embodiments the expected level constant for a homozygous deletion is about −0.4, −0.3, −0.2, −0.1, 0.0, 0.1, 0.2, 0.3 or about 0.4. Often the expected level constant for a homozygous deletion is about −0.1, −0.08, −0.06, −0.04, −0.02, 0.0, 0.02, 0.04, 0.06, 0.08 or about 0.10. Often the expected level constant for a homozygous deletion is about 0.

Expected Level Range

In some embodiments the presence or absence of a genetic variation or copy number variation (e.g., a maternal copy number variation, fetal copy number variation, or a maternal copy number variation and a fetal copy number variation) is determined by a level that falls within or outside of an expected level range. An expected level range is often determined according to an expected level. In some embodiments an expected level range is determined for a level comprising substantially no genetic variation or substantially no copy number variation. A suitable method can be used to determine an expected level range.

In some embodiments, an expected level range is defined according to a suitable uncertainty value calculated for a level. Non-limiting examples of an uncertainty value are a standard deviation, standard error, calculated variance, p-value, and mean absolute deviation (MAD). In some embodiments, an expected level range for a genetic variation or a copy number variation is determined, in part, by calculating the uncertainty value for a level (e.g., a first level, a second level, a first level and a second level). In some embodiments an expected level range is defined according to an uncertainty value calculated for a profile (e.g., a profile of normalized counts for a chromosome or segment thereof). In some embodiments, an uncertainty value is calculated for a level comprising substantially no genetic variation or substantially no copy number variation. In some embodiments, an uncertainty value is calculated for a first level, a second level or a first level and a second level. In some embodiments an uncertainty value is determined for a first level, a second level or a second level comprising a first level.

An expected level range is sometimes calculated, in part, by multiplying, adding, subtracting, or dividing an uncertainty value by a constant (e.g., a predetermined constant) n. A suitable mathematical procedure or combination of procedures can be used. The constant n (e.g., predetermined constant n) is sometimes referred to as a confidence interval. A selected confidence interval is determined according to the constant n that is selected. The constant n (e.g., the predetermined constant n, the confidence interval) can be determined by a suitable manner. The constant n can be a number or fraction of a number greater than zero. The constant n can be a whole number. Often the constant n is a number less than 10. In some embodiments the constant n is a number less than about 10, less than about 9, less than about 8, less than about 7, less than about 6, less than about 5, less than about 4, less than about 3, or less than about 2. In some embodiments the constant n is about 10, 9.5, 9, 8.5, 8, 7.5, 7, 6.5, 6, 5.5, 5, 4.5, 4, 3.5, 3, 2.5, 2 or 1. The constant n can be determined empirically from data derived from subjects (a pregnant female and/or a fetus) with a known genetic disposition.

Often an uncertainty value and constant n defines a range (e.g., an uncertainty cutoff). For example, sometimes an uncertainty value is a standard deviation (e.g., +/−5) and is multiplied by a constant n (e.g., a confidence interval) thereby defining a range or uncertainty cutoff (e.g., 5n to −5n).

In some embodiments, an expected level range for a genetic variation (e.g., a maternal copy number variation, fetal copy number variation, or a maternal copy number variation and fetal copy number variation) is the sum of an expected level plus a constant n times the uncertainty (e.g., n×sigma (e.g., 6 sigma)). In some embodiments the expected level range for a genetic variation or copy number variation designated by k can be defined by the formula:

(Expected Level Range)$_k$=(Expected Level)$_k$+$n\sigma$    Formula R where $\sigma$ is an uncertainty value, n is a constant (e.g., a predetermined constant) and the expected level range and expected level are for the genetic variation k (e.g., k=a heterozygous deletion, e.g., k=the absence of a genetic variation). For example, for an expected level equal to 1 (e.g., the absence of a copy number variation), an uncertainty value (i.e. a) equal to +/−0.05, and n=3, the expected level range is defined as 1.15 to 0.85. In some embodiments, the expected level range for a heterozygous duplication is determined as 1.65 to 1.35 when the expected level for a heterozygous duplication is 1.5, n=3, and the uncertainty value $\sigma$ is +/−0.05. In some embodiments the expected level range for a heterozygous deletion is determined as 0.65 to 0.35 when the expected level for a heterozygous duplication is 0.5, n=3, and the uncertainty value $\sigma$ is +/−0.05. In some embodiments the expected level range for a homozygous duplication is determined as 2.15 to 1.85 when the expected level for a heterozygous duplication is 2.0, n=3 and the uncertainty value $\sigma$ is +/−0.05. In some embodiments the expected level range for a homozygous deletion is determined as 0.15 to −0.15 when the expected level for a heterozygous duplication is 0.0, n=3 and the uncertainty value $\sigma$ is +/−0.05.

In some embodiments an expected level range for a homozygous copy number variation (e.g., a maternal, fetal or maternal and fetal homozygous copy number variation) is determined, in part, according to an expected level range for a corresponding heterozygous copy number variation. For example, sometimes an expected level range for a homozygous duplication comprises all values greater than an upper limit of an expected level range for a heterozygous duplication. In some embodiments an expected level range for a homozygous duplication comprises all values greater than or equal to an upper limit of an expected level range for a heterozygous duplication. In some embodiments an expected level range for a homozygous duplication comprises all values greater than an upper limit of an expected level range for a heterozygous duplication and less than the upper limit defined by the formula R where $\sigma$ is an uncertainty value and is a positive value, n is a constant and k is a homozygous duplication. In some embodiments an expected level range for a homozygous duplication comprises all values greater than or equal to an upper limit of an expected level range for a heterozygous duplication and less than or equal to the upper limit defined by the formula R where $\sigma$ is an uncertainty value, $\sigma$ is a positive value, n is a constant and k is a homozygous duplication.

In some embodiments, an expected level range for a homozygous deletion comprises all values less than a lower limit of an expected level range for a heterozygous deletion. In some embodiments an expected level range for a homozygous deletion comprises all values less than or equal to a lower limit of an expected level range for a heterozygous deletion. In some embodiments an expected level range for a homozygous deletion comprises all values less than a lower limit of an expected level range for a heterozygous deletion and greater than the lower limit defined by the formula R where $\sigma$ is an uncertainty value, $\sigma$ is a negative value, n is a constant and k is a homozygous deletion. In some embodiments an expected level range for a homozygous deletion comprises all values less than or equal to a lower limit of an expected level range for a heterozygous deletion and greater than or equal to the lower limit defined by the formula R where $\sigma$ is an uncertainty value, $\sigma$ is a negative value, n is a constant and k is a homozygous deletion.

An uncertainty value can be utilized to determine a threshold value. In some embodiments, a range (e.g., a threshold range) is obtained by calculating the uncertainty value determined from a raw, filtered and/or normalized counts. A range can be determined by multiplying the uncertainty value for a level (e.g. normalized counts of a level) by a predetermined constant (e.g., 1, 2, 3, 4, 5, 6, etc.) representing the multiple of uncertainty (e.g., number of standard deviations) chosen as a cutoff threshold (e.g., multiply by 3 for 3 standard deviations), whereby a range is generated, in some embodiments. A range can be determined by adding and/or subtracting a value (e.g., a predetermined value, an uncertainty value, an uncertainty value multiplied by a predetermined constant) to and/or from a level whereby a range is generated, in some embodiments. For example, for a level equal to 1, a standard deviation of +/−0.2, where a predetermined constant is 3, the range can be calculated as (1+3(0.2)) to (1+3(−0.2)), or 1.6 to 0.4. A range sometimes can define an expected range or expected level range for a copy number variation. In certain embodiments, some or all of the portions exceeding a threshold value, falling outside a range or falling inside a range of values, are removed as part of, prior to, or after a normalization process. In some embodiments, some or all of the portions exceeding a calculated threshold value, falling outside a range or falling inside a range are weighted or adjusted as part of, or prior to the normalization or classification process. Examples of weighting are described herein. The terms "redundant data", and "redundant mapped reads" as used herein refer to sample derived sequence reads that are identified as having already been assigned to a genomic location (e.g., base position) and/or counted for a portion.

In some embodiments an uncertainty value is determined according to the formula below:

$$Z = \frac{L_A - L_o}{\sqrt{\frac{\sigma_A^2}{N_A} + \frac{\sigma_o^2}{N_o}}}$$

Where Z represents the standardized deviation between two levels, L is the mean (or median) level and sigma is the standard deviation (or MAD). The subscript O denotes a segment of a profile (e.g., a second level, a chromosome, an NRV, a "euploid level", a level absent a copy number variation), and A denotes another segment of a profile (e.g., a first level, a level representing a copy number variation, a level representing an aneuploidy (e.g., a trisomy). The variable $N_o$ represents the total number of portions in the segment of the profile denoted by the subscript O. $N_A$ represents the total number of portions in the segment of the profile denoted by subscript A.

Categorizing a Copy Number Variation

A level (e.g., a first level) that significantly differs from another level (e.g., a second level) can often be categorized as a copy number variation (e.g., a maternal and/or fetal copy number variation, a fetal copy number variation, a deletion, duplication, insertion) according to an expected level range. In some embodiments, the presence of a copy number variation is categorized when a first level is significantly different from a second level and the first level falls within the expected level range for a copy number variation. For example, a copy number variation (e.g., a maternal and/or fetal copy number variation, a fetal copy number variation) can be categorized when a first level is significantly different from a second level and the first level falls within the expected level range for a copy number variation. In some embodiments a heterozygous duplication (e.g., a maternal or fetal, or maternal and fetal, heterozygous duplication) or heterozygous deletion (e.g., a maternal or fetal, or maternal and fetal, heterozygous deletion) is categorized when a first level is significantly different from a second level and the first level falls within the expected level range for a heterozygous duplication or heterozygous deletion, respectively. In some embodiments a homozygous duplication or homozygous deletion is categorized when a first level is significantly different from a second level and the first level falls within the expected level range for a homozygous duplication or homozygous deletion, respectively.

Level Adjustments

In some embodiments, one or more levels are adjusted. A process for adjusting a level often is referred to as padding. In some embodiments, multiple levels in a profile (e.g., a profile of a genome, a chromosome profile, a profile of a portion or segment of a chromosome) are adjusted. In some embodiments, about 1 to about 10,000 or more levels in a profile are adjusted. In some embodiments about 1 to about a 1000, 1 to about 900, 1 to about 800, 1 to about 700, 1 to about 600, 1 to about 500, 1 to about 400, 1 to about 300, 1 to about 200, 1 to about 100, 1 to about 50, 1 to about 25, 1 to about 20, 1 to about 15, 1 to about 10, or 1 to about 5 levels in a profile are adjusted. In some embodiments one level is adjusted. In some embodiments, a level (e.g., a first level of a normalized count profile) that significantly differs from a second level is adjusted. In some embodiments a level categorized as a copy number variation is adjusted. In some embodiments a level (e.g., a first level of a normalized count profile) that significantly differs from a second level is categorized as a copy number variation (e.g., a copy number variation, e.g., a maternal copy number variation) and is adjusted. In some embodiments, a level (e.g., a first level) is within an expected level range for a maternal copy number variation, fetal copy number variation, or a maternal copy number variation and a fetal copy number variation and the level is adjusted. In some embodiments, one or more levels (e.g., levels in a profile) are not adjusted. In some embodiments, a level (e.g., a first level) is outside an expected level range for a copy number variation and the level is not adjusted. Often, a level within an expected level range for the absence of a copy number variation is not adjusted. Any suitable number of adjustments can be made to one or more levels in a profile. In some embodiments, one or more levels are adjusted. In some embodiments 2 or more, 3 or more, 5 or more, 6 or more, 7 or more, 8 or more, 9 or more and sometimes 10 or more levels are adjusted.

In some embodiments, a value of a first level is adjusted according to a value of a second level. In some embodiments a first level, identified as representative of a copy number variation, is adjusted to the value of a second level, where the second level is often associated with no copy number variation. In certain embodiments, a value of a first level, identified as representative of a copy number variation, is adjusted so the value of the first level is about equal to a value of a second level.

An adjustment can comprise a suitable mathematical operation. In some embodiments an adjustment comprises one or more mathematical operations. In some embodiments a level is adjusted by normalizing, filtering, averaging, multiplying, dividing, adding or subtracting or combination thereof. In some embodiments a level is adjusted by a predetermined value or a constant. In some embodiments a level is adjusted by modifying the value of the level to the value of another level. For example, a first level may be adjusted by modifying its value to the value of a second level. A value in such cases may be a processed value (e.g., mean, normalized value and the like).

In some embodiments a level is categorized as a copy number variation (e.g., a maternal copy number variation) and is adjusted according to a predetermined value referred to herein as a predetermined adjustment value (PAV). Often a PAV is determined for a specific copy number variation. Often a PAV determined for a specific copy number variation (e.g., homozygous duplication, homozygous deletion, heterozygous duplication, heterozygous deletion) is used to adjust a level categorized as a specific copy number variation (e.g., homozygous duplication, homozygous deletion, heterozygous duplication, heterozygous deletion). In certain embodiments, a level is categorized as a copy number variation and is then adjusted according to a PAV specific to the type of copy number variation categorized. In some embodiments a level (e.g., a first level) is categorized as a maternal copy number variation, fetal copy number variation, or a maternal copy number variation and a fetal copy number variation and is adjusted by adding or subtracting a PAV from the level. Often a level (e.g., a first level) is categorized as a maternal copy number variation and is adjusted by adding a PAV to the level. For example, a level categorized as a duplication (e.g., a maternal, fetal or maternal and fetal homozygous duplication) can be adjusted by adding a PAV determined for a specific duplication (e.g., a homozygous duplication) thereby providing an adjusted level. Often a PAV determined for a copy number duplication is a negative value. In some embodiments providing an adjustment to a level representative of a duplication by utilizing a PAV determined for a duplication results in a reduction in the value of the level. In some embodiments, a level (e.g., a first level) that significantly differs from a second level is categorized as a copy number deletion (e.g., a homozygous deletion, heterozygous deletion, homozygous duplication, homozygous duplication) and the first level is adjusted by adding a PAV determined for a copy number deletion. Often a PAV determined for a copy number deletion is a positive value. In some embodiments providing an adjustment to a level representative of a deletion by utilizing a PAV determined for a deletion results in an increase in the value of the level.

A PAV can be any suitable value. Often a PAV is determined according to and is specific for a copy number variation (e.g., a categorized copy number variation). In certain embodiments a PAV is determined according to an expected level for a copy number variation (e.g., a categorized copy number variation) and/or a PAV factor. A PAV sometimes is determined by multiplying an expected level by a PAV factor. For example, a PAV for a copy number variation can be determined by multiplying an expected level determined for a copy number variation (e.g., a heterozygous deletion) by a PAV factor determined for the same copy number variation (e.g., a heterozygous deletion). For example, PAV can be determined by the formula below:

$$PAV_k = (\text{Expected Level})_k \times (\text{PAV factor})_k$$

for the copy number variation k (e.g., k=a heterozygous deletion)

A PAV factor can be any suitable value. In some embodiments a PAV factor for a homozygous duplication is between about −0.6 and about −0.4. In some embodiments a PAV factor for a homozygous duplication is about −0.60, −0.59, −0.58, −0.57, −0.56, −0.55, −0.54, −0.53, −0.52, −0.51, −0.50, −0.49, −0.48, −0.47, −0.46, −0.45, −0.44, −0.43, −0.42, −0.41 and −0.40. Often a PAV factor for a homozygous duplication is about −0.5.

For example, for an NRV of about 1 and an expected level of a homozygous duplication equal to about 2, the PAV for the homozygous duplication is determined as about −1 according to the formula above. In this case, a first level categorized as a homozygous duplication is adjusted by adding about −1 to the value of the first level, for example.

In some embodiments a PAV factor for a heterozygous duplication is between about −0.4 and about −0.2. In some embodiments a PAV factor for a heterozygous duplication is about −0.40, −0.39, −0.38, −0.37, −0.36, −0.35, −0.34, −0.33, −0.32, −0.31, −0.30, −0.29, −0.28, −0.27, −0.26, −0.25, −0.24, −0.23, −0.22, −0.21 and −0.20. Often a PAV factor for a heterozygous duplication is about −0.33.

For example, for an NRV of about 1 and an expected level of a heterozygous duplication equal to about 1.5, the PAV for the homozygous duplication is determined as about −0.495 according to the formula above. In this case, a first level categorized as a heterozygous duplication is adjusted by adding about −0.495 to the value of the first level, for example.

In some embodiments a PAV factor for a heterozygous deletion is between about 0.4 and about 0.2. In some embodiments a PAV factor for a heterozygous deletion is about 0.40, 0.39, 0.38, 0.37, 0.36, 0.35, 0.34, 0.33, 0.32, 0.31, 0.30, 0.29, 0.28, 0.27, 0.26, 0.25, 0.24, 0.23, 0.22, 0.21 and 0.20. Often a PAV factor for a heterozygous deletion is about 0.33.

For example, for an NRV of about 1 and an expected level of a heterozygous deletion equal to about 0.5, the PAV for the heterozygous deletion is determined as about 0.495 according to the formula above. In this case, a first level categorized as a heterozygous deletion is adjusted by adding about 0.495 to the value of the first level, for example.

In some embodiments a PAV factor for a homozygous deletion is between about 0.6 and about 0.4. In some embodiments a PAV factor for a homozygous deletion is about 0.60, 0.59, 0.58, 0.57, 0.56, 0.55, 0.54, 0.53, 0.52, 0.51, 0.50, 0.49, 0.48, 0.47, 0.46, 0.45, 0.44, 0.43, 0.42, 0.41 and 0.40. Often a PAV factor for a homozygous deletion is about 0.5.

For example, for an NRV of about 1 and an expected level of a homozygous deletion equal to about 0, the PAV for the homozygous deletion is determined as about 1 according to the formula above. In this case, a first level categorized as a homozygous deletion is adjusted by adding about 1 to the value of the first level, for example.

In certain embodiments, a PAV is about equal to or equal to an expected level for a copy number variation (e.g., the expected level of a copy number variation).

In some embodiments, counts of a level are normalized prior to making an adjustment. In certain embodiments, counts of some or all levels in a profile are normalized prior to making an adjustment. For example, counts of a level can be normalized according to counts of a reference level or an NRV. In certain embodiments, counts of a level (e.g., a second level) are normalized according to counts of a reference level or an NRV and the counts of all other levels (e.g., a first level) in a profile are normalized relative to the counts of the same reference level or NRV prior to making an adjustment.

In some embodiments, a level of a profile results from one or more adjustments. In certain embodiments, a level of a profile is determined after one or more levels in the profile are adjusted. In some embodiments, a level of a profile is re-calculated after one or more adjustments are made.

In some embodiments, a copy number variation (e.g., a maternal copy number variation, fetal copy number variation, or a maternal copy number variation and a fetal copy number variation) is determined (e.g., determined directly or indirectly) from an adjustment. For example, a level in a profile that was adjusted (e.g., an adjusted first level) can be identified as a maternal copy number variation. In some embodiments, the magnitude of the adjustment indicates the type of copy number variation (e.g., heterozygous deletion, homozygous duplication, and the like). In certain embodiments, an adjusted level in a profile can be identified as representative of a copy number variation according to the value of a PAV for the copy number variation. For example, for a given profile, PAV is about −1 for a homozygous duplication, about −0.5 for a heterozygous duplication, about 0.5 for a heterozygous deletion and about 1 for a homozygous deletion. In the preceding example, a level adjusted by about −1 can be identified as a homozygous duplication, for example. In some embodiments, one or more copy number variations can be determined from a profile or a level comprising one or more adjustments.

In certain embodiments, adjusted levels within a profile are compared. In some embodiments anomalies and errors are identified by comparing adjusted levels. For example, often one or more adjusted levels in a profile are compared and a particular level may be identified as an anomaly or error. In some embodiments an anomaly or error is identified within one or more portions making up a level. An anomaly or error may be identified within the same level (e.g., in a profile) or in one or more levels that represent portions that are adjacent, contiguous, adjoining or abutting. In some embodiments one or more adjusted levels are levels of portions that are adjacent, contiguous, adjoining or abutting where the one or more adjusted levels are compared and an anomaly or error is identified. An anomaly or error can be a peak or dip in a profile or level where a cause of the peak or dip is known or unknown. In certain embodiments adjusted levels are compared and an anomaly or error is identified where the anomaly or error is due to a stochastic, systematic, random or user error. In some embodiments adjusted levels are compared and an anomaly or error is removed from a profile. In certain embodiments, adjusted levels are compared and an anomaly or error is adjusted.

Determining Fetal Nucleic Acid Content

The amount of fetal nucleic acid (e.g., concentration, relative amount, absolute amount, copy number, and the like) in nucleic acid is determined in some embodiments. In certain embodiments, the amount of fetal nucleic acid in a sample is referred to as "fetal fraction". In some embodiments "fetal fraction" refers to the fraction of fetal nucleic acid in circulating cell-free nucleic acid in a sample (e.g., a blood sample, a serum sample, a plasma sample) obtained from a pregnant female. In some embodiments, a method in which a genetic variation is determined also can comprise determining fetal fraction. In some embodiments the presence or absence of a genetic variation is determined according to a fetal fraction (e.g., a fetal fraction determination for a sample). Determining fetal fraction can be performed in a suitable manner, non-limiting examples of which include methods described below.

Fetal fraction can be determined, in some embodiments, using methods described herein for determining fragment length. Cell-free fetal nucleic acid fragments generally are shorter than maternally-derived nucleic acid fragments (see e.g., Chan et al. (2004) Clin. Chem. 50:88-92; Lo et al. (2010) Sci. Transl. Med. 2:61ra91). Thus, fetal fraction can be determined, in some embodiments, by counting fragments under a particular length threshold and comparing the counts to the amount of total nucleic acid in the sample. Methods for counting nucleic acid fragments of a particular length are described in further detail below.

In certain embodiments, the amount of fetal nucleic acid is determined according to markers specific to a male fetus (e.g., Y-chromosome STR markers (e.g., DYS 19, DYS 385, DYS 392 markers); RhD marker in RhD-negative females), allelic ratios of polymorphic sequences, or according to one or more markers specific to fetal nucleic acid and not maternal nucleic acid (e.g., differential epigenetic biomarkers (e.g., methylation; described in further detail below) between mother and fetus, or fetal RNA markers in maternal blood plasma (see e.g., Lo, 2005, Journal of Histochemistry and Cytochemistry 53 (3): 293-296)).

Determination of fetal nucleic acid content (e.g., fetal fraction) sometimes is performed using a fetal quantifier assay (FQA) as described, for example, in U.S. Patent Application Publication No. 2010/0105049, which is hereby incorporated by reference. This type of assay allows for the detection and quantification of fetal nucleic acid in a maternal sample based on the methylation status of the nucleic acid in the sample. In certain embodiments, the amount of fetal nucleic acid from a maternal sample can be determined relative to the total amount of nucleic acid present, thereby providing the percentage of fetal nucleic acid in the sample. In certain embodiments, the copy number of fetal nucleic acid can be determined in a maternal sample. In certain embodiments, the amount of fetal nucleic acid can be determined in a sequence-specific (or portion-specific) manner and sometimes with sufficient sensitivity to allow for accurate chromosomal dosage analysis (for example, to detect the presence or absence of a fetal aneuploidy).

A fetal quantifier assay (FQA) can be performed in conjunction with any of the methods described herein. Such an assay can be performed by any method known in the art and/or described in U.S. Patent Application Publication No. 2010/0105049, such as, for example, by a method that can distinguish between maternal and fetal DNA based on differential methylation status, and quantify (i.e. determine the amount of) the fetal DNA. Methods for differentiating nucleic acid based on methylation status include, but are not limited to, methylation sensitive capture, for example, using a MBD2-Fc fragment in which the methyl binding domain of MBD2 is fused to the Fc fragment of an antibody (MBD-FC) (Gebhard et al. (2006) Cancer Res. 66(12):6118-28); methylation specific antibodies; bisulfite conversion methods, for example, MSP (methylation-sensitive PCR), COBRA, methylation-sensitive single nucleotide primer extension (Ms-SNuPE) or Sequenom MassCLEAVE™ technology; and the use of methylation sensitive restriction enzymes (e.g., digestion of maternal DNA in a maternal sample using one or more methylation sensitive restriction enzymes thereby enriching the fetal DNA). Methyl-sensitive enzymes also can be used to differentiate nucleic acid based on methylation status, which, for example, can preferentially or substantially cleave or digest at their DNA recognition sequence if the latter is non-methylated. Thus, an unmethylated DNA sample will be cut into smaller fragments than a methylated DNA sample and a hypermethylated DNA sample will not be cleaved. Except where explicitly stated, any method for differentiating nucleic acid based on methylation status can be used with the compositions and methods of the technology herein. The amount of fetal DNA can be determined, for example, by introducing one or more competitors at known concentrations during an amplification reaction. Determining the amount of fetal DNA also can be done, for example, by RT-PCR, primer extension, sequencing and/or counting. In certain instances, the amount of nucleic acid can be determined using BEAMing technology as described in U.S. Patent Application Publication No. 2007/0065823. In certain embodiments, the restriction efficiency can be determined and the efficiency rate is used to further determine the amount of fetal DNA.

In certain embodiments, a fetal quantifier assay (FQA) can be used to determine the concentration of fetal DNA in a maternal sample, for example, by the following method: a) determine the total amount of DNA present in a maternal sample; b) selectively digest the maternal DNA in a maternal sample using one or more methylation sensitive restriction enzymes thereby enriching the fetal DNA; c) determine the amount of fetal DNA from step b); and d) compare the amount of fetal DNA from step c) to the total amount of DNA from step a), thereby determining the concentration of fetal DNA in the maternal sample. In certain embodiments, the absolute copy number of fetal nucleic acid in a maternal sample can be determined, for example, using mass spectrometry and/or a system that uses a competitive PCR approach for absolute copy number measurements. See for example, Ding and Cantor (2003) PNAS USA 100:3059-3064, and U.S. Patent Application Publication No. 2004/0081993, both of which are hereby incorporated by reference.

In certain embodiments, fetal fraction can be determined based on allelic ratios of polymorphic sequences (e.g., single nucleotide polymorphisms (SNPs)), such as, for example, using a method described in U.S. Patent Application Publication No. 2011/0224087, which is hereby incorporated by reference. In such a method, nucleotide sequence reads are obtained for a maternal sample and fetal fraction is determined by comparing the total number of nucleotide sequence reads that map to a first allele and the total number of nucleotide sequence reads that map to a second allele at an informative polymorphic site (e.g., SNP) in a reference genome. In certain embodiments, fetal alleles are identified, for example, by their relative minor contribution to the mixture of fetal and maternal nucleic acids in the sample when compared to the major contribution to the mixture by the maternal nucleic acids. Accordingly, the relative abundance of fetal nucleic acid in a maternal sample can be determined as a parameter of the total number of unique sequence reads mapped to a target nucleic acid sequence on a reference genome for each of the two alleles of a polymorphic site.

The amount of fetal nucleic acid in extracellular nucleic acid can be quantified and used in conjunction with a method provided herein. Thus, in certain embodiments, methods of the technology described herein comprise an additional step of determining the amount of fetal nucleic acid. The amount of fetal nucleic acid can be determined in a nucleic acid sample from a subject before or after processing to prepare sample nucleic acid. In certain embodiments, the amount of fetal nucleic acid is determined in a sample after sample nucleic acid is processed and prepared, which amount is utilized for further assessment. In some embodiments, an outcome comprises factoring the fraction of fetal nucleic acid in the sample nucleic acid (e.g., adjusting counts, removing samples, making a call or not making a call).

The determination step can be performed before, during, at any one point in a method described herein, or after certain (e.g., aneuploidy detection, fetal gender determination) methods described herein. For example, to achieve a fetal gender or aneuploidy determination method with a given sensitivity or specificity, a fetal nucleic acid quantification method may be implemented prior to, during or after fetal gender or aneuploidy determination to identify those samples with greater than about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% or more fetal nucleic acid. In some embodiments, samples determined as having a certain threshold amount of fetal nucleic acid (e.g., about 15% or more fetal nucleic acid; about 4% or more fetal nucleic acid) are further analyzed for fetal gender or aneuploidy determination, or the presence or absence of aneuploidy or genetic variation, for example. In certain embodiments, determinations of, for example, fetal gender or the presence or absence of aneuploidy are selected (e.g., selected and communicated to a patient) only for samples having a certain threshold amount of fetal nucleic acid (e.g., about 15% or more fetal nucleic acid; about 4% or more fetal nucleic acid).

In some embodiments, the determination of fetal fraction or determining the amount of fetal nucleic acid is not required or necessary for identifying the presence or absence of a chromosome aneuploidy. In some embodiments, identifying the presence or absence of a chromosome aneuploidy does not require the sequence differentiation of fetal versus maternal DNA. In certain embodiments this is because the summed contribution of both maternal and fetal sequences in a particular chromosome, chromosome portion or segment thereof is analyzed. In some embodiments, identifying the presence or absence of a chromosome aneuploidy does not rely on a priori sequence information that would distinguish fetal DNA from maternal DNA.

Fetal Fraction Determination Based on Level

In some embodiments, a fetal fraction is determined according to a level categorized as representative of a maternal and/or fetal copy number variation. For example determining fetal fraction often comprises assessing an expected level for a maternal and/or fetal copy number variation utilized for the determination of fetal fraction. In some embodiments a fetal fraction is determined for a level (e.g., a first level) categorized as representative of a copy number variation according to an expected level range determined for the same type of copy number variation. Often a fetal fraction is determined according to an observed level that falls within an expected level range and is thereby categorized as a maternal and/or fetal copy number variation. In some embodiments a fetal fraction is determined when an observed level (e.g., a first level) categorized as a maternal and/or fetal copy number variation is different than the expected level determined for the same maternal and/or fetal copy number variation.

In some embodiments a level (e.g., a first level, an observed level), is significantly different than a second level, the first level is categorized as a maternal and/or fetal copy number variation, and a fetal fraction is determined according to the first level. In some embodiments a first level is an observed and/or experimentally obtained level that is significantly different than a second level in a profile and a fetal fraction is determined according to the first level. In some embodiments the first level is an average, mean or summed level and a fetal fraction is determined according to the first level. In certain embodiments a first level and a second level are observed and/or experimentally obtained levels and a fetal fraction is determined according to the first level. In some instances a first level comprises normalized counts for a first set of portions and a second level comprises normalized counts for a second set of portions and a fetal fraction is determined according to the first level. In some embodiments a first set of portions of a first level includes a copy number variation (e.g., the first level is representative of a copy number variation) and a fetal fraction is determined according to the first level. In some embodiments the first set of portions of a first level includes a homozygous or heterozygous maternal copy number variation and a fetal fraction is determined according to the first level. In some embodiments a profile comprises a first level for a first set of portions and a second level for a second set of portions, the second set of portions includes substantially no copy number variation (e.g., a maternal copy number variation, fetal copy number variation, or a maternal copy number variation and a fetal copy number variation) and a fetal fraction is determined according to the first level.

In some embodiments a level (e.g., a first level, an observed level), is significantly different than a second level, the first level is categorized as for a maternal and/or fetal copy number variation, and a fetal fraction is determined according to the first level and/or an expected level of the copy number variation. In some embodiments a first level is categorized as for a copy number variation according to an expected level for a copy number variation and a fetal fraction is determined according to a difference between the first level and the expected level. In certain embodiments a level (e.g., a first level, an observed level) is categorized as a maternal and/or fetal copy number variation, and a fetal fraction is determined as twice the difference between the first level and expected level of the copy number variation. In some embodiments a level (e.g., a first level, an observed level) is categorized as a maternal and/or fetal copy number variation, the first level is subtracted from the expected level thereby providing a difference, and a fetal fraction is determined as twice the difference. In some embodiments a level (e.g., a first level, an observed level) is categorized as a maternal and/or fetal copy number variation, an expected level is subtracted from a first level thereby providing a difference, and the fetal fraction is determined as twice the difference.

Often a fetal fraction is provided as a percent. For example, a fetal fraction can be divided by 100 thereby providing a percent value. For example, for a first level representative of a maternal homozygous duplication and having a level of 155 and an expected level for a maternal homozygous duplication having a level of 150, a fetal fraction can be determined as 10% (e.g., (fetal fraction=2× (155−150)).

In some embodiments a fetal fraction is determined from two or more levels within a profile that are categorized as copy number variations. For example, sometimes two or more levels (e.g., two or more first levels) in a profile are identified as significantly different than a reference level (e.g., a second level, a level that includes substantially no copy number variation), the two or more levels are categorized as representative of a maternal and/or fetal copy number variation and a fetal fraction is determined from each of the two or more levels. In some embodiments a fetal fraction is determined from about 3 or more, about 4 or more, about 5 or more, about 6 or more, about 7 or more, about 8 or more, or about 9 or more fetal fraction determinations within a profile. In some embodiments a fetal fraction is determined from about 10 or more, about 20 or more, about 30 or more, about 40 or more, about 50 or more, about 60 or more, about 70 or more, about 80 or more, or about 90 or more fetal fraction determinations within a profile. In some embodiments a fetal fraction is determined from about 100 or more, about 200 or more, about 300 or more, about 400 or more, about 500 or more, about 600 or more, about 700 or more, about 800 or more, about 900 or more, or about 1000 or more fetal fraction determinations within a profile. In some embodiments a fetal fraction is determined from about 10 to about 1000, about 20 to about 900, about 30 to about 700, about 40 to about 600, about 50 to about 500, about 50 to about 400, about 50 to about 300, about 50 to about 200, or about 50 to about 100 fetal fraction determinations within a profile.

In some embodiments a fetal fraction is determined as the average or mean of multiple fetal fraction determinations within a profile. In certain embodiments, a fetal fraction determined from multiple fetal fraction determinations is a mean (e.g., an average, a mean, a standard average, a median, or the like) of multiple fetal fraction determinations. Often a fetal fraction determined from multiple fetal fraction determinations is a mean value determined by a suitable method known in the art or described herein. In some embodiments a mean value of a fetal fraction determination is a weighted mean. In some embodiments a mean value of a fetal fraction determination is an unweighted mean. A mean, median or average fetal fraction determination (i.e., a mean, median or average fetal fraction determination value) generated from multiple fetal fraction determinations is sometimes associated with an uncertainty value (e.g., a variance, standard deviation, MAD, or the like). Before determining a mean, median or average fetal fraction value from multiple determinations, one or more deviant determinations are removed in some embodiments (described in greater detail herein).

Some fetal fraction determinations within a profile sometimes are not included in the overall determination of a fetal fraction (e.g., mean or average fetal fraction determination). In some embodiments a fetal fraction determination is derived from a first level (e.g., a first level that is significantly different than a second level) in a profile and the first level is not indicative of a genetic variation. For example, some first levels (e.g., spikes or dips) in a profile are generated from anomalies or unknown causes. Such values often generate fetal fraction determinations that differ significantly from other fetal fraction determinations obtained from true copy number variations. In some embodiments fetal fraction determinations that differ significantly from other fetal fraction determinations in a profile are identified and removed from a fetal fraction determination. For example, some fetal fraction determinations obtained from anomalous spikes and dips are identified by comparing them to other fetal fraction determinations within a profile and are excluded from the overall determination of fetal fraction.

In some embodiments, an independent fetal fraction determination that differs significantly from a mean, median or average fetal fraction determination is an identified, recognized and/or observable difference. In certain embodiments, the term "differs significantly" can mean statistically different and/or a statistically significant difference. An "independent" fetal fraction determination can be a fetal fraction determined (e.g., in some embodiments a single determination) from a specific level categorized as a copy number variation. Any suitable threshold or range can be used to determine that a fetal fraction determination differs significantly from a mean, median or average fetal fraction determination. In certain embodiments a fetal fraction determination differs significantly from a mean, median or average fetal fraction determination and the determination can be expressed as a percent deviation from the average or mean value. In certain embodiments a fetal fraction determination that differs significantly from a mean, median or average fetal fraction determination differs by about 10 percent or more. In some embodiments a fetal fraction determination that differs significantly from a mean, median or average fetal fraction determination differs by about 15 percent or more. In some embodiments a fetal fraction determination that differs significantly from a mean, median or average fetal fraction determination differs by about 15% to about 100% or more.

In certain embodiments a fetal fraction determination differs significantly from a mean, median or average fetal fraction determination according to a multiple of an uncertainty value associated with the mean or average fetal fraction determination. Often an uncertainty value and constant n (e.g., a confidence interval) defines a range (e.g., an uncertainty cutoff). For example, sometimes an uncertainty value is a standard deviation for fetal fraction determinations (e.g., +/−5) and is multiplied by a constant n (e.g., a confidence interval) thereby defining a range or uncertainty cutoff (e.g., 5n to −5n, sometimes referred to as 5 sigma). In some embodiments an independent fetal fraction determination falls outside a range defined by the uncertainty cutoff and is considered significantly different from a mean, median or average fetal fraction determination. For example, for a mean value of 10 and an uncertainty cutoff of 3, an independent fetal fraction greater than 13 or less than 7 is significantly different. In some embodiments a fetal fraction determination that differs significantly from a mean, median or average fetal fraction determination differs by more than n times the uncertainty value (e.g., n×sigma) where n is about equal to or greater than 1, 2, 3, 4, 5, 6, 7, 8, 9 or 10. In some embodiments a fetal fraction determination that differs significantly from a mean, median or average fetal fraction determination differs by more than n times the uncertainty value (e.g., n×sigma) where n is about equal to or greater than 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0.

In some embodiments, a level is representative of a fetal and/or maternal microploidy. In some embodiments a level (e.g., a first level, an observed level), is significantly different than a second level, the first level is categorized as a maternal and/or fetal copy number variation, and the first level and/or second level is representative of a fetal microploidy and/or a maternal microploidy. In certain embodiments a first level is representative of a fetal microploidy, In some embodiments a first level is representative of a maternal microploidy. Often a first level is representative of a fetal microploidy and a maternal microploidy. In some embodiments a level (e.g., a first level, an observed level), is significantly different than a second level, the first level is categorized as a maternal and/or fetal copy number variation, the first level is representative of a fetal and/or maternal microploidy and a fetal fraction is determined according to the fetal and/or maternal microploidy. In some instances a first level is categorized as a maternal and/or fetal copy number variation, the first level is representative of a fetal microploidy and a fetal fraction is determined according to the fetal microploidy. In some embodiments a first level is categorized as a maternal and/or fetal copy number variation, the first level is representative of a maternal microploidy and a fetal fraction is determined according to the maternal microploidy. In some embodiments a first level is categorized as a maternal and/or fetal copy number variation, the first level is representative of a maternal and a fetal microploidy and a fetal fraction is determined according to the maternal and fetal microploidy.

In some embodiments, a determination of a fetal fraction comprises determining a fetal and/or maternal microploidy. In some embodiments a level (e.g., a first level, an observed level), is significantly different than a second level, the first level is categorized as a maternal and/or fetal copy number variation, a fetal and/or maternal microploidy is determined according to the first level and/or second level and a fetal fraction is determined. In some embodiments a first level is categorized as a maternal and/or fetal copy number variation, a fetal microploidy is determined according to the first level and/or second level and a fetal fraction is determined according to the fetal microploidy. In certain embodiments a first level is categorized as a maternal and/or fetal copy number variation, a maternal microploidy is determined according to the first level and/or second level and a fetal fraction is determined according to the maternal microploidy. In some embodiments a first level is categorized as a maternal and/or fetal copy number variation, a maternal and fetal microploidy is determined according to the first level and/or second level and a fetal fraction is determined according to the maternal and fetal microploidy.

A fetal fraction often is determined when the microploidy of the mother is different from (e.g., not the same as) the microploidy of the fetus for a given level or for a level categorized as a copy number variation. In some embodiments a fetal fraction is determined when the mother is homozygous for a duplication (e.g., a microploidy of 2) and the fetus is heterozygous for the same duplication (e.g., a microploidy of 1.5). In some embodiments a fetal fraction is determined when the mother is heterozygous for a duplication (e.g., a microploidy of 1.5) and the fetus is homozygous for the same duplication (e.g., a microploidy of 2) or the duplication is absent in the fetus (e.g., a microploidy of 1). In some embodiments a fetal fraction is determined when the mother is homozygous for a deletion (e.g., a microploidy of 0) and the fetus is heterozygous for the same deletion (e.g., a microploidy of 0.5). In some embodiments a fetal fraction is determined when the mother is heterozygous for a deletion (e.g., a microploidy of 0.5) and the fetus is homozygous for the same deletion (e.g., a microploidy of 0) or the deletion is absent in the fetus (e.g., a microploidy of 1).

In certain embodiments, a fetal fraction cannot be determined when the microploidy of the mother is the same (e.g., identified as the same) as the microploidy of the fetus for a given level identified as a copy number variation. For example, for a given level where both the mother and fetus carry the same number of copies of a copy number variation, a fetal fraction is not determined, in some embodiments. For example, a fetal fraction cannot be determined for a level categorized as a copy number variation when both the mother and fetus are homozygous for the same deletion or homozygous for the same duplication. In certain embodiments, a fetal fraction cannot be determined for a level categorized as a copy number variation when both the mother and fetus are heterozygous for the same deletion or heterozygous for the same duplication. In embodiments where multiple fetal fraction determinations are made for a sample, determinations that significantly deviate from a mean, median or average value can result from a copy number variation for which maternal ploidy is equal to fetal ploidy, and such determinations can be removed from consideration.

In some embodiments the microploidy of a maternal copy number variation and fetal copy number variation is unknown. In some embodiments, in cases when there is no determination of fetal and/or maternal microploidy for a copy number variation, a fetal fraction is generated and compared to a mean, median or average fetal fraction determination. A fetal fraction determination for a copy number variation that differs significantly from a mean, median or average fetal fraction determination is sometimes because the microploidy of the mother and fetus are the same for the copy number variation. A fetal fraction determination that differs significantly from a mean, median or average fetal fraction determination is often excluded from an overall fetal fraction determination regardless of the source or cause of the difference. In some embodiments, the microploidy of the mother and/or fetus is determined and/or verified by a method known in the art (e.g., by targeted sequencing methods).

Additional Methods of Fetal Fraction Determination

Fetal fraction (e.g., for a sample) can be determined, in some embodiments, according to portion-specific fetal fraction estimates. Without being limited to theory, it has been determined herein that the amount reads from fetal CCF fragments (e.g., fragments of a particular length, or range of lengths) map with ranging frequencies to portions (e.g., within the same sample, e.g., within the same sequencing run). Also, without being limited to theory, it has been determined herein that certain portions, when compared among multiple samples, tend to have a similar representation of reads from fetal CCF fragments (e.g., fragments of a particular length, or range of lengths), and that the representation correlates with portion-specific fetal fractions (e.g., the relative amount, percentage or ratio of CCF fragments originating from a fetus).

In some embodiments portion-specific fetal fraction estimates are determined based in part on portion-specific parameters and their relation to fetal fraction. Portion-specific parameters can be any suitable parameter that is reflective of (e.g., correlates with) the amount or proportion of reads from CCF fragment lengths of a particular size (e.g., size range) in a portion. A portion-specific parameter can be an average, mean or median of portion-specific parameters determined for multiple samples. Any suitable portion-specific parameter can be used. Non-limiting examples of portion-specific parameters include FLR (e.g., FRS), an amount of reads having a length less than a selected fragment length, genomic coverage (i.e., coverage), mappability, counts (e.g., counts of sequence reads mapped to the portion, e.g., normalized counts, PERUN normalized counts), DNaseI-sensitivity, methylation state, acetylation, histone distribution, guanine-cytosine (GC) content, chromatin structure, the like or combinations thereof. A portion-specific parameter can be any suitable parameter that correlates with FLR and/or FRS in a portion-specific manner. In some embodiments, some or all portion-specific parameters are a direct or indirect representation of an FLR for a portion. In some embodiments a portion-specific parameter is not guanine-cytosine (GC) content.

In some embodiments a portion-specific parameter is any suitable value representing, correlated with or proportional to an amount of reads from CCF fragments where the reads mapped to a portion have a length less than a selected fragment length. In certain embodiments, a portion-specific parameter is a representation of the amount of reads derived from relatively short CCF fragments (e.g., about 200 base pairs or less) that map to a portion. CCF fragments having a length less than a selected fragment length often are relatively short CCF fragments, and sometimes a selected fragment length is about 200 base pairs or less (e.g., CCF fragments that are about 190, 180, 170, 160, 150, 140, 130, 120, 110, 100, 90, or 80 bases in length). The length of a CCF fragment or a read derived from a CCF fragment can be determined (e.g., deduced or inferred) by any suitable method (e.g., a sequencing method, a hybridization approach). In some embodiments the length of a CCF fragment is determined (e.g., deduced or inferred) by a read obtained from a paired-end sequencing method. In certain embodiments the length of a CCF fragment template is determined directly from the length of a read derived from the CCF fragment (e.g., single-end read).

Portion-specific parameters can be weighted or adjusted by one or more weighting factors. In some embodiments weighted or adjusted portion-specific parameters can provide portion-specific fetal fraction estimates for a sample (e.g., a test sample). In some embodiments weighting or adjusting generally converts the counts of a portion (e.g., reads mapped to a portion) or another portion-specific parameter into a portion-specific fetal fraction estimate, and such a conversion sometimes is considered a transformation.

In some embodiments a weighting factor is a coefficient or constant that, in part, describes and/or defines a relation between a fetal fraction (e.g., a fetal fraction determined from multiple samples) and a portion-specific parameter for multiple samples (e.g., a training set). In some embodiments a weighting factor is determined according to a relation for multiple fetal fraction determinations and multiple portion-specific parameters. A relation may be defined by one or more weighting factors and one or more weighting factors may be determined from a relation. In some embodiments a weighting factor (e.g., one or more weighting factors) is determined from a fitted relation for a portion according to (i) a fraction of fetal nucleic acid determined for each of multiple samples, and (ii) a portion-specific parameter for multiple samples.

A weighting factor can be any suitable coefficient, estimated coefficient or constant derived from a suitable relation (e.g., a suitable mathematical relation, an algebraic relation, a fitted relation, a regression, a regression analysis, a regression model). A weighting factor can be determined according to, derived from, or estimated from a suitable relation. In some embodiments weighting factors are estimated coefficients from a fitted relation. Fitting a relation for multiple samples is sometimes referred to herein as training a model. Any suitable model and/or method of fitting a relationship (e.g., training a model to a training set) can be used. Non-limiting examples of a suitable model that can be used include a regression model, linear regression model, simple regression model, ordinary least squares regression model, multiple regression model, general multiple regression model, polynomial regression model, general linear model, generalized linear model, discrete choice regression model, logistic regression model, multinomial logit model, mixed logit model, probit model, multinomial probit model, ordered logit model, ordered probit model, Poisson model, multivariate response regression model, multilevel model, fixed effects model, random effects model, mixed model, nonlinear regression model, nonparametric model, semiparametric model, robust model, quantile model, isotonic model, principal components model, least angle model, local model, segmented model, and errors-in-variables model. In some embodiments a fitted relation is not a regression model. In some embodiments a fitted relations is chosen from a decision tree model, support-vector machine model and neural network model. The result of training a model (e.g., a regression model, a relation) is often a relation that can be described mathematically where the relation comprises one or more coefficients (e.g., weighting factors). For example, for a linear least squared model, a general multiple regression model can be trained using fetal fraction values and a portion-specific parameter (e.g., coverage, e.g., see Example 7) resulting in a relationship described by equation (30) where the weighting factor $\beta$ is further defined in equations (31), (32) and (33). More complex multivariate models may determine one, two, three or more weighting factors. In some embodiments a model is trained according to fetal fraction and two or more portion-specific parameters (e.g., coefficients) obtained from multiple samples (e.g., fitted relationships fitted to multiple samples, e.g., by a matrix).

A weighting factor can be derived from a suitable relation (e.g., a suitable mathematical relation, an algebraic relation, a fitted relation, a regression, a regression analysis, a regression model) by a suitable method. In some embodiments fitted relations are fitted by an estimation, non-limiting examples of which include least squares, ordinary least squares, linear, partial, total, generalized, weighted, non-linear, iteratively reweighted, ridge regression, least absolute deviations, Bayesian, Bayesian multivariate, reduced-rank, LASSO, Weighted Rank Selection Criteria (WRSC), Rank Selection Criteria (RSC), an elastic net estimator (e.g., an elastic net regression) and combinations thereof.

A weighting factor can have any suitable value. In some embodiments a weighting factor is between about $-1 \times 10^{-2}$ and about $1 \times 10^{-2}$, between about $-1 \times 10^{-3}$ and about $1 \times 10^{-3}$, between about $-5 \times 10^{-4}$ and about $5 \times 10^{-4}$, or between about $-1 \times 10^{-4}$ and about $1 \times 10^{-4}$. In some embodiments the distribution of weighting factors for multiple samples is substantially symmetrical. A distribution of weighting factors for multiple samples is sometimes a normal distribution. A distribution of weighting factors for multiple samples sometimes is not a normal distribution. In some embodiments the width of a distribution of the weighting factors is dependent on the amount of reads from CCF fetal nucleic acid fragments. In some embodiments portions comprising higher fetal nucleic acid content generate larger coefficients (e.g., positive or negative, e.g., see FIG. 31). A weighting factor can be zero or a weighting factor may be greater than zero. In some embodiments about 70% or more, about 75% or more, about 80% or more, about 85% or more, about 90% or more, about 95% or more, or about 98% or more of the weighting factors for a portion are greater than zero.

A weighting factor can be determined for or associated with any suitable portion of a genome. A weighting factor can be determined for or associated with any suitable portion of any suitable chromosome. In some embodiments a weighting factor is determined for or associated with some or all portions in a genome. In some embodiments a weighting factor is determined for or associated with portions of some or all chromosomes in a genome. A weighting factor is sometimes determined for or associated with portions of selected chromosomes. A weighting factor can be determined for or associated with portions of one or more autosomes. A weighting factor can be determined for or associated with portions in a plurality of portions that include portions in autosomes or a subset thereof. In some embodiments a weighting factor is determined for or associated with portions of a sex chromosome (e.g. ChrX and/or ChrY). A weighting factor can be determined for or associated with portions of one or more autosomes and one or more sex chromosomes. In certain embodiments a weighting factor is determined for or associated with portions in a plurality of portions in all autosomes and chromosomes X and Y. A weighting factor can be determined for or associated with portions in a plurality of portions that does not include portions in an X and/or Y chromosome. In certain embodiments a weighting factor is determined for or associated with portions of a chromosome where the chromosome comprises an aneuploidy (e.g., a whole chromosome aneuploidy). In certain embodiments a weighting factor is determined for or associated only with portions of a chromosome where the chromosome is not aneuploid (e.g., a euploid chromosome). A weighting factor can be determined for or associated with portions in a plurality of portions that does not include portions in chromosomes 13, 18 and/or 21.

In some embodiments a weighting factor is determined for a portion according to one or more samples (e.g., a training set of samples). Weighting factors are often specific to a portion. In some embodiments one or more weighting factors are independently assigned to a portion. In some embodiments a weighting factor is determined according to a relation for a fetal fraction determination (e.g., a sample specific fetal fraction determination) for multiple samples and a portion-specific parameter determined according to multiple samples. Weighting factors are often determined from multiple samples, for example, from about 20 to about 100,000 or more, from about 100 to about 100,000 or more, from about 500 to about 100,000 or more, from about 1000 to about 100,000 or more, or from about 10,000 to about 100,000 or more samples. Weighting factors can be determined from samples that are euploid (e.g., samples from subjects comprising a euploid fetus, e.g., samples where no aneuploid chromosome is present). In some embodiments weighting factors are obtained from samples comprising an aneuploid chromosome (e.g., samples from subjects comprising a euploid fetus). In some embodiments weighting factors are determined from multiple samples from subjects having a euploid fetus and from subjects having a trisomy fetus. Weighting factors can be derived from multiple samples where the samples are from subjects having a male fetus and/or a female fetus.

A fetal fraction is often determined for one or more samples of a training set from which a weighting factor is derived. A fetal fraction from which a weighting factor is determined is sometimes a sample specific fetal fraction determination. A fetal fraction from which a weighting factor is determined can be determined by any suitable method described herein or known in the art. In some embodiments a determination of fetal nucleic acid content (e.g., fetal fraction) is performed using a suitable fetal quantifier assay (FQA) described herein or known in the art, non-limiting examples of which include fetal fraction determinations according to markers specific to a male fetus, based on allelic ratios of polymorphic sequences, according to one or more markers specific to fetal nucleic acid and not maternal nucleic acid, by use of methylation-based DNA discrimination (e.g., A. Nygren, et al., (2010) Clinical Chemistry 56(10):1627-1635), by a mass spectrometry method and/or a system that uses a competitive PCR approach, by a method described in U.S. Patent Application Publication No. 2010/0105049, which is hereby incorporated by reference, the like or combinations thereof. Often a fetal fraction is determined, in part, according to a level (e.g., one or more genomic section levels, a level of a profile) of a Y chromosome. In some embodiments a fetal fraction is determined according to a suitable assay of a Y chromosome (e.g., by comparing the amount of fetal-specific locus (such as the SRY locus on chromosome Y in male pregnancies) to that of a locus on any autosome that is common to both the mother and the fetus by using quantitative real-time PCR (e.g., Lo Y M, et al. (1998) Am J Hum Genet. 62:768-775.)).

Portion-specific parameters (e.g., for a test sample) can be weighted or adjusted by one or more weighting factors (e.g., weighting factors derived from a training set). For example, a weighting factor can be derived for a portion according to a relation of a portion-specific parameter and a fetal fraction determination for a training set of multiple samples. A portion-specific parameter of a test sample can then be adjusted and/or weighted according to the weighting factor derived from the training set. In some embodiments a portion-specific parameter from which a weighting factor is derived, is the same as the portion-specific parameter (e.g., of a test sample) that is adjusted or weighted (e.g., both parameters are an FLR). In certain embodiment, a portion-specific parameter, from which a weighting factor is derived, is different than the portion-specific parameter (e.g., of a test sample) that is adjusted or weighted. For example, a weighting factor may be determined from a relation between coverage (i.e., a portion-specific parameter) and fetal fraction for a training set of samples, and an FLR (i.e., another portion-specific parameter) for a portion of a test sample can be adjusted according to the weighting factor derived from coverage. Without being limited by theory, a portion-specific parameter (e.g., for a test sample) can sometimes be adjusted and/or weighted by a weighting factor derived from a different portion-specific parameter (e.g., of a training set) due to a relation and/or correlation between each portion-specific parameter and a common portion-specific FLR.

A portion-specific fetal fraction estimate can be determined for a sample (e.g., a test sample) by weighting a portion-specific parameter by a weighting factor determined for that portion. Weighting can comprise adjusting, converting and/or transforming a portion-specific parameter according to a weighting factor by applying any suitable mathematical manipulation, non-limiting examples of which include multiplication, division, addition, subtraction, integration, symbolic computation, algebraic computation, algorithm, trigonometric or geometric function, transformation (e.g., a Fourier transform), the like or combinations thereof. Weighting can comprise adjusting, converting and/or transforming a portion-specific parameter according to a weighting factor a suitable mathematical model (e.g., the model presented in Example 7).

In some embodiments a fetal fraction is determined for a sample according to one or more portion-specific fetal fraction estimates. In some embodiments a fetal fraction is determined (e.g., estimated) for a sample (e.g., a test sample) according to weighting or adjusting a portion-specific parameter for one or more portions. In certain embodiments a fraction of fetal nucleic acid for a test sample is estimated based on adjusted counts or an adjusted subset of counts. In certain embodiments a fraction of fetal nucleic acid for a test sample is estimated based on an adjusted FLR, an adjusted FRS, adjusted coverage, and/or adjusted mappability for a portion. In some embodiments about 1 to about 500,000, about 100 to about 300,000, about 500 to about 200,000, about 1000 to about 200,000, about 1500 to about 200,000, or about 1500 to about 50,000 portion-specific parameters are weighted or adjusted.

A fetal fraction (e.g., for a test sample) can be determined according to multiple portion-specific fetal fraction estimates (e.g., for the same test sample) by any suitable method. In some embodiments a method for increasing the accuracy of the estimation of a fraction of fetal nucleic acid in a test sample from a pregnant female comprises determining one or more portion-specific fetal fraction estimates where the estimate of fetal fraction for the sample is determined according to the one or more portion-specific fetal fraction estimates. In some embodiments estimating or determining a fraction of fetal nucleic acid for a sample (e.g., a test sample) comprises summing one or more portion-specific fetal fraction estimates. Summing can comprise determining an average, mean, median, AUC, or integral value according to multiple portion-specific fetal fraction estimates.

In some embodiments a method for increasing the accuracy of the estimation of a fraction of fetal nucleic acid in a test sample from a pregnant female, comprises obtaining counts of sequence reads mapped to portions of a reference genome, which sequence reads are reads of circulating cell-free nucleic acid from a test sample from a pregnant female, where at least a subset of the counts obtained are derived from a region of the genome that contributes a greater number of counts derived from fetal nucleic acid relative to total counts from the region than counts of fetal nucleic acid relative to total counts of another region of the genome. In some embodiments an estimate of the fraction of fetal nucleic acid is determined according to a subset of the portions, where the subset of the portions is selected according to portions to which are mapped a greater number of counts derived from fetal nucleic acid than counts of fetal nucleic acid of another portion. In some embodiments the subset of the portions is selected according to portions to which are mapped a greater number of counts derived from fetal nucleic acid, relative to non-fetal nucleic acid, than counts of fetal nucleic acid, relative to non-fetal nucleic acid, of another portion. The counts mapped to all or a subset of the portions can be weighted, thereby providing weighted counts. The weighted counts can be utilized for estimating the fraction of fetal nucleic acid, and the counts can be weighted according to portions to which are mapped a greater number of counts derived from fetal nucleic acid than counts of fetal nucleic acid of another portion. In some embodiments the counts are weighted according to portions to which are mapped a greater number of counts derived from fetal nucleic acid, relative to non-fetal nucleic acid, than counts of fetal nucleic acid, relative to non-fetal nucleic acid, of another portion.

A fetal fraction can be determined for a sample (e.g., a test sample) according to multiple portion-specific fetal fraction estimates for the sample where the portions-specific estimates are from portions of any suitable region or segment of a genome. Portion-specific fetal fraction estimates can be determined for one or more portions of a suitable chromosome (e.g., one or more selected chromosomes, one or more autosomes, a sex chromosome (e.g. ChrX and/or ChrY), an aneuploid chromosome, a euploid chromosome, the like or combinations thereof).

Portion-specific parameters, weighting factors, portion-specific fetal fraction estimates (e.g., weighting), and/or fetal fraction determinations can be determined by a suitable system, machine, apparatus, non-transitory computer-readable storage medium (e.g., with an executable program stored thereon), the like or a combination thereof. In certain embodiments portion-specific parameters, weighting factors, portion-specific fetal fraction estimates (e.g., weighting), and/or fetal fraction determinations are determined (e.g., in part) by a system or a machine comprising one or more microprocessors and memory. In some embodiments portion-specific parameters, weighting factors, portion-specific fetal fraction estimates (e.g., weighting), and/or fetal fraction determinations are determined (e.g., in part) by a non-transitory computer-readable storage medium with an executable program stored thereon, where the program instructs a microprocessor to perform the determination.

Fetal Ploidy

A fetal ploidy determination, in some embodiments, is used, in part, to make a determination of the presence or absence of a genetic variation (e.g., a chromosome aneuploidy, a trisomy). A fetal ploidy can be determined, in part, from a measure of fetal fraction determined by a suitable method of fetal fraction determination, including methods described herein. A fetal ploidy and/or the presence of a genetic variation (e.g., an aneuploidy) can be determined according to a fetal fraction. In some embodiments fetal ploidy is determined according to a fetal fraction determination and equation (8), (20), (21) or a variation or derivation thereof (Example 2). In some embodiments, fetal ploidy is determined by a method described below. In some embodiments each method described below requires a calculated reference count $F_i$ (sometimes represented as $f_i$) determined for a portion (i.e. a portion, i) of a genome for multiple samples where the ploidy of the fetus for portion i of the genome is euploid. In some embodiments an uncertainty value (e.g., a standard deviation, σ) is determined for the reference count $f_i$. In some embodiments a reference count $f_i$, an uncertainty value, a test sample count and/or a measured fetal fraction (F) are used to determine fetal ploidy according to a method described below. In some embodiments a reference count (e.g., an average, mean or median reference count) is normalized by a method described herein (e.g., portion-wise normalization, normalization by GC content, linear and nonlinear least squares regression, LOESS, GC LOESS, LOWESS, PERUN, RM, GCRM and/or combinations thereof). In some embodiments a reference count of a segment of a genome that is euploid is equal to 1 when the reference count is normalized by PERUN. In some embodiments both the reference count (e.g., for a fetus known to be euploid) and the counts of a test sample for a portion or segment of a genome are normalized by PERUN and the reference count is equal to 1. Likewise, in some embodiments, a reference count of a portion or segment of a genome that is euploid is equal to 1 when the counts are normalized by (i.e., divided by) a median of the reference count. For example, in some embodiments both the reference count (e.g., for a fetus that is euploid) and the counts of a test sample for a portion or segment of a genome are normalized by a median reference count, the normalized reference count is equal to 1 and the test sample count is normalized (e.g., divided by) the median reference count. In some embodiments both the reference count (e.g., for a fetus that is euploid) and the counts of a test sample for a portion or segment of a genome are normalized by GCRM, GC, RM or a suitable method. In some embodiments a reference count is an average, mean or median reference count. A reference count is often a normalized count for a portion (e.g., a normalized genomic section level). In some embodiments a reference count and the counts for a test sample are raw counts. A reference count, in some embodiments, is determined from an average, mean or median count profile. In some embodiments, a reference count is a calculated genomic section level. In some embodiments a reference count of a reference sample and a count of a test sample (e.g., a patient sample, e.g., $y_i$) are normalized by the same method or process.

In some embodiments a measurement of fetal fraction (F) is determined. This fetal fraction value can then be used to determine fetal ploidy according to equation (8), a derivation or a variation thereof. In some embodiments, a negative value is returned if the fetus is euploid and a positive value is returned if the fetus is not euploid. In some embodiments a negative value indicates the fetus is euploid for the segment of the genome considered. In certain embodiments, a value that is not negative indicates the fetus comprises an aneuploidy (e.g., a duplication). In certain embodiments, a value that is not negative indicates the fetus comprises a trisomy. In certain embodiments, any positive value indicates the fetus comprises an aneuploidy (e.g., a trisomy, a duplication).

In some embodiments a sum of square residuals is determined. For example, an equation representing the sum of square residuals derived from equation (8) is illustrated in equation (18). In some embodiments a sum of square residuals is determined from equation (8) for a ploidy value X set to a value of 1 (see equation (9)) and for a ploidy value set to a value of 3/2 (see equation (13)). In some embodiments the sum of square residuals (equations (9) and (13)) are determined for a segment of a genome or chromosome (e.g., for all portions of a reference genome i in a segment of the genome). For example, the sum of square residuals (e.g., equations (9) and (13)) can be determined for chromosome 21, 13, 18 or a portion thereof. In some embodiments, to determine a ploidy status of a fetus, the result of equation (13) is subtracted from equation (9) to arrive at a value, phi (e.g., see equation (14)). In certain embodiments, the sign (i.e. positive or negative) of the value phi determines the presence or absence of a fetal aneuploidy. In certain embodiments, a phi value (e.g., from equation (14)) that is negative indicates the absence of an aneuploidy (e.g., the fetus is euploid for portions of a reference genome i) and a phi value that is not negative indicates the presence of an aneuploidy (e.g., a trisomy).

In some embodiments the reference count $f_i$, the uncertainty value for the reference count a and/or the measured fetal fraction (F) are used in equations (9) and (13) to determine the sum of square residuals for the sum of all portions of a reference genome i. In some embodiments the reference count $f_i$, the uncertainty value for the reference count σ and/or the measured fetal fraction (F) are used in equations (9) and (13) to determine fetal ploidy. In some embodiments the counts (e.g., normalized counts, e.g., calculated genomic section level), represented by $y_i$ for portion i, for a test sample are used to determine the ploidy status of a fetus for portion i. For example, in certain embodiments, the ploidy status for a segment of a genome is determined according to a reference count $f_i$, an uncertainty value (e.g., from the reference count), a feta fraction (F) determined for a test sample and the counts $y_i$ determined for the test sample where the ploidy status is determined according to equation (14) or a derivation or variation thereof. In some embodiments the counts $y_i$ and/or reference counts are normalized by a method described herein (e.g., portion-wise normalization, normalization by GC content, linear and nonlinear least squares regression, LOESS, GC LOESS, LOWESS, PERUN, RM, GCRM and combinations thereof). In some embodiments a fetal ploidy status (e.g., euploid, aneuploid, trisomy) for a portion or segment of a genome or chromosome is determined by the non-limiting example described above and in the Examples section.

In some embodiments a fetal fraction is determined from a test sample, counts y are determined for a test sample and both are used to determine a ploidy for a fetus from a test sample. In certain embodiments of the method described here, the value of fetal ploidy represented by X is not fixed or assumed. In certain embodiments of the method described here, fetal fraction F is fixed. In some embodiments, a ploidy (e.g., a ploidy value) is determined for a portion or segment of a genome according to equation (20) or (21) (Example 2). In some embodiments of this method, a ploidy value is determined, where the value is close to 1, 3/2, or 5/4. In some embodiments a ploidy value of about 1 indicates a euploid fetus, a value of about 3/2 indicates a fetal trisomy and, in the case of twins, a value of about 5/4 indicates that one fetus comprises a trisomy and the other is euploid for the portion or segment of the genome considered. Additional information regarding determining the presence or absence of a fetal aneuploidy from a fetal ploidy determination is discussed in another section below.

In some embodiments, fetal fraction is determined, fixed at its determined value and fetal ploidy is determined from a regression. Any suitable regression can be utilized, non-limiting examples of which include a linear regression, a non-linear regression (e.g., a polynomial regression), and the like. In some embodiments, a linear regression is used according to equation (8), (20), (21) and/or a derivation or variation thereof. In some embodiments, the linear regression used is according to a sum of square residuals derived from equation (8), (20), (21) and/or a derivation or variation thereof. In some embodiments, fetal ploidy is determined according to equation (8), (20), (21) and/or a derivation or variation thereof and a regression is not used. In some embodiments, fetal ploidy is determined according to a sum of square residuals derived from equation (8), (20), (21)

and/or a derivation or variation thereof for multiple portions of a reference genome i and a regression is not used. A derivation of an equation is any variation of the equation obtained from a mathematical proof of an equation.

In some embodiments a reference count $f_i$ (described previously herein), an uncertainty value σ and/or a measured fetal fraction (F) are used in equations (20) and (21) to determine a fetal ploidy. In some embodiments a reference count $f_i$, an uncertainty value σ and/or a measured fetal fraction (F) are used in equations (20) or (21) to determine a fetal ploidy X for portion i or for a sum of multiple portions of a reference genome i (e.g., for the sum of all portions of a reference genome i for a chromosome or segment thereof). In some embodiments the counts (e.g., normalized counts, calculated genomic section level), represented by $y_i$ for portion i, for a test sample are used to determine the ploidy of a fetus for a segment of a genome represented by multiple portions of a reference genome i. For example, in certain embodiments, the ploidy X for a segment of a genome is determined according to a reference count $f_j$, an uncertainty value, a feta fraction (F) determined for a test sample and the counts $y_i$ determined for the test sample where the ploidy is determined according to equation (20), (21) or a derivation or variation thereof. In some embodiments the counts $y_i$ and/or reference counts are normalized by a method described herein (e.g., portion-wise normalization, normalization by GC content, linear and nonlinear least squares regression, LOESS, GC LOESS, LOWESS, PERUN, RM, GCRM and combinations thereof). In some embodiments the counts $y_i$ and/or reference counts are normalized and/or processed by the same method (e.g., portion-wise normalization, normalization by GC content, linear and nonlinear least squares regression, LOESS, GC LOESS, LOWESS, PERUN, RM, GCRM, a method described herein or combinations thereof). In some embodiments counts $y_i$ and $f_i$ are counts mapped to the same portion or segment of a genome or chromosome.

The uncertainty value σ can be a suitable measure of error, non-limiting examples of which include standard deviation, standard error, calculated variance, p-value, and/or mean absolute deviation (MAD). The uncertainty value σ can be determined for any suitable measurement, non-limiting examples of which include Z-scores, Z-values, t-values, p-values, cross-validation error, genomic section level, calculated genomic section levels, levels, counts, the like, or combinations thereof. In some embodiments σ is set to a value of 1. In some embodiments σ is not set to a value of 1. In some embodiments the value of σ is estimated and sometimes it is measured and/or calculated.

In some embodiments $M_i$ is the ploidy of the mother (i.e., maternal ploidy) for a portion of the genome i. In some embodiments $M_i$ is determined for the same patient (e.g., same test sample) from which $y_i$ is determined. In some embodiments the maternal ploidy $M_i$ is known or determined according to a method described herein. In some embodiments maternal ploidy is determined before or after padding (e.g., after making level adjustments). In certain embodiments $M_i$ is estimated or determined from visualizing a profile. In some embodiments the maternal ploidy $M_i$ is not known. In some embodiments the maternal ploidy $M_i$ is assumed. For example, in some embodiments it is assumed or known that the mother has no deletions and/or duplications in the segment of the genome being evaluated. In some embodiments it is assumed or known that maternal ploidy is 1. In some embodiments maternal ploidy is set to a value of 1 after padding (e.g., after making levels adjustments). In some embodiments maternal ploidy is ignored and is set to a value of 1. In some embodiments equation (21) is derived from equation (20) with the assumption that the mother has no deletions and/or duplications in the segment of the genome being evaluated.

In some embodiments a method for determining fetal ploidy is according to nucleic acid sequence reads for a test sample obtained from a pregnant female. In some embodiments the sequence reads are reads of circulating cell-free nucleic acid from a sample (e.g., a test sample). In some embodiments, a method for determining fetal ploidy comprises obtaining counts of sequence reads mapped to portions of a reference genome. In some embodiments the sequence reads are mapped to a subset of portions of the reference genome. In certain embodiments determining fetal ploidy comprises determining a fetal fraction. In some embodiments determining fetal ploidy comprises calculating or determining genomic section levels. In certain embodiments determining fetal ploidy comprises determining a fetal fraction and calculating or determining genomic section levels. A fetal fraction and calculated genomic section levels can be determined from the same test sample (e.g., same part of the test sample). In some embodiments the fetal fraction and the calculated genomic section levels are determined from the same reads obtained from the same test sample (e.g., same part of the test sample). In certain embodiments the fetal fraction and the calculated genomic section levels are determined from the same reads obtained from the same sequencing run and/or from the same flow cell. In some embodiments the fetal fraction and the calculated genomic section levels are determined from the same equipment and/or machine (e.g., sequencing apparatus, flow cell, or the like).

In some embodiments a method for determining fetal ploidy is determined according to a fetal fraction determination and normalized counts (e.g., calculated genomic section levels) where the fetal fraction determination and the normalized counts (e.g., calculated genomic section levels) are determined from different parts of a test sample (e.g., different aliquots, or e.g., different test samples taken at about the same time from the same subject or patient). For example, sometimes a fetal fraction is determined from a first part of a test sample and normalized counts and/or genomic section levels are determined from a second part of the test sample. In some embodiments the fetal fraction and the calculated genomic section levels are determined from different test samples (e.g., different parts of a test sample) taken from the same subject (e.g., patient). In some embodiments the fetal fraction and the calculated genomic section levels are determined from reads obtained at different times. In some embodiments the fetal fraction determination and the normalized counts (e.g., calculated genomic section levels) are determined from different equipment and/or from different machines (e.g., sequencing apparatus, flow cell, or the like).

Outcome

Methods described herein can provide a determination of the presence or absence of a genetic variation (e.g., fetal aneuploidy) for a sample, thereby providing an outcome (e.g., thereby providing an outcome determinative of the presence or absence of a genetic variation (e.g., fetal aneuploidy)). A genetic variation often includes a gain, a loss and/or alteration (e.g., duplication, deletion, fusion, insertion, mutation, reorganization, substitution or aberrant methylation) of genetic information (e.g., chromosomes, segments of chromosomes, polymorphic regions, translocated regions, altered nucleotide sequence, the like or combinations of the foregoing) that results in a detectable change in the genome or genetic information of a test subject with respect to a reference. Presence or absence of a genetic variation can be determined by transforming, analyzing and/or manipulating sequence reads that have been mapped to portions (e.g., counts, counts of genomic portions of a reference genome). Determining an outcome, in some embodiments, comprises analyzing nucleic acid from a pregnant female. In certain embodiments, an outcome is determined according to counts (e.g., normalized counts) obtained from a pregnant female where the counts are from nucleic acid obtained from the pregnant female.

Methods described herein sometimes determine presence or absence of a fetal aneuploidy (e.g., full chromosome aneuploidy, partial chromosome aneuploidy or segmental chromosomal aberration (e.g., mosaicism, deletion and/or insertion)) for a test sample from a pregnant female bearing a fetus. In certain embodiments methods described herein detect euploidy or lack of euploidy (non-euploidy) for a sample from a pregnant female bearing a fetus. Methods described herein sometimes detect trisomy for one or more chromosomes (e.g., chromosome 13, chromosome 18, chromosome 21 or combination thereof) or segment thereof.

In some embodiments, presence or absence of a genetic variation (e.g., a fetal aneuploidy) is determined by a method described herein, by a method known in the art or by a combination thereof. Presence or absence of a genetic variation generally is determined from counts of sequence reads mapped to portions of a reference genome. Counts of sequence reads utilized to determine presence or absence of a genetic variation sometimes are raw counts and/or filtered counts, and often are normalized counts. A suitable normalization process or processes can be used to generate normalized counts, non-limiting examples of which include portion-wise normalization, normalization by GC content, linear and nonlinear least squares regression, LOESS, GC LOESS, LOWESS, PERUN, RM, GCRM and combinations thereof. Normalized counts sometimes are expressed as one or more levels or levels in a profile for a particular set or sets of portions. Normalized counts sometimes are adjusted or padded prior to determining presence or absence of a genetic variation.

In some embodiments an outcome is determined according to one or more levels. In some embodiments, a determination of the presence or absence of a genetic variation (e.g., a chromosome aneuploidy) is determined according to one or more adjusted levels. In some embodiments a determination of the presence or absence of a genetic variation (e.g., a chromosome aneuploidy) is determined according to a profile comprising 1 to about 10,000 adjusted levels. Often a determination of the presence or absence of a genetic variation (e.g., a chromosome aneuploidy) is determined according to a profile comprising about 1 to about a 1000, 1 to about 900, 1 to about 800, 1 to about 700, 1 to about 600, 1 to about 500, 1 to about 400, 1 to about 300, 1 to about 200, 1 to about 100, 1 to about 50, 1 to about 25, 1 to about 20, 1 to about 15, 1 to about 10, or 1 to about 5 adjustments. In some embodiments a determination of the presence or absence of a genetic variation (e.g., a chromosome aneuploidy) is determined according to a profile comprising about 1 adjustment (e.g., one adjusted level). In some embodiments an outcome is determined according to one or more profiles (e.g., a profile of a chromosome or segment thereof) comprising one or more, 2 or more, 3 or more, 5 or more, 6 or more, 7 or more, 8 or more, 9 or more or sometimes 10 or more adjustments. In some embodiments, a determination of the presence or absence of a genetic variation (e.g., a chromosome aneuploidy) is determined according to a profile where some levels in a profile are not adjusted. In some embodiments, a determination of the presence or absence of a genetic variation (e.g., a chromosome aneuploidy) is determined according to a profile where adjustments are not made.

In some embodiments, an adjustment of a level (e.g., a first level) in a profile reduces a false determination or false outcome. In some embodiments, an adjustment of a level (e.g., a first level) in a profile reduces the frequency and/or probability (e.g., statistical probability, likelihood) of a false determination or false outcome. A false determination or outcome can be a determination or outcome that is not accurate. A false determination or outcome can be a determination or outcome that is not reflective of the actual or true genetic make-up or the actual or true genetic disposition (e.g., the presence or absence of a genetic variation) of a subject (e.g., a pregnant female, a fetus and/or a combination thereof). In some embodiments a false determination or outcome is a false negative determination. In some embodiments a negative determination or negative outcome is the absence of a genetic variation (e.g., aneuploidy, copy number variation). In some embodiments a false determination or false outcome is a false positive determination or false positive outcome. In some embodiments a positive determination or positive outcome is the presence of a genetic variation (e.g., aneuploidy, copy number variation). In some embodiments, a determination or outcome is utilized in a diagnosis. In some embodiments, a determination or outcome is for a fetus.

Presence or absence of a genetic variation (e.g., fetal aneuploidy) sometimes is determined without comparing counts for a set of portions to a reference. Counts measured for a test sample and are in a test region (e.g., a set of portions of interest) are referred to as "test counts" herein. Test counts sometimes are processed counts, averaged or summed counts, a representation, normalized counts, or one or more levels or levels as described herein. In certain embodiments test counts are averaged or summed (e.g., an average, mean, median, mode or sum is calculated) for a set of portions, and the averaged or summed counts are compared to a threshold or range. Test counts sometimes are expressed as a representation, which can be expressed as a ratio or percentage of counts for a first set of portions to counts for a second set of portions. In certain embodiments a first set of portions is for one or more test chromosomes (e.g., chromosome 13, chromosome 18, chromosome 21, or combination thereof) and sometimes a second set of portions is for a genome or a part of a genome (e.g., autosomes or autosomes and sex chromosomes). In some embodiments, a first set of portions is for one or more sex chromosomes (e.g., chromosome X, chromosome Y, or combination thereof) and sometimes a second set of portions is for one or more autosomes. In some embodiments, a first set of portions is for one or more first regions of a test chromosomes (e.g., chromosome X, chromosome Y, or combination thereof) and sometimes a second set of portions is for one or more second regions of a test chromosome (e.g., chromosome X, chromosome Y, or combination thereof) or the entire test chromosome. In certain embodiments a representation is compared to a threshold or range. In certain embodiments test counts are expressed as one or more levels or levels for normalized counts over a set of portions, and the one or more levels or levels are compared to a threshold or range. Test counts (e.g., averaged or summed counts, representation, normalized counts, one or more levels or levels) above or below a particular threshold, in a particular range or outside a particular range sometimes are determinative of the presence of a genetic variation or lack of euploidy (e.g., not euploidy). Test counts (e.g., averaged or summed counts, representation, normalized counts, one or more levels or levels) below or above a particular threshold, in a particular range or outside a particular range sometimes are determinative of the absence of a genetic variation or euploidy.

Presence or absence of a genetic variation (e.g., fetal aneuploidy) sometimes is determined by comparing counts, non-limiting examples of which include test counts, reference counts, raw counts, filtered counts, averaged or summed counts, representations (e.g., chromosome representations), normalized counts, one or more levels or levels (e.g., for a set of portions, e.g., genomic section levels, profiles), Z-scores, the like or combinations thereof. In some embodiments test counts are compared to a reference (e.g., reference counts). A reference (e.g., a reference count) can be a suitable determination of counts, non-limiting examples of which include raw counts, filtered counts, averaged or summed counts, representations (e.g., chromosome representations), normalized counts, one or more levels or levels (e.g., for a set of portions, e.g., genomic section levels, profiles), Z-scores, the like or combinations thereof. Reference counts often are counts for a euploid test region or from a segment of a genome or chromosome that is euploid. In some embodiments reference counts and test counts are obtained from the same sample and/or the same subject. In some embodiments reference counts are from different samples and/or from different subjects. In some embodiments reference counts are determined from and/or compared to a corresponding segment of the genome from which the test counts are derived and/or determined. A corresponding segment refers to a segment, portion or set of portions that map to the same location of a reference genome. In some embodiments reference counts are determined from and/or compared to a different segment of the genome from which the test counts are derived and/or determined.

In certain embodiments, test counts sometimes are for a first set of portions and a reference includes counts for a second set of portions different than the first set of portions. Reference counts sometimes are for a nucleic acid sample from the same pregnant female from which the test sample is obtained. In certain embodiments reference counts are for a nucleic acid sample from one or more pregnant females different than the female from which the test sample was obtained. In some embodiments, a first set of portions is in chromosome 13, chromosome 18, chromosome 21, a segment thereof or combination of the foregoing, and the second set of portions is in another chromosome or chromosomes or segment thereof. In a non-limiting example, where a first set of portions is in chromosome 21 or segment thereof, a second set of portions often is in another chromosome (e.g., chromosome 1, chromosome 13, chromosome 14, chromosome 18, chromosome 19, segment thereof or combination of the foregoing). A reference often is located in a chromosome or segment thereof that is typically euploid. For example, chromosome 1 and chromosome 19 often are euploid in fetuses owing to a high rate of early fetal mortality associated with chromosome 1 and chromosome 19 aneuploidies. A measure of deviation between the test counts and the reference counts can be generated.

In certain embodiments a reference comprises counts for the same set of portions as for the test counts, where the counts for the reference are from one or more reference samples (e.g., often multiple reference samples from multiple reference subjects). A reference sample often is from one or more pregnant females different than a female from which a test sample is obtained. A measure of deviation (e.g., a measure of uncertainty, an uncertainty value) between the test counts and the reference counts can be generated. In some embodiments a measure of deviation is determined from the test counts. In some embodiments a measure of deviation is determined from the reference counts. In some embodiments a measure of deviation is determined from an entire profile or a subset of portions within a profile.

A suitable measure of deviation can be selected, non-limiting examples of which include standard deviation, average absolute deviation, median absolute deviation, maximum absolute deviation, standard score (e.g., z-value, z-score, normal score, standardized variable) and the like. In some embodiments, reference samples are euploid for a test region and deviation between the test counts and the reference counts is assessed. In some embodiments a determination of the presence or absence of a genetic variation is according to the number of deviations (e.g., measures of deviations, MAD) between test counts and reference counts for a segment or portion of a genome or chromosome. In some embodiments the presence of a genetic variation is determined when the number of deviations between test counts and reference counts is greater than about 1, greater than about 1.5, greater than about 2, greater than about 2.5, greater than about 2.6, greater than about 2.7, greater than about 2.8, greater than about 2.9, greater than about 3, greater than about 3.1, greater than about 3.2, greater than about 3.3, greater than about 3.4, greater than about 3.5, greater than about 4, greater than about 5, or greater than about 6. For example, sometimes a test count differs from a reference count by more than 3 measures of deviation (e.g., 3 sigma, 3 MAD) and the presence of a genetic variation is determined. In some embodiments a test count obtained from a pregnant female is larger than a reference count by more than 3 measures of deviation (e.g., 3 sigma, 3 MAD) and the presence of a fetal chromosome aneuploidy (e.g., a fetal trisomy) is determined. A deviation of greater than three between test counts and reference counts often is indicative of a non-euploid test region (e.g., presence of a genetic variation). Test counts significantly above reference counts, which reference counts are indicative of euploidy, sometimes are determinative of a trisomy. In some embodiments a test count obtained from a pregnant female is less than a reference count by more than 3 measures of deviation (e.g., 3 sigma, 3 MAD) and the presence of a fetal chromosome aneuploidy (e.g., a fetal monosomy) is determined. Test counts significantly below reference counts, which reference counts are indicative of euploidy, sometimes are determinative of a monosomy.

In some embodiments the absence of a genetic variation is determined when the number of deviations between test counts and reference counts is less than about 3.5, less than about 3.4, less than about 3.3, less than about 3.2, less than about 3.1, less than about 3.0, less than about 2.9, less than about 2.8, less than about 2.7, less than about 2.6, less than about 2.5, less than about 2.0, less than about 1.5, or less than about 1.0. For example, sometimes a test count differs from a reference count by less than 3 measures of deviation (e.g., 3 sigma, 3 MAD) and the absence of a genetic variation is determined. In some embodiments a test count obtained from a pregnant female differs from a reference count by less than 3 measures of deviation (e.g., 3 sigma, 3 MAD) and the absence of a fetal chromosome aneuploidy (e.g., a fetal euploid) is determined. In some embodiments (e.g., deviation of less than three between test counts and reference counts (e.g., 3-sigma for standard deviation) often is indicative of a euploid test region (e.g., absence of a genetic variation). A measure of deviation between test counts for a test sample and reference counts for one or more reference subjects can be plotted and visualized (e.g., z-score plot).

Any other suitable reference can be factored with test counts for determining presence or absence of a genetic variation (or determination of euploid or non-euploid) for a test region of a test sample. For example, a fetal fraction determination can be factored with test counts to determine the presence or absence of a genetic variation. A suitable process for quantifying fetal fraction can be utilized, non-limiting examples of which include a mass spectrometric process, sequencing process or combination thereof.

In some embodiments the presence or absence of a fetal chromosomal aneuploidy (e.g., a trisomy) is determined, in part, from a fetal ploidy determination. In some embodiments a fetal ploidy is determined by a suitable method described herein. In some certain embodiments a fetal ploidy determination of about 1.20 or greater, 1.25 or greater, 1.30 or greater, about 1.35 or greater, about 1.4 or greater, or about 1.45 or greater indicates the presence of a fetal chromosome aneuploidy (e.g., the presence of a fetal trisomy). In some embodiments a fetal ploidy determination of about 1.20 to about 2.0, about 1.20 to about 1.9, about 1.20 to about 1.85, about 1.20 to about 1.8, about 1.25 to about 2.0, about 1.25 to about 1.9, about 1.25 to about 1.85, about 1.25 to about 1.8, about 1.3 to about 2.0, about 1.3 to about 1.9, about 1.3 to about 1.85, about 1.3 to about 1.8, about 1.35 to about 2.0, about 1.35 to about 1.9, about 1.35 to about 1.8, about 1.4 to about 2.0, about 1.4 to about 1.85 or about 1.4 to about 1.8 indicates the presence of a fetal chromosome aneuploidy (e.g., the presence of a fetal trisomy). In some embodiments the fetal aneuploidy is a trisomy. In some embodiments the fetal aneuploidy is a trisomy of chromosome 13, 18 and/or 21.

In some embodiments a fetal ploidy of less than about 1.35, less than about 1.30, less than about 1.25, less than about 1.20 or less than about 1.15 indicates the absence of a fetal aneuploidy (e.g., the absence of a fetal trisomy, e.g., euploid). In some embodiments a fetal ploidy determination of about 0.7 to about 1.35, about 0.7 to about 1.30, about 0.7 to about 1.25, about 0.7 to about 1.20, about 0.7 to about 1.15, about 0.75 to about 1.35, about 0.75 to about 1.30, about 0.75 to about 1.25, about 0.75 to about 1.20, about 0.75 to about 1.15, about 0.8 to about 1.35, about 0.8 to about 1.30, about 0.8 to about 1.25, about 0.8 to about 1.20, or about 0.8 to about 1.15 indicates the absence of a fetal chromosome aneuploidy (e.g., the absence of a fetal trisomy, e.g., euploid).

In some embodiments a fetal ploidy of less than about 0.8, less than about 0.75, less than about 0.70 or less than about 0.6 indicates the presence of a fetal aneuploidy (e.g., the presence of a chromosome deletion). In some embodiments a fetal ploidy determination of about 0 to about 0.8, about 0 to about 0.75, about 0 to about 0.70, about 0 to about 0.65, about 0 to about 0.60, about 0.1 to about 0.8, about 0.1 to about 0.75, about 0.1 to about 0.70, about 0.1 to about 0.65, about 0.1 to about 0.60, about 0.2 to about 0.8, about 0.2 to about 0.75, about 0.2 to about 0.70, about 0.2 to about 0.65, about 0.2 to about 0.60, about 0.25 to about 0.8, about 0.25 to about 0.75, about 0.25 to about 0.70, about 0.25 to about 0.65, about 0.25 to about 0.60, about 0.3 to about 0.8, about 0.3 to about 0.75, about 0.3 to about 0.70, about 0.3 to about 0.65, about 0.3 to about 0.60 indicates the presence of a fetal chromosome aneuploidy (e.g., the presence of a chromosome deletion). In some embodiments the fetal aneuploidy determined is a whole chromosome deletion.

In some embodiments a determination of the presence or absence of a fetal aneuploidy (e.g., according to one or more of the ranges of a ploidy determination above) is determined according to a call zone. In certain embodiments a call is made (e.g., a call determining the presence or absence of a genetic variation, e.g., an outcome) when a value (e.g. a ploidy value, a fetal fraction value, a level of uncertainty) or collection of values falls within a pre-defined range (e.g., a zone, a call zone). In some embodiments a call zone is defined according to a collection of values that are obtained from the same patient sample. In certain embodiments a call zone is defined according to a collection of values that are derived from the same chromosome or segment thereof. In some embodiments a call zone based on a ploidy determination is defined according a level of confidence (e.g., high level of confidence, e.g., low level of uncertainty) and/or a fetal fraction. In some embodiments a call zone is defined according to a ploidy determination and a fetal fraction of about 2.0% or greater, about 2.5% or greater, about 3% or greater, about 3.25% or greater, about 3.5% or greater, about 3.75% or greater, or about 4.0% or greater. For example, in some embodiments a call is made that a fetus comprises a trisomy 21 based on a ploidy determination of greater than 1.25 with a fetal fraction determination of 2% or greater or 4% or greater for a sample obtained from a pregnant female bearing a fetus. In certain embodiments, for example, a call is made that a fetus is euploid based on a ploidy determination of less than 1.25 with a fetal fraction determination of 2% or greater or 4% or greater for a sample obtained from a pregnant female bearing a fetus. In some embodiments a call zone is defined by a confidence level of about 99% or greater, about 99.1% or greater, about 99.2% or greater, about 99.3% or greater, about 99.4% or greater, about 99.5% or greater, about 99.6% or greater, about 99.7% or greater, about 99.8% or greater or about 99.9% or greater. In some embodiments a call is made without using a call zone. In some embodiments a call is made using a call zone and additional data or information. In some embodiments a call is made based on a ploidy value without the use of a call zone. In some embodiments a call is made without calculating a ploidy value. In some embodiments a call is made based on visual inspection of a profile (e.g., visual inspection of genomic section levels). A call can be made by any suitable method based in full, or in part, upon determinations, values and/or data obtained by methods described herein, non-limiting examples of which include a fetal ploidy determination, a fetal fraction determination, maternal ploidy, uncertainty and/or confidence determinations, portion levels, levels, profiles, z-scores, expected chromosome representations, measured chromosome representations, counts (e.g., normalized counts, raw counts), fetal or maternal copy number variations (e.g., categorized copy number variations), significantly different levels, adjusted levels (e.g., padding), the like or combinations thereof.

In some embodiments a no-call zone is where a call is not made. In some embodiments a no-call zone is defined by a value or collection of values that indicate low accuracy, high risk, high error, low level of confidence, high level of uncertainty, the like or a combination thereof. In some embodiments a no-call zone is defined, in part, by a fetal fraction of about 5% or less, about 4% or less, about 3% or less, about 2.5% or less, about 2.0% or less, about 1.5% or less or about 1.0% or less.

In some embodiments, a method for determining the presence or absence of a genetic variation (e.g., fetal aneuploidy) is performed with an accuracy of at least about 90% to about 100%. For example, the presence or absence of a genetic variation may be determined with an accuracy of at least about 91%, 92%, 93%, 94%, 95%, 96%, 97%, 98%, 99%, 99.1%, 99.2%, 99.3%, 99.4%, 99.5%, 99.6%, 99.7%, 99.8% or 99.9%. In some embodiments, the presence or absence of a genetic variation is determined with an accuracy that is about the same or higher than the accuracy using other methods of genetic variation determination (e.g., karyotype analysis). In some embodiments, the presence or absence of a genetic variation is determined with an accuracy having confidence interval (CI) of about 80% to about 100%. For example, the confidence interval (CI) can be about 81%, 82%, 83%, 84%, 85%, 86%, 87%, 88%, 89%, 90%, 91%, 92%, 93%, 94%, 95%, 96%, 97%, 98%, or 99%.

Outcome sometimes can be determined in terms of sequence tag density. "Sequence tag density" refers to the normalized value of sequence tags or reads for a defined genomic section where the sequence tag density is used for comparing different samples and for subsequent analysis. The value of the sequence tag density often is normalized within a sample. In some embodiments, normalization can be performed by counting the number of tags falling within each genomic section; obtaining a median value of the total sequence tag count for each chromosome; obtaining a median value of all of the autosomal values; and using this value as a normalization constant to account for the differences in total number of sequence tags obtained for different samples. A sequence tag density sometimes is about 1 for a disomic chromosome. Sequence tag densities can vary according to sequencing artifacts, most notably G/C bias, which can be corrected by use of an external standard or internal reference (e.g., derived from substantially all of the sequence tags (genomic sequences), which may be, for example, a single chromosome or a calculated value from all autosomes, in some embodiments). Thus, dosage imbalance of a chromosome or chromosomal regions can be inferred from the percentage representation of the locus among other mappable sequenced tags of the specimen. Dosage imbalance of a particular chromosome or chromosomal regions therefore can be quantitatively determined and be normalized. Methods for sequence tag density normalization and quantification are discussed in further detail below.

In some embodiments, a proportion of all of the sequence reads are from a sex chromosome (e.g., chromosome X, chromosome Y) or a chromosome involved in an aneuploidy (e.g., chromosome 13, chromosome 18, chromosome 21), and other sequence reads are from other chromosomes. By taking into account the relative size of the sex chromosome or chromosome involved in the aneuploidy (e.g., "target chromosome": chromosome 21) compared to other chromosomes, one could obtain a normalized frequency, within a reference range, of target chromosome-specific sequences, in some embodiments. If the fetus has an aneuploidy, for example, in a target chromosome, then the normalized frequency of the target chromosome-derived sequences is statistically greater than the normalized frequency of non-target chromosome-derived sequences, thus allowing the detection of the aneuploidy. The degree of change in the normalized frequency will be dependent on the fractional concentration of fetal nucleic acids in the analyzed sample, in some embodiments.

A genetic variation sometimes is associated with medical condition. An outcome determinative of a genetic variation is sometimes an outcome determinative of the presence or absence of a condition (e.g., a medical condition), disease, syndrome or abnormality or, includes, detection of a condition, disease, syndrome or abnormality (e.g., non-limiting examples listed in Table 1). In certain embodiments a diagnosis comprises assessment of an outcome. An outcome determinative of the presence or absence of a condition (e.g., a medical condition), disease, syndrome or abnormality by methods described herein can sometimes be independently verified by further testing (e.g., by karyotyping and/or amniocentesis). Analysis and processing of data can provide one or more outcomes. The term "outcome" as used herein can refer to a result of data processing that facilitates determining the presence or absence of a genetic variation (e.g., an aneuploidy, a copy number variation). In certain embodiments the term "outcome" as used herein refers to a conclusion that predicts and/or determines the presence or absence of a genetic variation (e.g., an aneuploidy, a copy number variation). In certain embodiments the term "outcome" as used herein refers to a conclusion that predicts and/or determines a risk or probability of the presence or absence of a genetic variation (e.g., an aneuploidy, a copy number variation) in a subject (e.g., a fetus). A diagnosis sometimes comprises use of an outcome. For example, a health practitioner may analyze an outcome and provide a diagnosis bases on, or based in part on, the outcome. In some embodiments, determination, detection or diagnosis of a condition, syndrome or abnormality (e.g., listed in Table 1) comprises use of an outcome determinative of the presence or absence of a genetic variation. In some embodiments, an outcome based on counted mapped sequence reads or transformations thereof is determinative of the presence or absence of a genetic variation. In certain embodiments, an outcome generated utilizing one or more methods (e.g., data processing methods) described herein is determinative of the presence or absence of one or more conditions, syndromes or abnormalities listed in Table 1. In certain embodiments a diagnosis comprises a determination of a presence or absence of a condition, syndrome or abnormality. Often a diagnosis comprises a determination of a genetic variation as the nature and/or cause of a condition, syndrome or abnormality. In certain embodiments an outcome is not a diagnosis. An outcome often comprises one or more numerical values generated using a processing method described herein in the context of one or more considerations of probability. A consideration of risk or probability can include, but is not limited to: an uncertainty value, a measure of variability, confidence level, sensitivity, specificity, standard deviation, coefficient of variation (CV) and/or confidence level, Z-scores, Chi values, Phi values, ploidy values, fitted fetal fraction, area ratios, median level, the like or combinations thereof. A consideration of probability can facilitate determining whether a subject is at risk of having, or has, a genetic variation, and an outcome determinative of a presence or absence of a genetic disorder often includes such a consideration.

An outcome sometimes is a phenotype. An outcome sometimes is a phenotype with an associated level of confidence (e.g., an uncertainty value, e.g., a fetus is positive for trisomy 21 with a confidence level of 99%; a pregnant female is carrying a male fetus with a confidence level of 95%; a test subject is negative for a cancer associated with a genetic variation at a confidence level of 95%). Different methods of generating outcome values sometimes can produce different types of results. Generally, there are four types of possible scores or calls that can be made based on outcome values generated using methods described herein: true positive, false positive, true negative and false negative. The terms "score", "scores", "call" and "calls" as used herein refer to calculating the probability that a particular genetic variation is present or absent in a subject/sample. The value of a score may be used to determine, for example, a variation, difference, or ratio of mapped sequence reads that may correspond to a genetic variation. For example, calculating a positive score for a selected genetic variation or portion from a data set, with respect to a reference genome can lead to an identification of the presence or absence of a genetic variation, which genetic variation sometimes is associated with a medical condition (e.g., cancer, preeclampsia, trisomy, monosomy, and the like). In some embodiments, an outcome comprises a level, a profile and/or a plot (e.g., a profile plot). In those embodiments in which an outcome comprises a profile, a suitable profile or combination of profiles can be used for an outcome. Non-limiting examples of profiles that can be used for an outcome include z-score profiles, p-value profiles, chi value profiles, phi value profiles, the like, and combinations thereof.

An outcome generated for determining the presence or absence of a genetic variation sometimes includes a null result (e.g., a data point between two clusters, a numerical value with a standard deviation that encompasses values for both the presence and absence of a genetic variation, a data set with a profile plot that is not similar to profile plots for subjects having or free from the genetic variation being investigated). In some embodiments, an outcome indicative of a null result still is a determinative result, and the determination can include the need for additional information and/or a repeat of the data generation and/or analysis for determining the presence or absence of a genetic variation.

An outcome can be generated after performing one or more processing steps described herein, in some embodiments. In certain embodiments, an outcome is generated as a result of one of the processing steps described herein, and in some embodiments, an outcome can be generated after each statistical and/or mathematical manipulation of a data set is performed. An outcome pertaining to the determination of the presence or absence of a genetic variation can be expressed in a suitable form, which form comprises without limitation, a probability (e.g., odds ratio, p-value), likelihood, value in or out of a cluster, value over or under a threshold value, value within a range (e.g., a threshold range), value with a measure of variance or confidence, or risk factor, associated with the presence or absence of a genetic variation for a subject or sample. In certain embodiments, comparison between samples allows confirmation of sample identity (e.g., allows identification of repeated samples and/or samples that have been mixed up (e.g., mislabeled, combined, and the like)).

In some embodiments, an outcome comprises a value above or below a predetermined threshold or cutoff value (e.g., greater than 1, less than 1), and an uncertainty or confidence level associated with the value. In certain embodiments a predetermined threshold or cutoff value is an expected level or an expected level range. An outcome also can describe an assumption used in data processing. In certain embodiments, an outcome comprises a value that falls within or outside a predetermined range of values (e.g., a threshold range) and the associated uncertainty or confidence level for that value being inside or outside the range. In some embodiments, an outcome comprises a value that is equal to a predetermined value (e.g., equal to 1, equal to zero), or is equal to a value within a predetermined value range, and its associated uncertainty or confidence level for that value being equal or within or outside a range. An outcome sometimes is graphically represented as a plot (e.g., profile plot).

As noted above, an outcome can be characterized as a true positive, true negative, false positive or false negative. The term "true positive" as used herein refers to a subject correctly diagnosed as having a genetic variation. The term "false positive" as used herein refers to a subject wrongly identified as having a genetic variation. The term "true negative" as used herein refers to a subject correctly identified as not having a genetic variation. The term "false negative" as used herein refers to a subject wrongly identified as not having a genetic variation. Two measures of performance for any given method can be calculated based on the ratios of these occurrences: (i) a sensitivity value, which generally is the fraction of predicted positives that are correctly identified as being positives; and (ii) a specificity value, which generally is the fraction of predicted negatives correctly identified as being negative.

In certain embodiments, one or more of sensitivity, specificity and/or confidence level are expressed as a percentage. In some embodiments, the percentage, independently for each variable, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome is not due to chance) in certain embodiments is expressed as a Z-score, a p-value, or the results of a t-test. In some embodiments, a measured variance, confidence interval, sensitivity, specificity and the like (e.g., referred to collectively as confidence parameters) for an outcome can be generated using one or more data processing manipulations described herein. Specific examples of generating outcomes and associated confidence levels are described in the Examples section and in international patent application no. PCT/US12/59123 (WO2013/052913) the entire content of which is incorporated herein by reference, including all text, tables, equations and drawings.

The term "sensitivity" as used herein refers to the number of true positives divided by the number of true positives plus the number of false negatives, where sensitivity (sens) may be within the range of $0 \le sens \le 1$. The term "specificity" as used herein refers to the number of true negatives divided by the number of true negatives plus the number of false positives, where sensitivity (spec) may be within the range of $0 \le spec \le 1$. In some embodiments a method that has sensitivity and specificity equal to one, or 100%, or near one (e.g., between about 90% to about 99%) sometimes is selected. In some embodiments, a method having a sensitivity equaling 1, or 100% is selected, and in certain embodiments, a method having a sensitivity near 1 is selected (e.g., a sensitivity of about 90%, a sensitivity of about 91%, a sensitivity of about 92%, a sensitivity of about 93%, a sensitivity of about 94%, a sensitivity of about 95%, a sensitivity of about 96%, a sensitivity of about 97%, a sensitivity of about 98%, or a sensitivity of about 99%). In some embodiments, a method having a specificity equaling 1, or 100% is selected, and in certain embodiments, a method having a specificity near 1 is selected (e.g., a specificity of about 90%, a specificity of about 91%, a specificity of about 92%, a specificity of about 93%, a specificity of about 94%, a specificity of about 95%, a specificity of about 96%, a specificity of about 97%, a specificity of about 98%, or a specificity of about 99%).

Ideally, the number of false negatives equal zero or close to zero, so that no subject is wrongly identified as not having at least one genetic variation when they indeed have at least one genetic variation. Conversely, an assessment often is made of the ability of a prediction algorithm to classify negatives correctly, a complementary measurement to sensitivity. Ideally, the number of false positives equal zero or close to zero, so that no subject is wrongly identified as having at least one genetic variation when they do not have the genetic variation being assessed.

In some embodiments, presence or absence of a genetic variation (e.g., chromosome aneuploidy) is determined for a fetus. In such embodiments, presence or absence of a fetal genetic variation (e.g., fetal chromosome aneuploidy) is determined.

In certain embodiments, presence or absence of a genetic variation (e.g., chromosome aneuploidy) is determined for a sample. In such embodiments, presence or absence of a genetic variation in sample nucleic acid (e.g., chromosome aneuploidy) is determined. In some embodiments, a variation detected or not detected resides in sample nucleic acid from one source but not in sample nucleic acid from another source. Non-limiting examples of sources include placental nucleic acid, fetal nucleic acid, maternal nucleic acid, cancer cell nucleic acid, non-cancer cell nucleic acid, the like and combinations thereof. In non-limiting examples, a particular genetic variation detected or not detected (i) resides in placental nucleic acid but not in fetal nucleic acid and not in maternal nucleic acid; (ii) resides in fetal nucleic acid but not maternal nucleic acid; or (iii) resides in maternal nucleic acid but not fetal nucleic acid.

After one or more outcomes have been generated, an outcome often is used to provide a determination of the presence or absence of a genetic variation and/or associated medical condition. An outcome typically is provided to a health care professional (e.g., laboratory technician or manager; physician or assistant). Often an outcome is provided by an outcome module. In certain embodiments an outcome is provided by a plotting module. In certain embodiments an outcome is provided on a peripheral or component of a machine or machine. For example, sometimes an outcome is provided by a printer or display. In some embodiments, an outcome determinative of the presence or absence of a genetic variation is provided to a healthcare professional in the form of a report, and in certain embodiments the report comprises a display of an outcome value and an associated confidence parameter. Generally, an outcome can be displayed in a suitable format that facilitates determination of the presence or absence of a genetic variation and/or medical condition. Non-limiting examples of formats suitable for use for reporting and/or displaying data sets or reporting an outcome include digital data, a graph, a 2D graph, a 3D graph, and 4D graph, a picture, a pictograph, a chart, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, nomogram, and the like, and combination of the foregoing. Various examples of outcome representations are shown in the drawings and are described in the Examples.

Generating an outcome can be viewed as a transformation of nucleic acid sequence reads into a representation of a subject's cellular nucleic acid, in certain embodiments. A representation of a subject's cellular nucleic acid often reflects a dosage or copy number for a particular chromosome or portion thereof, and the representation thereby often is a property of the subject's nucleic acid. Converting a multitude of relatively small sequence reads to a representation of a relatively large chromosome, for example, can be viewed as a transformation. As an illustration, in a process for generating a representation of chromosome 21, which is about 47 million bases in length, using reads of approximately 36 base pairs in length, many thousands of reads that are at least 100,000 times smaller than the chromosome are transformed into a representation of the significantly larger chromosome. Generating such a representation of a chromosome typically involves several manipulations of reads (e.g., mapping, filtering and/or normalizing) to arrive at a representation of the relatively large chromosome, as described herein. Multiple manipulations often are utilized, which can require the use of one or more computers, often multiple computers coordinated in parallel.

When providing a representation of a chromosome for a fetal chromosome using a sample from a pregnant female, such a transformation further is apparent given that the majority of reads often are from maternal nucleic acid and a minority of reads often is from fetal nucleic acid. Reads of maternal nucleic acid often dominate reads of fetal nucleic acid, and the majority of maternal nucleic acid reads often masks a representation of a fetal chromosome. A typically large background of maternal reads can obscure differences between fetal and maternal chromosome nucleic acid and obtaining a representation of a fetal chromosome against such a background involves a process that de-convolutes the contribution of maternal reads, as described herein.

In some embodiments, an outcome results from a transformation of sequence reads from a subject (e.g., a pregnant female), into a representation of an existing structure (e.g., a genome, a chromosome or segment thereof) present in a subject (e.g., a mother and/or fetus). In some embodiments, an outcome comprises a transformation of sequence reads from a first subject (e.g., a pregnant female), into a composite representation of structures (e.g., a genome, a chromosome or segment thereof), and a second transformation of the composite representation that yields a representation of a structure present in a first subject (e.g., a pregnant female) and/or a second subject (e.g., a fetus). In some embodiments, an outcome comprises a transformation of sequence reads from a first subject (e.g., a female subject, a pregnant female), into a representation of structures (e.g., a genome, a chromosome or segment thereof) present in a second subject (e.g., a fetus).

A transformative method herein sometimes comprises determining the presence or absence of a trisomic chromosome (i.e., chromosome trisomy) in a fetus (e.g., T21, T18 and/or T13) from nucleic acid reads in a sample obtained from a pregnant female subject carrying the fetus. In some embodiments, a transformative method herein may comprise preparing (e.g., determining, visualizing, displaying, providing) a representation of a chromosome (e.g., chromosome copy number, chromosome dosage) for a fetus from nucleic acid reads in a sample obtained from a pregnant female subject carrying the fetus. In the latter embodiments, a representation of a chromosome for a fetus often is for chromosome 13, chromosome 18 and/or chromosome 21.

Use of Outcomes

A health care professional, or other qualified individual, receiving a report comprising one or more outcomes determinative of the presence or absence of a genetic variation can use the displayed data in the report to make a call regarding the status of the test subject or patient. The healthcare professional can make a recommendation based on the provided outcome, in some embodiments. A health care professional or qualified individual can provide a test subject or patient with a call or score with regards to the presence or absence of the genetic variation based on the outcome value or values and associated confidence parameters provided in a report, in some embodiments. In certain embodiments, a score or call is made manually by a healthcare professional or qualified individual, using visual observation of the provided report. In certain embodiments, a score or call is made by an automated routine, sometimes embedded in software, and reviewed by a healthcare professional or qualified individual for accuracy prior to providing information to a test subject or patient. The term "receiving a report" as used herein refers to obtaining, by a communication means, a written and/or graphical representation comprising an outcome, which upon review allows a healthcare professional or other qualified individual to make a determination as to the presence or absence of a genetic variation in a test subject or patient. The report may be generated by a computer or by human data entry, and can be communicated using electronic means (e.g., over the internet, via computer, via fax, from one network location to another location at the same or different physical sites), or by a other method of sending or receiving data (e.g., mail service, courier service and the like). In some embodiments the outcome is transmitted to a health care professional in a suitable medium, including, without limitation, in verbal, document, or file form. The file may be, for example, but not limited to, an auditory file, a computer readable file, a paper file, a laboratory file or a medical record file.

The term "providing an outcome" and grammatical equivalents thereof, as used herein also can refer to a method for obtaining such information, including, without limitation, obtaining the information from a laboratory (e.g., a laboratory file). A laboratory file can be generated by a laboratory that carried out one or more assays or one or more data processing steps to determine the presence or absence of the medical condition. The laboratory may be in the same location or different location (e.g., in another country) as the personnel identifying the presence or absence of the medical condition from the laboratory file. For example, the laboratory file can be generated in one location and transmitted to another location in which the information therein will be transmitted to the pregnant female subject. The laboratory file may be in tangible form or electronic form (e.g., computer readable form), in certain embodiments.

In some embodiments, an outcome can be provided to a health care professional, physician or qualified individual from a laboratory and the health care professional, physician or qualified individual can make a diagnosis based on the outcome. In some embodiments, an outcome can be provided to a health care professional, physician or qualified individual from a laboratory and the health care professional, physician or qualified individual can make a diagnosis based, in part, on the outcome along with additional data and/or information and other outcomes.

A healthcare professional or qualified individual, can provide a suitable recommendation based on the outcome or outcomes provided in the report. Non-limiting examples of recommendations that can be provided based on the provided outcome report includes, surgery, radiation therapy, chemotherapy, genetic counseling, after birth treatment solutions (e.g., life planning, long term assisted care, medicaments, symptomatic treatments), pregnancy termination, organ transplant, blood transfusion, the like or combinations of the foregoing. In some embodiments the recommendation is dependent on the outcome based classification provided (e.g., Down's syndrome, Turner syndrome, medical conditions associated with genetic variations in T13, medical conditions associated with genetic variations in T18).

Laboratory personnel (e.g., a laboratory manager) can analyze values (e.g., test counts, reference counts, level of deviation) underlying a determination of the presence or absence of a genetic variation (or determination of euploid or non-euploid for a test region). For calls pertaining to presence or absence of a genetic variation that are close or questionable, laboratory personnel can re-order the same test, and/or order a different test (e.g., karyotyping and/or amniocentesis in the case of fetal aneuploidy determinations), that makes use of the same or different sample nucleic acid from a test subject.

Genetic Variations and Medical Conditions

The presence or absence of a genetic variance can be determined using a method, apparatus or machine described herein. In certain embodiments, the presence or absence of one or more genetic variations is determined according to an outcome provided by methods, machines and apparatuses described herein. A genetic variation generally is a particular genetic phenotype present in certain individuals, and often a genetic variation is present in a statistically significant sub-population of individuals. In some embodiments, a genetic variation is a chromosome abnormality (e.g., aneuploidy), partial chromosome abnormality or mosaicism, each of which is described in greater detail herein. Non-limiting examples of genetic variations include one or more deletions (e.g., micro-deletions), duplications (e.g., micro-duplications), insertions, mutations, polymorphisms (e.g., single-nucleotide polymorphisms), fusions, repeats (e.g., short tandem repeats), distinct methylation sites, distinct methylation patterns, the like and combinations thereof. An insertion, repeat, deletion, duplication, mutation or polymorphism can be of any length, and in some embodiments, is about 1 base or base pair (bp) to about 250 megabases (Mb) in length. In some embodiments, an insertion, repeat, deletion, duplication, mutation or polymorphism is about 1 base or base pair (bp) to about 1,000 kilobases (kb) in length (e.g., about 10 bp, 50 bp, 100 bp, 500 bp, 1 kb, 5 kb, 10 kb, 50 kb, 100 kb, 500 kb, or 1000 kb in length).

A genetic variation is sometime a deletion. In certain embodiments a deletion is a mutation (e.g., a genetic aberration) in which a part of a chromosome or a sequence of DNA is missing. A deletion is often the loss of genetic material. Any number of nucleotides can be deleted. A deletion can comprise the deletion of one or more entire chromosomes, a segment of a chromosome, an allele, a gene, an intron, an exon, any non-coding region, any coding region, a segment thereof or combination thereof. A deletion can comprise a microdeletion. A deletion can comprise the deletion of a single base.

A genetic variation is sometimes a genetic duplication. In certain embodiments a duplication is a mutation (e.g., a genetic aberration) in which a part of a chromosome or a sequence of DNA is copied and inserted back into the genome. In certain embodiments a genetic duplication (i.e. duplication) is any duplication of a region of DNA. In some embodiments a duplication is a nucleic acid sequence that is repeated, often in tandem, within a genome or chromosome. In some embodiments a duplication can comprise a copy of one or more entire chromosomes, a segment of a chromosome, an allele, a gene, an intron, an exon, any non-coding region, any coding region, segment thereof or combination thereof. A duplication can comprise a microduplication. A duplication sometimes comprises one or more copies of a duplicated nucleic acid. A duplication sometimes is characterized as a genetic region repeated one or more times (e.g., repeated 1, 2, 3, 4, 5, 6, 7, 8, 9 or 10 times). Duplications can range from small regions (thousands of base pairs) to whole chromosomes in some instances. Duplications frequently occur as the result of an error in homologous recombination or due to a retrotransposon event. Duplications have been associated with certain types of proliferative diseases. Duplications can be characterized using genomic microarrays or comparative genetic hybridization (CGH).

A genetic variation is sometimes an insertion. An insertion is sometimes the addition of one or more nucleotide base pairs into a nucleic acid sequence. An insertion is sometimes a microinsertion. In certain embodiments an insertion comprises the addition of a segment of a chromosome into a genome, chromosome, or segment thereof. In certain embodiments an insertion comprises the addition of an allele, a gene, an intron, an exon, any non-coding region, any coding region, segment thereof or combination thereof into a genome or segment thereof. In certain embodiments an insertion comprises the addition (i.e., insertion) of nucleic acid of unknown origin into a genome, chromosome, or segment thereof. In certain embodiments an insertion comprises the addition (i.e. insertion) of a single base.

As used herein a "copy number variation" generally is a class or type of genetic variation or chromosomal aberration. A copy number variation can be a deletion (e.g. micro-deletion), duplication (e.g., a micro-duplication) or insertion (e.g., a micro-insertion). Often, the prefix "micro" as used herein sometimes is a segment of nucleic acid less than 5 Mb in length. A copy number variation can include one or more deletions (e.g. micro-deletion), duplications and/or insertions (e.g., a micro-duplication, micro-insertion) of a segment of a chromosome. In certain embodiments a duplication comprises an insertion. In certain embodiments an insertion is a duplication. In certain embodiments an insertion is not a duplication. For example, often a duplication of a sequence in a portion increases the counts for a portion in which the duplication is found. Often a duplication of a sequence in a portion increases the level. In certain embodiments, a duplication present in portions making up a first level increases the level relative to a second level where a duplication is absent. In certain embodiments an insertion increases the counts of a portion and a sequence representing the insertion is present (i.e., duplicated) at another location within the same portion. In certain embodiments an insertion does not significantly increase the counts of a portion or level and the sequence that is inserted is not a duplication of a sequence within the same portion. In certain embodiments an insertion is not detected or represented as a duplication and a duplicate sequence representing the insertion is not present in the same portion.

In some embodiments a copy number variation is a fetal copy number variation. Often, a fetal copy number variation is a copy number variation in the genome of a fetus. In some embodiments a copy number variation is a maternal and/or fetal copy number variation. In certain embodiments a maternal and/or fetal copy number variation is a copy number variation within the genome of a pregnant female (e.g., a female subject bearing a fetus), a female subject that gave birth or a female capable of bearing a fetus. A copy number variation can be a heterozygous copy number variation where the variation (e.g., a duplication or deletion) is present on one allele of a genome. A copy number variation can be a homozygous copy number variation where the variation is present on both alleles of a genome. In some embodiments a copy number variation is a heterozygous or homozygous fetal copy number variation. In some embodiments a copy number variation is a heterozygous or homozygous maternal and/or fetal copy number variation. A copy number variation sometimes is present in a maternal genome and a fetal genome, a maternal genome and not a fetal genome, or a fetal genome and not a maternal genome.

"Ploidy" is a reference to the number of chromosomes present in a fetus or mother. In certain embodiments "ploidy" is the same as "chromosome ploidy". In humans, for example, autosomal chromosomes are often present in pairs. For example, in the absence of a genetic variation, most humans have two of each autosomal chromosome (e.g., chromosomes 1-22). The presence of the normal complement of 2 autosomal chromosomes in a human is often referred to as euploid. "Microploidy" is similar in meaning to ploidy. "Microploidy" often refers to the ploidy of a segment of a chromosome. The term "microploidy" sometimes is a reference to the presence or absence of a copy number variation (e.g., a deletion, duplication and/or an insertion) within a chromosome (e.g., a homozygous or heterozygous deletion, duplication, or insertion, the like or absence thereof). "Ploidy" and "microploidy" sometimes are determined after normalization of counts of a level in a profile. Thus, a level representing an autosomal chromosome pair (e.g., a euploid) is often normalized to a ploidy of 1. Similarly, a level within a segment of a chromosome representing the absence of a duplication, deletion or insertion is often normalized to a microploidy of 1. Ploidy and microploidy are often portion-specific (e.g., portion-specific) and sample-specific. Ploidy is often defined as integral multiples of ½, with the values of 1, ½, 0, 3/2, and 2 representing euploid (e.g., 2 chromosomes), 1 chromosome present (e.g., a chromosome deletion), no chromosome present, 3 chromosomes (e.g., a trisomy) and 4 chromosomes, respectively. Likewise, microploidy is often defined as integral multiples of ½, with the values of 1, ½, 0, 3/2, and 2 representing euploid (e.g., no copy number variation), a heterozygous deletion, homozygous deletion, heterozygous duplication and homozygous duplication, respectively. Some examples of ploidy values for a fetus are provided in Table 2.

In certain embodiments the microploidy of a fetus matches the microploidy of the mother of the fetus (i.e., the pregnant female subject). In certain embodiments the microploidy of a fetus matches the microploidy of the mother of the fetus and both the mother and fetus carry the same heterozygous copy number variation, homozygous copy number variation or both are euploid. In certain embodiments the microploidy of a fetus is different than the microploidy of the mother of the fetus. For example, sometimes the microploidy of a fetus is heterozygous for a copy number variation, the mother is homozygous for a copy number variation and the microploidy of the fetus does not match (e.g., does not equal) the microploidy of the mother for the specified copy number variation.

A microploidy is often associated with an expected level. For example, sometimes a level (e.g., a level in a profile, sometimes a level that includes substantially no copy number variation) is normalized to a value of 1 (e.g., a ploidy of 1, a microploidy of 1) and the microploidy of a homozygous duplication is 2, a heterozygous duplication is 1.5, a heterozygous deletion is 0.5 and a homozygous deletion is zero.

A genetic variation for which the presence or absence is identified for a subject is associated with a medical condition in certain embodiments. Thus, technology described herein can be used to identify the presence or absence of one or more genetic variations that are associated with a medical condition or medical state. Non-limiting examples of medical conditions include those associated with intellectual disability (e.g., Down Syndrome), aberrant cell-proliferation (e.g., cancer), presence of a micro-organism nucleic acid (e.g., virus, bacterium, fungus, yeast), and preeclampsia.

Non-limiting examples of genetic variations, medical conditions and states are described hereafter.

Fetal Gender

In some embodiments, the prediction of a fetal gender or gender related disorder (e.g., sex chromosome aneuploidy) can be determined by a method, machine or apparatus described herein. Gender determination generally is based on a sex chromosome. In humans, there are two sex chromosomes, the X and Y chromosomes. The Y chromosome contains a gene, SRY, which triggers embryonic development as a male. The Y chromosomes of humans and other mammals also contain other genes needed for normal sperm production. Individuals with XX are female and XY are male and non-limiting variations, often referred to as sex chromosome aneuploidies, include X0, XYY, XXX and XXY. In certain embodiments, males have two X chromosomes and one Y chromosome (XXY; Klinefelter's Syndrome), or one X chromosome and two Y chromosomes (XYY syndrome; Jacobs Syndrome), and some females have three X chromosomes (XXX; Triple X Syndrome) or a single X chromosome instead of two (X0; Turner Syndrome). In certain embodiments, only a portion of cells in an individual are affected by a sex chromosome aneuploidy which may be referred to as a mosaicism (e.g., Turner mosaicism). Other cases include those where SRY is damaged (leading to an XY female), or copied to the X (leading to an XX male).

In some embodiments, a method in which fetal gender is determined can also comprise determining fetal fraction and/or presence or absence of a fetal genetic variation (e.g., fetal chromosome aneuploidy). Determining presence or absence of a fetal genetic variation can be performed in a suitable manner, non-limiting examples of which include karyotype analysis, amniocentesis, circulating cell-free nucleic acid analysis, cell-free fetal DNA analysis, nucleotide sequence analysis, sequence read quantification, targeted approaches, amplification-based approaches, mass spectrometry-based approaches, differential methylation-based approaches, differential digestion-based approaches, polymorphism-based approaches, hybridization-based approaches (e.g., using probes), and the like.

In certain cases, it can be beneficial to determine the gender of a fetus in utero. For example, a patient (e.g., pregnant female) with a family history of one or more sex-linked disorders may wish to determine the gender of the fetus she is carrying to help assess the risk of the fetus inheriting such a disorder. Sex-linked disorders include, without limitation, X-linked and Y-linked disorders. X-linked disorders include X-linked recessive and X-linked dominant disorders. Examples of X-linked recessive disorders include, without limitation, immune disorders (e.g., chronic granulomatous disease (CYBB), Wiskott-Aldrich syndrome, X-linked severe combined immunodeficiency, X-linked agammaglobulinemia, hyper-IgM syndrome type 1, IPEX, X-linked lymphoproliferative disease, Properdin deficiency), hematologic disorders (e.g., Hemophilia A, Hemophilia B, X-linked sideroblastic anemia), endocrine disorders (e.g., androgen insensitivity syndrome/Kennedy disease, KAL1 Kallmann syndrome, X-linked adrenal hypoplasia congenital), metabolic disorders (e.g., ornithine transcarbamylase deficiency, oculocerebrorenal syndrome, adrenoleukodystrophy, glucose-6-phosphate dehydrogenase deficiency, pyruvate dehydrogenase deficiency, Danon disease/glycogen storage disease Type IIb, Fabry's disease, Hunter syndrome, Lesch-Nyhan syndrome, Menkes disease/occipital horn syndrome), nervous system disorders (e.g., Coffin-Lowry syndrome, MASA syndrome, X-linked alpha thalassemia mental retardation syndrome, Siderius X-linked mental retardation syndrome, color blindness, ocular albinism, Norrie disease, choroideremia, Charcot-Marie-Tooth disease (CMTX2-3), Pelizaeus-Merzbacher disease, SMAX2), skin and related tissue disorders (e.g., dyskeratosis congenital, hypohidrotic ectodermal dysplasia (EDA), X-linked ichthyosis, X-linked endothelial corneal dystrophy), neuromuscular disorders (e.g., Becker's muscular dystrophy/Duchenne, centronuclear myopathy (MTM1), Conradi-Hünermann syndrome, Emery-Dreifuss muscular dystrophy 1), urologic disorders (e.g., Alport syndrome, Dent's disease, X-linked nephrogenic diabetes insipidus), bone/tooth disorders (e.g., AMELX Amelogenesis imperfecta), and other disorders (e.g., Barth syndrome, McLeod syndrome, Smith-Fineman-Myers syndrome, Simpson-Golabi-Behmel syndrome, Mohr-Tranebjærg syndrome, Nasodigitoacoustic syndrome). Examples of X-linked dominant disorders include, without limitation, X-linked hypophosphatemia, Focal dermal hypoplasia, Fragile X syndrome, Aicardi syndrome, Incontinentia pigmenti, Rett syndrome, CHILD syndrome, Lujan-Fryns syndrome, and Orofaciodigital syndrome 1. Examples of Y-linked disorders include, without limitation, male infertility, retinitis pigmentosa, and azoospermia.

Chromosome Abnormalities

In some embodiments, the presence or absence of a fetal chromosome abnormality can be determined by using a method, machine or apparatus described herein. Chromosome abnormalities include, without limitation, a gain or loss of an entire chromosome or a region of a chromosome comprising one or more genes. Chromosome abnormalities include monosomies, trisomies, polysomies, loss of heterozygosity, translocations, deletions and/or duplications of one or more nucleotide sequences (e.g., one or more genes), including deletions and duplications caused by unbalanced translocations. The term "chromosomal abnormality", "aneuploidy" and/or "aneuploid" as used herein refers to a deviation between the structure of the subject chromosome and a normal homologous chromosome. The term "normal" refers to the predominate karyotype or banding pattern found in healthy individuals of a particular species, for example, a euploid genome (in humans, 46,XX or 46,XY). As different organisms have widely varying chromosome complements, the term "aneuploidy" and "aneuploid" does not refer to a particular number of chromosomes, but rather to the situation in which the chromosome content within a given cell or cells of an organism is abnormal. In some embodiments, the term "aneuploidy" and "aneuploid" herein refers to an imbalance of genetic material caused by a loss or gain of a whole chromosome, or part of a chromosome. An "aneuploidy" can refer to one or more deletions and/or insertions of a segment of a chromosome. The term "euploid", in some embodiments, refers a normal complement of chromosomes.

The term "monosomy" as used herein refers to lack of one chromosome of the normal complement. Partial monosomy can occur in unbalanced translocations or deletions, in which only a segment of the chromosome is present in a single copy. Monosomy of sex chromosomes (45, X) causes Turner syndrome, for example. The term "disomy" refers to the presence of two copies of a chromosome. For organisms such as humans that have two copies of each chromosome (those that are diploid or "euploid"), disomy is the normal condition. For organisms that normally have three or more copies of each chromosome (those that are triploid or above), disomy is an aneuploid chromosome state. In uniparental disomy, both copies of a chromosome come from the same parent (with no contribution from the other parent).

The term "trisomy" as used herein refers to the presence of three copies, instead of two copies, of a particular chromosome. The presence of an extra chromosome 21, which is found in human Down syndrome, is referred to as "Trisomy 21." Trisomy 18 and Trisomy 13 are two other human autosomal trisomies. Trisomy of sex chromosomes can be seen in females (e.g., 47, XXX in Triple X Syndrome) or males (e.g., 47, XXY in Klinefelter's Syndrome; or 47, XYY in Jacobs Syndrome). In some embodiments, a trisomy is a duplication of most or all of an autosome. In certain embodiments a trisomy is a whole chromosome aneuploidy resulting in three instances (e.g., three copies) of a particular type of chromosome (e.g., instead of two instances (i.e., a pair) of a particular type of chromosome for a euploid).

The terms "tetrasomy" and "pentasomy" as used herein refer to the presence of four or five copies of a chromosome, respectively. Although rarely seen with autosomes, sex chromosome tetrasomy and pentasomy have been reported in humans, including XXXX, XXXY, XXYY, XYYY, XXXXX, XXXXY, XXXYY, XXYYY and XYYYY.

Chromosome abnormalities can be caused by a variety of mechanisms. Mechanisms include, but are not limited to (i) nondisjunction occurring as the result of a weakened mitotic checkpoint, (ii) inactive mitotic checkpoints causing nondisjunction at multiple chromosomes, (iii) merotelic attachment occurring when one kinetochore is attached to both mitotic spindle poles, (iv) a multipolar spindle forming when more than two spindle poles form, (v) a monopolar spindle forming when only a single spindle pole forms, and (vi) a tetraploid intermediate occurring as an end result of the monopolar spindle mechanism.

The terms "partial monosomy" and "partial trisomy" as used herein refer to an imbalance of genetic material caused by loss or gain of part of a chromosome. A partial monosomy or partial trisomy can result from an unbalanced translocation, where an individual carries a derivative chromosome formed through the breakage and fusion of two different chromosomes. In this situation, the individual would have three copies of part of one chromosome (two normal copies and the segment that exists on the derivative chromosome) and only one copy of part of the other chromosome involved in the derivative chromosome.

The term "mosaicism" as used herein refers to aneuploidy in some cells, but not all cells, of an organism. Certain chromosome abnormalities can exist as mosaic and non-mosaic chromosome abnormalities. For example, certain trisomy 21 individuals have mosaic Down syndrome and some have non-mosaic Down syndrome. Different mechanisms can lead to mosaicism. For example, (i) an initial zygote may have three 21st chromosomes, which normally would result in simple trisomy 21, but during the course of cell division one or more cell lines lost one of the 21st chromosomes; and (ii) an initial zygote may have two 21st chromosomes, but during the course of cell division one of the 21st chromosomes were duplicated. Somatic mosaicism likely occurs through mechanisms distinct from those typically associated with genetic syndromes involving complete or mosaic aneuploidy. Somatic mosaicism has been identified in certain types of cancers and in neurons, for example. In certain instances, trisomy 12 has been identified in chronic lymphocytic leukemia (CLL) and trisomy 8 has been identified in acute myeloid leukemia (AML). Also, genetic syndromes in which an individual is predisposed to breakage of chromosomes (chromosome instability syndromes) are frequently associated with increased risk for various types of cancer, thus highlighting the role of somatic aneuploidy in carcinogenesis. Methods and protocols described herein can identify presence or absence of non-mosaic and mosaic chromosome abnormalities.

Tables 1A and 1B present a non-limiting list of chromosome conditions, syndromes and/or abnormalities that can be potentially identified by methods, machines and apparatuses described herein. Table 1B is from the DECIPHER database as of Oct. 6, 2011 (e.g., version 5.1, based on positions mapped to GRCh37; available at uniform resource locator (URL) dechipher.sanger.ac.uk).

TABLE 1A

| Chromosome | Abnormality | Disease Association |
|---|---|---|
| X | XO | Turner's Syndrome |
| Y | XXY | Klinefelter syndrome |
| Y | XYY | Double Y syndrome |
| Y | XXX | Trisomy X syndrome |
| Y | XXXX | Four X syndrome |
| Y | Xp21 deletion | Duchenne's/Becker syndrome, congenital adrenal hypoplasia, chronic granulomatus disease |
| Y | Xp22 deletion | steroid sulfatase deficiency |
| Y | Xq26 deletion | X-linked lymphoproliferative disease |
| 1 | 1p (somatic) monosomy trisomy | neuroblastoma |
| 2 | monosomy trisomy 2q | growth retardation, developmental and mental delay, and minor physical abnormalities |
| 3 | monosomy trisomy (somatic) | Non-Hodgkin's lymphoma |
| 4 | monosomy trisomy (somatic) | Acute non lymphocytic leukemia (ANLL) |
| 5 | 5p | Cri du chat; Lejeune syndrome |
| 5 | 5q (somatic) monosomy trisomy | myelodysplastic syndrome |
| 6 | monosomy trisomy (somatic) | clear-cell sarcoma |
| 7 | 7q11.23 deletion | William's syndrome |
| 7 | monosomy trisomy | monosomy 7 syndrome of childhood; somatic: renal cortical adenomas; myelodysplastic syndrome |

TABLE 1A-continued

| Chromosome | Abnormality | Disease Association |
|---|---|---|
| 8 | 8q24.1 deletion | Langer-Giedon syndrome |
| 8 | monosomy trisomy | myelodysplastic syndrome; Warkany syndrome; somatic: chronic myelogenous leukemia |
| 9 | monosomy 9p | Alfi's syndrome |
| 9 | monosomy 9p partial trisomy | Rethore syndrome |
| 9 | trisomy | complete trisomy 9 syndrome; mosaic trisomy 9 syndrome |
| 10 | Monosomy trisomy (somatic) | ALL or ANLL |
| 11 | 11p- | Aniridia; Wilms tumor |
| 11 | 11q- | Jacobsen Syndrome |
| 11 | monosomy (somatic) trisomy | myeloid lineages affected (ANLL, MDS) |
| 12 | monosomy trisomy (somatic) | CLL, Juvenile granulosa cell tumor (JGCT) |
| 13 | 13q- | 13q-syndrome; Orbeli syndrome |
| 13 | 13q14 deletion | retinoblastoma |
| 13 | monosomy trisomy | Patau's syndrome |
| 14 | monosomy trisomy (somatic) | myeloid disorders (MDS, ANLL, atypical CML) |
| 15 | 15q11-q13 deletion monosomy | Prader-Willi, Angelman's syndrome |
| 15 | trisomy (somatic) | myeloid and lymphoid lineages affected, e.g., MDS, ANLL, ALL, CLL) |
| 16 | 16q13.3 deletion | Rubenstein-Taybi |
| 3 | monosomy trisomy (somatic) | papillary renal cell carcinomas (malignant) |
| 17 | 17p-(somatic) | 17p syndrome in myeloid malignancies |
| 17 | 17q11.2 deletion | Smith-Magenis |
| 17 | 17q13.3 | Miller-Dieker |
| 17 | monosomy trisomy (somatic) | renal cortical adenomas |
| 17 | 17p11.2-12 trisomy | Charcot-Marie Tooth Syndrome type 1; HNPP |
| 18 | 18p- | 18p partial monosomy syndrome or Grouchy Lamy Thieffry syndrome |
| 18 | 18q- | Grouchy Lamy Salmon Landry Syndrome |
| 18 | monosomy trisomy | Edwards Syndrome |
| 19 | monosomy trisomy | |
| 20 | 20p- | trisomy 20p syndrome |
| 20 | 20p11.2-12 deletion | Alagille |
| 20 | 20q- | somatic: MDS, ANLL, polycythemia vera, chronic neutrophilic leukemia |
| 20 | monosomy trisomy (somatic) | papillary renal cell carcinomas (malignant) |
| 21 | monosomy trisomy | Down's syndrome |
| 22 | 22q11.2 deletion | DiGeorge's syndrome, velocardiofacial syndrome, conotruncal anomaly face syndrome, autosomal dominant Opitz G/BBB syndrome, Caylor cardiofacial syndrome |
| 22 | monosomy trisomy | complete trisomy 22 syndrome |

TABLE 1B

| Syndrome | Chromosome | Start | End | Interval (Mb) | Grade |
|---|---|---|---|---|---|
| 12q14 microdeletion syndrome | 12 | 65,071,919 | 68,645,525 | 3.57 | |
| 15q13.3 microdeletion syndrome | 15 | 30,769,995 | 32,701,482 | 1.93 | |
| 15q24 recurrent microdeletion syndrome | 15 | 74,377,174 | 76,162,277 | 1.79 | |
| 15q26 overgrowth syndrome | 15 | 99,357,970 | 102,521,392 | 3.16 | |
| 16p11.2 microduplication syndrome | 16 | 29,501,198 | 30,202,572 | 0.70 | |
| 16p11.2-p12.2 microdeletion syndrome | 16 | 21,613,956 | 29,042,192 | 7.43 | |
| 16p13.11 recurrent microdeletion (neurocognitive disorder susceptibility locus) | 16 | 15,504,454 | 16,284,248 | 0.78 | |
| 16p13.11 recurrent microduplication (neurocognitive disorder susceptibility locus) | 16 | 15,504,454 | 16,284,248 | 0.78 | |
| 17q21.3 recurrent microdeletion syndrome | 17 | 43,632,466 | 44,210,205 | 0.58 | 1 |
| 1p36 microdeletion syndrome | 1 | 10,001 | 5,408,761 | 5.40 | 1 |
| 1q21.1 recurrent microdeletion (susceptibility locus for neurodevelopmental disorders) | 1 | 146,512,930 | 147,737,500 | 1.22 | 3 |
| 1q21.1 recurrent microduplication (possible susceptibility locus for neurodevelopmental disorders) | 1 | 146,512,930 | 147,737,500 | 1.22 | 3 |
| 1q21.1 susceptibility locus for Thrombocytopenia-Absent Radius (TAR) syndrome | 1 | 145,401,253 | 145,928,123 | 0.53 | 3 |
| 22q11 deletion syndrome (Velocardiofacial/DiGeorge syndrome) | 22 | 18,546,349 | 22,336,469 | 3.79 | 1 |
| 22q11 duplication syndrome | 22 | 18,546,349 | 22,336,469 | 3.79 | 3 |
| 22q11.2 distal deletion syndrome | 22 | 22,115,848 | 23,696,229 | 1.58 | |
| 22q13 deletion syndrome (Phelan-Mcdermid syndrome) | 22 | 51,045,516 | 51,187,844 | 0.14 | 1 |
| 2p15-16.1 microdeletion syndrome | 2 | 57,741,796 | 61,738,334 | 4.00 | |
| 2q33.1 deletion syndrome | 2 | 196,925,089 | 205,206,940 | 8.28 | 1 |
| 2q37 monosomy | 2 | 239,954,693 | 243,102,476 | 3.15 | 1 |
| 3q29 microdeletion syndrome | 3 | 195,672,229 | 197,497,869 | 1.83 | |
| 3q29 microduplication syndrome | 3 | 195,672,229 | 197,497,869 | 1.83 | |
| 7q11.23 duplication syndrome | 7 | 72,332,743 | 74,616,901 | 2.28 | |
| 8p23.1 deletion syndrome | 8 | 8,119,295 | 11,765,719 | 3.65 | |
| 9q subtelomeric deletion syndrome | 9 | 140,403,363 | 141,153,431 | 0.75 | 1 |
| Adult-onset autosomal dominant leukodystrophy (ADLD) | 5 | 126,063,045 | 126,204,952 | 0.14 | |
| Angelman syndrome (Type 1) | 15 | 22,876,632 | 28,557,186 | 5.68 | 1 |
| Angelman syndrome (Type 2) | 15 | 23,758,390 | 28,557,186 | 4.80 | 1 |
| ATR-16 syndrome | 16 | 60,001 | 834,372 | 0.77 | 1 |
| AZFa | Y | 14,352,761 | 15,154,862 | 0.80 | |
| AZFb | Y | 20,118,045 | 26,065,197 | 5.95 | |
| AZFb + AZFc | Y | 19,964,826 | 27,793,830 | 7.83 | |
| AZFc | Y | 24,977,425 | 28,033,929 | 3.06 | |
| Cat-Eye Syndrome (Type I) | 22 | 1 | 16,971,860 | 16.97 | |
| Charcot-Marie-Tooth syndrome type 1A (CMT1A) | 17 | 13,968,607 | 15,434,038 | 1.47 | 1 |
| Cri du Chat Syndrome (5p deletion) | 5 | 10,001 | 11,723,854 | 11.71 | 1 |
| Early-onset Alzheimer disease with cerebral amyloid angiopathy | 21 | 27,037,956 | 27,548,479 | 0.51 | |
| Familial Adenomatous Polyposis | 5 | 112,101,596 | 112,221,377 | 0.12 | |
| Hereditary Liability to Pressure Palsies (HNPP) | 17 | 13,968,607 | 15,434,038 | 1.47 | 1 |
| Leri-Weill dyschondrostosis (LWD) - SHOX deletion | X | 751,878 | 867,875 | 0.12 | |
| Leri-Weill dyschondrostosis (LWD) - SHOX deletion | X | 460,558 | 753,877 | 0.29 | |
| Miller-Dieker syndrome (MDS) | 17 | 1 | 2,545,429 | 2.55 | 1 |
| NF1-microdeletion syndrome | 17 | 29,162,822 | 30,218,667 | 1.06 | 1 |
| Pelizaeus-Merzbacher disease | X | 102,642,051 | 103,131,767 | 0.49 | |
| Potocki-Lupski syndrome (17p11.2 duplication syndrome) | 17 | 16,706,021 | 20,482,061 | 3.78 | |
| Potocki-Shaffer syndrome | 11 | 43,985,277 | 46,064,560 | 2.08 | 1 |
| Prader-Willi syndrome (Type 1) | 15 | 22,876,632 | 28,557,186 | 5.68 | 1 |
| Prader-Willi Syndrome (Type 2) | 15 | 23,758,390 | 28,557,186 | 4.80 | 1 |
| RCAD (renal cysts and diabetes) | 17 | 34,907,366 | 36,076,803 | 1.17 | |
| Rubinstein-Taybi Syndrome | 16 | 3,781,464 | 3,861,246 | 0.08 | 1 |
| Smith-Magenis Syndrome | 17 | 16,706,021 | 20,482,061 | 3.78 | 1 |
| Sotos syndrome | 5 | 175,130,402 | 177,456,545 | 2.33 | 1 |
| Split hand/foot malformation 1 (SHFM1) | 7 | 95,533,860 | 96,779,486 | 1.25 | |
| Steroid sulphatase deficiency (STS) | X | 6,441,957 | 8,167,697 | 1.73 | |
| WAGR 11p13 deletion syndrome | 11 | 31,803,509 | 32,510,988 | 0.71 | |
| Williams-Beuren Syndrome (WBS) | 7 | 72,332,743 | 74,616,901 | 2.28 | 1 |

TABLE 1B-continued

| Syndrome | Chromosome | Start | End | Interval (Mb) | Grade |
|---|---|---|---|---|---|
| Wolf-Hirschhorn Syndrome | 4 | 10,001 | 2,073,670 | 2.06 | 1 |
| Xq28 (MECP2) duplication | X | 152,749,900 | 153,390,999 | 0.64 | |

Grade 1 conditions often have one or more of the following characteristics; pathogenic anomaly; strong agreement amongst geneticists; highly penetrant; may still have variable phenotype but some common features; all cases in the literature have a clinical phenotype; no cases of healthy individuals with the anomaly; not reported on DVG databases or found in healthy population; functional data confirming single gene or multi-gene dosage effect; confirmed or strong candidate genes; clinical management implications defined; known cancer risk with implication for surveillance; multiple sources of information (OMIM, GeneReviews, Orphanet, Unique, Wikipedia); and/or available for diagnostic use (reproductive counseling).

Grade 2 conditions often have one or more of the following characteristics; likely pathogenic anomaly; highly penetrant; variable phenotype with no consistent features other than DD; small number of cases/reports in the literature; all reported cases have a clinical phenotype; no functional data or confirmed pathogenic genes; multiple sources of information (OMIM, GeneReviews, Orphanet, Unique, Wikipedia); and/or may be used for diagnostic purposes and reproductive counseling.

Grade 3 conditions often have one or more of the following characteristics; susceptibility locus; healthy individuals or unaffected parents of a proband described; present in control populations; non penetrant; phenotype mild and not specific; features less consistent; no functional data or confirmed pathogenic genes; more limited sources of data; possibility of second diagnosis remains a possibility for cases deviating from the majority or if novel clinical finding present; and/or caution when using for diagnostic purposes and guarded advice for reproductive counseling.

Preeclampsia

In some embodiments, the presence or absence of preeclampsia is determined by using a method, machine or apparatus described herein. Preeclampsia is a condition in which hypertension arises in pregnancy (i.e. pregnancy-induced hypertension) and is associated with significant amounts of protein in the urine. In certain embodiments, preeclampsia also is associated with elevated levels of extracellular nucleic acid and/or alterations in methylation patterns. For example, a positive correlation between extracellular fetal-derived hypermethylated RASSF1A levels and the severity of pre-eclampsia has been observed. In certain examples, increased DNA methylation is observed for the H19 gene in preeclamptic placentas compared to normal controls.

Preeclampsia is one of the leading causes of maternal and fetal/neonatal mortality and morbidity worldwide. Circulating cell-free nucleic acids in plasma and serum are novel biomarkers with promising clinical applications in different medical fields, including prenatal diagnosis. Quantitative changes of cell-free fetal (cff)DNA in maternal plasma as an indicator for impending preeclampsia have been reported in different studies, for example, using real-time quantitative PCR for the male-specific SRY or DYS 14 loci. In cases of early onset preeclampsia, elevated levels may be seen in the first trimester. The increased levels of cffDNA before the onset of symptoms may be due to hypoxia/reoxygenation within the intervillous space leading to tissue oxidative stress and increased placental apoptosis and necrosis. In addition to the evidence for increased shedding of cffDNA into the maternal circulation, there is also evidence for reduced renal clearance of cffDNA in preeclampsia. As the amount of fetal DNA is currently determined by quantifying Y-chromosome specific sequences, alternative approaches such as measurement of total cell-free DNA or the use of gender-independent fetal epigenetic markers, such as DNA methylation, offer an alternative. Cell-free RNA of placental origin is another alternative biomarker that may be used for screening and diagnosing preeclampsia in clinical practice. Fetal RNA is associated with subcellular placental particles that protect it from degradation. Fetal RNA levels sometimes are ten-fold higher in pregnant females with preeclampsia compared to controls, and therefore is an alternative biomarker that may be used for screening and diagnosing preeclampsia in clinical practice.

Pathogens

In some embodiments, the presence or absence of a pathogenic condition is determined by a method or apparatus described herein. A pathogenic condition can be caused by infection of a host by a pathogen including, but not limited to, a bacterium, virus or fungus. Since pathogens typically possess nucleic acid (e.g., genomic DNA, genomic RNA, mRNA) that can be distinguishable from host nucleic acid, methods, machines and apparatuses provided herein can be used to determine the presence or absence of a pathogen. Often, pathogens possess nucleic acid with characteristics unique to a particular pathogen such as, for example, epigenetic state and/or one or more sequence variations, duplications and/or deletions. Thus, methods provided herein may be used to identify a particular pathogen or pathogen variant (e.g. strain).

Cancers

In some embodiments, the presence or absence of a cell proliferation disorder (e.g., a cancer) is determined by using a method, machine or apparatus described herein. For example, levels of cell-free nucleic acid in serum can be elevated in patients with various types of cancer compared with healthy patients. Patients with metastatic diseases, for example, can sometimes have serum DNA levels approximately twice as high as non-metastatic patients. Patients with metastatic diseases may also be identified by cancer-specific markers and/or certain single nucleotide polymorphisms or short tandem repeats, for example. Non-limiting examples of cancer types that may be positively correlated with elevated levels of circulating DNA include breast cancer, colorectal cancer, gastrointestinal cancer, hepatocellular cancer, lung cancer, melanoma, non-Hodgkin lymphoma, leukemia, multiple myeloma, bladder cancer, hepatoma, cervical cancer, esophageal cancer, pancreatic cancer, and prostate cancer. Various cancers can possess, and can sometimes release into the bloodstream, nucleic acids with characteristics that are distinguishable from nucleic acids from non-cancerous healthy cells, such as, for example, epigenetic state and/or sequence variations, duplications and/or deletions. Such characteristics can, for example, be specific to a particular type of cancer. Thus, it is further contemplated that a method provided herein can be used to identify a particular type of cancer.

Software can be used to perform one or more steps in the processes described herein, including but not limited to; counting, data processing, generating an outcome, and/or providing one or more recommendations based on generated outcomes, as described in greater detail hereafter.

Machines, Software and Interfaces

Certain processes and methods described herein (e.g., quantifying, mapping, normalizing, range setting, adjusting, categorizing, counting and/or determining sequence reads, counts, levels (e.g., levels) and/or profiles) often cannot be performed without a computer, microprocessor, software, module or other machine. Methods described herein typically are computer-implemented methods, and one or more portions of a method sometimes are performed by one or more processors (e.g., microprocessors), computers, or microprocessor controlled machines. Embodiments pertaining to methods described in this document generally are applicable to the same or related processes implemented by instructions in systems, machines and computer program products described herein. Embodiments pertaining to methods described in this document generally can be applicable to the same or related processes implemented by a non-transitory computer-readable storage medium with an executable program stored thereon, where the program instructs a microprocessor to perform the method, or a part thereof. In some embodiments, processes and methods described herein (e.g., quantifying, counting and/or determining sequence reads, counts, levels and/or profiles) are performed by automated methods. In some embodiments one or more steps and a method described herein is carried out by a microprocessor and/or computer, and/or carried out in conjunction with memory. In some embodiments, an automated method is embodied in software, modules, microprocessors, peripherals and/or a machine comprising the like, that determine sequence reads, counts, mapping, mapped sequence tags, levels, profiles, normalizations, comparisons, range setting, categorization, adjustments, plotting, outcomes, transformations and identifications. As used herein, software refers to computer readable program instructions that, when executed by a microprocessor, perform computer operations, as described herein.

Sequence reads, counts, levels, and profiles derived from a test subject (e.g., a patient, a pregnant female) and/or from a reference subject can be further analyzed and processed to determine the presence or absence of a genetic variation. Sequence reads, counts, levels and/or profiles sometimes are referred to as "data" or "data sets". In some embodiments, data or data sets can be characterized by one or more features or variables (e.g., sequence based [e.g., GC content, specific nucleotide sequence, the like], function specific [e.g., expressed genes, cancer genes, the like], location based [genome specific, chromosome specific, portion or portion-specific], the like and combinations thereof). In certain embodiments, data or data sets can be organized into a matrix having two or more dimensions based on one or more features or variables. Data organized into matrices can be organized using any suitable features or variables. A non-limiting example of data in a matrix includes data that is organized by maternal age, maternal ploidy, and fetal contribution. In certain embodiments, data sets characterized by one or more features or variables sometimes are processed after counting.

Machines, software and interfaces may be used to conduct methods described herein. Using machines, software and interfaces, a user may enter, request, query or determine options for using particular information, programs or processes (e.g., mapping sequence reads, processing mapped data and/or providing an outcome), which can involve implementing statistical analysis algorithms, statistical significance algorithms, statistical algorithms, iterative steps, validation algorithms, and graphical representations, for example. In some embodiments, a data set may be entered by a user as input information, a user may download one or more data sets by a suitable hardware media (e.g., flash drive), and/or a user may send a data set from one system to another for subsequent processing and/or providing an outcome (e.g., send sequence read data from a sequencer to a computer system for sequence read mapping; send mapped sequence data to a computer system for processing and yielding an outcome and/or report).

A system typically comprises one or more machines. Each machine comprises one or more of memory, one or more microprocessors, and instructions. Where a system includes two or more machines, some or all of the machines may be located at the same location, some or all of the machines may be located at different locations, all of the machines may be located at one location and/or all of the machines may be located at different locations. Where a system includes two or more machines, some or all of the machines may be located at the same location as a user, some or all of the machines may be located at a location different than a user, all of the machines may be located at the same location as the user, and/or all of the machine may be located at one or more locations different than the user.

A system sometimes comprises a computing machine and a sequencing apparatus or machine, where the sequencing apparatus or machine is configured to receive physical nucleic acid and generate sequence reads, and the computing apparatus is configured to process the reads from the sequencing apparatus or machine. The computing machine sometimes is configured to determine the presence or absence of a genetic variation (e.g., copy number variation; fetal chromosome aneuploidy) from the sequence reads.

A user may, for example, place a query to software which then may acquire a data set via internet access, and in certain embodiments, a programmable microprocessor may be prompted to acquire a suitable data set based on given parameters. A programmable microprocessor also may prompt a user to select one or more data set options selected by the microprocessor based on given parameters. A programmable microprocessor may prompt a user to select one or more data set options selected by the microprocessor based on information found via the internet, other internal or external information, or the like. Options may be chosen for selecting one or more data feature selections, one or more statistical algorithms, one or more statistical analysis algorithms, one or more statistical significance algorithms, iterative steps, one or more validation algorithms, and one or more graphical representations of methods, machines, apparatuses, computer programs or a non-transitory computer-readable storage medium with an executable program stored thereon.

Systems addressed herein may comprise general components of computer systems, such as, for example, network servers, laptop systems, desktop systems, handheld systems, personal digital assistants, computing kiosks, and the like. A computer system may comprise one or more input means such as a keyboard, touch screen, mouse, voice recognition or other means to allow the user to enter data into the system. A system may further comprise one or more outputs, including, but not limited to, a display screen (e.g., CRT or LCD), speaker, FAX machine, printer (e.g., laser, ink jet, impact, black and white or color printer), or other output useful for providing visual, auditory and/or hardcopy output of information (e.g., outcome and/or report).

In a system, input and output means may be connected to a central processing unit which may comprise among other components, a microprocessor for executing program instructions and memory for storing program code and data. In some embodiments, processes may be implemented as a single user system located in a single geographical site. In certain embodiments, processes may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by a provider, or it may be implemented as an internet based service where the user accesses a web page to enter and retrieve information. Accordingly, in certain embodiments, a system includes one or more machines, which may be local or remote with respect to a user. More than one machine in one location or multiple locations may be accessed by a user, and data may be mapped and/or processed in series and/or in parallel. Thus, a suitable configuration and control may be utilized for mapping and/or processing data using multiple machines, such as in local network, remote network and/or "cloud" computing platforms.

A system can include a communications interface in some embodiments. A communications interface allows for transfer of software and data between a computer system and one or more external devices. Non-limiting examples of communications interfaces include a modem, a network interface (such as an Ethernet card), a communications port, a PCMCIA slot and card, and the like. Software and data transferred via a communications interface generally are in the form of signals, which can be electronic, electromagnetic, optical and/or other signals capable of being received by a communications interface. Signals often are provided to a communications interface via a channel. A channel often carries signals and can be implemented using wire or cable, fiber optics, a phone line, a cellular phone link, an RF link and/or other communications channels. Thus, in an example, a communications interface may be used to receive signal information that can be detected by a signal detection module.

Data may be input by a suitable device and/or method, including, but not limited to, manual input devices or direct data entry devices (DDEs). Non-limiting examples of manual devices include keyboards, concept keyboards, touch sensitive screens, light pens, mouse, tracker balls, joysticks, graphic tablets, scanners, digital cameras, video digitizers and voice recognition devices. Non-limiting examples of DDEs include bar code readers, magnetic strip codes, smart cards, magnetic ink character recognition, optical character recognition, optical mark recognition, and turnaround documents.

In some embodiments, output from a sequencing apparatus or machine may serve as data that can be input via an input device. In certain embodiments, mapped sequence reads may serve as data that can be input via an input device. In certain embodiments, nucleic acid fragment size (e.g., length) may serve as data that can be input via an input device. In certain embodiments, output from a nucleic acid capture process (e.g., genomic region origin data) may serve as data that can be input via an input device. In certain embodiments, a combination of nucleic acid fragment size (e.g., length) and output from a nucleic acid capture process (e.g., genomic region origin data) may serve as data that can be input via an input device. In certain embodiments, simulated data is generated by an in silico process and the simulated data serves as data that can be input via an input device. The term "in silico" refers to research and experiments performed using a computer. In silico processes include, but are not limited to, mapping sequence reads and processing mapped sequence reads according to processes described herein.

A system may include software useful for performing a process described herein, and software can include one or more modules for performing such processes (e.g., sequencing module, logic processing module, data display organization module). The term "software" refers to computer readable program instructions that, when executed by a computer, perform computer operations. Instructions executable by the one or more microprocessors sometimes are provided as executable code, that when executed, can cause one or more microprocessors to implement a method described herein. A module described herein can exist as software, and instructions (e.g., processes, routines, subroutines) embodied in the software can be implemented or performed by a microprocessor. For example, a module (e.g., a software module) can be a part of a program that performs a particular process or task. The term "module" refers to a self-contained functional unit that can be used in a larger machine or software system. A module can comprise a set of instructions for carrying out a function of the module. A module can transform data and/or information. Data and/or information can be in a suitable form. For example, data and/or information can be digital or analogue. In certain embodiments, data and/or information sometimes can be packets, bytes, characters, or bits. In some embodiments, data and/or information can be any gathered, assembled or usable data or information. Non-limiting examples of data and/or information include a suitable media, pictures, video, sound (e.g. frequencies, audible or non-audible), numbers, constants, a value, objects, time, functions, instructions, maps, references, sequences, reads, mapped reads, levels, ranges, thresholds, signals, displays, representations, or transformations thereof. A module can accept or receive data and/or information, transform the data and/or information into a second form, and provide or transfer the second form to an machine, peripheral, component or another module. A module can perform one or more of the following non-limiting functions: mapping sequence reads, providing counts, assembling portions, providing or determining a level, providing a count profile, normalizing (e.g., normalizing reads, normalizing counts, and the like), providing a normalized count profile or levels of normalized counts, comparing two or more levels, providing uncertainty values, providing or determining expected levels and expected ranges (e.g., expected level ranges, threshold ranges and threshold levels), providing adjustments to levels (e.g., adjusting a first level, adjusting a second level, adjusting a profile of a chromosome or a segment thereof, and/or padding), providing identification (e.g., identifying a copy number variation, genetic variation or aneuploidy), categorizing, plotting, and/or determining an outcome, for example. A microprocessor can, in certain embodiments, carry out the instructions in a module. In some embodiments, one or more microprocessors are required to carry out instructions in a module or group of modules. A module can provide data and/or information to another module, machine or source and can receive data and/or information from another module, machine or source.

A computer program product sometimes is embodied on a tangible computer-readable medium, and sometimes is tangibly embodied on a non-transitory computer-readable medium. A module sometimes is stored on a computer readable medium (e.g., disk, drive) or in memory (e.g., random access memory). A module and microprocessor capable of implementing instructions from a module can be located in a machine or in a different machine. A module and/or microprocessor capable of implementing an instruction for a module can be located in the same location as a user (e.g., local network) or in a different location from a user (e.g., remote network, cloud system). In embodiments in which a method is carried out in conjunction with two or more modules, the modules can be located in the same machine, one or more modules can be located in different machine in the same physical location, and one or more modules may be located in different machines in different physical locations.

A machine, in some embodiments, comprises at least one microprocessor for carrying out the instructions in a module. Counts of sequence reads mapped to portions of a reference genome sometimes are accessed by a microprocessor that executes instructions configured to carry out a method described herein. Counts that are accessed by a microprocessor can be within memory of a system, and the counts can be accessed and placed into the memory of the system after they are obtained. In some embodiments, a machine includes a microprocessor (e.g., one or more microprocessors) which microprocessor can perform and/or implement one or more instructions (e.g., processes, routines and/or subroutines) from a module. In some embodiments, a machine includes multiple microprocessors, such as microprocessors coordinated and working in parallel. In some embodiments, a machine operates with one or more external microprocessors (e.g., an internal or external network, server, storage device and/or storage network (e.g., a cloud)). In some embodiments, a machine comprises a module. In certain embodiments a machine comprises one or more modules. A machine comprising a module often can receive and transfer one or more of data and/or information to and from other modules. In certain embodiments, a machine comprises peripherals and/or components. In certain embodiments a machine can comprise one or more peripherals or components that can transfer data and/or information to and from other modules, peripherals and/or components. In certain embodiments a machine interacts with a peripheral and/or component that provides data and/or information. In certain embodiments peripherals and components assist a machine in carrying out a function or interact directly with a module. Non-limiting examples of peripherals and/or components include a suitable computer peripheral, I/O or storage method or device including but not limited to scanners, printers, displays (e.g., monitors, LED, LCT or CRTs), cameras, microphones, pads (e.g., ipads, tablets), touch screens, smart phones, mobile phones, USB I/O devices, USB mass storage devices, keyboards, a computer mouse, digital pens, modems, hard drives, jump drives, flash drives, a microprocessor, a server, CDs, DVDs, graphic cards, specialized I/O devices (e.g., sequencers, photo cells, photo multiplier tubes, optical readers, sensors, etc.), one or more flow cells, fluid handling components, network interface controllers, ROM, RAM, wireless transfer methods and devices (Bluetooth, WiFi, and the like,), the world wide web (www), the internet, a computer and/or another module.

Software often is provided on a program product containing program instructions recorded on a computer readable medium, including, but not limited to, magnetic media including floppy disks, hard disks, and magnetic tape; and optical media including CD-ROM discs, DVD discs, magneto-optical discs, flash drives, RAM, floppy discs, the like, and other such media on which the program instructions can be recorded. In online implementation, a server and web site maintained by an organization can be configured to provide software downloads to remote users, or remote users may access a remote system maintained by an organization to remotely access software. Software may obtain or receive input information. Software may include a module that specifically obtains or receives data (e.g., a data receiving module that receives sequence read data and/or mapped read data) and may include a module that specifically processes the data (e.g., a processing module that processes received data (e.g., filters, normalizes, provides an outcome and/or report). The terms "obtaining" and "receiving" input information refers to receiving data (e.g., sequence reads, mapped reads) by computer communication means from a local, or remote site, human data entry, or any other method of receiving data. The input information may be generated in the same location at which it is received, or it may be generated in a different location and transmitted to the receiving location. In some embodiments, input information is modified before it is processed (e.g., placed into a format amenable to processing (e.g., tabulated)). In some embodiments, provided are computer program products, such as, for example, a computer program product comprising a computer usable medium having a computer readable program code embodied therein, the computer readable program code adapted to be executed to implement a method comprising: (a) obtaining sequence reads of sample nucleic acid from a test subject; (b) mapping the sequence reads obtained in (a) to a known genome, which known genome has been divided into portions; (c) counting the mapped sequence reads within the portions; (d) generating a sample normalized count profile by normalizing the counts for the portions obtained in (c); and (e) determining the presence or absence of a genetic variation from the sample normalized count profile in (d).

Software can include one or more algorithms in certain embodiments. An algorithm may be used for processing data and/or providing an outcome or report according to a finite sequence of instructions. An algorithm often is a list of defined instructions for completing a task. Starting from an initial state, the instructions may describe a computation that proceeds through a defined series of successive states, eventually terminating in a final ending state. The transition from one state to the next is not necessarily deterministic (e.g., some algorithms incorporate randomness). By way of example, and without limitation, an algorithm can be a search algorithm, sorting algorithm, merge algorithm, numerical algorithm, graph algorithm, string algorithm, modeling algorithm, computational genometric algorithm, combinatorial algorithm, machine learning algorithm, cryptography algorithm, data compression algorithm, parsing algorithm and the like. An algorithm can include one algorithm or two or more algorithms working in combination. An algorithm can be of any suitable complexity class and/or parameterized complexity. An algorithm can be used for calculation and/or data processing, and in some embodiments, can be used in a deterministic or probabilistic/predictive approach. An algorithm can be implemented in a computing environment by use of a suitable programming language, non-limiting examples of which are C, C++, Java, Perl, Python, Fortran, and the like. In some embodiments, an algorithm can be configured or modified to include margin of errors, statistical analysis, statistical significance, and/or comparison to other information or data sets (e.g., applicable when using a neural net or clustering algorithm).

In certain embodiments, several algorithms may be implemented for use in software. These algorithms can be trained with raw data in some embodiments. For each new raw data sample, the trained algorithms may produce a representative processed data set or outcome. A processed data set sometimes is of reduced complexity compared to the parent data set that was processed. Based on a processed set, the performance of a trained algorithm may be assessed based on sensitivity and specificity, in some embodiments. An algorithm with the highest sensitivity and/or specificity may be identified and utilized, in certain embodiments.

In certain embodiments, simulated (or simulation) data can aid data processing, for example, by training an algorithm or testing an algorithm. In some embodiments, simulated data includes hypothetical various samplings of different groupings of sequence reads. Simulated data may be based on what might be expected from a real population or may be skewed to test an algorithm and/or to assign a correct classification. Simulated data also is referred to herein as "virtual" data. Simulations can be performed by a computer program in certain embodiments. One possible step in using a simulated data set is to evaluate the confidence of an identified results, e.g., how well a random sampling matches or best represents the original data. One approach is to calculate a probability value (p-value), which estimates the probability of a random sample having better score than the selected samples. In some embodiments, an empirical model may be assessed, in which it is assumed that at least one sample matches a reference sample (with or without resolved variations). In some embodiments, another distribution, such as a Poisson distribution for example, can be used to define the probability distribution.

A system may include one or more microprocessors in certain embodiments. A microprocessor can be connected to a communication bus. A computer system may include a main memory, often random access memory (RAM), and can also include a secondary memory. Memory in some embodiments comprises a non-transitory computer-readable storage medium. Secondary memory can include, for example, a hard disk drive and/or a removable storage drive, representing a floppy disk drive, a magnetic tape drive, an optical disk drive, memory card and the like. A removable storage drive often reads from and/or writes to a removable storage unit. Non-limiting examples of removable storage units include a floppy disk, magnetic tape, optical disk, and the like, which can be read by and written to by, for example, a removable storage drive. A removable storage unit can include a computer-usable storage medium having stored therein computer software and/or data.

A microprocessor may implement software in a system. In some embodiments, a microprocessor may be programmed to automatically perform a task described herein that a user could perform. Accordingly, a microprocessor, or algorithm conducted by such a microprocessor, can require little to no supervision or input from a user (e.g., software may be programmed to implement a function automatically). In some embodiments, the complexity of a process is so large that a single person or group of persons could not perform the process in a timeframe short enough for determining the presence or absence of a genetic variation.

In some embodiments, secondary memory may include other similar means for allowing computer programs or other instructions to be loaded into a computer system. For example, a system can include a removable storage unit and an interface device. Non-limiting examples of such systems include a program cartridge and cartridge interface (such as that found in video game devices), a removable memory chip (such as an EPROM, or PROM) and associated socket, and other removable storage units and interfaces that allow software and data to be transferred from the removable storage unit to a computer system.

One entity can generate counts of sequence reads, map the sequence reads to portions, count the mapped reads, and utilize the counted mapped reads in a method, system, machine, apparatus or computer program product described herein, in some embodiments. Counts of sequence reads mapped to portions sometimes are transferred by one entity to a second entity for use by the second entity in a method, system, machine, apparatus or computer program product described herein, in certain embodiments.

In some embodiments, one entity generates sequence reads and a second entity maps those sequence reads to portions in a reference genome in some embodiments. The second entity sometimes counts the mapped reads and utilizes the counted mapped reads in a method, system, machine or computer program product described herein. In certain embodiments the second entity transfers the mapped reads to a third entity, and the third entity counts the mapped reads and utilizes the mapped reads in a method, system, machine or computer program product described herein. In certain embodiments the second entity counts the mapped reads and transfers the counted mapped reads to a third entity, and the third entity utilizes the counted mapped reads in a method, system, machine or computer program product described herein. In embodiments involving a third entity, the third entity sometimes is the same as the first entity. That is, the first entity sometimes transfers sequence reads to a second entity, which second entity can map sequence reads to portions in a reference genome and/or count the mapped reads, and the second entity can transfer the mapped and/or counted reads to a third entity. A third entity sometimes can utilize the mapped and/or counted reads in a method, system, machine or computer program product described herein, where the third entity sometimes is the same as the first entity, and sometimes the third entity is different from the first or second entity.

In some embodiments, one entity obtains blood from a pregnant female, optionally isolates nucleic acid from the blood (e.g., from the plasma or serum), and transfers the blood or nucleic acid to a second entity that generates sequence reads from the nucleic acid.

Figure 24:
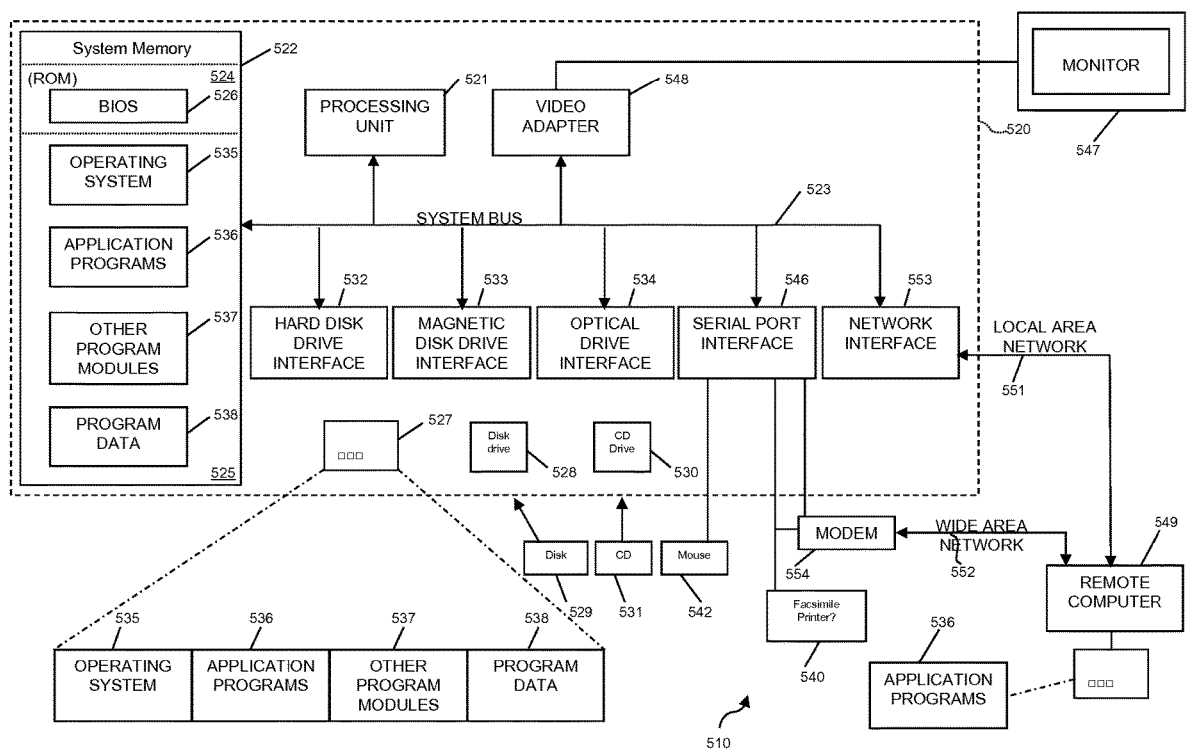
FIG. 24 shows an illustrative embodiment of a system in which certain embodiments of the technology may be implemented.

FIG. 24 illustrates a non-limiting example of a computing environment 510 in which various systems, methods, algorithms, and data structures described herein may be implemented. The computing environment 510 is only one example of a suitable computing environment and is not intended to suggest any limitation as to the scope of use or functionality of the systems, methods, and data structures described herein. Neither should computing environment 510 be interpreted as having any dependency or requirement relating to any one or combination of components illustrated in computing environment 510. A subset of systems, methods, and data structures shown in FIG. 24 can be utilized in certain embodiments. Systems, methods, and data structures described herein are operational with numerous other general purpose or special purpose computing system environments or configurations. Examples of known computing systems, environments, and/or configurations that may be suitable include, but are not limited to, personal computers, server computers, thin clients, thick clients, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The operating environment 510 of FIG. 24 includes a general purpose computing device in the form of a computer 520, including a processing unit 521, a system memory 522, and a system bus 523 that operatively couples various system components including the system memory 522 to the processing unit 521. There may be only one or there may be more than one processing unit 521, such that the microprocessor of computer 520 includes a single central-processing unit (CPU), or a plurality of processing units, commonly referred to as a parallel processing environment. The computer 520 may be a conventional computer, a distributed computer, or any other type of computer.

The system bus 523 may be any of several types of bus structures including a memory bus or memory controller, a peripheral bus, and a local bus using any of a variety of bus architectures. The system memory may also be referred to as simply the memory, and includes read only memory (ROM) 524 and random access memory (RAM). A basic input/output system (BIOS) 526, containing the basic routines that help to transfer information between elements within the computer 520, such as during start-up, is stored in ROM 524. The computer 520 may further include a hard disk drive interface 527 for reading from and writing to a hard disk, not shown, a magnetic disk drive 528 for reading from or writing to a removable magnetic disk 529, and an optical disk drive 530 for reading from or writing to a removable optical disk 531 such as a CD ROM or other optical media.

The hard disk drive 527, magnetic disk drive 528, and optical disk drive 530 are connected to the system bus 523 by a hard disk drive interface 532, a magnetic disk drive interface 533, and an optical disk drive interface 534, respectively. The drives and their associated computer-readable media provide nonvolatile storage of computer-readable instructions, data structures, program modules and other data for the computer 520. Any type of computer-readable media that can store data that is accessible by a computer, such as magnetic cassettes, flash memory cards, digital video disks, Bernoulli cartridges, random access memories (RAMs), read only memories (ROMs), and the like, may be used in the operating environment.

A number of program modules may be stored on the hard disk, magnetic disk 529, optical disk 531, ROM 524, or RAM, including an operating system 535, one or more application programs 536, other program modules 537, and program data 538. A user may enter commands and information into the personal computer 520 through input devices such as a keyboard 540 and pointing device 542. Other input devices (not shown) may include a microphone, joystick, game pad, satellite dish, scanner, or the like. These and other input devices are often connected to the processing unit 521 through a serial port interface 546 that is coupled to the system bus, but may be connected by other interfaces, such as a parallel port, game port, or a universal serial bus (USB). A monitor 547 or other type of display device is also connected to the system bus 523 via an interface, such as a video adapter 548. In addition to the monitor, computers typically include other peripheral output devices (not shown), such as speakers and printers.

The computer 520 may operate in a networked environment using logical connections to one or more remote computers, such as remote computer 549. These logical connections may be achieved by a communication device coupled to or a part of the computer 520, or in other manners. The remote computer 549 may be another computer, a server, a router, a network PC, a client, a peer device or other common network node, and typically includes many or all of the elements described above relative to the computer 520, although only a memory storage device 550 has been illustrated in FIG. 24. The logical connections depicted in FIG. 24 include a local-area network (LAN) 551 and a wide-area network (WAN) 552. Such networking environments are commonplace in office networks, enterprise-wide computer networks, intranets and the Internet, which all are types of networks.

When used in a LAN-networking environment, the computer 520 is connected to the local network 551 through a network interface or adapter 553, which is one type of communications device. When used in a WAN-networking environment, the computer 520 often includes a modem 554, a type of communications device, or any other type of communications device for establishing communications over the wide area network 552. The modem 554, which may be internal or external, is connected to the system bus 523 via the serial port interface 546. In a networked environment, program modules depicted relative to the personal computer 520, or portions thereof, may be stored in the remote memory storage device. It is appreciated that the network connections shown are non-limiting examples and other communications devices for establishing a communications link between computers may be used.

Modules

One or more modules can be utilized in a method described herein, non-limiting examples of which include a logic processing module, data display organization module, sequencing module, mapping module, counting module, filtering module, weighting module, normalization module, GC bias module, level module, comparison module, range setting module, categorization module, adjustment module, plotting module, representation module, relationship module, outcome module and/or data display organization module, the like or combination thereof. Modules are sometimes controlled by a microprocessor. In certain embodiments a module or a machine comprising one or more modules, gather, assemble, receive, obtain, access, recover provide and/or transfer data and/or information to or from another module, machine, component, peripheral or operator of a machine. In some embodiments, data and/or information (e.g., sequencing reads) are provided to a module by a machine comprising one or more of the following: one or more flow cells, a camera, a detector (e.g., a photo detector, a photo cell, an electrical detector (e.g., an amplitude modulation detector, a frequency and phase modulation detector, a phase-locked loop detector), a counter, a sensor (e.g., a sensor of pressure, temperature, volume, flow, weight), a fluid handling device, a printer, a display (e.g., an LED, LCT or CRT), the like or combinations thereof. For example, sometimes an operator of a machine provides a constant, a threshold value, a formula or a predetermined value to a module. A module is often configured to transfer data and/or information to or from another module or machine. A module can receive data and/or information from another module, non-limiting examples of which include a logic processing module, sequencing module, mapping module, counting module, filtering module, weighting module, normalization module, GC bias module, level module, comparison module, range setting module, categorization module, plotting module, representation module, relationship module, outcome module and/or data display organization module, the like or combination thereof. A module can manipulate and/or transform data and/or information. Data and/or information derived from or transformed by a module can be transferred to another suitable machine and/or module, non-limiting examples of which include a logic processing module, data display organization module, sequencing module, mapping module, counting module, filtering module, weighting module, normalization module, GC bias module, level module, comparison module, range setting module, categorization module, adjustment module, plotting module, representation module, relationship module, outcome module and/or data display organization module, the like or combination thereof. A machine comprising a module can comprise at least one microprocessor. In some embodiments, data and/or information are received by and/or provided by a machine comprising a module. A machine comprising a module can include a microprocessor (e.g., one or more microprocessors) which microprocessor can perform and/or implement one or more instructions (e.g., processes, routines and/or subroutines) of a module. In some embodiments, a module operates with one or more external microprocessors (e.g., an internal or external network, server, storage device and/or storage network (e.g., a cloud)).

Logic Processing Module

In certain embodiments a logic processing module orchestrates, controls, limits, organizes, orders, distributes, partitions, transforms and/or regulates data and/or information or the transfer of data and/or information to and from one or more other modules, peripherals or devices.

Data Display Organization Module

In certain embodiments a data display organization module processes and/or transforms data and/or information into a suitable visual medium non-limiting examples of which include images, video and/or text (e.g., numbers, letters and symbols). In some embodiments a data display organization module processes, transforms and/or transfers data and/or information for presentation on a suitable display (e.g., a monitor, LED, LCD, CRT, the like or combinations thereof), a printer, a suitable peripheral or device. In some embodiments a data display organization module processes, transforms data and/or information into a visual representation of a fetal or maternal genome, chromosome or part thereof.

Sequencing Module

In some embodiments, a sequence module obtains, generates, gathers, assembles, manipulates, transforms, processes, transforms and/or transfers sequence reads. A "sequence receiving module" as used herein is the same as a "sequencing module". A machine comprising a sequencing module can be any machine that determines the sequence of a nucleic acid utilizing a sequencing technology known in the art. In some embodiments a sequencing module can align, assemble, fragment, complement, reverse complement, error check, or error correct sequence reads.

Mapping Module

Sequence reads can be mapped by a mapping module or by a machine comprising a mapping module, which mapping module generally maps reads to a reference genome or segment thereof. A mapping module can map sequencing reads by a suitable method known in the art. In some embodiments, a mapping module or a machine comprising a mapping module is required to provide mapped sequence reads.

Counting Module

Counts can be provided by a counting module or by a machine comprising a counting module. In some embodiments a counting module counts sequence reads mapped to a reference genome. In some embodiments a counting module generates, assembles, and/or provides counts according to a counting method known in the art. In some embodiments, a counting module or a machine comprising a counting module is required to provide counts.

Filtering Module

Filtering portions (e.g., portions of a reference genome) can be provided by a filtering module (e.g., by a machine comprising a filtering module). In some embodiments, a filtering module is required to provide filtered portion data (e.g., filtered portions) and/or to remove portions from consideration. In certain embodiments a filtering module removes counts mapped to a portion from consideration. In certain embodiments a filtering module removes counts mapped to a portion from a determination of a level or a profile. A filtering module can filter data (e.g., counts, counts mapped to portions, portions, portion levels, normalized counts, raw counts, and the like) by one or more filtering methods known in the art or described herein.

Weighting Module

Weighting portions (e.g., portions of a reference genome) can be provided by a weighting module (e.g., by a machine comprising a weighting module). In some embodiments, a weighting module is required to weight genomics sections and/or provide weighted portion values. A weighting module can weight portions by one or more weighting methods known in the art or described herein.

Normalization Module

Normalized data (e.g., normalized counts) can be provided by a normalization module (e.g., by a machine comprising a normalization module). In some embodiments, a normalization module is required to provide normalized data (e.g., normalized counts) obtained from sequencing reads. A normalization module can normalize data (e.g., counts, filtered counts, raw counts) by one or more normalization methods described herein (e.g., PERUN, hybrid normalization, the like or combinations thereof) or known in the art.

GC Bias Module

Determining GC bias (e.g., determining GC bias for each of the portions of a reference genome (e.g., portions, portions of a reference genome)) can be provided by a GC bias module (e.g., by a machine comprising a GC bias module). In some embodiments, a GC bias module is required to provide a determination of GC bias. In some embodiments a GC bias module provides a determination of GC bias from a fitted relationship (e.g., a fitted linear relationship) between counts of sequence reads mapped to each of the portions of a reference genome and GC content of each portion. A GC bias module sometimes is part of a normalization module (e.g., PERUN normalization module).

Level Module

Determining levels (e.g., levels) and/or calculating genomic section levels for portions of a reference genome can be provided by an level module (e.g., by a machine comprising a level module). In some embodiments, a level module is required to provide a level or a calculated genomic section level (e.g., according to Equation A, B, L, M, N, O and/or Q). In some embodiments a level module provides a level from a fitted relationship (e.g., a fitted linear relationship) between a GC bias and counts of sequence reads mapped to each of the portions of a reference genome. In some embodiments a level module calculates a genomic section level as part of PERUN. In some embodiments, a level module provides a genomic section level (i.e., $L_i$) according to equation $L_i = (m_i - G_i S) I^{-1}$ where $G_i$ is the GC bias, $m_i$ is measured counts mapped to each portion of a reference genome, i is a sample, and I is the intercept and S is the slope of the a fitted relationship (e.g., a fitted linear relationship) between a GC bias and counts of sequence reads mapped to each of the portions of a reference genome.

Comparison Module

A first level can be identified as significantly different from a second level by a comparison module or by a machine comprising a comparison module. In some embodiments, a comparison module or a machine comprising a comparison module is required to provide a comparison between two levels.

Range Setting Module

Expected ranges (e.g., expected level ranges) for various copy number variations (e.g., duplications, insertions and/or deletions) or ranges for the absence of a copy number variation can be provided by a range setting module or by a machine comprising a range setting module. In certain embodiments, expected levels are provided by a range setting module or by a machine comprising a range setting module. In some embodiments, a range setting module or a machine comprising a range setting module is required to provide expected levels and/or ranges.

Categorization Module

A copy number variation (e.g., a maternal and/or fetal copy number variation, a fetal copy number variation, a duplication, insertion, deletion) can be categorized by a categorization module or by a machine comprising a categorization module. In certain embodiments a copy number variation (e.g., a maternal and/or fetal copy number variation) is categorized by a categorization module. In certain embodiments a level (e.g., a first level) determined to be significantly different from another level (e.g., a second level) is identified as representative of a copy number variation by a categorization module. In certain embodiments the absence of a copy number variation is determined by a categorization module. In some embodiments, a determination of a copy number variation can be determined by a machine comprising a categorization module. A categorization module can be specialized for categorizing a maternal and/or fetal copy number variation, a fetal copy number variation, a duplication, deletion or insertion or lack thereof or combination of the foregoing. For example, a categorization module that identifies a maternal deletion can be different than and/or distinct from a categorization module that identifies a fetal duplication. In some embodiments, a categorization module or a machine comprising a categorization module is required to identify a copy number variation or an outcome determinative of a copy number variation.

Adjustment Module

In some embodiments, adjustments of a level (e.g., adjustments to genomic section levels, a level of a profile, a level of a copy number variation, a level of one or more portions, the like or combinations thereof) are made by an adjustment module or by a machine comprising an adjustment module. In some embodiments, an adjustment module or a machine comprising an adjustment module is required to adjust a level. A level adjusted by methods described herein can be independently verified and/or adjusted by further testing (e.g., by targeted sequencing of maternal and or fetal nucleic acid).

Plotting Module

In some embodiments a plotting module processes and/or transforms data and/or information into a suitable visual medium, non-limiting examples of which include a chart, plot, graph, the like or combinations thereof. In some embodiments a plotting module processes, transforms and/or transfers data and/or information for presentation on a suitable display (e.g., a monitor, LED, LCD, CRT, the like or combinations thereof), a printer, a suitable peripheral or device. In certain embodiments a plotting module provides a visual display of a count, a level, and/or a profile. In some embodiments a data display organization module processes, transforms data and/or information into a visual representation of a fetal or maternal genome, chromosome or part thereof. In some embodiments, a plotting module or a machine comprising a plotting module is required to plot a count, a level or a profile.

Relationship Module

In certain embodiments, a relationship module processes and/or transforms data and/or information into a relationship. In certain embodiments, a relationship is generated by and/or transferred from a relationship module.

Outcome Module

The presence or absence of a genetic variation (an aneuploidy, a fetal aneuploidy, a copy number variation) is, in some embodiments, identified by an outcome module or by a machine comprising an outcome module. In certain embodiments a genetic variation is identified by an outcome module. Often a determination of the presence or absence of an aneuploidy is identified by an outcome module. In some embodiments, an outcome determinative of a genetic variation (an aneuploidy, a copy number variation) can be identified by an outcome module or by a machine comprising an outcome module. An outcome module can be specialized for determining a specific genetic variation (e.g., a trisomy, a trisomy 21, a trisomy 18). For example, an outcome module that identifies a trisomy 21 can be different than and/or distinct from an outcome module that identifies a trisomy 18. In some embodiments, an outcome module or a machine comprising an outcome module is required to identify a genetic variation or an outcome determinative of a genetic variation (e.g., an aneuploidy, a copy number variation). A genetic variation or an outcome determinative of a genetic variation identified by methods described herein can be independently verified by further testing (e.g., by targeted sequencing of maternal and/or fetal nucleic acid).

Transformations

As noted above, data sometimes is transformed from one form into another form. The terms "transformed", "transformation", and grammatical derivations or equivalents thereof, as used herein refer to an alteration of data from a physical starting material (e.g., test subject and/or reference subject sample nucleic acid) into a digital representation of the physical starting material (e.g., sequence read data), and in some embodiments includes a further transformation into one or more numerical values or graphical representations of the digital representation that can be utilized to provide an outcome. In certain embodiments, the one or more numerical values and/or graphical representations of digitally represented data can be utilized to represent the appearance of a test subject's physical genome (e.g., virtually represent or visually represent the presence or absence of a genomic insertion, duplication or deletion; represent the presence or absence of a variation in the physical amount of a sequence associated with medical conditions). A virtual representation sometimes is further transformed into one or more numerical values or graphical representations of the digital representation of the starting material. These methods can transform physical starting material into a numerical value or graphical representation, or a representation of the physical appearance of a test subject's genome.

In some embodiments, transformation of a data set facilitates providing an outcome by reducing data complexity and/or data dimensionality. Data set complexity sometimes is reduced during the process of transforming a physical starting material into a virtual representation of the starting material (e.g., sequence reads representative of physical starting material). A suitable feature or variable can be utilized to reduce data set complexity and/or dimensionality. Non-limiting examples of features that can be chosen for use as a target feature for data processing include GC content, fetal gender prediction, fragment size (e.g., length of CCF fragments, reads or a suitable representation thereof (e.g., FRS)), fragment sequence, identification of chromosomal aneuploidy, identification of particular genes or proteins, identification of cancer, diseases, inherited genes/traits, chromosomal abnormalities, a biological category, a chemical category, a biochemical category, a category of genes or proteins, a gene ontology, a protein ontology, co-regulated genes, cell signaling genes, cell cycle genes, proteins pertaining to the foregoing genes, gene variants, protein variants, co-regulated genes, co-regulated proteins, amino acid sequence, nucleotide sequence, protein structure data and the like, and combinations of the foregoing. Non-limiting examples of data set complexity and/or dimensionality reduction include; reduction of a plurality of sequence reads to profile plots, reduction of a plurality of sequence reads to numerical values (e.g., normalized values, Z-scores, p-values); reduction of multiple analysis methods to probability plots or single points; principle component analysis of derived quantities; and the like or combinations thereof.

Certain System, Machine and Computer Program Product Embodiments

In certain aspects provided is a computer implemented method for determining the presence or absence of a genetic variation, comprising (a) obtaining counts of nucleotide sequence reads mapped to genomic sections of a reference genome, which sequence reads are: (i) reads of circulating cell-free nucleic acid from a test sample from a pregnant female, and (ii) reads from nucleic acid fragments having lengths that are less than a selected fragment length; (b) normalizing the counts, thereby generating normalized counts of sequence reads mapped to the genomic sections; and (c) determining the presence or absence of a genetic variation according to the normalized counts.

Provided also in certain aspects is a system comprising one or more microprocessors and memory, which memory comprises instructions executable by the one or more microprocessors and which memory comprises counts of nucleotide sequence reads mapped to genomic sections of a reference genome, which sequence reads are (i) reads of circulating cell-free nucleic acid from a test sample from a pregnant female, and (ii) reads from nucleic acid fragments having lengths that are less than a selected fragment length; and which instructions executable by the one or more microprocessors are configured to (a) normalize the counts, thereby generating normalized counts of sequence reads mapped to the genomic sections; and (b) determine the presence or absence of a genetic variation according to the normalized counts.

Also provided in certain aspects is a machine comprising one or more microprocessors and memory, which memory comprises instructions executable by the one or more microprocessors and which memory comprises counts of nucleotide sequence reads mapped to genomic sections of a reference genome, which sequence reads are (i) reads of circulating cell-free nucleic acid from a test sample from a pregnant female, and (ii) reads from nucleic acid fragments having lengths that are less than a selected fragment length; and which instructions executable by the one or more microprocessors are configured to (a) normalize the counts, thereby generating normalized counts of sequence reads mapped to the genomic sections; and (b) determine the presence or absence of a genetic variation according to the normalized counts.

Provided also in certain embodiments is a computer program product tangibly embodied on a computer-readable medium, comprising instructions that when executed by one or more microprocessors are configured to (a) access counts of nucleotide sequence reads mapped to genomic sections of a reference genome, which sequence reads are: (i) reads of circulating cell-free nucleic acid from a test sample from a pregnant female, and (ii) reads from nucleic acid fragments having lengths that are less than a selected fragment length (b) normalize the counts, thereby generating normalized counts of sequence reads mapped to the genomic sections; and (c) determine the presence or absence of a genetic variation according to the normalized counts.

Also provided herein is system comprising one or more microprocessors and memory, which memory comprises instructions executable by the one or more microprocessors and which memory comprises nucleotide sequence reads mapped to portions of a reference genome, which sequence reads are reads of circulating cell-free nucleic acid from a test sample from a pregnant female, and which instructions executable by the one or more microprocessors are configured to (a) weight, using a microprocessor, (i) the counts of the sequence reads mapped to each portion, or (ii) other portion-specific parameter, to a portion-specific fraction of fetal nucleic acid according to a weighting factor independently associated with each portion, thereby providing portion-specific fetal fraction estimates according to the weighting factors, where each of the weighting factors have been determined from a fitted relation for each portion between (i) a fraction of fetal nucleic acid for each of multiple samples, and (ii) counts of sequence reads mapped to each portion, or other portion-specific parameter, for the multiple samples and (b) estimate a fraction of fetal nucleic acid for the test sample based on the portion-specific fetal fraction estimates.

Also provided herein is a machine comprising one or more microprocessors and memory, which memory comprises instructions executable by the one or more microprocessors and which memory comprises nucleotide sequence reads mapped to portions of a reference genome, which sequence reads are reads of circulating cell-free nucleic acid from a test sample from a pregnant female, and which instructions executable by the one or more microprocessors are configured to (a) weight, using a microprocessor, (i) the counts of the sequence reads mapped to each portion, or (ii) other portion-specific parameter, to a portion-specific fraction of fetal nucleic acid according to a weighting factor independently associated with each portion, thereby providing portion-specific fetal fraction estimates according to the weighting factors, where each of the weighting factors have been determined from a fitted relation for each portion between (i) a fraction of fetal nucleic acid for each of multiple samples, and (ii) counts of sequence reads mapped to each portion, or other portion-specific parameter, for the multiple samples and (b) estimate a fraction of fetal nucleic acid for the test sample based on the portion-specific fetal fraction estimates.

Also provided herein is a non-transitory computer-readable storage medium with an executable program stored thereon, where the program instructs a microprocessor to perform the following: (a) access nucleotide sequence reads mapped to portions of a reference genome, which sequence reads are reads of circulating cell-free nucleic acid from a test sample from a pregnant female, (b) weight, using a microprocessor, (i) the counts of the sequence reads mapped to each portion, or (ii) other portion-specific parameter, to a portion-specific fraction of fetal nucleic acid according to a weighting factor independently associated with each portion, thereby providing portion-specific fetal fraction estimates according to the weighting factors, where each of the weighting factors have been determined from a fitted relation for each portion between (i) a fraction of fetal nucleic acid for each of multiple samples, and (ii) counts of sequence reads mapped to each portion, or other portion-specific parameter, for the multiple samples and (c) estimate a fraction of fetal nucleic acid for the test sample based on the portion-specific fetal fraction estimates.

In certain embodiments, a system, machine and/or computer program product comprises a counting module configured to count reads mapped to genomic sections of a reference genome or portion thereof (e.g., subset of genomic sections, selected set of genomic sections). A counting module often is configured to count reads from nucleic acid fragments having lengths that are less than a selected fragment length. The counts sometimes are raw, filtered, normalized counts or combination of the foregoing. In some embodiments, a counting module can normalize the counts, for example, using any suitable normalization process described herein or known in the art.

In some embodiments, a system, machine and/or computer program product comprises a count comparison module. A count comparison module often is configured to compare the number of counts of reads counted by a counting module, thereby making a count comparison. A count comparison module often is configured to access, receive, utilize, store, search for and/or align counts of reads (e.g., from a counting module or normalization module). A count comparison module often is configured to provide a suitable comparison between counts, non-limiting examples of which comparison include a simple comparison (e.g., match or no match between counts of reads mapped to a first set of genomic sections compared to a second set of genomic sections), mathematical comparison (e.g., ratio, percentage), statistical comparison (e.g., multiple comparisons, multiple testing, standardization (e.g., z-score analyses)), the like and combinations thereof. A suitable count comparison value can be provided by a count comparison module, non-limiting examples of which include presence or absence of a match between counts, a ratio, percentage, z-score, a value coupled with a measure of variance or uncertainty (e.g., standard deviation, median absolute deviation, confidence interval), the like and combinations thereof. A count comparison module sometimes is configured to transmit a comparison value to another module or machine, such as a genetic variation module, display machine or printer machine, for example.

In certain embodiments, a system, machine and/or computer program product comprises a genetic variation module. A genetic variation module sometimes is configured to provide a determination of the presence or absence of a genetic variation according to counts of reads mapped to genomic sections of a reference genome. A genetic variation module sometimes is configured to provide a determination of the presence or absence of a genetic variation according to a comparison of counts. A genetic variation module often is configured to access, receive, utilize, store, search for and/or align one or more comparisons from a count comparison module and/or counts from a counting module. A genetic variation module can determine the presence or absence of a genetic variation from one or more comparisons or from counts in a suitable manner. A genetic variation module sometimes determines whether there is a significant difference between counts for different sets of genomic sections in a reference genome. The significance of a difference can be determined by a genetic variation module in a suitable manner (e.g., percent difference, z-score analysis). A genetic variation module sometimes determines whether a count determination or a comparison of counts is in a particular category. For example, a genetic variation module may categorize a particular comparison to a particular ratio threshold or a range of ratios associated with a euploid determination, or a particular ratio threshold or range of ratios associated with an aneuploid determination. In another non-limiting example, a genetic variation module may categorize a particular count determination to a particular count threshold or a range of counts associated with a euploid determination, or a particular count threshold or range of counts associated with an aneuploid determination. A genetic variation module can provide an outcome in a suitable format, which sometimes is a call pertaining to a genetic variation optionally associated with a measure of variance or uncertainty (e.g., standard deviation, median absolute deviation, accuracy (e.g., within a particular confidence interval). A genetic variation module sometimes is configured to transmit a determination of the presence or absence of a genetic variation to another module or machine, such as a display machine or printer, for example.

A machine or system comprising a module described herein (e.g., a reference comparison module) can comprise one or more microprocessors. In some embodiments, a machine or system can include multiple microprocessors, such as microprocessors coordinated and working in parallel. A microprocessor (e.g., one or more microprocessors) in a system or machine can perform and/or implement one or more instructions (e.g., processes, routines and/or subroutines) in a module described herein. A module described herein sometimes is located in memory or associated with a machine or system. In some embodiments, a module described herein operates with one or more external microprocessors (e.g., an internal or external network, server, storage device and/or storage network (e.g., a cloud)). In some embodiments, a module described herein is configured to access, gather, assemble and/or receive data and/or information from another module, machine or system (e.g., component, peripheral). In some embodiments, a module described herein is configured to provide and/or transfer data and/or information to another module, machine or system (e.g., component, peripheral). In some embodiments, a module described herein is configured to access, accept, receive and/or gather input data and/or information from an operator of a machine or system (i.e., user). For example, sometimes a user provides a constant, a threshold value, a formula and/or a predetermined value to a module. A module described herein sometimes is configured to transform data and/or information it accesses, receives, gathers and/or assembles.

In certain embodiments, a system, machine and/or computer program product comprises (i) a sequencing module configured to obtain and/or access nucleic acid sequence reads and/or partial nucleotide sequence reads; (ii) a mapping module configured to map nucleic acid sequence reads to portions of a reference genome; (iii) a counting module configured to provide counts of nucleic acid sequence reads mapped to portions of a reference genome; (iv) a normalization module configured to provide normalized counts; (v) a comparison module configured to provide an identification of a first elevation that is significantly different than a second elevation; (vi) a range setting module configured to provide one or more expected level ranges; (vii) a categorization module configured to identify an elevation representative of a copy number variation; (viii) an adjustment module configured to adjust a level identified as a copy number variation; (ix) a plotting module configured to graph and display a level and/or a profile; (x) an outcome module configured to determine the presence or absence of a genetic variation, or determine an outcome (e.g., outcome determinative of the presence or absence of a fetal aneuploidy); (xi) a data display organization module configured to display a genetic variation determination; (xii) a logic processing module configured to perform one or more of map sequence reads, count mapped sequence reads, normalize counts and generate an outcome; (xiii) a count comparison module, (xiv) fetal fraction module configured to provide a fetal fraction determination; (xv) a genetic variation module configured to provide a determination of the presence or absence of a genetic variation; or (xvi) combination of two or more of the foregoing.

In some embodiments a sequencing module and mapping module are configured to transfer sequence reads from the sequencing module to the mapping module. The mapping module and counting module sometimes are configured to transfer mapped sequence reads from the mapping module to the counting module. In some embodiments, the normalization module and/or comparison module are configured to transfer normalized counts to the comparison module and/or range setting module. The comparison module, range setting module and/or categorization module independently are configured to transfer (i) an identification of a first elevation that is significantly different than a second elevation and/or (ii) an expected level range from the comparison module and/or range setting module to the categorization module, in some embodiments. In certain embodiments, the categorization module and the adjustment module are configured to transfer an elevation categorized as a copy number variation from the categorization module to the adjustment module. In some embodiments, the adjustment module, plotting module and the outcome module are configured to transfer one or more adjusted levels from the adjustment module to the plotting module or outcome module. The normalization module sometimes is configured to transfer mapped normalized sequence read counts to one or more of the comparison module, range setting module, categorization module, adjustment module, outcome module or plotting module.

EXAMPLES

The following examples are provided by way of illustration only and not by way of limitation. Thus, the examples set forth below illustrate certain embodiments and do not limit the technology. Those of skill in the art will readily recognize a variety of non-critical parameters that could be changed or modified to yield essentially the same or similar results.

Example 1

PERUN and General Methods for Detecting Conditions Associated with Genetic Variations The methods and underlying theory described herein can be utilized to detect various conditions associated with genetic variation and provide an outcome determinative of, or determine the presence or absence of a genetic variation.

Removal of Uninformative Portions of a Reference Genome

Multiple attempts to remove uninformative portions of a reference genome have indicated that portion selection has the potential to improve classification.

Equation A:

$$M = LI + GS \quad \text{(A)}$$

The various terms in Eq. A have the following meanings:
  M: measured counts, representing the primary information polluted by unwanted variation.
  L: chromosomal level—this is the desired output from the data processing procedure. L indicates fetal and/or maternal aberrations from euploid. This is the quantity that is masked both by stochastic errors and by the systematic biases. The chromosomal level L is both sample specific and portion-specific.
  G: GC bias coefficient measured using linear model, LOESS, or any equivalent approach. G represents secondary information, extracted from M and from a set of portion-specific GC content values, usually derived from the reference genome (but may be derived from actually observed GC contents as well). G is sample specific and does not vary along the genomic position. It encapsulates a portion of the unwanted variation.
  I: Intercept of the linear model. This model parameter is fixed for a given experimental setup, independent on the sample, and portion-specific.
  S: Slope of the linear model. This model parameter is fixed for a given experimental setup, independent on the sample, and portion-specific.

The quantities M and G are measured. Initially, the portion-specific values I and S are unknown. To evaluate unknown I and S, we must assume that L=1 for all portions of a reference genome in euploid samples. The assumption is not always true, but one can reasonably expect that any samples with deletions/duplications will be overwhelmed by samples with normal chromosomal levels. A linear model applied to the euploid samples extracts the I and S parameter values specific for the selected portion (assuming L=1). The same procedure is applied to all the portions of a reference genome in the human genome, yielding a set of intercepts I and slopes S for every genomic location. Cross-validation randomly selects a work set containing 90% of all LDTv2CE euploids and uses that subset to train the model. The random selection is repeated 100 times, yielding a set of 100 slopes and 100 intercepts for every portion.

Extraction of Chromosomal Level from Measured Counts
Assuming that the model parameter values/and S are available for every portion, measurements M collected on a new test sample are used to evaluate the chromosomal level according to the following Equation B:

$$L = (M - GS)/I \quad \text{(B)}$$

As in Eq. A, the GC bias coefficient G is evaluated as the slope of the regression between the portion-wise measured raw counts M and the GC content of the reference genome. The chromosomal level L is then used for further analyses (Z-values, maternal deletions/duplications, fetal microdeletions/microduplications, fetal gender, sex aneuploidies, and so on). The procedure encapsulated by Eq. B is named Parameterized Error Removal and Unbiased Normalization (PERUN).

Example 2

Examples of Formulas

Provided below are non-limiting examples of mathematical and/or statistical formulas that can be used in methods described herein.

Z-scores and p-values calculated from Z-scores associated with deviations from the expected level of 1 can then be evaluated in light of the estimate for uncertainty in the average level. The p-values are based on a t-distribution whose order is determined by the number of portions of a reference genome in a peak. Depending on the desired level of confidence, a cutoff can suppress noise and allow unequivocal detection of the actual signal.

Equation 1

$$Z = \frac{\Delta_1 - \Delta_z}{\sqrt{\sigma_1^2\left(\frac{1}{N_1} + \frac{1}{n_1}\right) + \sigma_2^2\left(\frac{1}{N_2} + \frac{1}{n_2}\right)}} \quad (1)$$

Equation 1 can be used to directly compare peak level from two different samples, where N and n refer to the numbers of portions of a reference genome in the entire chromosome and within the aberration, respectively. The order of the t-test that will yield a p-value measuring the similarity between two samples is determined by the number of portions of a reference genome in the shorter of the two deviant stretches.

Equation 8 can be utilized to incorporate fetal fraction, maternal ploidy, and median reference counts into a classification scheme for determining the presence or absence of a genetic variation with respect to fetal aneuploidy.

Equation 8:

$$y_i = (1-F)M_i f_i + FX f_i \quad (8)$$

where $Y_i$ represents the measured counts for a portion in the test sample corresponding to the portion in the median count profile, F represents the fetal fraction, X represents the fetal ploidy, and $M_i$ represents maternal ploidy assigned to each portion. Possible values used for X in equation (8) are: 1 if the fetus is euploid; 3/2, if the fetus is triploid; and, 5/4, if there are twin fetuses and one is affected and one is not. 5/4 is used in the case of twins where one fetus is affected and the other not, because the term F in equation (8) represents total fetal DNA, therefore all fetal DNA must be taken into account. In some embodiments, large deletions and/or duplications in the maternal genome can be accounted for by assigning maternal ploidy, $M_i$, to each portion or portion. Maternal ploidy often is assigned as a multiple of ½, and can be estimated using portion-wise normalization, in some embodiments. Because maternal ploidy often is a multiple of ½, maternal ploidy can be readily accounted for, and therefore will not be included in further equations to simplify derivations.

When evaluating equation (8) at X=1, (e.g., euploid assumption), the fetal fraction is canceled out and the following equation results for the sum of squared residuals.

Equation 9

$$\varphi_E = \sum_{i=1}^{N} \frac{1}{\sigma_i^2}(y_i - f_i)^2 = \quad (9)$$

$$\sum_{i=1}^{N} \frac{y_i^2}{\sigma_i^2} - 2\sum_{i=1}^{N} \frac{y_i f_i}{\sigma_i^2} + \sum_{i=1}^{N} \frac{f_i^2}{\sigma_i^2} = \Xi_{yy} - 2\Xi_{fy} + \Xi_{ff}$$

To simplify equation (9) and subsequent calculations, the following equations are utilized.

$$\Xi_{yy} = \sum_{i=1}^{N} \frac{y_i^2}{\sigma_i^2} \quad (10)$$

$$\Xi_{ff} = \sum_{i=1}^{N} \frac{f_i^2}{\sigma_i^2} \quad (11)$$

$$\Xi_{fy} = \sum_{i=1}^{N} \frac{y_i f_i}{\sigma_i^2}. \quad (12)$$

When evaluating equation (8) at X=3/2 (e.g., triploid assumption), the following equation results for the sum of the squared residuals.

Equation 13

$$\varphi_T = \sum_{i=1}^{N} \frac{1}{\sigma_i^2}\left(y_i - f_i - \frac{1}{2}Ff_i\right)^2 \quad (13)$$

$$= \Xi_{yy} - 2\Xi_{fy} + \Xi_{ff} + F(\Xi_{ff} - \Xi_{fy}) + \frac{1}{4}F^2\Xi_{ff}$$

The difference between equations (9) and (13) forms the functional result (e.g., phi) that can be used to test the null hypothesis (e.g., euploid, X=1) against the alternative hypothesis (e.g., trisomy singleton, X=3/2):

Equation 14

$$\varphi = \varphi_E - \varphi_T = F(\Xi_{fy} - \Xi_{ff}) - \frac{1}{4}F^2\Xi_{ff} \quad (14)$$

Equation 18

$$\varphi = \sum_{i=1}^{N} \frac{1}{\sigma_i^2}[y_i - (1-F)M_i f_i - FX f_i]^2 \quad (18)$$

$$= \sum_{i=1}^{N} \frac{1}{\sigma_i^2}\left[\begin{array}{c} y_i^2 - (1-F)M_i f_i y_i - 2FX f_i y_i + (1-F)^2 M_i^2 f_i^2 + \\ 2F(1-F)XM_i f_i^2 + F^2 X^2 f_i^2 \end{array}\right]$$

Optimal ploidy value sometimes is given by Equation 20:

$$X = \frac{\sum_{i=1}^{N} \frac{f_i y_i}{\sigma_i^2} - (1-F)\sum_{i=1}^{N} \frac{M_i f_i^2}{\sigma_i^2}}{F\sum_{i=1}^{N} \frac{f_i^2}{\sigma_i^2}} \quad (20)$$

The term for maternal ploidy, $M_i$, can be omitted from some mathematical derivations. The resulting expression for X corresponds to the relatively simple, and often most frequently occurring, special case of when the mother has no deletions or duplications in the chromosome or chromosomes being evaluated.

Equation 21

$$X = \frac{\Xi_{fy} - (1-F)\Xi_{ff}}{F\Xi_{ff}} = \frac{\Xi_{fy}}{F\Xi_{ff}} - \frac{1-F}{F} = 1 + \frac{1}{F}\left(\frac{\Xi_{fy}}{\Xi_{ff}} - 1\right) \quad (21)$$

$Xi_{ff}$ and $Xi_{fy}$ are given by equations (11) and (12), respectively. In embodiments where all experimental errors are negligible, solving equation (21) results in a value of 1 for euploids where $Xi_{ff} = Xi_{fy}$. In certain embodiments where all experimental errors are negligible, solving equation (21) results in a value of 3/2 for triploids (see equation (15) for triploid relationship between $Xi_{ff}$ and $Xi_{fy}$.

TABLE 2

| Pregnancy Status | Fetal Chr21 | Fetal Chr18 | Fetal Chr13 | Fetal ChrX | Fetal ChrY |
|---|---|---|---|---|---|
| Female T21 | $P_{ij}^F = 3/2$ | $P_{ij}^F = 1$ | $P_{ij}^F = 1$ | $P_{ij}^F = 1$ | $P_{ij}^F = 0$ |
| Female T18 | $P_{ij}^F = 1$ | $P_{ij}^F = 3/2$ | $P_{ij}^F = 1$ | $P_{ij}^F = 1$ | $P_{ij}^F = 0$ |
| Female T13 | $P_{ij}^F = 1$ | $P_{ij}^F = 1$ | $P_{ij}^F = 3/2$ | $P_{ij}^F = 1$ | $P_{ij}^F = 0$ |
| Male T21 | $P_{ij}^F = 3/2$ | $P_{ij}^F = 1$ | $P_{ij}^F = 1$ | $P_{ij}^F = 1/2$ | $P_{ij}^F = 1/2$ |
| Male T18 | $P_{ij}^F = 1$ | $P_{ij}^F = 3/2$ | $P_{ij}^F = 1$ | $P_{ij}^F = 1/2$ | $P_{ij}^F = 1/2$ |
| Male T13 | $P_{ij}^F = 1$ | $P_{ij}^F = 1$ | $P_{ij}^F = 3/2$ | $P_{ij}^F = 1/2$ | $P_{ij}^F = 1/2$ |
| Male Euploid | $P_{ij}^F = 1$ | $P_{ij}^F = 1$ | $P_{ij}^F = 1$ | $P_{ij}^F = 1/2$ | $P_{ij}^F = 1/2$ |
| Turner | $P_{ij}^F = 1$ | $P_{ij}^F = 1$ | $P_{ij}^F = 1$ | $P_{ij}^F = 1/2$ | $P_{ij}^F = 0$ |
| Jacobs | $P_{ij}^F = 1$ | $P_{ij}^F = 1$ | $P_{ij}^F = 1$ | $P_{ij}^F = 1/2$ | $P_{ij}^F = 1$ |
| Klinefelter | $P_{ij}^F = 1$ | $P_{ij}^F = 1$ | $P_{ij}^F = 1$ | $P_{ij}^F = 1$ | $P_{ij}^F = 1/2$ |
| TripleX | $P_{ij}^F = 1$ | $P_{ij}^F = 1$ | $P_{ij}^F = 1$ | $P_{ij}^F = 3/2$ | $P_{ij}^F = 0$ |

Example 3

Portion Selection Using FRS

Portions of the human reference genome designated HG19 were first pre-filtered using a PERUN-based method that removes portions with high variability, low mappability and binds with a large percentage of repetitive elements. Portions (as selected for LDTv2) with high variability, low mappability, and a large fraction of repetitive sequences were excluded. For each 50 kb portion (e.g., portion), a fetal ratio statistic was computed for paired end sequence reads from CCF fragments less than 150 bases and from CCF fragments less than 600 bases. The FRS was then averaged across 264 non-pooled samples processed using TruSeq Biochemistry library preparation with automated bead cleanup. Portions with FRS>median (FRS) were selected and are shown in TABLE 4 with reference to chromosome-specific start and end positions. Chromosome-specific start and end positions in TABLE 4 reference nucleotide base positions in human reference genome HG19.

All portions with FRS>median (FRS) were plotted concurrently with the number of unique exon start positions in each respective portion. A significant correlation was shown for regions of genes that contain an overrepresentation of small fragments (FIGS. 1-9). A significantly stronger correlation was shown with GC content (percentage of GC bases in a 50 kb portion) and FRS (Table 3).

Portion selection was further restricted to portions (i.e., portions) of the genome where FRS>median (FRS) for chromosomal trisomy detection. Applying this approach on a preliminary data set of 264 samples provided consistent classification margins despite discarding 50% of the data. Conversely, restricting portions where FRS<median (FRS), the classification margin was dramatically reduced, suggesting a dilution of fetal DNA for analyses (FIGS. 10-11).

Figure 10:
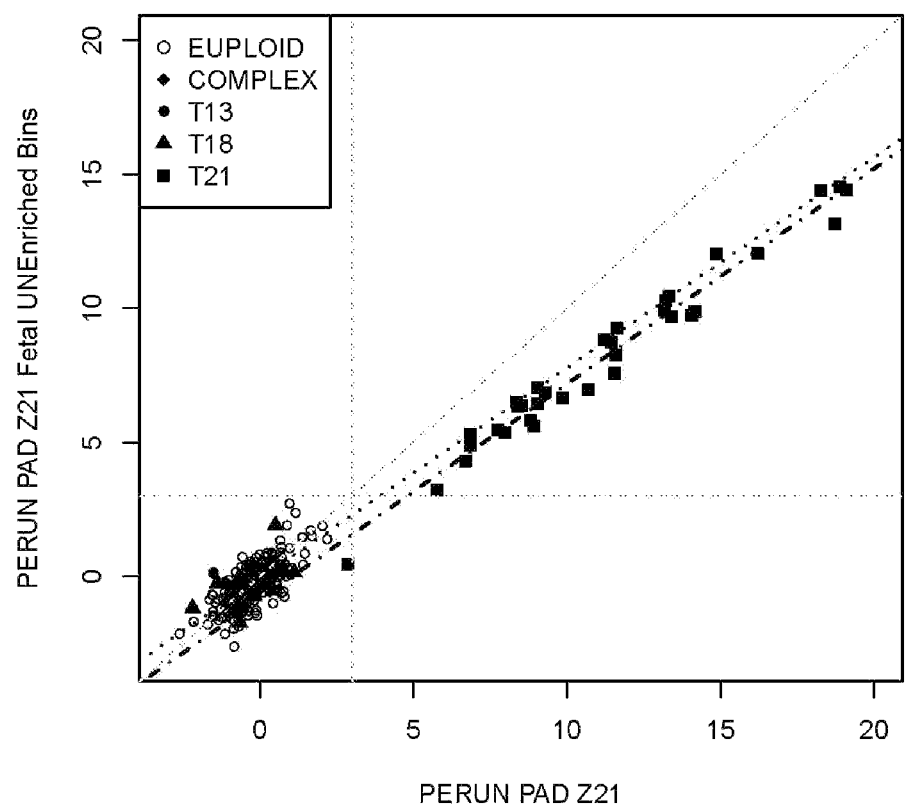
FIG. 10 shows PERUN PAD with LOESS Z scores (X-axis) verse PERUN PAD with LOESS Z scores based on "fetal unenriched" portions (Y-axis) for chromosome 21. The four quadrants represent concordance and discordance. The quadrant lines are drawn at Z=3. The top right and bottom left quadrants are separated by a grey dashed diagonal line. The dash-dot line is a regression line for non-T21 samples only. The dotted line is a regression line for T21 samples based on high FRS portions.
Figure 11:
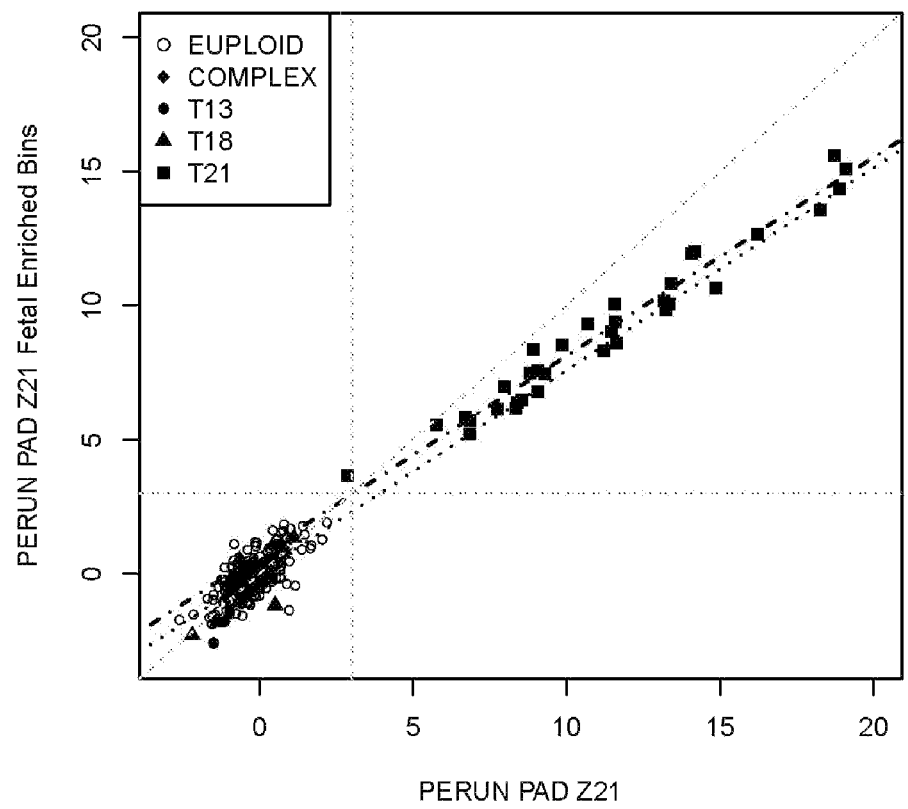
FIG. 11 shows PERUN PAD with LOESS Z scores (X-axis) verse PERUN PAD with LOESS Z scores based on "fetal enriched" portions (i.e., portions with high FRS) (Y-axis) for chromosome 21. The four quadrants represent concordance and discordance. The quadrant lines are drawn at Z=3. The top right and bottom left quadrants are separated by a grey dashed diagonal line. The dash-dot line is a regression line for non-T21 samples only. The dotted line is a regression line for T21 samples based on high FRS portions.

In FIG. 10 and FIG. 11 there are two regression lines, one for non-T21 samples only (dash-dot line) and the other for T21 samples (dotted line). The regression line for T21 samples based on high FRS portions was above the regression line for non-T21 samples based on high FRS (FIG. 10). Conversely, this similar regression was lower than non-T21 samples when comparing Z scores calculated on low FRS portions (FIG. 11). This suggests that the use of high FRS portions can improve the accuracy of outcome determinations, as the Z scores tend to be larger for T21 samples.

TABLE 3

Spearman Partial Correlation[Corr(X, Y|Z)]

|  | Truseq_FRS | genecountperbin | gccontent |
|---|---|---|---|
|  | Partial Correlation | | |
| Truseq_FRS | 1.000 | | |
| genecountperbin | 0.350 | 1.000 | |
| gccontent | 0.543 | 0.115 | 1.000 |
|  | Pvalue | | |
| Truseq_FRS | 0 | | |
| genecountperbin | 0 | 0 | |
| gccontent | 0 | 2.66E−148 | 0 |

Example 4

Detection of Trisomy 21 Using a Combination of Sequence-based Separation and Length-based Analysis Plasma samples containing circulating cell-free DNA obtained from pregnant females are tested for trisomy 21 using the following method.

Sequence-based Separation

A SURESELECT custom capture library is obtained from Agilent which includes a set of custom designed biotinylated capture RNAs. The capture RNAs are designed according to nucleotide sequences specific to chromosome 21 (test chromosome) and specific to chromosome 14 (reference chromosome) and are identified by Agilent's EARRAY web-based design tool. 100 independent capture RNAs are designed for each of chromosome 14 and chromosome 21. Single copy nucleotide sequences in the range of 40 to 60 base pairs that are unique to chromosome 14 or 21 and are AT-rich are selected for the custom capture RNA design.

Sample nucleic acid, which is cell-free circulating plasma nucleic acid from a pregnant woman in the first trimester of pregnancy, is split into two tubes and incubated with either chromosome 21 capture RNA or chromosome 14 capture RNA for 24 hours at 65° C., according to the manufacturer's instruction. After hybridization, captured target fragments and captured reference fragments (collectively referred to as captured fragments) are selected by pulling down the bioti-nylated RNA/fragment hybrids by using streptavidin-coated magnetic beads (DYNAL DYNAMAG-2, Invitrogen, Carlsbad, Calif.), and purified with the MINELUTE PCR Purification Kit (Qiagen, Germantown, Md.). Capture RNA is digested and the remaining DNA fragments are amplified according to the manufacturer's instruction.

Length-based Analysis

Samples containing separated nucleic acid fragments from above are hybridized under non-stringent hybridization conditions to poly-inosine probes comprising biotinylated inosine, which probes are longer than the DNA fragments to which they hybridize and are 500 base pairs in length. In some embodiments, hybridization is performed overnight at 65° C. in 6×SSC and 1% SDS In some embodiments, hybridization is performed overnight at 43° C. in 1.0M NaCl, 50 mM sodium phosphate buffer (pH 7.4), 1.0 mM EDTA, 2% (w/v) sodium dodecyl sulfate, 0.1% (w/v) gelatin, 50 µg/ml tRNA and 30% (v/v) formamide. Four 30 minute washes are performed at 55° C. in 1.2×SSC (1×SSC is 0.15M NaCl plus 0.015M sodium citrate), 10 mM sodium phosphate (pH 7.4), 1.0 mM EDTA and 0.5% (w/v) sodium dodecyl sulfate. After hybridization, unhybridized probe portions are digested using Exonuclease I (New England Biolabs, Ipswich, Mass.) and Phosphodiesterase II (Worthington Biochemical Corp., Lakewood, N.J.). The probe-fragment duplexes are denatured at 95° C. for two minutes and the probes are separated away from the fragments (i.e., pulled down) using streptavidin-coated magnetic beads (DYNAL DYNAMAG-2, Invitrogen, Carlsbad, Calif.), and purified with the MINELUTE PCR Purification Kit (Qiagen, Germantown, Md.). Trimmed, isolated and purified poly-inosine probes are measured for mass using MALDI mass spectrometry. Probe length, and thus corresponding fragment length, is extrapolated from the mass peaks for each probe length species by comparison to mass peaks for biotinylated poly-inosine standards of known length.

Determination of Trisomy 21

The relative amount of each fragment length species is determined based on the amplitude of the mass peaks for each probe length species. Fragments of 150 base pairs or less are quantified for chromosome 14 and chromosome 21. Samples with substantially equal amounts of fragments from chromosome 14 and chromosome 21 are determined as euploid for chromosome 21. Samples with a statistically significantly higher amount of fragments from chromosome 21 versus chromosome 14 (e.g., 2% elevation in fragments from chromosome 21 versus chromosome 14) are determined as triploid for chromosome 21.

Example 5

Trisomy Detection Using Fragment Length Filtering and Chromosome Representation

In this example, maternal samples containing cell-free nucleic acid were classified as carrying a euploid fetus or a fetus having an aneuploidy (i.e., trisomy 13, trisomy 18, trisomy 21) based on nucleotide sequence read counts from a subset of fragments having certain length parameters. Samples were obtained from the Women and Infants Hospital (WI study; Palomaki et al. (2011) Genet. Med. 13(11): 913-20). Nucleotide sequence reads (36-base reads) for each sample were obtained using an Illumina paired-end sequencing platform (Illumina, Inc., San Diego, Calif.). Paired-end nucleotide sequence reads were aligned to a reference genome (build 37 (hg19)) using the BOWTIE 2 beta 3 aligner program and fragment length was determined based on the alignments of the paired-end reads.

Certain nucleotide sequence reads were filtered out according to the following nucleic acid fragment length parameters: 1) fragments having lengths greater than or equal to 120 bases; 2) fragments having lengths greater than or equal to 130 bases; 3) fragments having lengths greater than or equal to 140 bases; 4) fragments having lengths greater than or equal to 150 bases; 5) fragments having lengths greater than or equal to 160 bases; or 6) fragments having lengths greater than or equal to 170 bases. Thus, paired end reads corresponding to fragments equal to or longer than a given length threshold (e.g., 120 bases, 130 bases, 140 bases, 150 bases, 160 base, 170 bases) were filtered out and paired end reads corresponding to fragments shorter than a given length threshold were retained for analysis.

Chromosome representations for chromosome 13, chromosome 18 and chromosome 21 were calculated for data sets presented in FIG. 23 using 1) unfiltered sequence reads and 2) length-filtered sequence reads at a threshold of 150 base fragments. Chromosome representation for each of chromosome 13, 18 and 21 were calculated according to the following:

Chromosome 13 (Chr 13) representation=Σ Chr 13 sequence read counts (unfiltered)/Σ all autosomal sequence read counts (unfiltered)

Chromosome 13 (Chr 13) representation=Σ Chr 13 sequence read counts (filtered)/Σ all autosomal sequence read counts (filtered)

Chromosome 18 (Chr 18) representation=Σ Chr 18 sequence read counts (unfiltered)/Σ all autosomal sequence read counts (unfiltered)

Chromosome 18 (Chr 18) representation=Σ Chr 18 sequence read counts (filtered)/Σ all autosomal sequence read counts (filtered)

Chromosome 21 (Chr 21) representation=Σ Chr 21 sequence read counts (unfiltered)/Σ all autosomal sequence read counts (unfiltered)

Chromosome 21 (Chr 21) representation=Σ Chr 21 sequence read counts (filtered)/Σ all autosomal sequence read counts (filtered)

Figure 13:
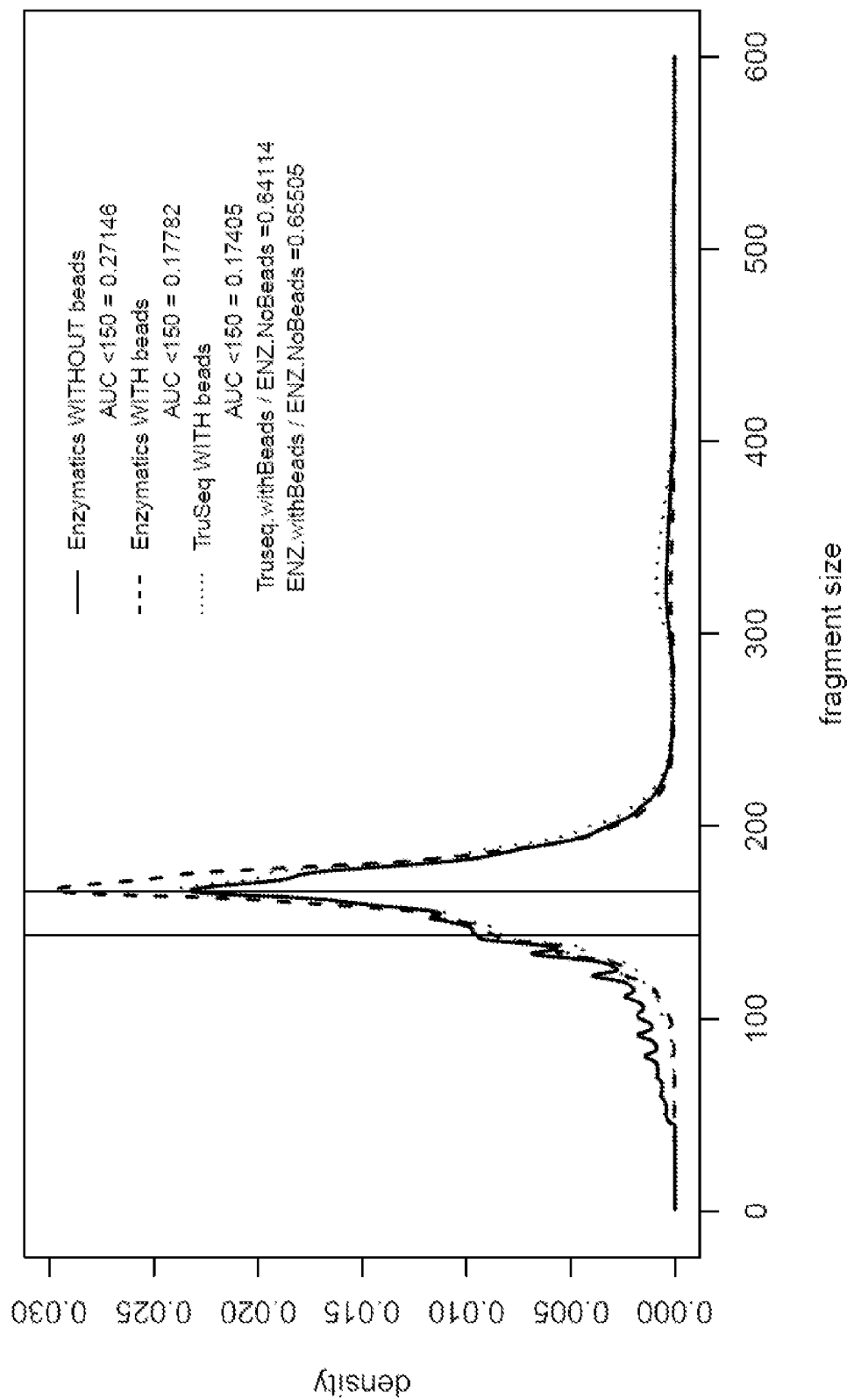
FIG. 13 shows a distribution of fragment lengths for three different library preparation methods. They include enzymatic with automated bead cleanup, enzymatic without automated bead cleanup, and TRUSEQ with automated bead cleanup. The vertical lines represent 143 base and 166 base fragment sizes.
Figure 14:
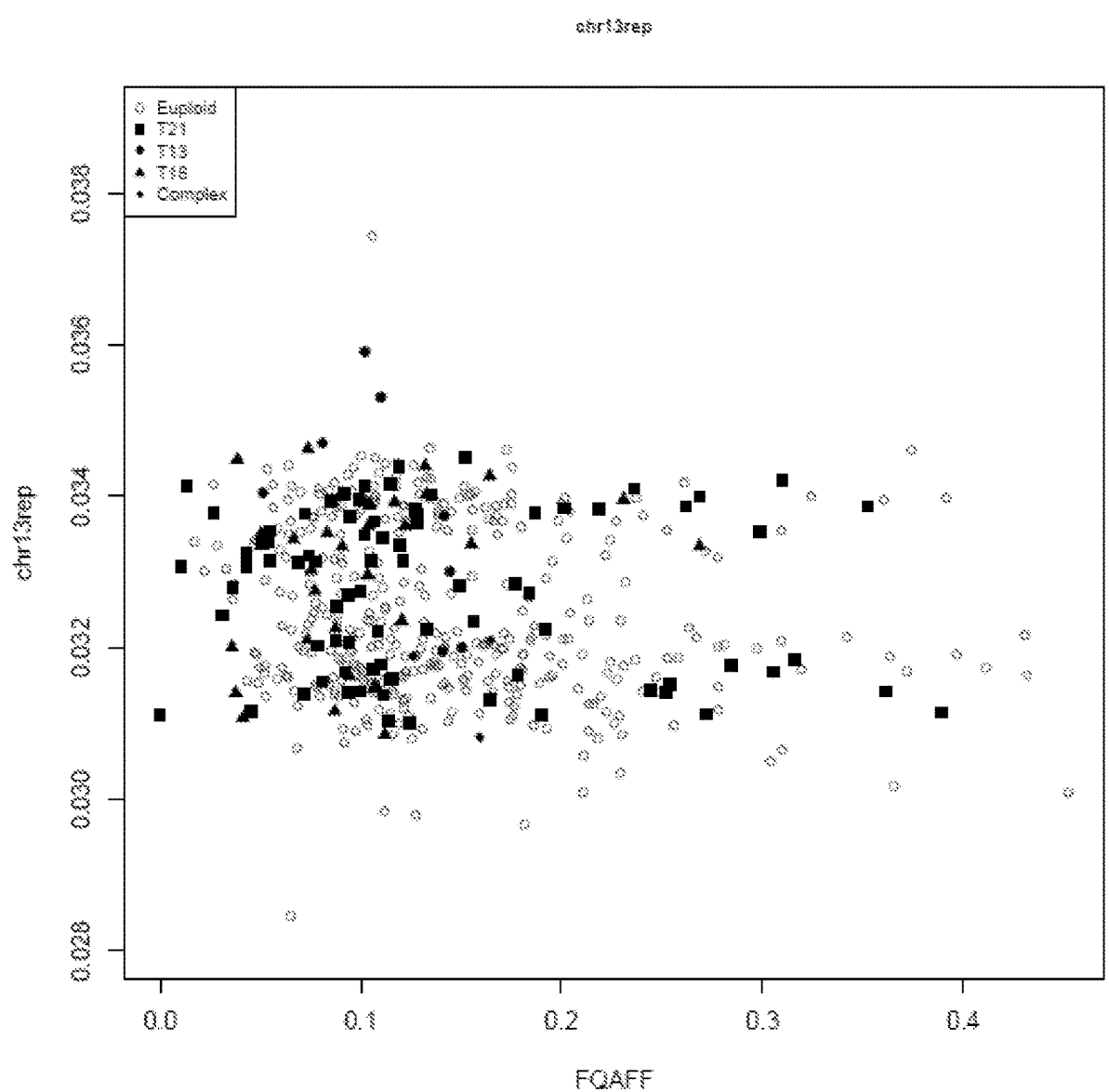
FIG. 14 shows chromosome 13 representation without a fragment size filter.
Figure 15:
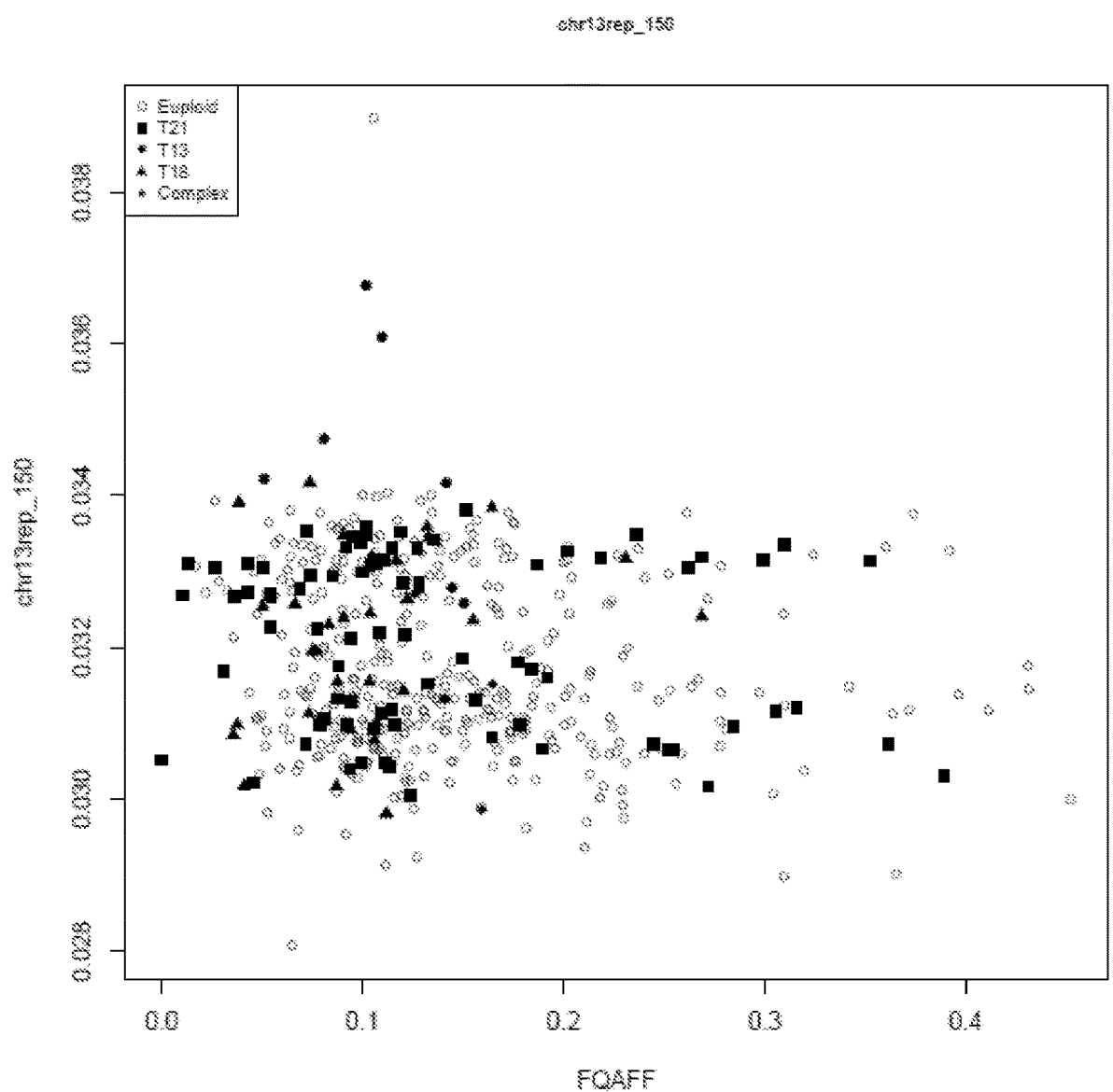
FIG. 15 shows chromosome 13 representation with a fragment size filter at 150 bases.
Figure 16:
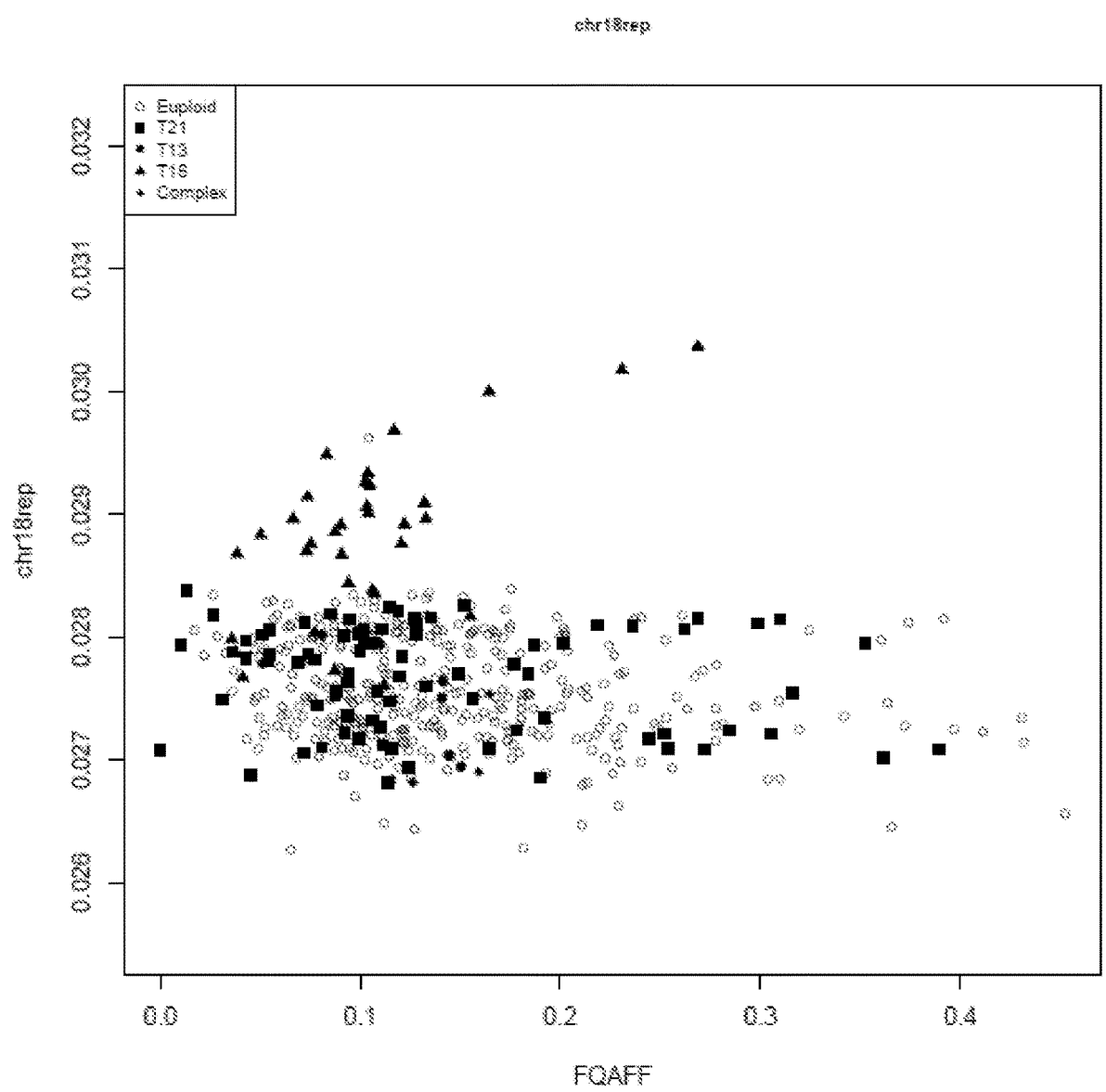
FIG. 16 shows chromosome 18 representation without a fragment size filter.
Figure 17:
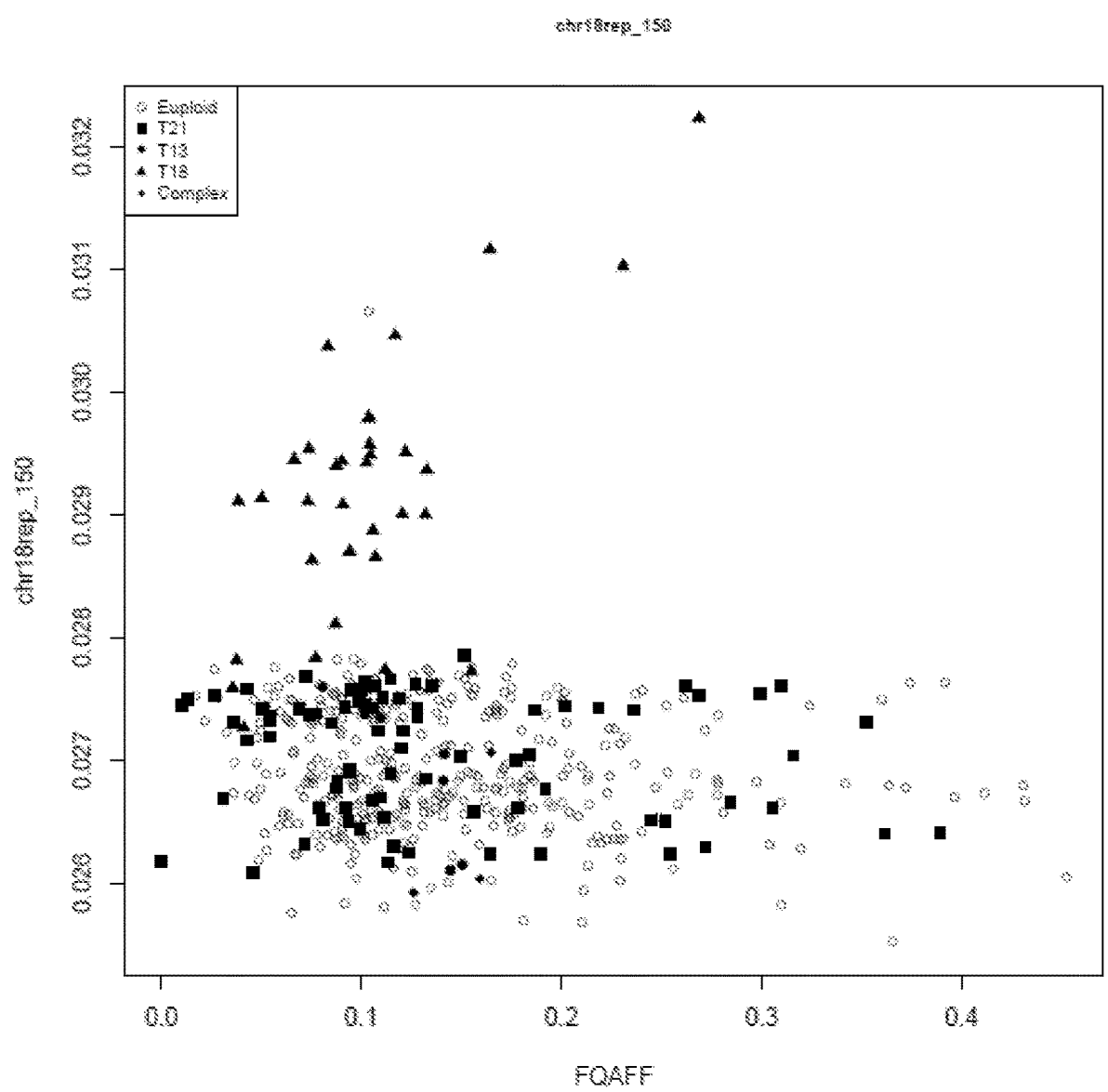
FIG. 17 shows chromosome 18 representation with a fragment size filter at 150 bases.
Figure 18:
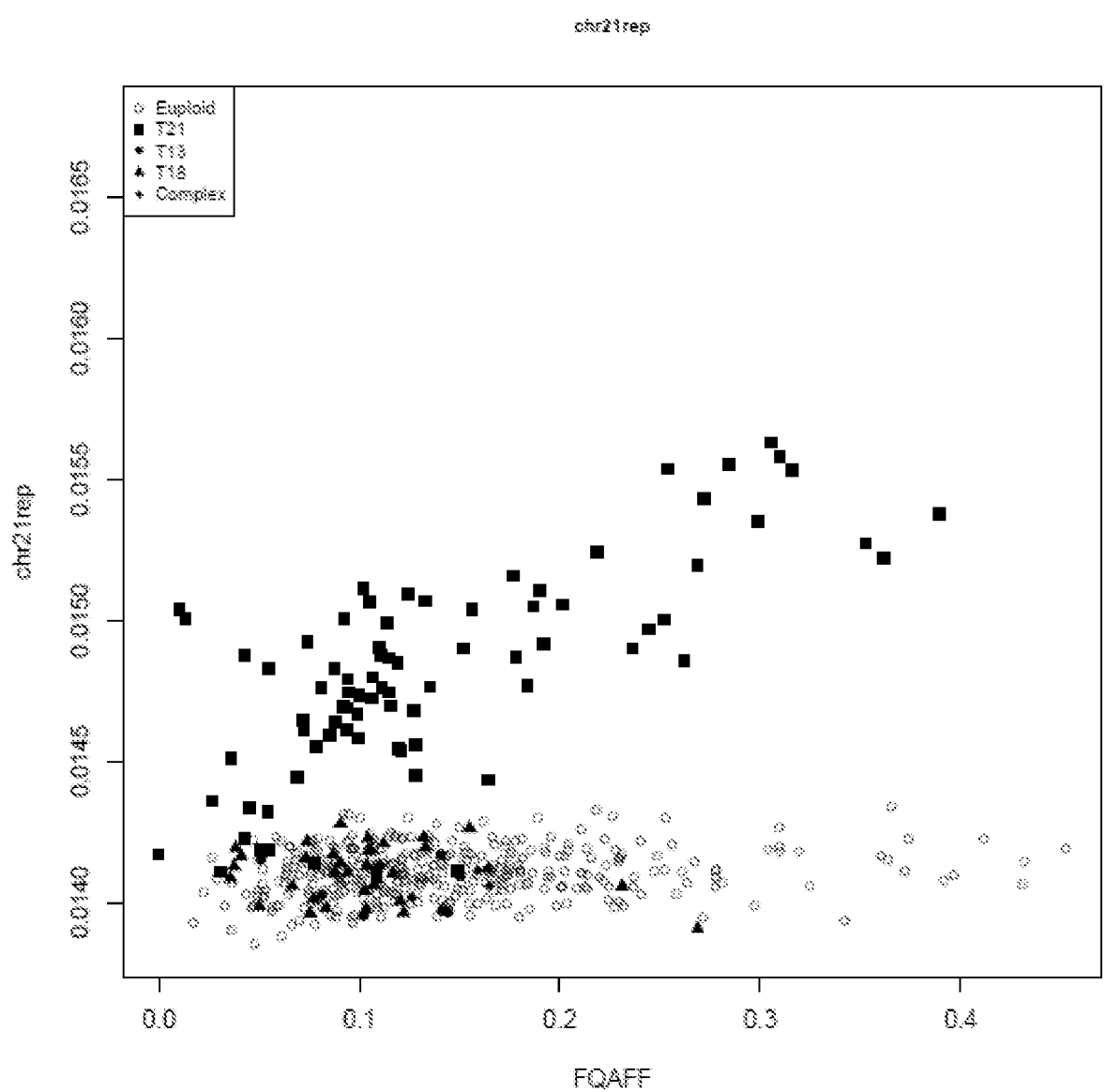
FIG. 18 shows chromosome 21 representation without a fragment size filter.
Figure 19:
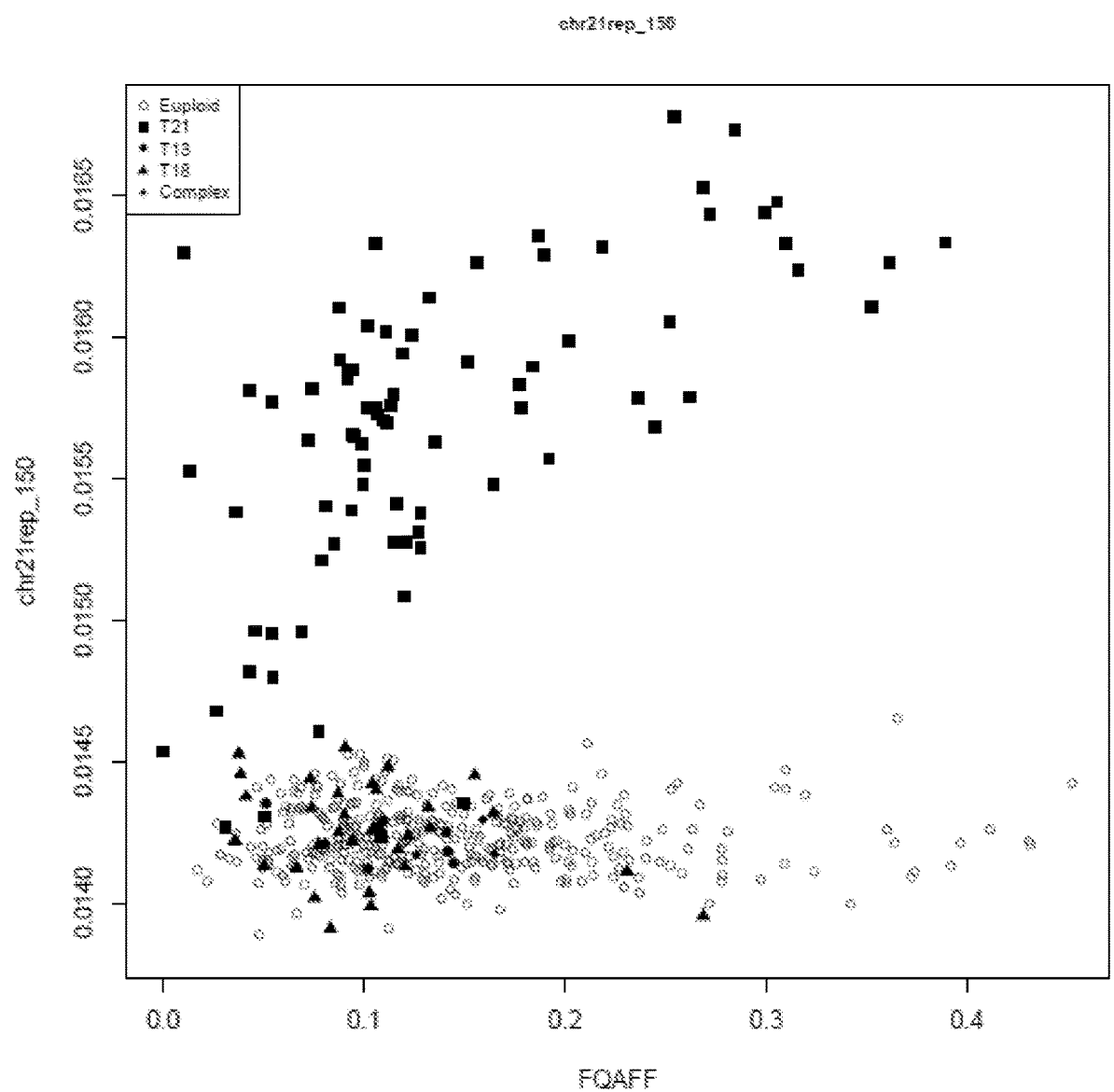
FIG. 19 shows chromosome 21 representation with a fragment size filter at 150 bases.

FIGS. 14, 16 and 18 show chromosome representations for chromosomes 13, 18 and 21, respectively, using unfiltered sequence reads. FIGS. 15, 17 and 19 show chromosome representations for chromosomes 13, 18 and 21, respectively, using length-filtered sequence reads. For filtered data sets, chromosome representation increased for trisomy samples due in part to an increase in fetal contributed sequence data. Although this increase in chromosome representation can increase power to detect chromosomal abnormalities, the variance of chromosome representation for non-trisomy samples increased due to an approximate 63-82% reduction in read counts. Example distributions of read counts at various fragment length threshold values is illustrated in FIG. 13 and presented in Table 5 below.

TABLE 5

| Threshold (fragment lengths) | Mean AUC (% of reads less than threshold) |
|---|---|
| 120 | 0.027 |
| 130 | 0.049 |
| 140 | 0.092 |
| 150 | 0.175 |
| 160 | 0.294 |
| 170 | 0.508 |
| ALL | 1 |

Mean area under the curve (AUC) values for reads from fragments less than a certain length were determined to illustrate the overall reduction of reads (i.e. sequence coverage) seen on average.

For a given assay that generates about 15 million sequence reads (or 0.2× coverage of the human genome), exclusion of reads greater than 150 bases, for example, is equivalent to about 0.035× coverage.

Figure 20:
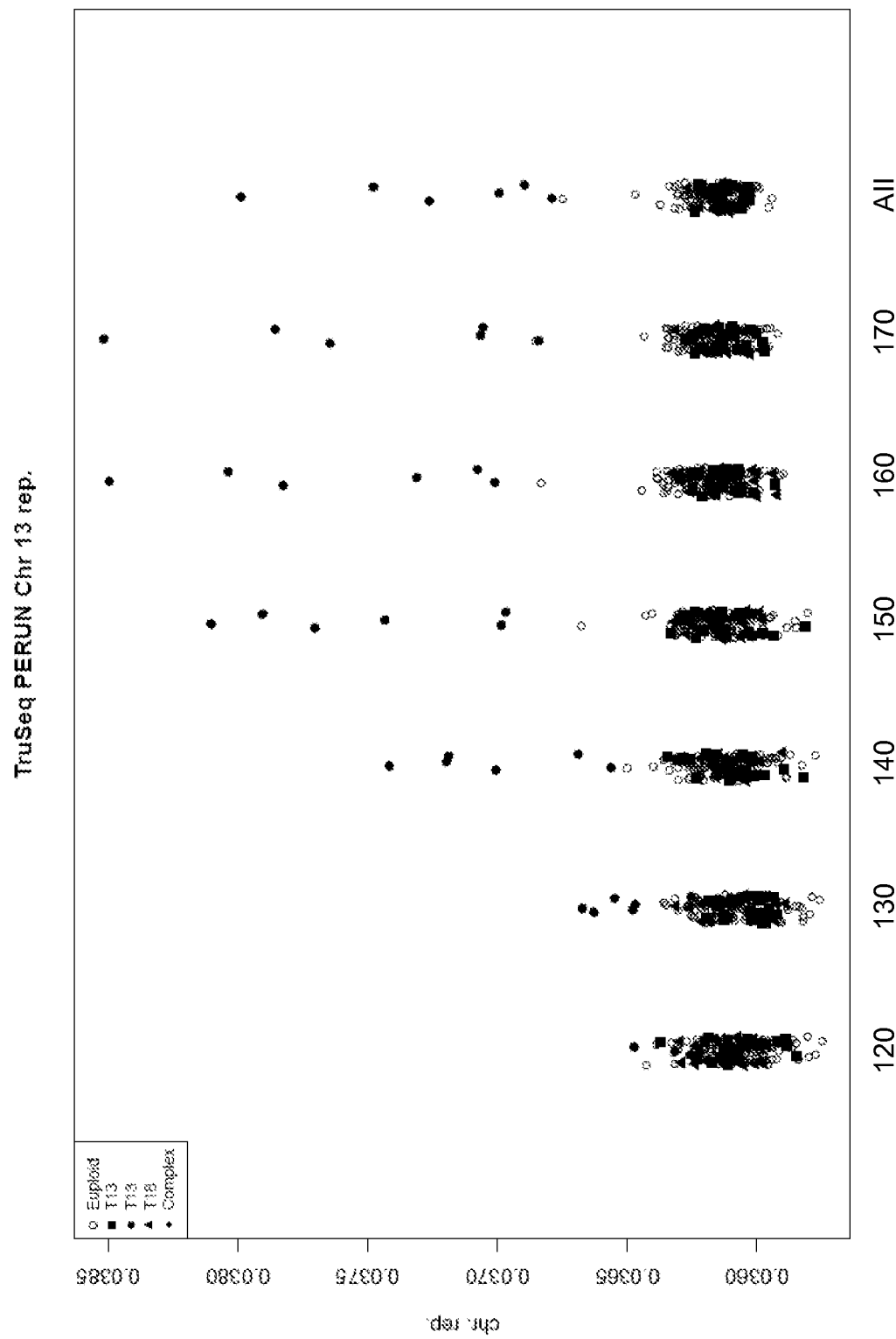
FIG. 20 shows chromosome 13 representation (PERUN PAD with LOESS) with variable fragment size filters.
Figure 21:
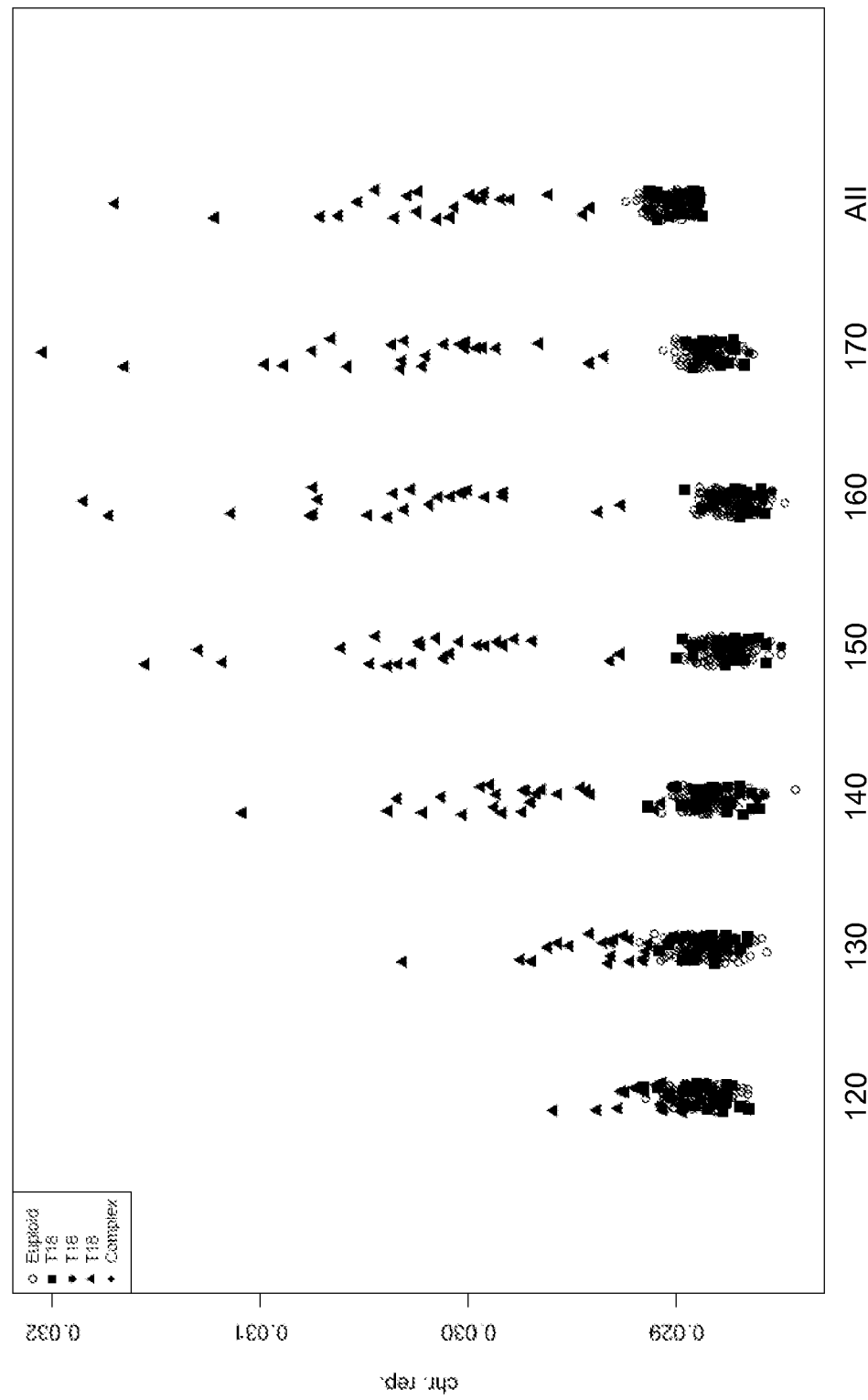
FIG. 21 shows chromosome 18 representation (PERUN PAD with LOESS) with variable fragment size filters.
Figure 22:
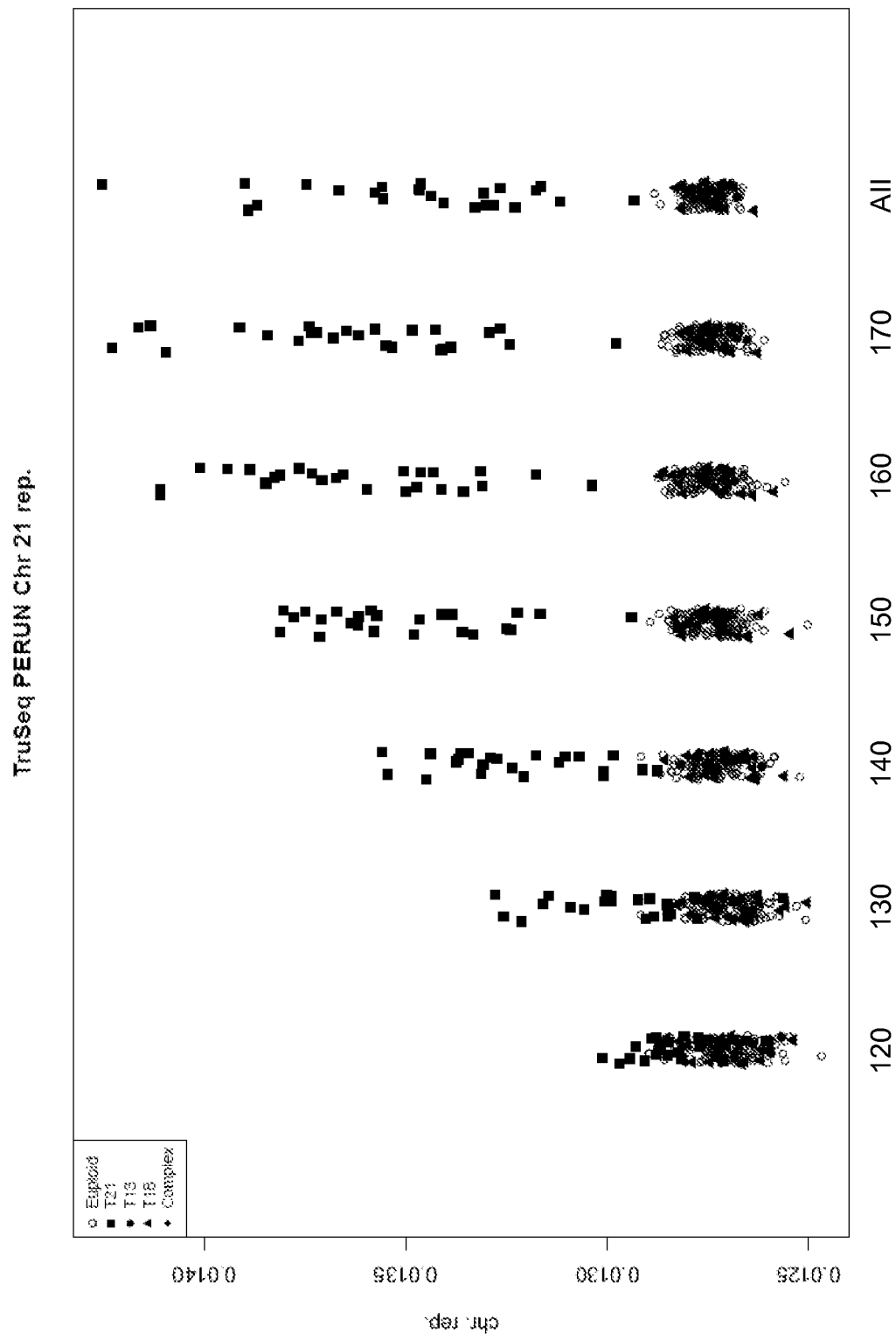
FIG. 22 shows chromosome 21 representation (PERUN PAD with LOESS) with variable fragment size filters.

To determine an optimal fragment size threshold for chromosome representation, fragment size threshold was varied from 120 to 170 bases, at 10 base increments. Chromosome representation (i.e. for chromosomes 13, 18, and 21) was calculated after sequence read count normalization (i.e., PERUN PADDED with LOESS) for each length-filtered data set (paired-end reads) and for an unfiltered data set (single-end reads; also referred to as "all"). Chromosome 13, 18 and 21 representations are presented in FIGS. 20, 21 and 22, respectively. Chromosome representation for the filtered data sets at the 150, 160 and 170 base threshold was fairly consistent with the unfiltered data set. The following tables present observed specificity and sensitivity for chromosome 13, 18 and 21 trisomy detection at the respective Z-score cutoff values (i.e., 3.95 for chromosome 13, 3.95 for chromosome 18, and 3 for chromosome 21). Z-score values were based on flow cell-specific median and data set-specific historic and population MAD values. Additionally, 10-fold cross validation of Receiver Operating Characteristic (ROC) analyses were conducted (i.e., 10-fold stratified cross-validation, repeated 100 times) and the average area under the curve (AUC; i.e., a measure of accuracy) for each analysis (calculated by summing up all the sensitivity times (1-specificity) values and implemented using R package ROCR) is presented in Tables 6, 7, and 8 below.

TABLE 6

| Threshold (fragment lengths) | CHROMOSOME 13 (Z = 3.95) | | |
|---|---|---|---|
| | ROC AUC | Specificity | Sensitivity |
| 120 | 0.85 | 1.00 | 0.00 |
| 130 | 0.99 | 1.00 | 0.67 |
| 140 | 1.00 | 1.00 | 1.00 |
| 150 | 1.00 | 0.99 | 1.00 |
| 160 | 1.00 | 0.99 | 1.00 |
| 170 | 1.00 | 0.99 | 1.00 |
| ALL | 1.00 | 0.99 | 1.00 |

TABLE 7

| Threshold (fragment lengths) | CHROMOSOME 18 (Z = 3.95) | | |
|---|---|---|---|
| | ROC AUC | Specificity | Sensitivity |
| 120 | 0.77 | 1.00 | 0.04 |
| 130 | 0.98 | 1.00 | 0.26 |
| 140 | 1.00 | 1.00 | 0.91 |
| 150 | 1.00 | 1.00 | 1.00 |
| 160 | 1.00 | 1.00 | 1.00 |
| 170 | 1.00 | 1.00 | 1.00 |
| ALL | 1.00 | 1.00 | 0.91 |

TABLE 8

| Threshold (fragment lengths) | CHROMOSOME 21 (Z = 3) | | |
|---|---|---|---|
| | ROC AUC | Specificity | Sensitivity |
| 120 | 0.83 | 1.00 | 0.08 |
| 130 | 0.88 | 1.00 | 0.44 |
| 140 | 0.97 | 1.00 | 0.88 |
| 150 | 1.00 | 1.00 | 0.92 |
| 160 | 1.00 | 1.00 | 1.00 |
| 170 | 1.00 | 1.00 | 0.96 |
| ALL | 1.00 | 1.00 | 1.00 |

The data show that despite a significant reduction in sequence coverage for length-filtered samples, trisomies can be identified using filtered samples at certain fragment length thresholds (e.g., 150 bases, 160 bases) with similar accuracy, sensitivity and specificity compared to unfiltered samples.

Example 6

Figure 25B:
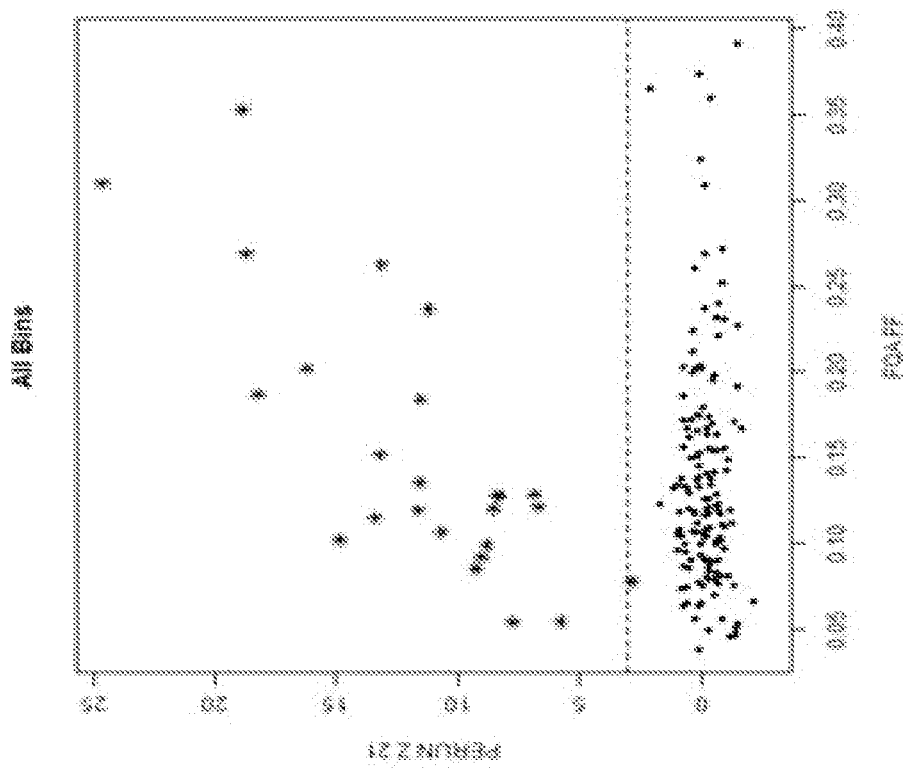
FIG. 25B shows a relation of FQA fetal fraction estimates (x-axis) vs. Z-scores of PERUN normalized counts (y-axis) for Chr21 obtained from pregnant females with a trisomy 21 fetus (indicated by an asterisk) or euploid fetus (indicated by circles) for all portions of Chr21 from which counts were obtained.
Figure 25A:
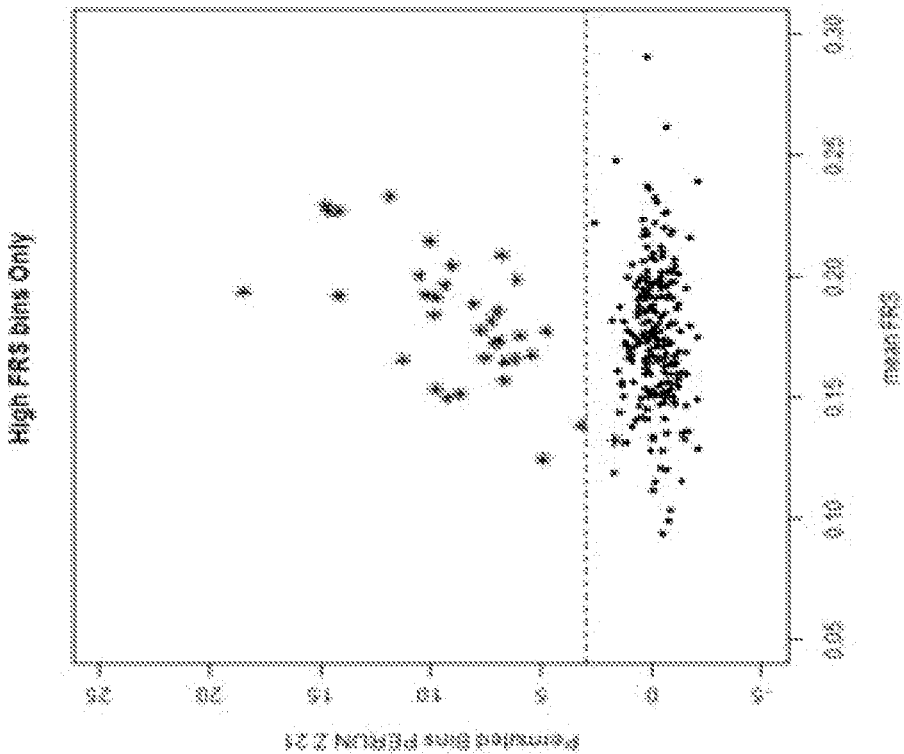
FIG. 25A shows a relation of the mean FRS of a subset of portions of Chr21 (x-axis) to the Z-scores of PERUN normalized counts (y-axis) for the same subset of portions for samples obtained from pregnant females with a trisomy 21 fetus (indicated by an asterisk) or euploid fetus (indicated by circles). Each portion in the subset of portions selected for FIG. 25A have an FRS greater than the median FRS determined for all portions of chromosome 21 from which counts were obtained.

This example illustrates, in part, a relationship between fetal fraction and fetal ratio statistic (FRS). As shown in FIGS. 25A and 25B, a plot of Z-scores v. the median FRS per sample showed remarkable similarity to a plot of Z-scores v. FQA based estimates of fetal fraction. Moreover, the median FRS per trisomy 21 samples restricted to High FRS portions (FIG. 25A, above dashed line) was 0.188 and the median FRS per trisomy 21 samples for all portions (FIG. 25B, above dashed line) was 0.172. For non-trisomy Chr21 samples, the median FRS for High FRS portions was 0.181 (FIG. 25A, below dashed line) and the median FRS for all portions was 0.166 (FIG. 25B, below dashed line). This suggested that trisomy 21 samples do indeed have a slightly higher portion representation than non-trisomy 21 samples, in particular to portions with a higher propensity of fetal contribution.

Figure 26:
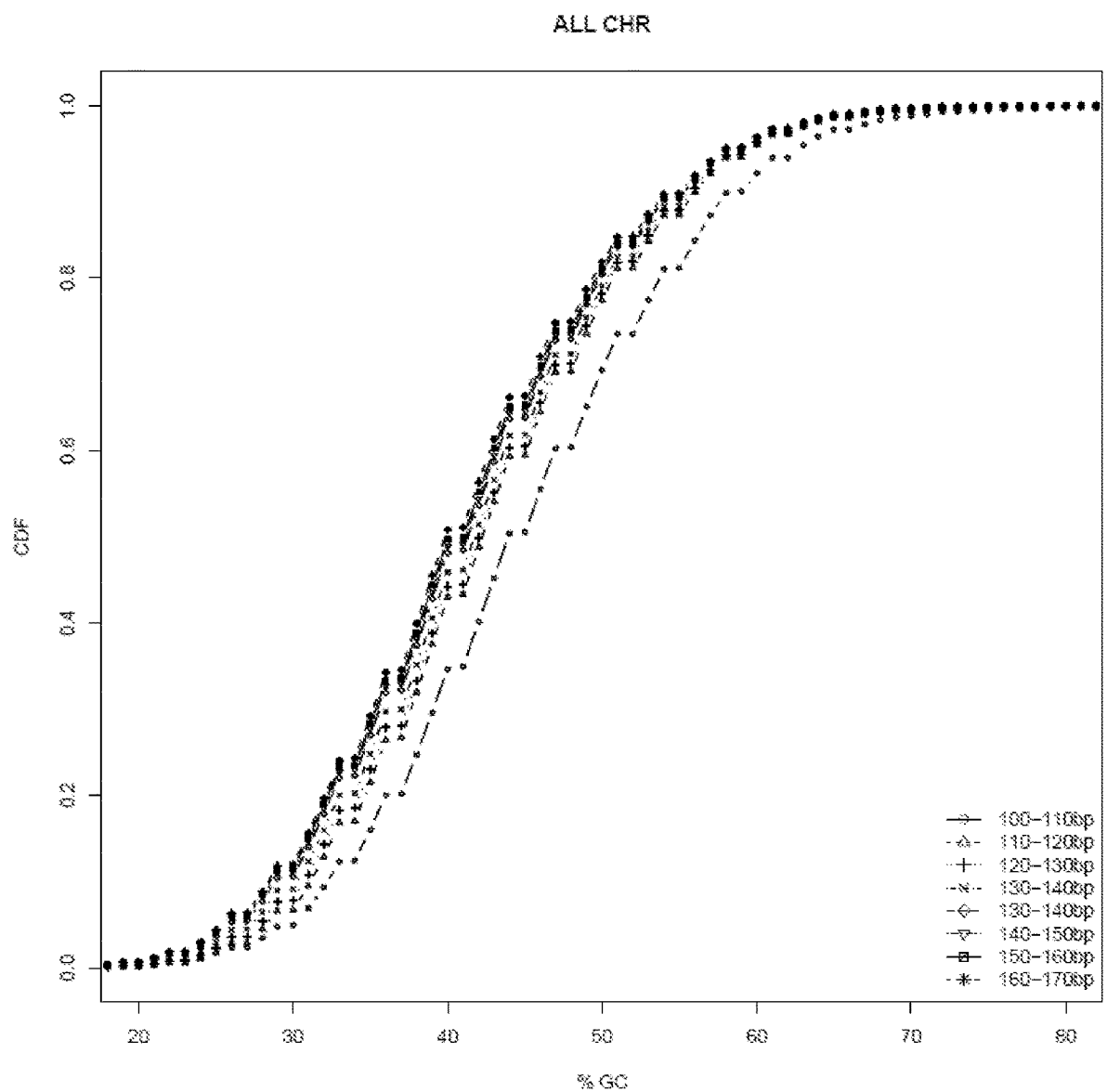
FIG. 26 shows a relation of GC content per read (x-axis) to the cumulative distribution function based on read length (CDF, y-axis) for reads of the indicated range of fragment lengths (shown in bottom right insert) for chromosome 21.

As shown in FIG. 26, it was determined that reads of varying fragment lengths comprise different GC content. Smaller fragments, which are known to be more fetal in origin, showed higher GC content compared to larger fragments. The difference in GC content was also related to how FRS correlated with GC content and gene density, as bins with higher FRS were positively correlated to GC content per bin. These subtle GC differences in fragment length can be leveraged to provide fetal fraction information. For example, GC difference, fragment length and/or fragment length dispersion across the human reference genome can be used to predict the fetal or maternal origin of fragments. This data demonstrated that GC content per read can be used to estimate fetal contribution.

Figure 27:
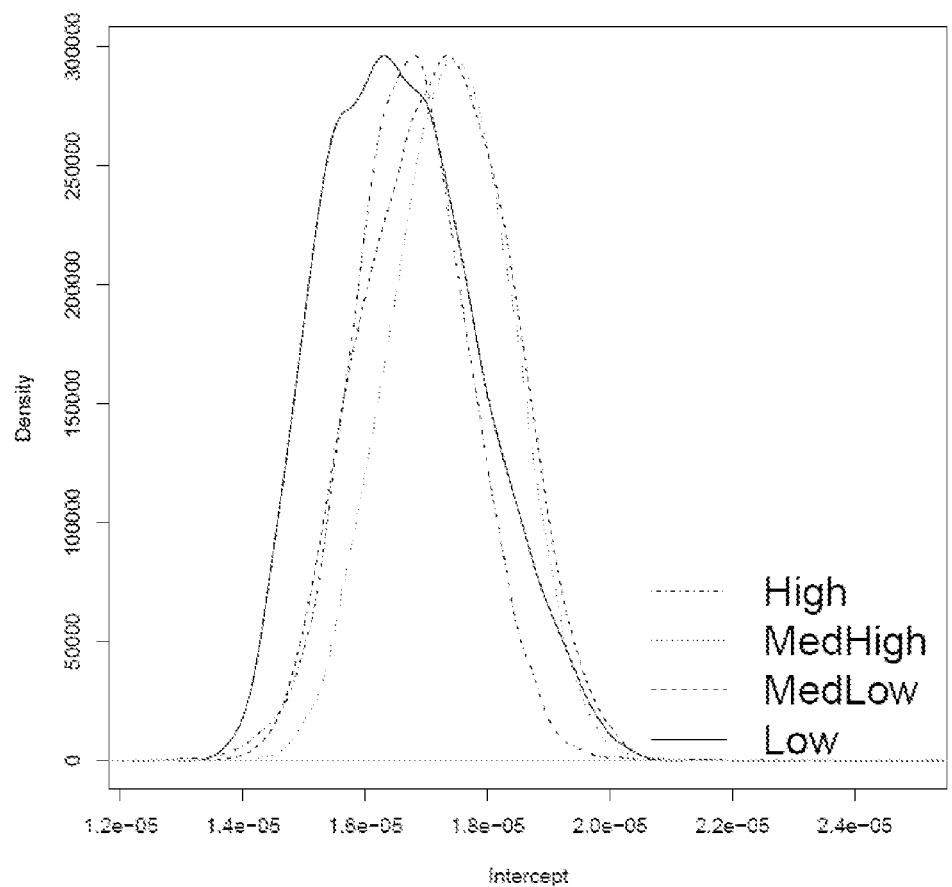
FIG. 27 shows a distribution of PERUN intercepts (x-axis) partitioned into quantiles (High, Medium High, Medium Low, and Low) according to FRS per bins.
Figure 28:
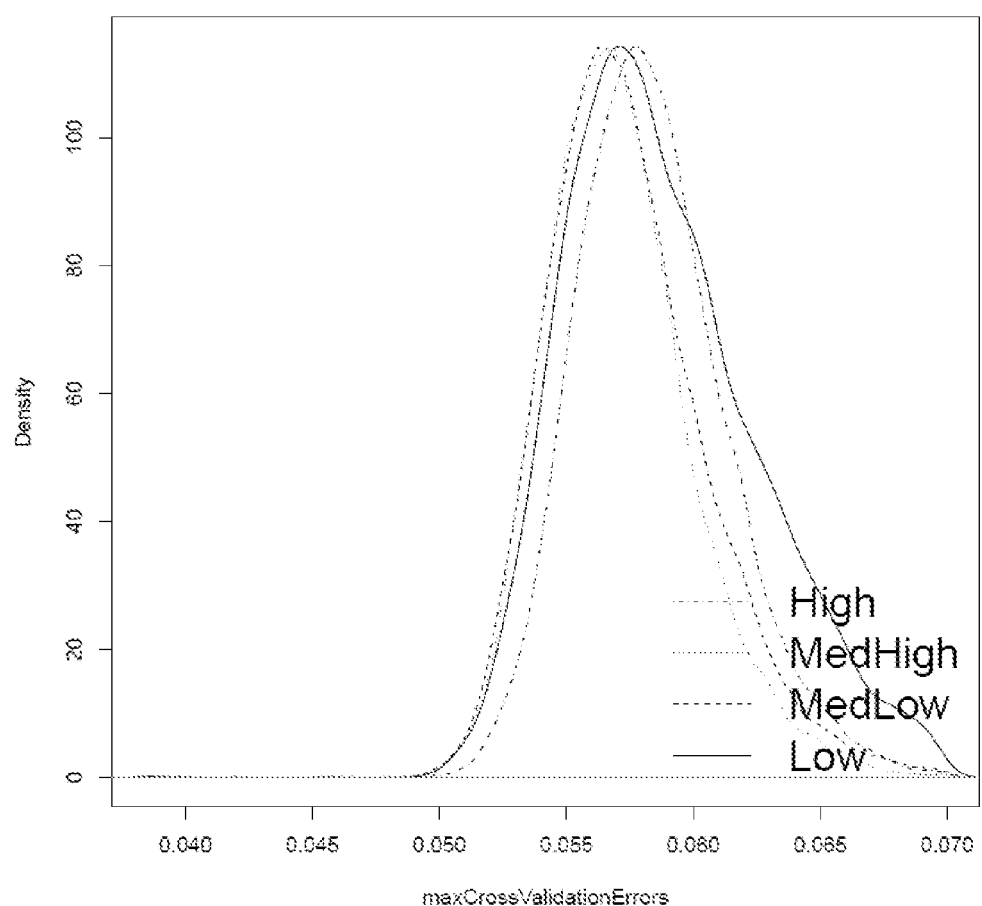
FIG. 28 shows a distribution of PERUN Max Cross Validation Errors (x-axis) partitioned into quantiles (High, Medium High, Medium Low, and Low) according to FRS per bins.

PERUN is the region specific additive correction to remove GC biases in read depth of coverage. This normalization procedure involved a trained estimate of two region specific parameters, the slope, i.e. the impact of GC bias, and intercept, i.e. the base level coverage in absence of GC bias. The distribution of PERUN intercepts partitioned into FRS quantiles suggested that increasing FRS increases PERUN intercepts (FIG. 27). Overall, the genomic regions with the smallest FRS tended to have the lowest intercepts, possibly due to reduction of fetal contribution relative to the overall coverage representation. In addition, initial efforts for region selection incorporated the maximum cross validation errors, where larger values indicated an increase in variability of coverage. FIG. 28 shows a distribution of the maximum cross validation errors partitioned into quantiles. The extreme quantiles (high and low) exhibited the largest variability in region stability. As extreme FRS genomic regions are potentially more sensitive to fetal contribution, the increased variability in maximum cross validation errors may in fact be due to the variability of fetal signal.

Example 7

Bin-based Fetal Fraction

This example demonstrates a method for quantifying the amount of circulating cell-free fetal DNA in a maternal blood sample using sequencing coverage data. The technology encompasses a method known herein as Bin-based Fetal Fraction (BFF) which uses sequencing coverage maps to quantify the fraction of fetal DNA in a maternal blood sample. The method takes advantage of machine-learning methods to build a model relating sequencing coverage to fetal fraction.

The first step of the BFF method was to obtain genomic coverage data. Genomic coverage data was obtained from a sequencing run and alignment. This coverage data then served as a predictor for fetal fraction. Coverage predictor variables can be generated by any suitable method, including but not limited to discrete genomic bins, variable-size bins, or point-based views of a smoothed coverage map.

The second step of the BFF method was to train a model for estimating fetal fraction from the coverage data predictors (e.g., parameters). In this example, a general multiple regression model was trained using simple least-squares to estimate fetal fraction directly from the known proportional sequencing level of a particular bin. This approach may be extended to a multivariate multiple regression model to predict bins that are known to be proportional to the fetal fraction (from which the fetal fraction, in turn, may be derived). Similarly, if bins are correlated, multivariate-response models may be trained to account for correlated responses. The following is an example in its simplest form:

The multiple regression model was chosen as equation 30 below;

$$Y_{ff} = X_{bin}\beta + \varepsilon \qquad \text{Equation (30)},$$

where $X_{bin}$ is an m×p matrix of bin counts, $Y_{ff}$ is an m×1 vector of m number of training samples and p number of predictor bins, $\varepsilon$ is a noise vector with the expectation $E(\varepsilon)=0$, where the covariance $Cov(\varepsilon)=\sigma^2 I$ where I is the identity matrix (i.e. errors are homoscedastic), and rank $(X_{bin}) \leq p$. The vector $Y_{ff}$ corresponded to a bin with levels known to be proportional to fetal fraction.

Without loss of generality, we assumed that $X_{bin}$ was centered by its mean. Thus $\beta$, the p×1 vector of regression coefficients, may be estimated from solving the normal equations for $\hat{\beta}$ as;

$$(\widehat{X_{bin}^T X_{bin}})\hat{\beta} = X_{bin}^T Y_{ff} \qquad \text{Equation (31)}.$$

The extension to the multivariate multiple response model simply extended the previous model to have multiple response variables, or as a matrix $Y_{ff}$ of size m×n where n is a number of different bins that have levels proportional to fetal fraction. The model is hence;

$$Y_{ff} = X_{bin} B + E \qquad \text{Equation (32)},$$

where E is a noise matrix with parallel assumptions to the multiple model. The matrix of coefficients B may be estimated by solving for $\hat{B}$ in;

$$(\widehat{X_{bin}^T X_{bin}})\hat{B} = X_{bin}^T Y_{ff} \qquad \text{Equation (33)},$$

where $\hat{B}$ is a p×n matrix.

If rank $rank(X_{bin}) \leq p$, then the problem may be decomposed into any number of suitable regression models to account for multicollinearilty. In addition to this, estimators of $\hat{B}$ of reduced-rank may also be found so that the $rank(\hat{B}) \leq \min(n,p)$, accounting for the potential correlation within the multivariate response. The resulting estimators may then be averaged or weighted together by a suitable method.

The BFF approach is not limited to this regression method. Many suitable machine-learning methods can be used, including but not limited to other multiple regression methods, multivariate-response regression, decision trees, support-vector machines, and neural networks, to improve estimation. There are also methods which may relax the assumptions and provide for high dimensional estimation so that all relevant bins may be incorporate into the model. Non-limiting examples of such estimators are constraint-based ones such as Reduced-Rank, LASSO, Weighted Rank Selection Criteria (WRSC), Rank Selection Criteria (RSC), and Elastic Net Estimators which have shown to improve the predictive power.

Fetal fraction predictions were also improved through the measurement and incorporation of genomic coverage biases into the pipeline. These biases can come from a number of sources, including but not limited to GC content, DNase1-hypersensitivity, mappability, and chromatin structure. Such profiles can be quantified on a per-sample basis and used to adjust the genomic coverage data, or added as predictors or constraints to the fetal fraction model.

Figure 29:
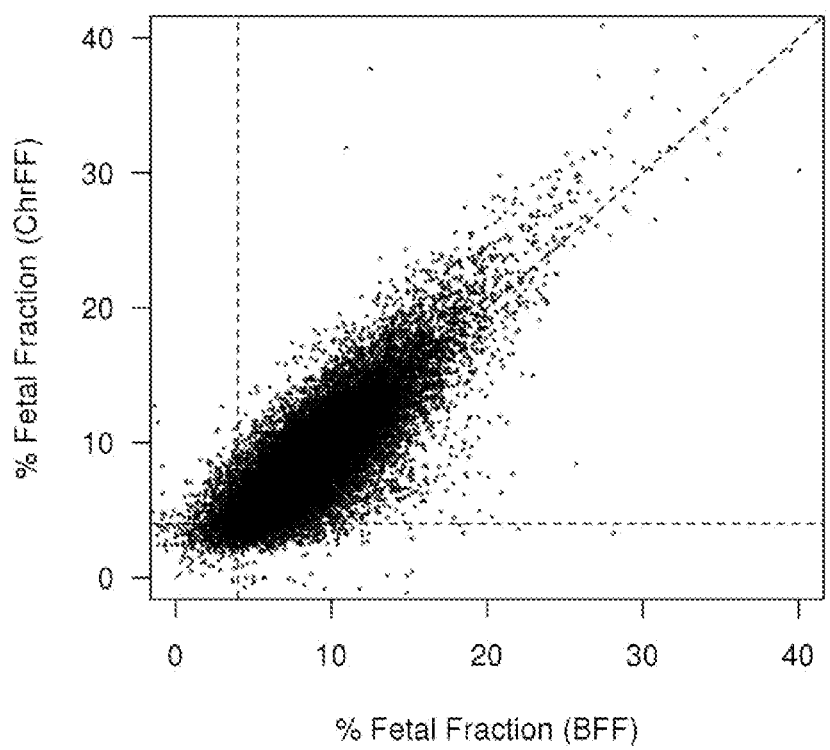
FIG. 29 shows a correlation (R=0.81, RMedSE=1.5) of fetal fraction percentages predicted for 19,312 test samples from a BFF model based on 6000 training samples (x-axis) compared to fetal fraction percentages determined from Chromosome Y levels (ChrFF, y-axis).

For example, the multiple-regression approach was trained on 6000 male euploid samples, using the relative level of chromosome Y coverage across all bins as the true value of fetal fraction (ChrFF). To prevent circularity with the detection of common trisomies, the model was trained only on autosomal coverage bins, and did not include chromosomes 13, 18, or 21. The model demonstrated strong performance on test data, consisting of 19,312 independent samples (FIG. 29).

Figure 30:
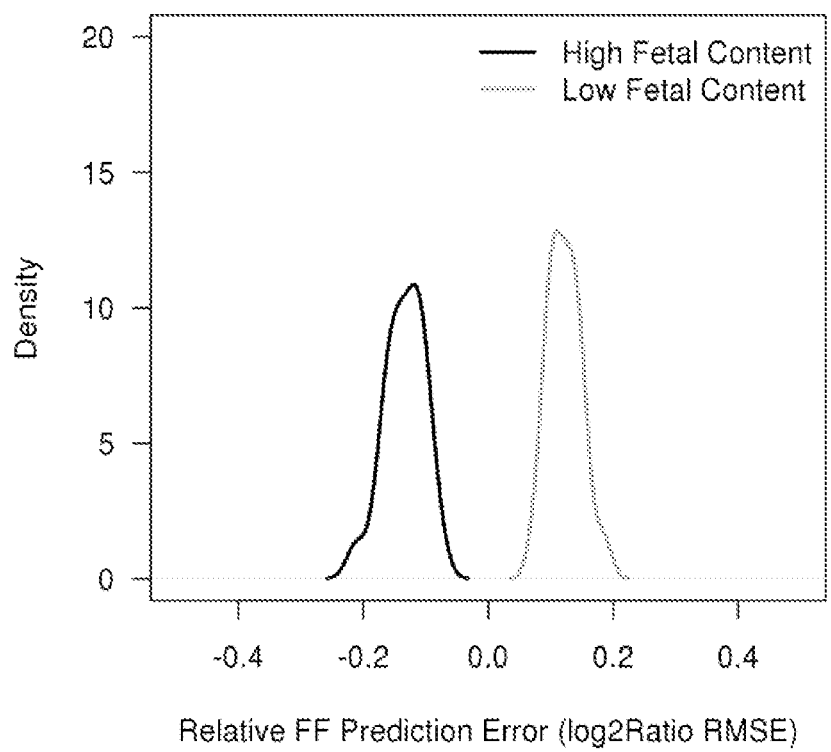
FIG. 30 shows relative prediction error (x-axis) for bins (i.e., portions) with high fetal fraction content (distribution shown on the left) and low fetal fraction content (distribution shown on the right) based on FRS. Bins with high fetal content have better performance and lower error. Predictive scores are based on an elastic-net regression procedure, with bootstrapping used to obtain density profiles.
Figure 31:
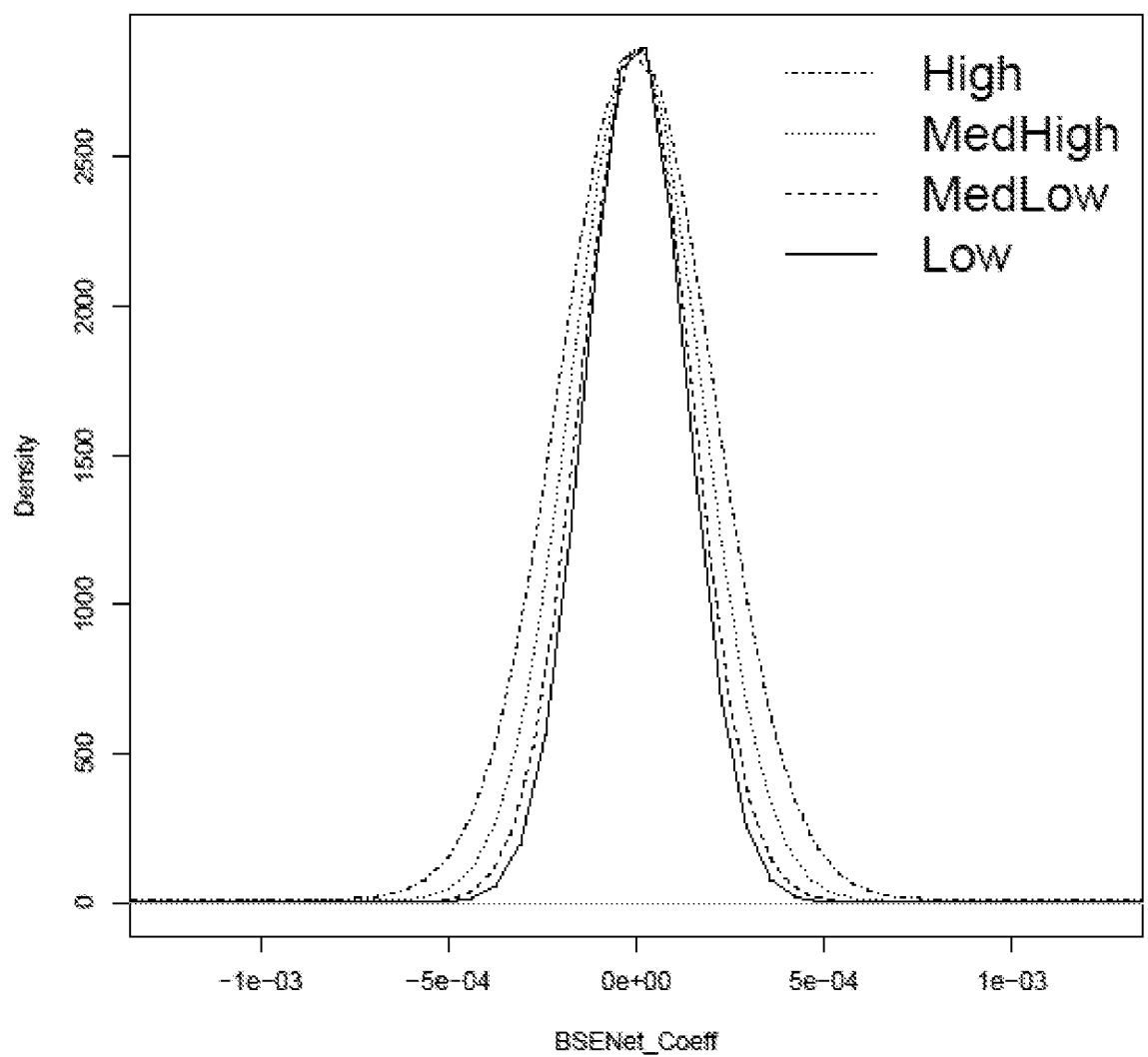
FIG. 31 shows four distributions of model coefficients (x-axis) determined using an elastic-net regression procedure on subsets of bins separated according to fetal fraction content (e.g., low, medium-low, medium-high, high). Bins with higher fetal fraction content tend to produce larger coefficients (positive or negative).

The strong performance of BFF is driven by the bins and regions that tend to attract fetal DNA. These regions tend to have higher coverage variance, and the model makes use of this variation. A bootstrap approach was used to compare models trained exclusively on bins with high or low fetal fraction representation (based on FRS). The bins with higher fetal content were found to be better predictors of fetal fraction (FIG. 30). This corresponded with the finding that models built on bins with higher fetal representation tend to have larger regression coefficients (FIG. 31).

Figure 32:
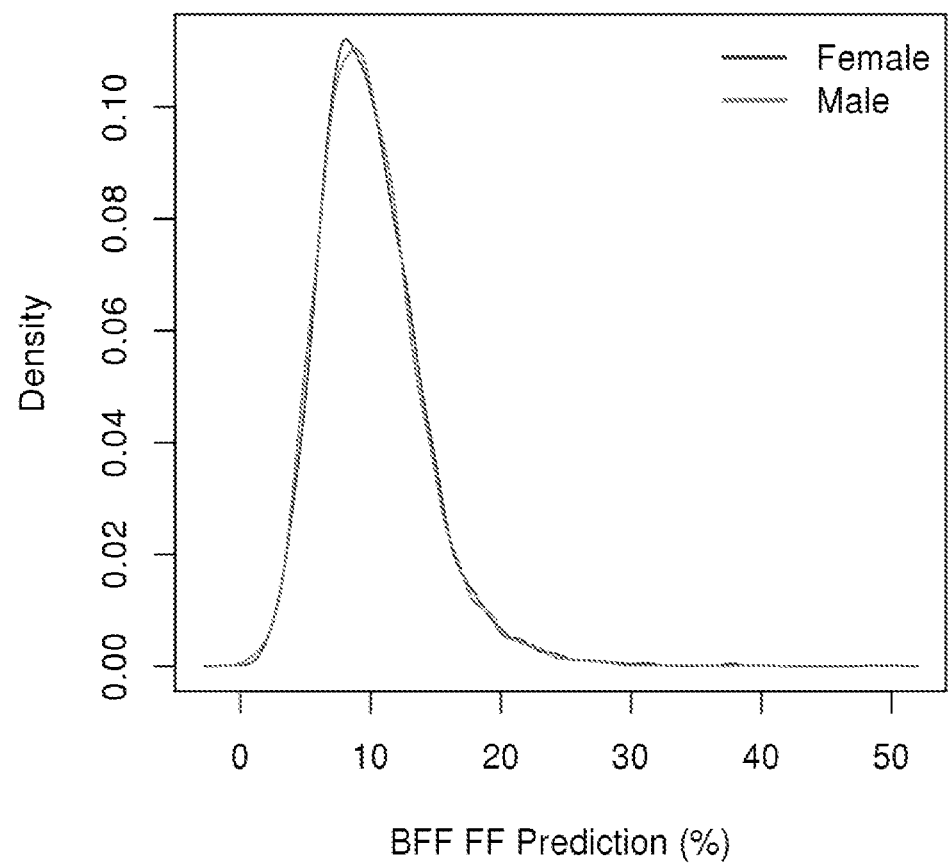
FIG. 32 shows two distributions for fetal fraction estimates (x-axis) determined using a BFF method for female and male test samples. The two distributions substantially overlap. Male and female fetuses showed no difference in the distribution of fetal fraction (KS-test P=0.49).

While the example training set included only male samples, predictions were made on both female samples and male trisomy samples, for which the fetal fraction can be independently estimated using the trisomy chromosomal representation. The fetal fraction estimation of male and female samples showed no difference in overall distribution (FIG. 32). This demonstrates that BFF is not systematically biased for estimating fetal fraction on one gender compared to the other.

Example 8

Examples of Embodiments

The examples set forth below illustrate certain embodiments and do not limit the technology.

A1. A method for estimating a fraction of fetal nucleic acid in a test sample from a pregnant female, comprising:
  (a) obtaining counts of sequence reads mapped to portions of a reference genome, which sequence reads are reads of circulating cell-free nucleic acid from a test sample from a pregnant female;
  (b) weighting, using a microprocessor, (i) the counts of the sequence reads mapped to each portion, or (ii) other portion-specific parameter, to a portion-specific fraction of fetal nucleic acid according to a weighting factor independently associated with each portion, thereby providing portion-specific fetal fraction estimates according to the weighting factors,
  wherein each of the weighting factors have been determined from a fitted relation for each portion between (i) a fraction of fetal nucleic acid for each of multiple samples, and (ii) counts of sequence reads mapped to each portion, or other portion-specific parameter, for the multiple samples; and (c) estimating a fraction of fetal nucleic acid for the test sample based on the portion-specific fetal fraction estimates.

A2. The method of embodiment A1, wherein the weighting factors are associated with portions in a plurality of portions in all autosomes and chromosomes X and Y.

A2.1. The method of embodiment A1, wherein the weighting factors are associated with portions in a plurality of portions that does not include portions in chromosome Y.

A3. The method of embodiment A2.1, wherein the weighting factors are associated with portions in a plurality of portions that does not include portions in chromosomes X and Y.

A4. The method of embodiment A2, wherein the weighting factors are associated with portions in a plurality of portions that include portions in autosomes or subset thereof.

A5. The method of embodiment A3 or A4, wherein the weighting factors are associated with portions in a plurality of portions that does not include portions in chromosomes 13, 18 and 21.

A6. The method of any one of embodiments A1 to A5, wherein the counts in (b)(i) or (b)(ii) are normalized counts.

A7. The method of embodiment A6, wherein the normalized counts have reduced guanine-cytosine (GC) bias with respect to raw counts.

A8. The method of embodiment A6 or A7, wherein the normalized counts are a product of a bin-wise normalization, normalization by GC content, linear least squares regression, nonlinear least squares regression, LOESS, GC LOESS, LOWESS, PERUN, repeat masking (RM), GC-normalization and repeat masking (GCRM), conditional quantile normalization (cQn), or combination thereof.

A9. The method of any one of embodiments A1 to A8, wherein estimating the fraction of fetal nucleic acid for the test sample comprises averaging or summing the portion-specific fetal fraction estimates.

A10. The method of any one of embodiments A1 to A9, wherein the portion-specific parameter is one portion-specific parameter or is one of two or more portion-specific parameters.

A11. The method of any one of embodiments A1 to A10, wherein the portion-specific parameter is chosen from genomic coverage, an amount of reads having a length less than a selected fragment length, mappability, DNaseI-sensitivity, methylation state, acetylation, histone distribution and chromatin structure.

A12. The method of any one of embodiments A1 to A10, wherein the portion-specific parameter is guanine-cytosine (GC) content.

A13. The method of any one of embodiments A1 to A10, wherein the portion-specific parameter is not guanine-cytosine (GC) content.

A14. The method of embodiment A11, wherein the amount of reads having a length less than a selected fragment length is determined according to a ratio of X to Y, wherein X is the amount of reads derived from circulating cell-free (CCF) fragments having a length less than a first selected fragment length, and Y is the amount of reads derived from CCF fragments having a length less than a second selected fragment length.

A15. The method of embodiment A14, wherein the first selected fragment length is about 140 to about 160 bases and the second selected fragment length is about 500 to about 700 bases.

A16. The method of embodiment A15, wherein the first selected fragment length is about 150 bases and the second selected fragment length is about 600 bases.

A17. The method of any one of embodiments A14 to A16, wherein the weighting factor for each portion is related to the average ratio for the portion for the multiple samples.

A18. The method of any one of embodiments A1 to A16, wherein the weighting factor for each portion is proportional to the average amount of reads from CCF fetal nucleic acid fragments mapped to the portion for the multiple samples.

A19. The method of any one of embodiments A1 to A18, wherein the portions are chosen from discrete genomic bins, genomic bins having sequential sequences of predetermined length, variable-size bins, point-based views of a smoothed coverage map, and a combination thereof.

A20. The method of any one of embodiments A1 to A19, wherein the multiple samples are from subjects having a euploid fetus.

A21. The method of any one of embodiments A1 to A19, wherein the multiple samples are from subjects having a trisomy fetus.

A22. The method of any one of embodiments A1 to A19, wherein the multiple samples are from subjects having a euploid fetus and from subjects having a trisomy fetus.

A23. The method of any one of embodiments A1 to A22, wherein the multiple samples are from subjects having a male fetus.

A24. The method of embodiment A23, wherein the fraction of fetal nucleic acid is determined according to an assay of chromosome Y.

A25. The method of any one of embodiments A1 to A24, wherein the counts in about 1,500 portions to about 200,000 portions are adjusted.

A25.1. The method of embodiment A25, wherein each of the portions are about 10 contiguous kilobases to about 75 contiguous kilobases from the reference genome.

A26. The method of any one of embodiments A1 to A25.1, wherein about 75% or more of the weighting factors are greater than zero.

A26.1. The method of embodiment A26, wherein about 85% or more of the weighting factors are greater than zero.

A26.2. The method of embodiment A26.1, wherein about 95% or more of the weighting factors are greater than zero.

A27. The method of any one of embodiments A1 to A26.2, wherein the width of a distribution of the weighting factors is dependent on the amount of reads from CCF fetal nucleic acid fragments.

A28. The method of any one of embodiments A1 to A27, wherein a distribution of the weighting factors is substantially symmetrical.

A28.1. The method of any one of embodiments A1 to A27, wherein a distribution of the weighting factors is substantially normal.

A29. The method of any one of embodiments A1 to A28.1, wherein the weighting factors are estimated coefficients from the fitted relations.

A30. The method of any one of embodiments A1 to A29, which comprises estimating coefficients from the relation for each portion between (i) the fraction of fetal nucleic acid for each of multiple samples, and (ii) counts of sequence reads mapped to each portion, or other portion-specific parameter, for the multiple samples.

A31. The method of embodiment A29 or A30, wherein each of the fitted relations is a regression model and the weighting factors are, or are based on, regression coefficients from the fitted relations.

A32. The method of embodiment A31, wherein the regression model is chosen from a linear regression model, simple regression model, ordinary least squares regression model, multiple regression model, general multiple regression model, polynomial regression model, general linear model, generalized linear model, discrete choice regression model, logistic regression model, multinomial logit model, mixed logit model, probit model, multinomial probit model, ordered logit model, ordered probit model, Poisson model, multivariate response regression model, multilevel model, fixed effects model, random effects model, mixed model, nonlinear regression model, nonparametric model, semiparametric model, robust model, quantile model, isotonic model, principal components model, least angle model, local model, segmented model, and errors-in-variables model.

A33. The method of embodiment A29 or A30, wherein the each of the fitted relations is not a regression model.

A34. The method of embodiment A33, wherein each of the fitted relations is chosen from a decision tree model, support-vector machine model and neural network model.

A35. The method of any one of embodiments A1 to A34, wherein the fitted relations are fitted by an estimation chosen from least squares, ordinary least squares, linear, partial, total, generalized, weighted, non-linear, iteratively reweighted, ridge regression, least absolute deviations, Bayesian, Bayesian multivariate, reduced-rank, LASSO, elastic net estimator and combination thereof.

A36. The method of any one of embodiments A1 to A35, comprising, prior to (a), determining the sequence reads by sequencing circulating cell-free nucleic acid from a test subject.

A37. The method of embodiment A36, comprising, prior to (a), mapping the sequence reads to the portions of the reference genome.

A38. The method of embodiment A36 or A37, comprising, prior to (a), isolating the circulating cell-free nucleic acid from the test sample.

A39. The method of embodiment A38, comprising, prior to (a), isolating the test sample from the test subject.

A40. The method of any one of embodiments A1 to A39, which comprises determining the presence or absence of a fetal chromosome aneuploidy for the test sample based on the estimated fraction of fetal nucleic acid.

A41. The method of embodiment A40, wherein the fetal chromosome aneuploidy is a trisomy.

A42. The method of embodiment A41, wherein the trisomy is chosen from a trisomy of chromosome 21, chromosome 18, chromosome 13 or combination thereof.

A43. The method of embodiment A41 or A42, wherein the presence or absence of the trisomy is determined with a sensitivity of 95% or greater or a specificity of 95% or greater, or a sensitivity of 95% or greater and a specificity of 95% or greater.

A44. A system comprising one or more microprocessors and memory,
which memory comprises instructions executable by the one or more microprocessors and which memory comprises nucleotide sequence reads mapped to portions of a reference genome, which sequence reads are reads of circulating cell-free nucleic acid from a test sample from a pregnant female, and which instructions executable by the one or more microprocessors are configured to:

(a) weight, using a microprocessor, (i) the counts of the sequence reads mapped to each portion, or (ii) other portion-specific parameter, to a portion-specific fraction of fetal nucleic acid according to a weighting factor independently associated with each portion, thereby providing portion-specific fetal fraction estimates according to the weighting factors,
wherein each of the weighting factors have been determined from a fitted relation for each portion between (i) a fraction of fetal nucleic acid for each of multiple samples, and (ii) counts of sequence reads mapped to each portion, or other portion-specific parameter, for the multiple samples; and
(b) estimate a fraction of fetal nucleic acid for the test sample based on the portion-specific fetal fraction estimates.

A45. A machine comprising one or more microprocessors and memory,
which memory comprises instructions executable by the one or more microprocessors and which memory comprises nucleotide sequence reads mapped to portions of a reference genome, which sequence reads are reads of circulating cell-free nucleic acid from a test sample from a pregnant female, and which instructions executable by the one or more microprocessors are configured to:

(a) weight, using a microprocessor, (i) the counts of the sequence reads mapped to each portion, or (ii) other portion-specific parameter, to a portion-specific fraction of fetal nucleic acid according to a weighting factor independently associated with each portion, thereby providing portion-specific fetal fraction estimates according to the weighting factors,
wherein each of the weighting factors have been determined from a fitted relation for each portion between (i) a fraction of fetal nucleic acid for each of multiple samples, and (ii) counts of sequence reads mapped to each portion, or other portion-specific parameter, for the multiple samples; and
(b) estimate a fraction of fetal nucleic acid for the test sample based on the portion-specific fetal fraction estimates.

A46. A non-transitory computer-readable storage medium with an executable program stored thereon, wherein the program instructs a microprocessor to perform the following:

(a) access nucleotide sequence reads mapped to portions of a reference genome, which sequence reads are reads of circulating cell-free nucleic acid from a test sample from a pregnant female;
(b) weight, using a microprocessor, (i) the counts of the sequence reads mapped to each portion, or (ii) other portion-specific parameter, to a portion-specific fraction of fetal nucleic acid according to a weighting factor independently associated with each portion, thereby providing portion-specific fetal fraction estimates according to the weighting factors,
wherein each of the weighting factors have been determined from a fitted relation for each portion between (i) a fraction of fetal nucleic acid for each of multiple samples, and (ii) counts of sequence reads mapped to each portion, or other portion-specific parameter, for the multiple samples; and
(c) estimate a fraction of fetal nucleic acid for the test sample based on the portion-specific fetal fraction estimates.

B1. A method for estimating a fraction of fetal nucleic acid in a test sample from a pregnant female, comprising:

(a) obtaining counts of sequence reads mapped to portions of a reference genome, which sequence reads are reads of circulating cell-free nucleic acid from a test sample from a pregnant female;

(b)(i) adjusting, using a microprocessor, the counts of the sequence reads mapped to each portion according to a weighting factor independently assigned to each portion, thereby providing adjusted counts for the portions, or (b)(ii) selecting, using a microprocessor, a subset of portions, thereby providing a subset of counts, wherein the adjusting in (b)(i) or the selecting in (b)(ii) is according to portions to which an increased amount of reads from fetal nucleic acid are mapped; and (c) estimating a fraction of fetal nucleic acid for the test sample based on the adjusted counts or the subset of counts.

B2. The method of embodiment B1, wherein the portions to which an increased amount of reads from fetal nucleic acid are mapped are determined according to a ratio of X to Y, wherein X is the amount of reads derived from circulating cell-free (CCF) fragments having a length less than a first selected fragment length, and Y is the amount of reads derived from CCF fragments having a length less than a second selected fragment length.

B3. The method of embodiment B2, wherein the ratio is an average ratio for multiple samples.

B4. The method of embodiment B3, wherein the weighting factor is determined, or portions are selected, according to a portion having an average ratio greater than the average ratio averaged for the portions.

B5. The method of any one of embodiments B2 to B4, wherein the first selected fragment length is about 140 to about 160 bases and the second selected fragment length is about 500 to about 700 bases.

B6. The method of embodiment B5, wherein the first selected fragment length is about 150 bases and the second selected fragment length is about 600 bases.

B7. A system comprising one or more microprocessors and memory, which memory comprises instructions executable by the one or more microprocessors and which memory comprises nucleotide sequence reads mapped to portions of a reference genome, which sequence reads are reads of circulating cell-free nucleic acid from a test sample from a pregnant female, and which instructions executable by the one or more microprocessors are configured to:

(a)(i) adjust, using a microprocessor, the counts of the sequence reads mapped to each portion according to a weighting factor independently assigned to each portion, thereby providing adjusted counts for the portions, or (a)(ii) select, using a microprocessor, a subset of portions, thereby providing a subset of counts, wherein the adjusting in (b)(i) or the selecting in (b)(ii) is according to portions to which an increased amount of reads from fetal nucleic acid are mapped; and (b) estimate a fraction of fetal nucleic acid for the test sample based on the adjusted counts or the subset of counts.

B8. A machine comprising one or more microprocessors and memory, which memory comprises instructions executable by the one or more microprocessors and which memory comprises nucleotide sequence reads mapped to portions of a reference genome, which sequence reads are reads of circulating cell-free nucleic acid from a test sample from a pregnant female, and which instructions executable by the one or more microprocessors are configured to:

(a)(i) adjust, using a microprocessor, the counts of the sequence reads mapped to each portion according to a weighting factor independently assigned to each portion, thereby providing adjusted counts for the portions, or (a)(ii) select, using a microprocessor, a subset of portions, thereby providing a subset of counts, wherein the adjusting in (b)(i) or the selecting in (b)(ii) is according to portions to which an increased amount of reads from fetal nucleic acid are mapped; and (b) estimate a fraction of fetal nucleic acid for the test sample based on the adjusted counts or the subset of counts.

B9. A non-transitory computer-readable storage medium with an executable program stored thereon, wherein the program instructs a microprocessor to perform the following:

(a) access nucleotide sequence reads mapped to portions of a reference genome, which sequence reads are reads of circulating cell-free nucleic acid from a test sample from a pregnant female;

(b)(i) adjust, using a microprocessor, the counts of the sequence reads mapped to each portion according to a weighting factor independently assigned to each portion, thereby providing adjusted counts for the portions, or (b)(ii) select, using a microprocessor, a subset of portions, thereby providing a subset of counts, wherein the adjusting in (b)(i) or the selecting in (b)(ii) is according to portions to which an increased amount of reads from fetal nucleic acid are mapped; and (c) estimate a fraction of fetal nucleic acid for the test sample based on the adjusted counts or the subset of counts.

C1. A method for increasing the accuracy of the estimation of a fraction of fetal nucleic acid in a test sample from a pregnant female, comprising: obtaining counts of sequence reads mapped to portions of a reference genome, which sequence reads are reads of circulating cell-free nucleic acid from a test sample from a pregnant female; wherein at least a subset of the counts obtained are derived from a region of the genome that contributes a greater number of counts derived from fetal nucleic acid relative to total counts from the region than counts of fetal nucleic acid relative to total counts of another region of the genome.

C2. The method of embodiment C1, comprising:

adjusting, using a microprocessor, the counts of the sequence reads mapped to each portion according to a weighting factor independently assigned to each portion, thereby providing adjusted counts for the portions, or selecting, using a microprocessor, a subset of portions, thereby providing a subset of counts; and estimating a fraction of fetal nucleic acid for the test sample based on the adjusted counts or the subset of counts.

C3. The method of embodiment C1 or C2, wherein the region of the genome that contributes a greater number of counts derived from fetal nucleic acid is determined according to a ratio of X to Y, wherein X is the amount of reads derived from circulating cell-free (CCF) fragments having a length less than a first selected fragment length, and Y is the amount of reads derived from CCF fragments having a length less than a second selected fragment length.

C4. The method of embodiment C3, wherein the ratio is an average ratio for multiple samples.

C5. The method of embodiment C4, wherein the weighting factor is determined, or portions are selected, according to a portion having an average ratio greater than the average ratio averaged for the portions.

C6. The method of any one of embodiments C3 to C5, wherein the first selected fragment length is about 140 to about 160 bases and the second selected fragment length is about 500 to about 700 bases.

C7. The method of embodiment C6, wherein the first selected fragment length is about 150 bases and the second selected fragment length is about 600 bases.

* * *

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The technology illustratively described herein suitably can be practiced in the absence of any element(s) not specifically disclosed herein. Thus, for example, in each instance herein any of the terms "comprising," "consisting essentially of," and "consisting of" can be replaced with either of the other two terms. The terms and expressions which have been employed are used as terms of description and not of limitation, and use of such terms and expressions do not exclude any equivalents of the features shown and described or segments thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed can be resorted to by those skilled in the art, and such modifications and variations are considered within the scope of this technology.

Certain embodiments of the technology are set forth in the claim(s) that follow(s).

What is claimed is:

1. A computer-implemented, fetal gender-independent, fetal ploidy independent and fetal polymorphism-independent method for determining a fraction of fetal nucleic acid in a test sample from sequenced test sample nucleic acid, the method comprising:

(a) receiving into a memory counts of sequence reads of sequenced test sample nucleic acid that are mapped to corresponding portions of a reference genome, which test sample nucleic acid comprises circulating cell-free (CCF) nucleic acid from blood of a pregnant female bearing a fetus;

(b) receiving into a memory a set of weighting factors that have been calculated for the corresponding portions of the reference genome from a fitted relation between (i) a fraction of fetal nucleic acid for each of multiple training samples, and (ii) counts of sequence reads mapped to each of the multiple training samples, wherein at least one weighting factor corresponds to each of the corresponding portions and is indicative of the fraction of fetal nucleic acid in each of the corresponding portions;

(c) assigning, using a microprocessor, the set of weighting factors to the corresponding portions of the reference genome, wherein each of the corresponding portions is independently associated with a corresponding weighting factor;

(d) generating, using a microprocessor, portion-specific fetal fraction calculations for the corresponding portions according to (i) the count of the sequence reads of the sequenced test sample nucleic acid mapped to the portion of the reference genome for each portion of the sequenced test sample, and (ii) the assigned weighting factor for each portion of the sequenced test sample; and (e) determining, using a microprocessor, a fraction of fetal nucleic acid for the test sample based on the portion-specific fetal fraction calculations.

2. The method of claim 1, wherein the weighting factors are associated with portions in a plurality of portions corresponding to autosomes.

3. The method of claim 2, wherein the weighting factors are associated with portions that do not correspond to any one or more of chromosomes 13, 18, and 21.

4. The method of claim 1, wherein the counts in (a) or (b)(ii) are normalized counts.

5. The method of claim 4, wherein the normalized counts have reduced guanine-cytosine (GC) bias with respect to raw counts.

6. The method of claim 1, wherein determining the fraction of fetal nucleic acid for the test sample comprises averaging or summing the portion-specific fetal fraction calculations.

7. The method of claim 1, wherein the weighting factor for each corresponding portion is related to the average ratio for the corresponding portion for the multiple training samples.

8. The method of claim 1, wherein the weighting factor for each corresponding portion is proportional to the average number of reads from CCF fetal nucleic acid fragments mapped to the corresponding portion for the multiple samples.

9. The method of claim 1, wherein the corresponding portions are chosen from discrete genomic bins, genomic bins having sequential sequences of predetermined length, variable-size bins, point-based views of a smoothed coverage map, or a combination thereof.

10. The method of claim 1, wherein each of the portions are about 10 contiguous kilobases to about 75 contiguous kilobases from the reference genome.

11. The method of claim 1, wherein about 75% or more of the weighting factors are greater than zero.

12. The method of claim 1, wherein the weighting factors are estimated coefficients from the fitted relations in (b).

13. The method of claim 1, which further comprises estimating coefficients for each portion from the fitted relations in (b).

14. The method of claim 12, wherein each of the fitted relations in (b) is a regression model and the weighting factors are, or are based on, regression coefficients from the fitted relations.

15. The method of claim 1, wherein the fitted relations in (b) are fitted by an estimation chosen from least squares, ordinary least squares, linear, partial, total, generalized, weighted, non-linear, iteratively reweighted, ridge regression, least absolute deviations, Bayesian, Bayesian multivariate, reduced-rank, LASSO, elastic net estimator, and any combination thereof.

16. The method of claim 1, further comprising, prior to (a), sequencing the test sample nucleic acid by a massively parallel sequencing process, thereby generating sequence reads; and mapping at least some of the sequence reads to a subset of the portions of the reference genome and counting the sequence reads mapped to the subset of the portions, thereby obtaining counts of sequence reads mapped to the subset of the portions, wherein each portion in the subset of the portions corresponds to a portion of the reference genome based on an observed proportion of fetal nucleic acid, a specific fragment length ratio, or a predetermined sequence length of the each portion, and wherein the number of portions in the subset of the portions is less than the number of portions of the reference genome.

17. The method of claim 1, further comprising outputting a classification of the presence or absence of a fetal chromosome copy number variation for the test sample based on the fraction of fetal nucleic acid determined in (e).

18. The method of claim 17, wherein the fetal chromosome copy number variation is an aneuploidy.

19. The method of claim 18, wherein the aneuploidy is a trisomy that is determined with a sensitivity of 95% or greater or a specificity of 95% or greater, or a sensitivity of 95% or greater and a specificity of 95% or greater.

20. The method of claim 16, wherein the test sample is sequenced at a fold coverage less than 1.

* * * * *

UNITED STATES PATENT AND TRADEMARK OFFICE
CERTIFICATE OF CORRECTION

PATENT NO. : 10,622,094 B2
APPLICATION NO. : 14/311070
DATED : April 14, 2020
INVENTOR(S) : Sung K. Kim et al.

Page 1 of 1

It is certified that error appears in the above-identified patent and that said Letters Patent is hereby corrected as shown below:

In the Claims

In Column 168, Line 35, In Claim 2, Line 2, after "with portions" delete "in a plurality of portions".

Signed and Sealed this
Twenty-sixth Day of May, 2020

Andrei Iancu
*Director of the United States Patent and Trademark Office*